(12) United States Patent
Sharpe et al.

(10) Patent No.: US 9,885,016 B2
(45) Date of Patent: Feb. 6, 2018

(54) COMPOSITIONS AND METHODS FOR MODULATING AN IMMUNE RESPONSE

(71) Applicant: President and Fellows of Harvard College, Cambridge, MA (US)

(72) Inventors: Arlene H. Sharpe, Cambridge, MA (US); Peter T. Sage, Cambridge, MA (US); Loise M. Francisco, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/707,596

(22) Filed: May 8, 2015

(65) Prior Publication Data

US 2016/0032245 A1  Feb. 4, 2016

Related U.S. Application Data

(63) Continuation of application No. PCT/US2013/069197, filed on Nov. 8, 2013.

(60) Provisional application No. 61/724,424, filed on Nov. 9, 2012.

(51) Int. Cl.
| | |
|---|---|
| *C12N 5/0783* | (2010.01) |
| *A61K 9/00* | (2006.01) |
| *A61K 39/00* | (2006.01) |

(52) U.S. Cl.
CPC .......... *C12N 5/0636* (2013.01); *A61K 9/0019* (2013.01); *A61K 39/0005* (2013.01); *C12N 5/0637* (2013.01); *C12N 2501/515* (2013.01); *C12N 2501/599* (2013.01)

(58) Field of Classification Search
None
See application file for complete search history.

(56) References Cited

FOREIGN PATENT DOCUMENTS

| | | |
|---|---|---|
| WO | 2010-003002 A2 | 1/2010 |
| WO | 2012-063875 A1 | 5/2012 |

OTHER PUBLICATIONS

Good-Jacobson et al., Nat Immunol. Jun. 2010;11(6):535-542.*
Kawamoto et al., Science. Apr. 27, 2012;336(6080):485-489.*
Wollenberg, I., et al., "Regulation of the Germinal Center Reaction by Foxp3+ Follicular Regulatory T Cells," The Journal of Immunology, 187(9): pp. 4553-4560 (2011).
Wu, H.Y., et al., "Suppression of Murine SLE by Oral Anti-CD3: Inducible CD4+CD25-LAP+ Regulatory T Cells Control the Expansion of IL-17+ Follicular Helper T Cells," Lupus 18(7): pp. 586-596 (2009).
King, C., et al., "T Follicular Helper (TFH) Cells in Normal and Dysregulated Immune Responses," Annual Review of Immunology, vol. 26, pp. 741-766 (2008).
Sage, P.T., et al., "The Receptor PD-1 Controls Follicular Regulatory T Cells in the Lymph Nodes and Blood," Nature Immunology, 14(2): pp. 152-161 (2012).

* cited by examiner

*Primary Examiner* — Daniel C Gamett
(74) *Attorney, Agent, or Firm* — Elmore Patent Law Group; Darlene A. Vanstone; Carolyn S. Elmore

(57) ABSTRACT

The invention provides methods of modulating follicular regulatory T (TFR) cell-mediated immune responses, follicular helper T (TFH) cell-mediated immune responses or both, and the use of those methods in the treatment of diseases or conditions mediated by TFR or TFH cells. The invention also provides novel methods for identifying TFR and TFH cells in a population of cells. The invention also provides compositions comprising TFR cells that have enhanced suppressive activity as compared wild type TFR cells. The invention also provides compositions comprising T follicular regulatory (TFR) cells isolated from the peripheral blood of a subject wherein the composition is enriched for TFR cells. Methods of making and using the compositions of the invention to modulate an immune response are also provided.

15 Claims, 109 Drawing Sheets

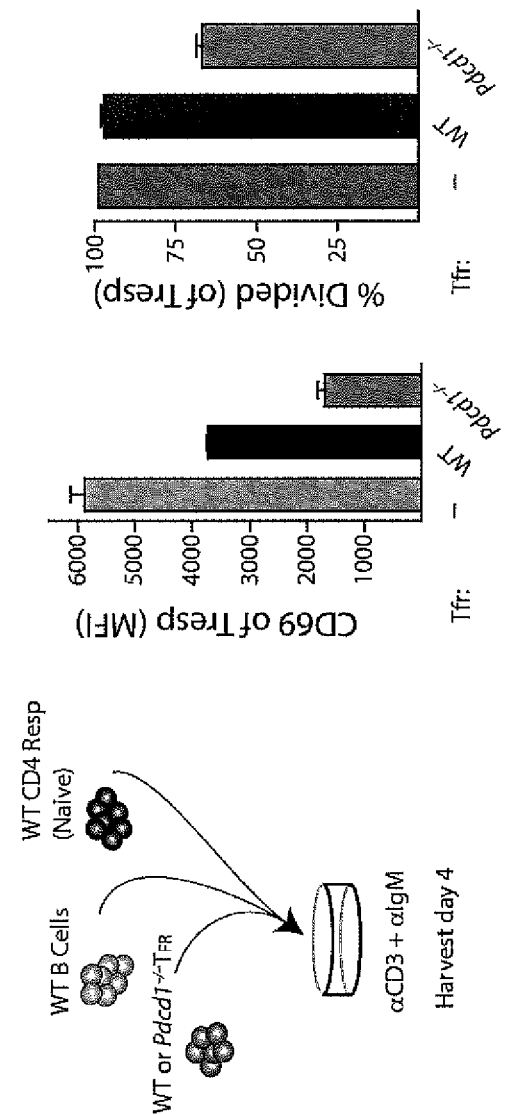

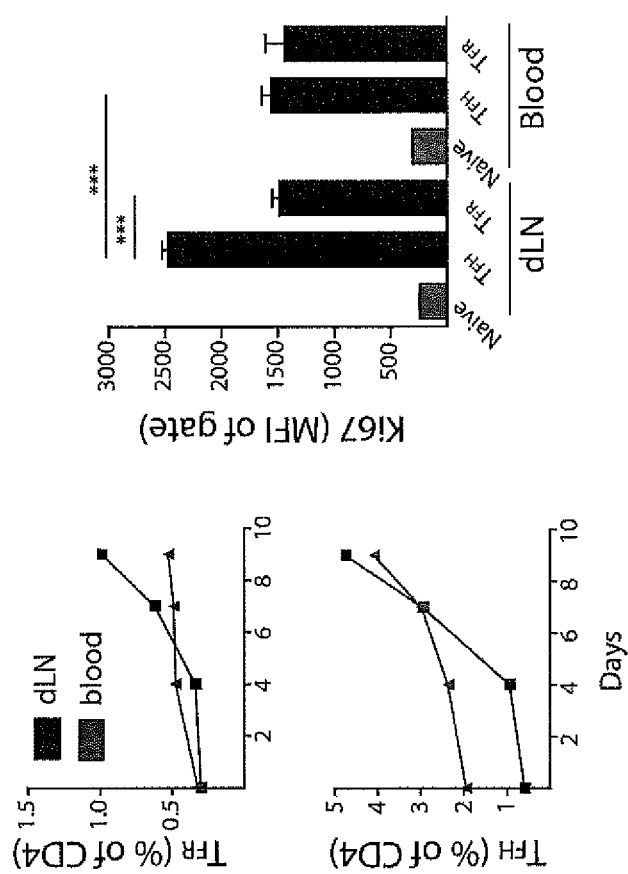

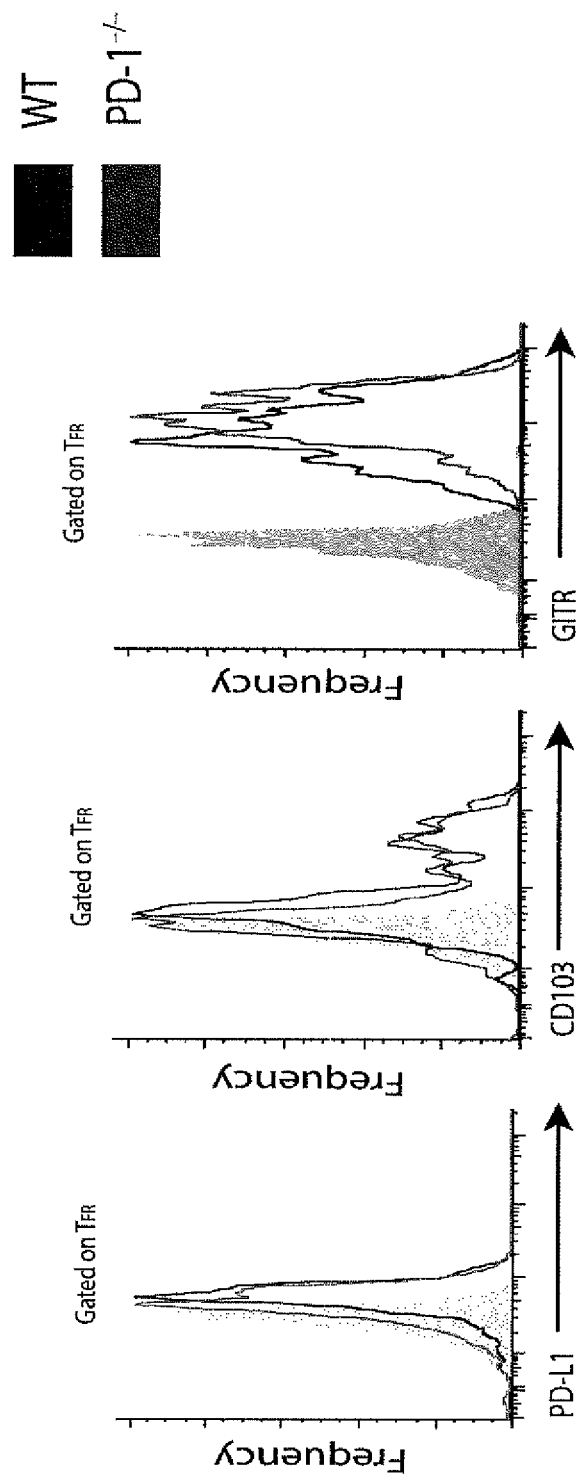

COMPOSITIONS AND METHODS FOR MODULATING AN IMMUNE RESPONSE

RELATED APPLICATIONS

This application is a continuation of PCT/US2013/069197, filed Nov. 8, 2013 which claims the benefit of U.S. Provisional Application No. 61/724,424, filed on Nov. 9, 2012. The entire teachings of the above applications are incorporated herein by reference.

GOVERNMENT SUPPORT

This invention was made with government support under grant numbers T32 AI070085; R01 AI40614, P01 78897 and T32 HL007627 awarded by The National Institutes of Health. The Government has certain rights in the invention.

BACKGROUND OF THE INVENTION

Regulation of immune responses is central for the prevention of inflammatory and autoimmune disorders. While downregulation of the immune system can be achieved by way of immunosuppressive therapy, agents that generally suppress the immune system leave subjects susceptible to other disorders, including infections and cancers. A means for controlling the aberrant activation of an immune response to specific antigens would be a major advance in the treatment of autoimmune disorders, graft versus host disease and the side effects of gene therapy, as it would allow downregulation of the immune response against a particular target antigen, but would otherwise leave the immune system functional against invading pathogens and tumor associated antigens. Conversely, methods of specifically improving immunogenicity of specific antigens to which immune responses are desired would be of tremendous benefit in promoting desired immune responses, for example in the context of vaccination and promoting responsiveness to antigens including tumor antigens.

T helper (Th) cells are a class of CD4+ cells that function to regulate the proliferation of B cells and B cell responses. Th cells play an importance role in humoral immunity and immunopathology. Follicular helper T cells ($T_{FH}$) are a recently defined subset of CD4+ T cells that are essential for helping cognate B cells form and maintain the germinal center (GC) reaction, and for development of humoral immune responses. These cells are universally defined by expression of the chemokine receptor CXCR5, which directs them to the B cell follicles via gradients of the chemokine CXCL13[1]. $T_{FH}$ cells also express the transcription factor Bcl6 (which represses Blimp-1/Prdm1) and high levels of the costimulatory receptor ICOS, which are both critical for their differentiation and maintenance[1-4]. In addition, $T_{FH}$ cells secrete large amounts of IL-21, which aids in GC formation, isotype switching and plasma cell formation[5]. In humans and mice functionally similar $T_{FH}$ cells can be found in secondary lymphoid organs. CXCR5+ $T_{FH}$ cells are also present in peripheral blood and seen at elevated levels in individuals with autoantibodies, including systemic lupus erythematosis, myasthenia gravis and juvenile dermatomyositis patients. However, the function of these circulating $T_{FH}$ remains unclear[6-9].

Regulatory T cells (Tregs) have pluripotent anti-inflammatory effects on multiple cell types. In particular they control the activation of innate and adaptive immune cells. Tregs acting in an antigen-specific manner reduce effector T cell activation and function, for example, after effector 'T' cells have successfully mounted an attack against an invading pathogen, or to suppress reactivity to self-antigen and thereby prevent autoimmune disease.

Two subsets of Tregs are classified according to the location at which they develop in vivo. Naturally occurring Tregs (nTreg) develop in the thymus and suppress self-reactive immune responses in the periphery, whereas adaptive Tregs (aTreg) develop in the periphery from conventional CD4+ T cells to ensure tolerance to harmless antigens, including those derived from, for example, food and intestinal flora. Both subsets of Treg cells are characterized by expression of high levels of CD25 and the transcription factor Foxp3. Tregs are thought to inhibit the antigen-specific expansion and/or activation of self-reactive effector T cells and to secrete suppressive cytokines, including TGF or IL-10, Because of their potential to provide antigen-specific immune regulation without generalized immunosuppression, Tregs have been contemplated for use in cell-based therapy for inflammatory or autoimmune disorders.

T follicular regulatory ($T_{FR}$) cells are newly defined subset of CD4+CXCR5+ cells which are positive for the transcription factors FoxP3, Bcl6 and Prdm1/Blimp1 and function to inhibit the germinal center response[21-23].

PD-1 has been identified as a receptor which binds to PD-L1 and PD-L2. PD-1 is a member of the immunoglobulin gene superfamily. PD-1 (Ishida et al. (1992) *EMBO J.* 11:3887; Shinohara et al. (1994) *Genomics* 23:704; U.S. Pat. No. 5,698,520) has an extracellular region containing immunoglobulin superfamily domain, a transmembrane domain, and an intracellular region including alp immunoreceptor tyrosine-based inhibitory motif (ITIM). PD-1 transmits a negative signal to immune cells, similar to CTLA4. PD-1 ligand proteins are expressed on the surface of antigen presenting cells, and other cell types, and can provide a costimulatory signal to immune cells or can transmit downmodulatory signals to immune cells, depending upon the protein to which they bind. While transmission of an inhibitory signal leads to downmodulation in immune cell responses (and a resulting downmodulation in the overall immune response), the prevention of an inhibitory signal (e.g., by using a non-activating antibody against PD-1) in immune cells leads to upmodulation of immune cell responses (and a resulting upmodulation of an immune response).

$T_{FH}$ cells express high levels of programmed death (PD) 1 receptor (CD279). Signaling through PD-1 attenuates TCR signals and inhibits T cell expansion, cytokine production and cytolytic function. In addition, PD-1 promotes the development of induced regulatory T (iTreg) cells from naïve lymphocytes[10-14]. PD-1 has two ligands, PD-L1 (B7-H1) and PD-L2 (B7-DC). PD-L1 is more widely expressed than PD-L2, but PD-L1 and PD-L2 both can be expressed on GC B cells and dendritic cells[15]. Perturbation studies suggest critical roles for this pathway in regulating humoral immune responses. However, there are conflicting reports as to the function of the PD-1 pathway in controlling humoral immunity. Some studies have found that humoral responses are attenuated[16-18], while others have seen that humoral responses are heightened[19, 20] when PD-1:PD-L interactions are prevented.

PD-1 also is found on $T_{FR}$ cells. These cells originate from natural regulatory T cell precursors, but express similar levels of ICOS, CXCR5 and PD-1 as $T_{FH}$ cells. Since ICOS, CXCR5 and PD-1 have been widely used to identify and purify '$T_{FH}$ cells', it seems likely that the inability to define clear functions for PD-1 in GC responses derives from experimental systems containing mixtures of stimulatory T$_{FH}$ cells and inhibitory T$_{FR}$ cells.

The present inventors have discovered that PD-1:PD-L1 interactions limit TFR cell differentiation and function. This discovery has elucidated novel approaches to modulating an immune response for use in therapy.

This discovery has also elucidated novel cell markers for identifying and separating TFR and TFH cells from all other cell types. These markers are also useful for selectively modifying TFR-mediated and/or TFH mediated immune responses in vivo and in vitro.

SUMMARY OF THE INVENTION

The invention is based, in part on the discovery that PD-1 regulates immune responses by inhibiting differentiation and function of TFR cells in both lymph nodes and blood. This discovery has led to strategies for modulating an immune response in vivo and in vitro by altering the interaction of PD-1 receptors on TFR cells with PD-1 ligands.

The invention is also based in part on the discovery of cell markers on TFH and THR cells that enable such cells to be more easily identified, distinguished and tracked in vivo and/or separated into highly purified homogenous cell populations of TFH cells or TFR cells. Such markers make it possible to add specificity and reliability in detecting TFR or TFH cells either in situ, in circulation, or as disseminated cells which is particularly useful for example in monitoring disease burden and in tracking the responses of TFH cells and TFR cells to particular stimuli such as agents intended to modulate TFH and TFR cell-mediated immune responses. These markers are also useful for selectively modifying TFR cell-mediated, and/or TFH cell-mediated immune responses in vivo and in vitro.

In one embodiment the invention provides TFR cells having enhanced suppressive activity as compared to wild type TFR cells. In one embodiment, the invention provides compositions comprising TFR cells having enhanced suppressive activity. TFR cells having enhanced suppressive activity as compared to wild type TFR cells are characterized by their greater capacity for antibody inhibition as compared to WT TFR, as measured by an in vivo or in vitro assays for antibody suppression. In one embodiment, the enhanced TFR cells have an increase in capacity of at least 2 fold to inhibit antibody production as compared to WT TFR cells.

In one embodiment the invention provides methods for generating TFR cells having enhanced suppressive activity. In accordance with the invention, TFR cells having enhanced suppressive activity may be prepared, ex vivo, from a starting population of cells which comprise TFR cells and/or TFR precursor cells such as FoxP3+ T regulatory (Treg) cells, isolated from the blood, tissues or organs of one or more subjects. The starting population of cells may optionally be sorted based on surface markers for Tcells and Tcell subsets. The starting population of cells is expanded and/or activated in the presence of a PD-1 receptor antagonist or PD-1 ligand inhibitor. The expanded/activated cells may optionally be sorted based on surface markers for T cells and T cell subsets to obtain a composition of cells enriched for a particular T cell subset (e.g. TFR cells or TFH cells).

The present inventors have also discovered that TFR cells derived from the peripheral blood of a subject are potent inhibitors of TFH mediated antibody production but do no inhibit other arms of the immune system. Therefore, the invention provides compositions comprising TFR cells isolated from the peripheral blood of a subject. The compositions may be enriched for the peripheral blood TFR cells by purifying TFR cells from other PMBCs and optionally sorting for TFR cells based on surface markers. Compositions of TFR cells derived from peripheral blood may also be expanded and/or activated to produce a clonal population of TFR cells based on the original population of TFR cells derived from the peripheral blood of the patient.

Compositions comprising TFH cells which are also present in the peripheral blood of a subject may be provided in the same manner. The inventors have discovered that such compositions, particularly when enriched for TFH cells, are capable of rapidly upregulating an antibody response in vitro and in vivo.

The inventors have also discovered that increasing the ratio of TFR cells to TFH cells in a subject prior to, or during an immune response by the subject, inhibits antibody production. Therefore, the invention provides a method for suppressing an immune response in a subject wherein suppression of an immune response is desired, comprising increasing the ratio of TFR cells to TFH cells by administering a composition enriched with TFR cells derived from the peripheral blood of a subject (or an expanded/activated population thereof) or administering a composition comprising TFR cells having enhanced suppressive activity.

The invention also provides methods of promoting rapid antibody production in a subject comprising increasing the number of TFH cells in a patient by administering a composition enriched with TFH cells derived from the peripheral blood of a subject (or an expanded/activated population thereof).

The compositions of TFR cells and TFH cells of the invention are also useful as adjuvants as a part of a vaccination regimen. When used in this manner, the compositions enhance the efficacy of such vaccines.

The invention further provides compositions and methods for suppressing pathogenic antibody responses in a patient comprising selectively modulating differentially expressed receptors on TFR cells, TFH cells, or both TFR cells and TFH cells with agents capable of modulating such receptors in amounts effective to suppress a pathogenic antibody response.

The invention further provides compositions and methods for enhancing a protective antibody response in a patient comprising selectively modulating differentially expressed receptors on TFR cells, TFH cells, or both TFR cells and TFH cells with agents capable of modulating such receptors in amounts effective to enhance a protective antibody response in a patient.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 4G. Design of assay to analyze capacity of T$_{FR}$ cells to inhibit activation of naïve CD4 T cells. WT and PD-1$^{-/-}$ mice were immunized with MOG/CFA and T$_{FR}$ cells were sorted from draining lymph nodes and plated 1:1:1 with CFSE-labeled CD4 naïve WT (CD4$^+$CD62L$^+$FoxP3$^-$) responder cells and WT GL7$^-$B220$^+$ B cells from MOG/CFA immunized mice along with anti-CD3 and anti-IgM for 4 days. 3 days later samples were analyzed by flow cytometry.

FIG. 4H. PD-1$^{-/-}$ T$_{FR}$ cells suppress activation of naïve T cells to a greater extent than WT T$_{FR}$ cells. T responders from suppression assays from FIG. 4G were analyzed for CD69 expression by measuring CFSE dilution. % divided indicates percent of cells that have gone through at least one division.

FIG. 4I. PD-1$^{-/-}$ T$_{FR}$ cells suppress activation of naïve T cells to a greater extent than WT T$_{FR}$ cells. T responders from suppression assays from FIG. 4G were analyzed for CD69 proliferation by measuring CFSE dilution. % divided indicates percent of cells that have gone through at least one division.

FIG. 5B. Quantitation of blood T$_{FH}$ and T$_{FR}$ cells following MOG/CFA immunization. Mice were immunized as in FIG. 5A and sacrificed on the indicated days. Blood was collected and cells stained and gated as in FIG. 5A.

FIG. 5C. Ki67 expression in blood and lymph node T$_{FH}$, T$_{FR}$ and nave (CD4$^+$ICOS$^-$CXCR5$^-$) cells 7 days after MOG/CFA immunization. All data indicates means+/−standard error of 5 mice and is representative of at least two independent experiments. * P<0.05,  P<0.005, * P<0.0005.

FIG. 11A. Comparison of PD-L1, CD103 and GITR expression on WT and PD-1$^{-/-}$ T Follicular Regulatory Cells. WT or PD-1$^{-/-}$ mice were immunized with MOG (35-55) and 7 days later draining lymph nodes were stained. T$_{FR}$ (CD4$^+$ICOS$^+$CXCR5$^+$FoxP3$^+$CD19$^-$) cells were analyzed for surface expression of PD-L1.

FIG. 11B. Comparison of PD-L1, CD103 and GITR expression on WT and PD-1$^{-/-}$ T Follicular Regulatory Cells. WT or PD-1$^{-/-}$ mice were immunized with MOG (35-55) and 7 days later draining lymph nodes were stained. T$_{FR}$ (CD4$^+$ICOS$^+$CXCR5$^+$FoxP3$^+$CD19$^-$) cells were analyzed for surface expression of CD103.

FIG. 11C. Comparison of PD-L1, CD103 and GITR expression on WT and PD-1$^{-/-}$ T Follicular Regulatory Cells. WT or PD-1$^{-/-}$ mice were immunized with MOG (35-55) and 7 days later draining lymph nodes were stained. T$_{FR}$ (CD4$^+$ICOS$^+$CXCR5$^+$FoxP3$^+$CD19$^-$) cells were analyzed for surface expression of GITR.

Figure 20A:
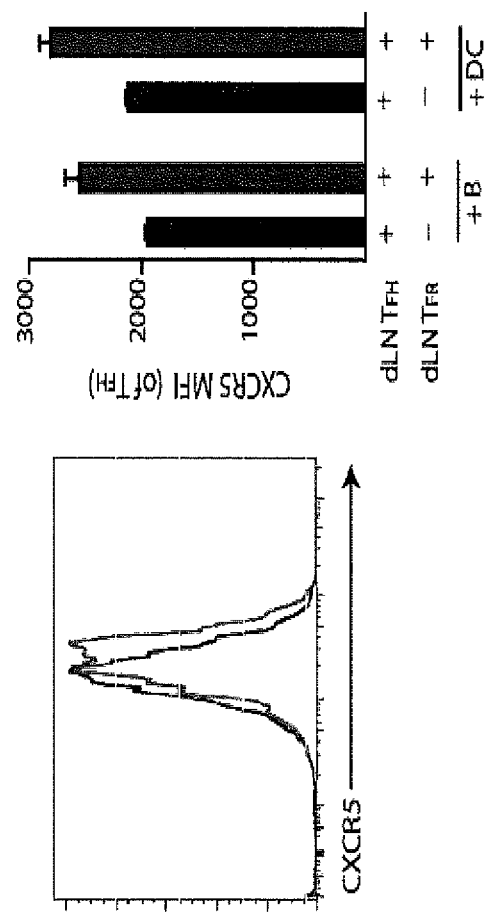
FIG. 20A. TFR cells suppress TFH activation and B cell class switch recombination in vitro. dLN TFR suppression assays in which dLN TFH CD4+ICOS+CXCR5+GITR−CD19−) and/or TFR (CD4+ICOS+CXCR5+GITR+CD19−) cells were plated with either B cells or DCs (isolated from the dLN of WT mice immunized with NP-OVA 7 days previously) for 5-6 days with anti-CD3 and anti-IgM. TFH cells were gated as CD4+CD19−FoxP3− and stained for surface expression of CXCR5. Representative histograms (left) and quantification (right) are shown. Data indicate means+/−standard error of replicate wells and representative of at least 3 independent experiments.
Figure 20B:
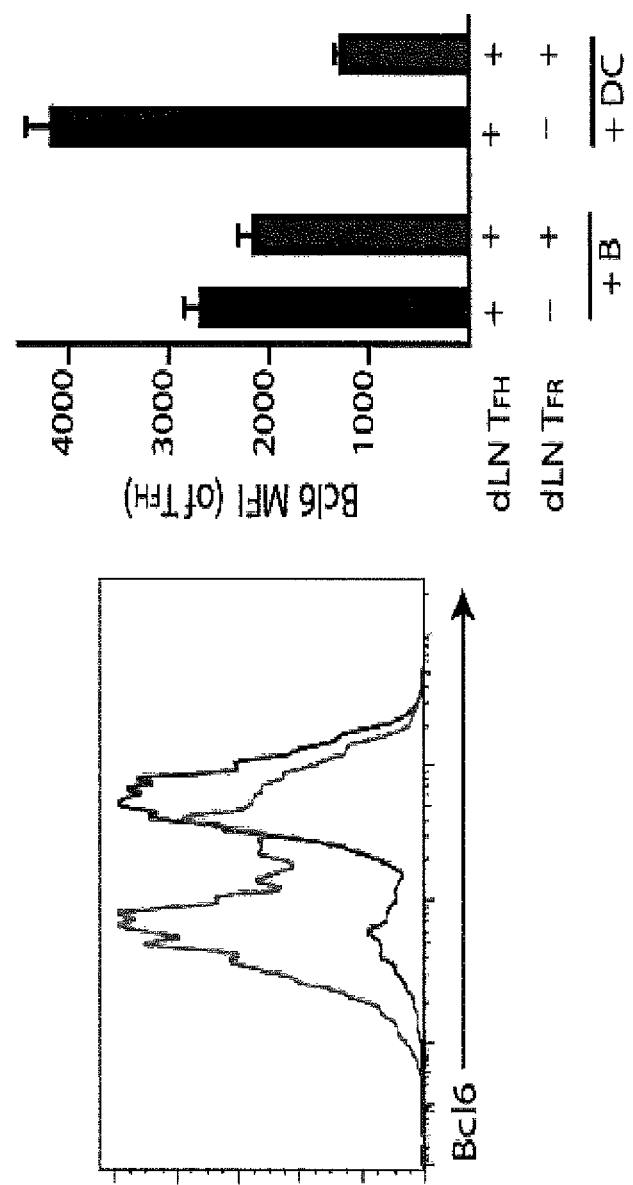
FIG. 20B. TFH cells gated as in FIG. 20A were intracellularly stained for (B) Bcl6 with representative histograms (left) and quantification (right) shown. Data indicate means+/−standard error of replicate wells and representative of at least 3 independent experiments.
Figure 20C:
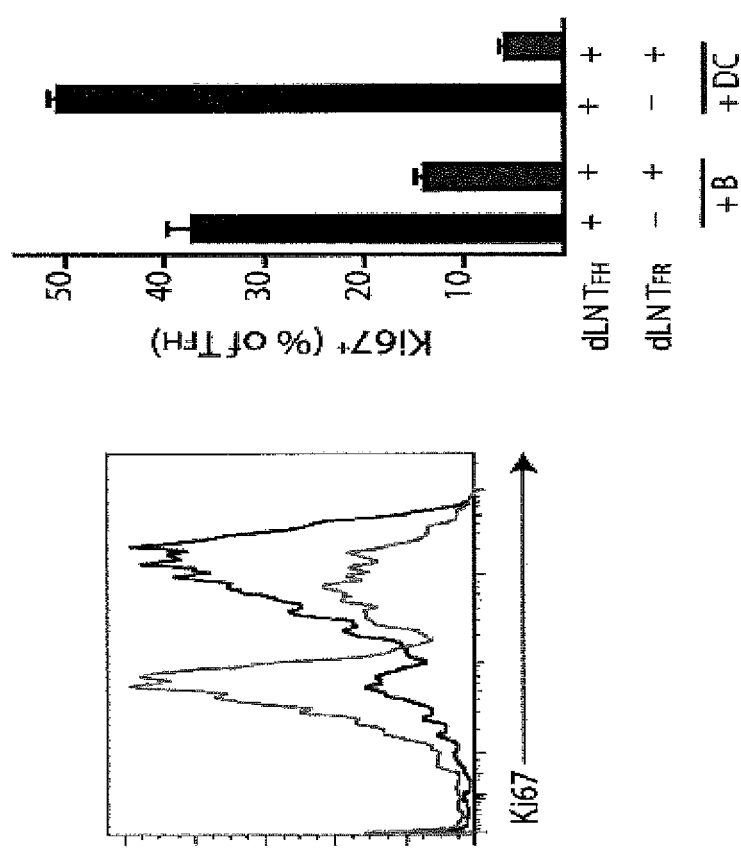
FIG. 20C. TFH cells gated as in FIG. 20A were intracellularly stained for (Ki67, with representative histograms (left) and quantification (right) shown. Data indicate means+/−standard error of replicate wells and representative of at least 3 independent experiments.
Figure 20D:
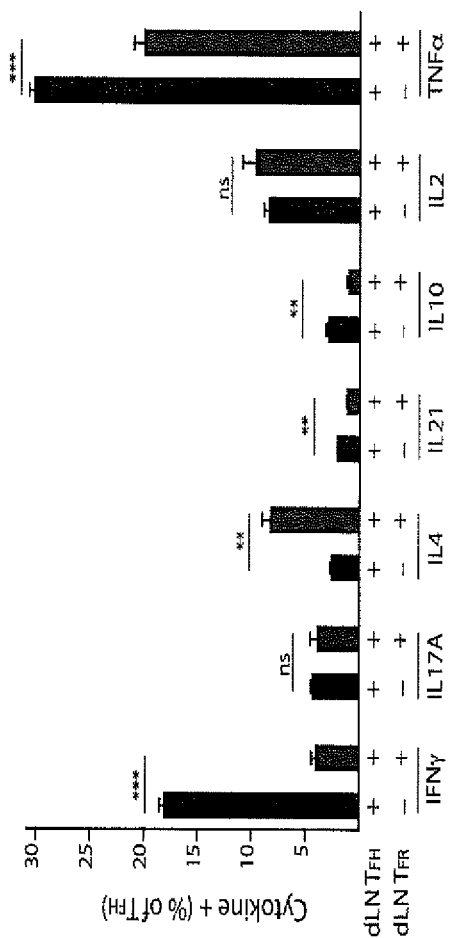
FIG. 20D. Intracellular cytokine staining in TFH cells from suppression assays in which dLN TFH and/or TFR cells were plated with B cells as in FIG. 20A. Data indicate means+/−standard error of replicate wells and representative of at least 3 independent experiments.
Figures 20E, 20F:
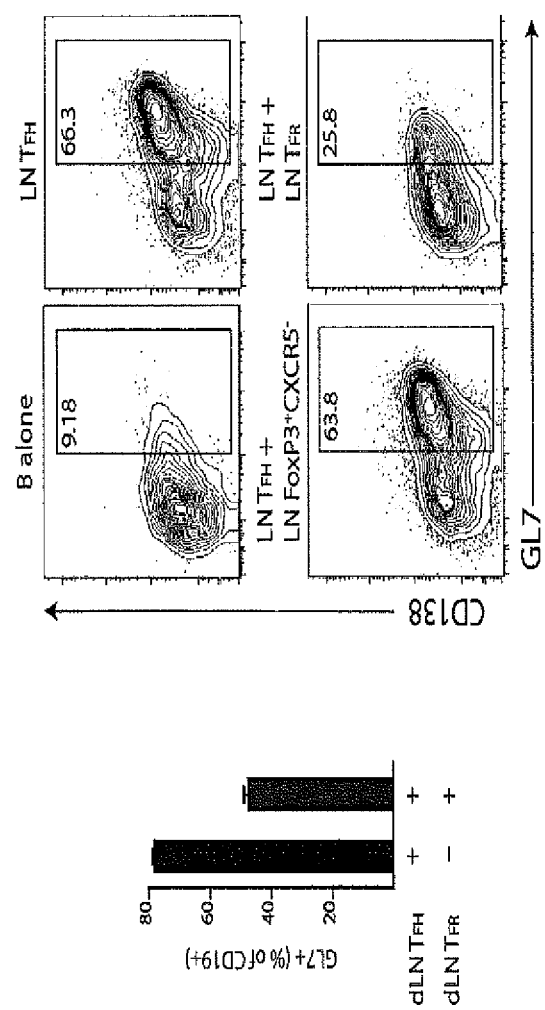
FIG. 20E. B cells from suppression assays in which dLN TFH and/or TFR cells were plated with B cells as in FIG. 20A and quantified for surface expression of GL7. Data indicate means+/−standard error of replicate wells and representative of at least 3 independent experiments.
FIG. 20F. Analyses of B cells from suppression assays in which no TFH or TFR cells were added, TFH cells alone were added, TFH and dLN FoxP3+CXCR5− cells from WT unimmunized mice were added, or TFH and TFR cells were added; B cells were stained for GL7 and CD138. Plots are pregated on CD19+CD4−.
Figure 20H:
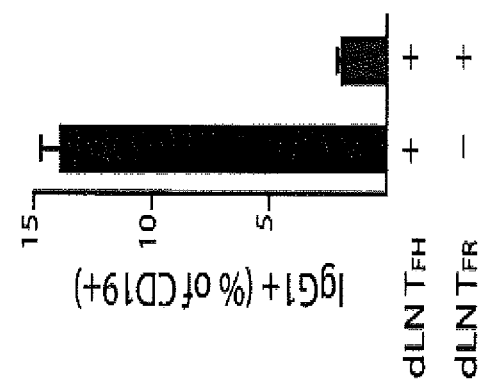
FIG. 20G. Intracellular expression of Ki67 in B cells from suppression assays in which dLN TFH and/or TFR cells were plated with B cells as in FIG. 20A. Data indicate means+/−standard error of replicate wells and representative of at least 3 independent experiments.

FIG. 20H. Intracellular expression of IgG1 in B cells from suppression assays in which dLN TFH and/or TFR cells were plated with B cells as in FIG. 20A. Data indicate means+/−standard error of replicate wells and representative of at least 3 independent experiments.

Figure 20G:
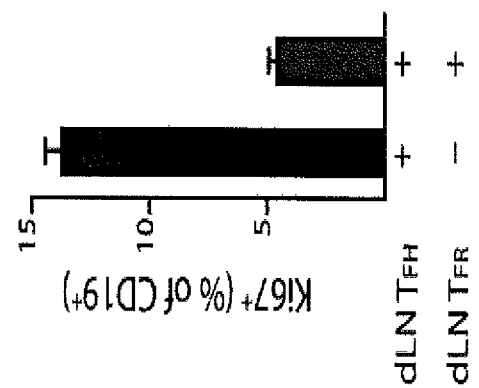
Figure 20I:
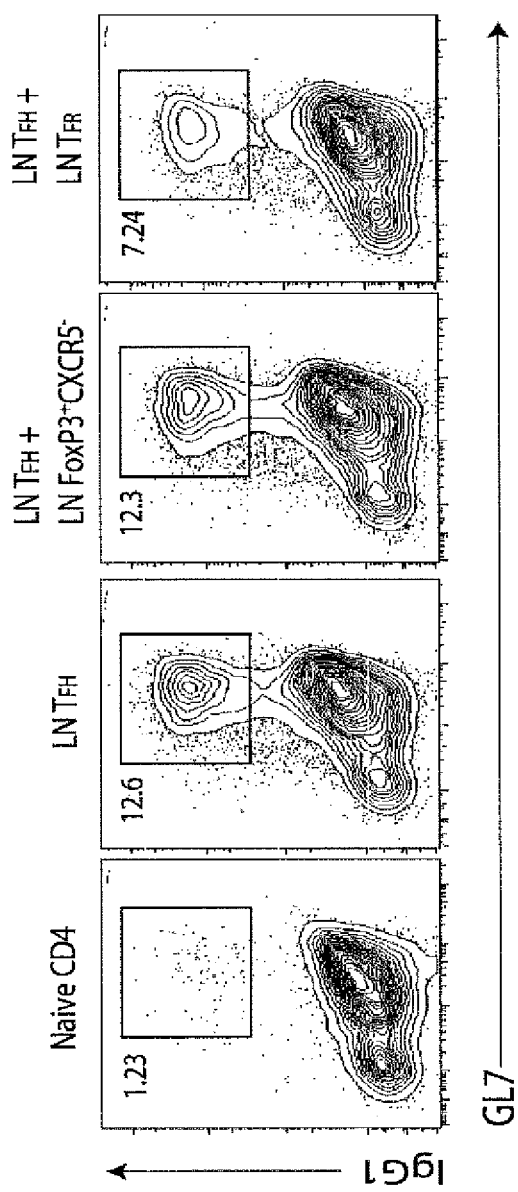

FIG. 20I. Surface staining of GL7 and intracellular staining of IgG1 in B cells from suppression assays in which B cells were cultured with with dLN TFH cells alone, or with CD4+FoxP3+CXCR5− cells from LN of unimmunized FoxP3 GFP reporter mice, or dLN TFR cells. B cells cultured with CD4+CXCR5−FoxP3−CD62L+ naïve cells were included as controls. Data indicate means+/−standard error of replicate wells and representative of at least 3 independent experiments.

Figure 21A:
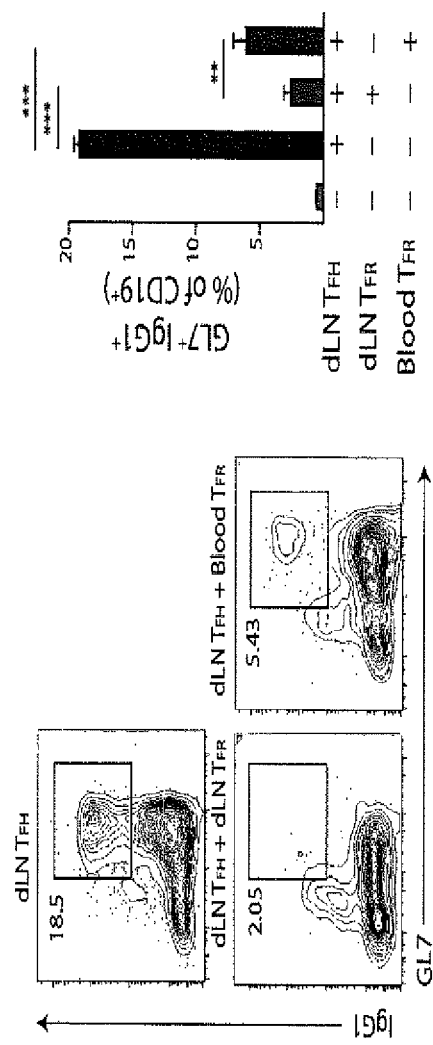

FIG. 21A. Blood TFR cells are less suppressive than LN TFR cells. GL7 and IgG1 expression in B cells from suppression assays in which dLN or blood TFR (CD4+ICOS+CXCR5+GITR+CD19−) cells from WT mice immunized 7 days previously were added to dLN TFH cells and B cells as in (FIG. 6A) for 6 days. Gating strategy (left) and quantification (right) are shown. Plots are pregated on CD4+CD19−FoxP3−. Data indicate means+/−standard error of at least 3 independent experiments.

Figure 21B:
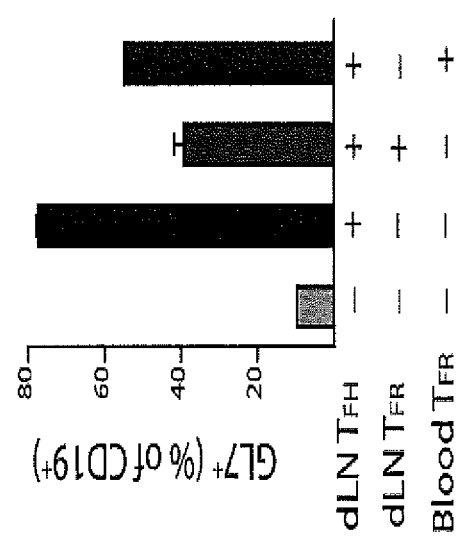

FIG. 21B. GL7 expression on B cells from suppression assays with dLN TFR cells and blood TFR cells as in FIG. 21A.

Figure 21C:
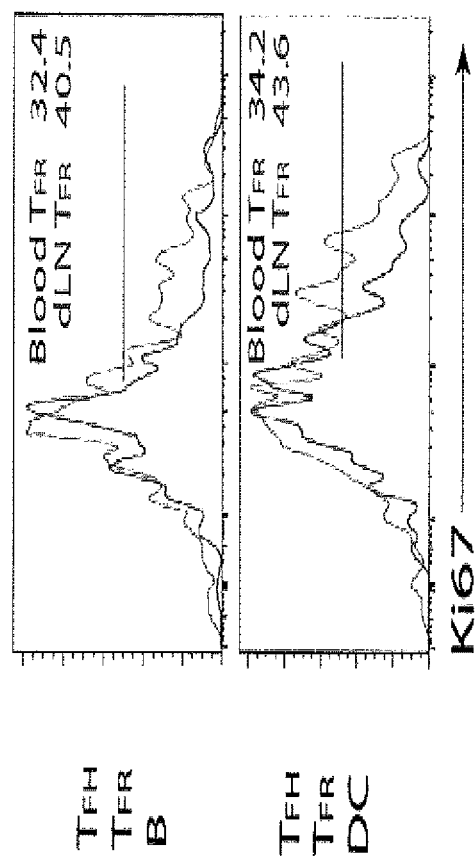

FIG. 21C. Intracellular Ki67 staining in TFR cells from suppression assays in which dLN TFH cells were plated with either B cells or DCs along with dLN TFR cells or blood TFR cells. Histograms are pregated on CD4+CD19−FoxP3+. Data for individual plots that are representative of at least two experiments.

Figures 21D, 21E:
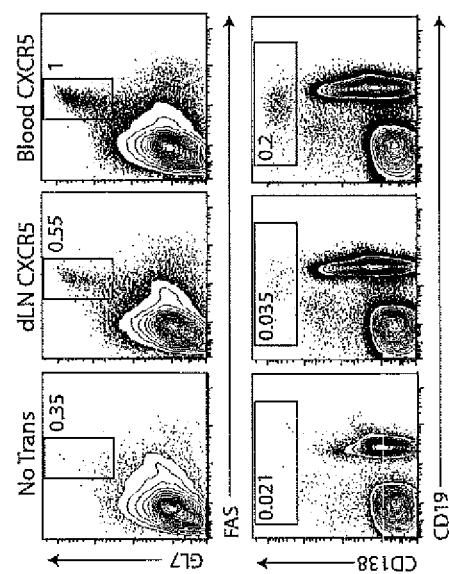

FIG. 21D. Blood TFH and TFR cells are capable of eliciting more potent B cell activation in vivo. Actin$^{CFP}$-Fox$^{GFP}$ mice were immunized with NP-OVA and 7 days later 2×10$^4$ blood or dLN CD4$^+$ICOS$^+$CXCR5$^+$ (TFH and TFR) cells (with the same TFH/TFR ratio) were adoptively transferred to CD28 deficient mice that were then immunized with NP-OVA. 7 days later draining lymph nodes were harvested and B cells were stained for GL7 and FAS (plots are pregated on CD19) or (E) CD138 and CD19 (pregated on live cells). Data for individual plots that are representative of at least two experiments.

FIG. 21E. Blood TFH and TFR cells are capable of eliciting more potent B cell activation in vivo. Actin$^{CFP}$-Fox$^{GFP}$ mice were immunized with NP-OVA and 7 days later 2×10$^4$ blood or dLN CD4$^+$ICOS$^+$CXCR5$^+$ (TFH and TFR) cells (with the same TFH/TFR ratio) were adoptively transferred to CD28 deficient mice that were then immunized with NP-OVA. 7 days later draining lymph nodes were harvested and B cells were stained for CD138 and CD19 (pregated on live cells). Data for individual plots that are representative of at least two experiments.

Figure 22A:
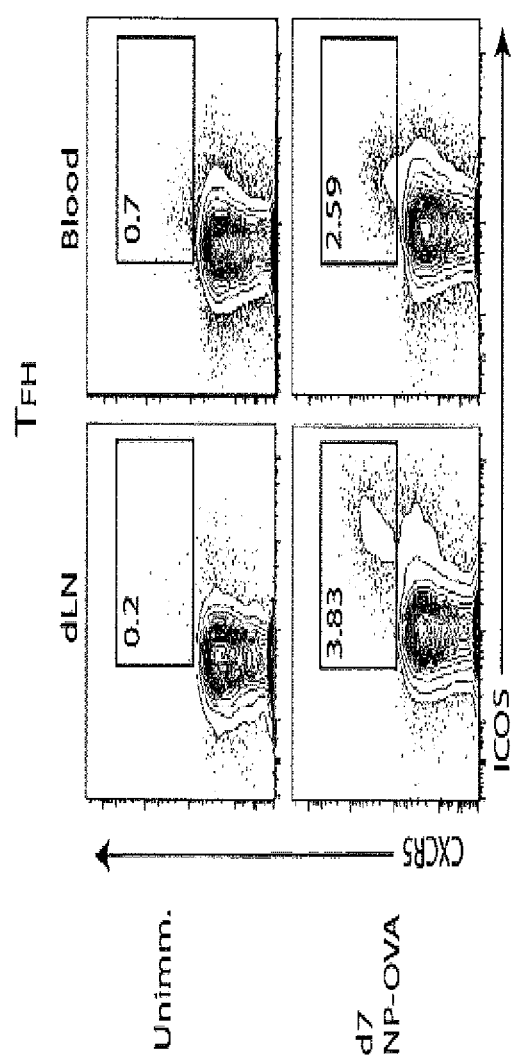

FIG. 22A. TFH and TFR cells from the circulation show decreased expression of CXCR5 and ICOS compared to lymph node TFH and TFR cells. WT mice were immunized (or not) with NP-OVA in CFA subcutaneously and 7 days later the draining lymph node and blood were collected and analyzed by flow cytometry. Populations of ICOS$^+$CXCR5$^+$ T follicular helper (TFH) cells in the lymph node (LN; left) and blood (right) of WT mice. Plots are pregated on CD4$^+$FoxP3$^-$CD19.

Figures 22B, 22C:
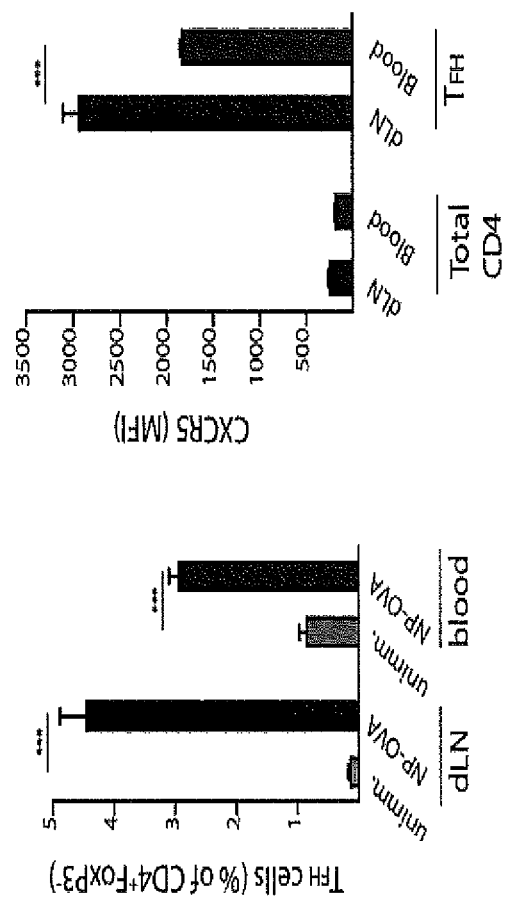

FIG. 22B. Quantification of TFH cells in lymph node (left) and blood (right) from plots as in FIG. 22A. Total CD4+CD19− cells "Total CD4" are included as controls.

FIG. 22C Quantification of CXCR5 expression, on lymph node and blood TFH cells gated as in FIG. 22A.

Figures 22D, 22E:
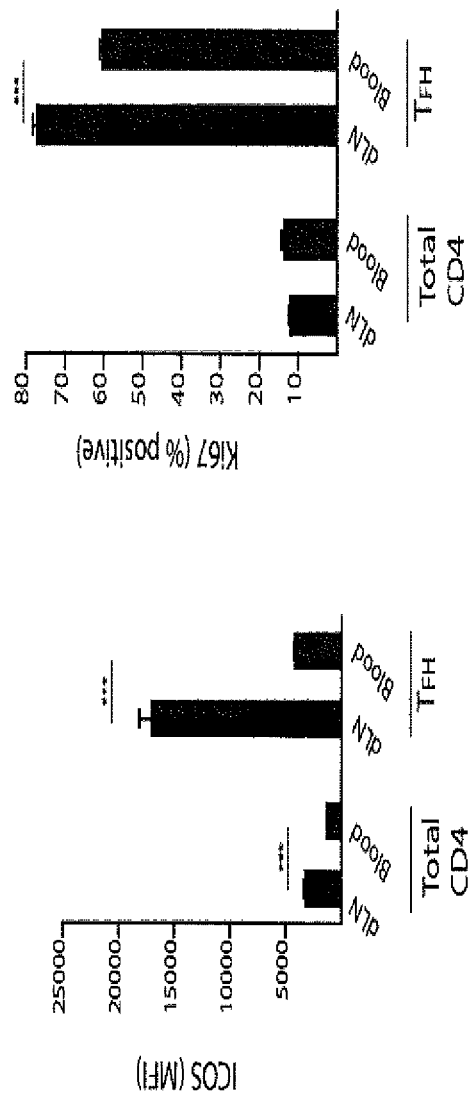

FIG. 22D. ICOS expression on lymph node and blood TFH cells gated as in FIG. 22A.

FIG. 22E. Quantification of Ki67 expression on lymph node and blood TFH cells gated as in FIG. 22A.

Figure 22F:
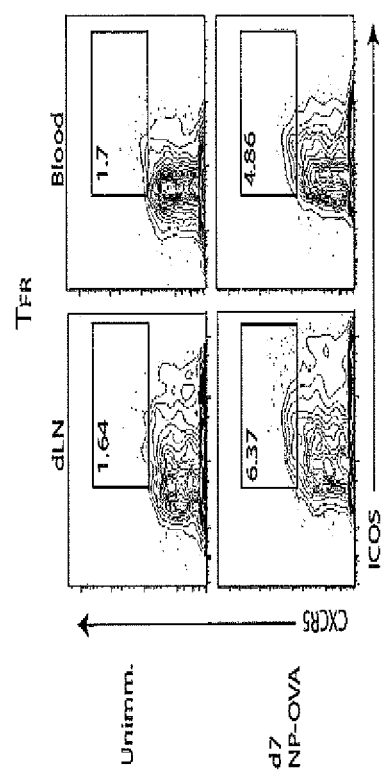

FIG. 22F. Populations of ICOS$^+$CXCR5$^+$ T follicular regulatory (TFR) cells in the lymph node and blood of WT mice immunized or not with NP-OVA 7 days previously. Plots are pregated on CD4$^+$FoxP3CD19$^-$.

Figures 22G, 22H:
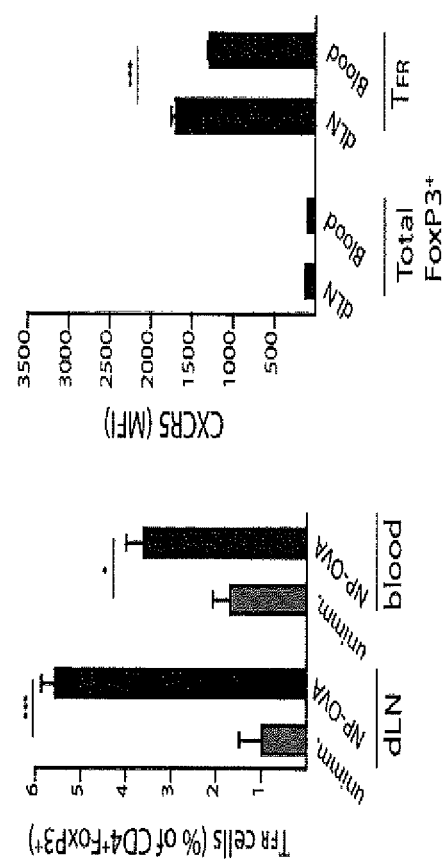

FIG. 22G. Draining LN TFR cells expressed lower levels of CXCR5 than dLN TFH cells.

FIG. 22H. Blood TFR cells expressed even lower levels of CXCR5 than dLN TFR cells.

Figures 22I, 22J:
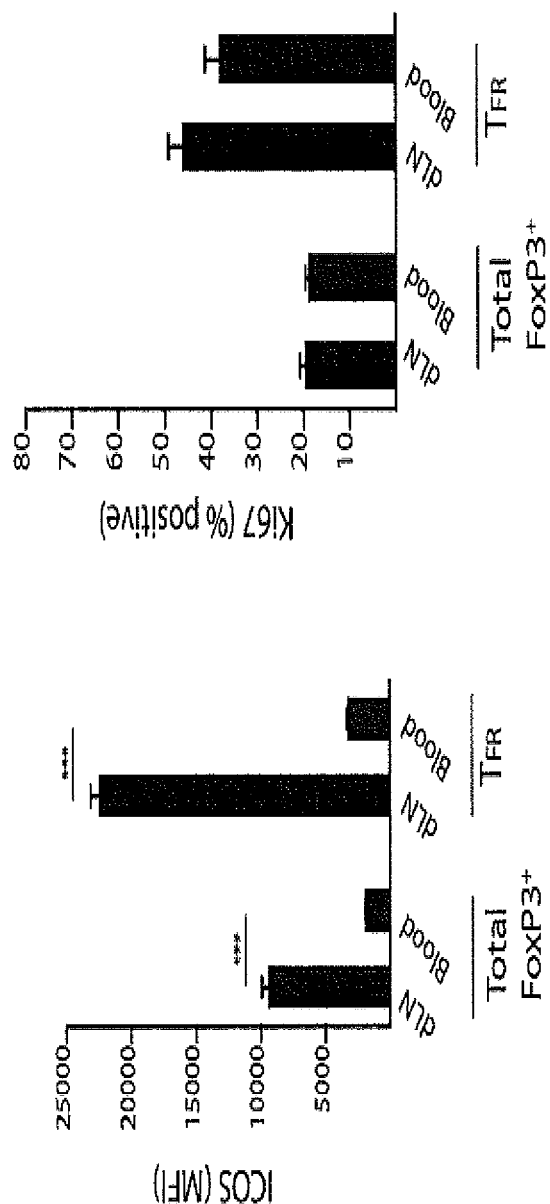

FIG. 22I. ICOS expression was also greatly attenuated in blood TFR cells compared to dLN TFR cells.

FIG. 22J. Ki67 intracellular staining revealed that there were similar proportions of dLN and blood TFR cells in cell cycle.

Figure 23:
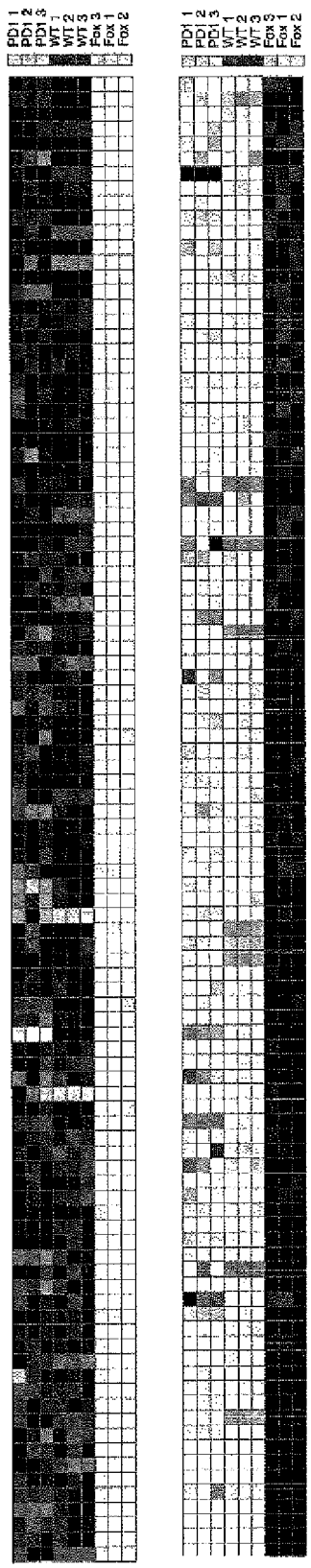

FIG. 23. Comparison of TFR and Treg gene expression signatures (left) Top hits (oriented top to bottom) and (right) bottom hits (oriented bottom to top) of differentially expressed genes in WT CD4+ICOS+CXCR5+ GITR+ TFR cells (WT) compared to CD4+CXCR5−FoxP3+ non-TFR Tregs (Fox) in microarray analysis. PD-1 deficient TFR cells (PD1) (which have increased suppressive capacity) are also shown. Each row indicates one gene. Data indicate top 100 and bottom 100 hits comparing WT TFR to Tregs. Black indicates row maximum expression, white indicates row minimum expression.

Figure 24:
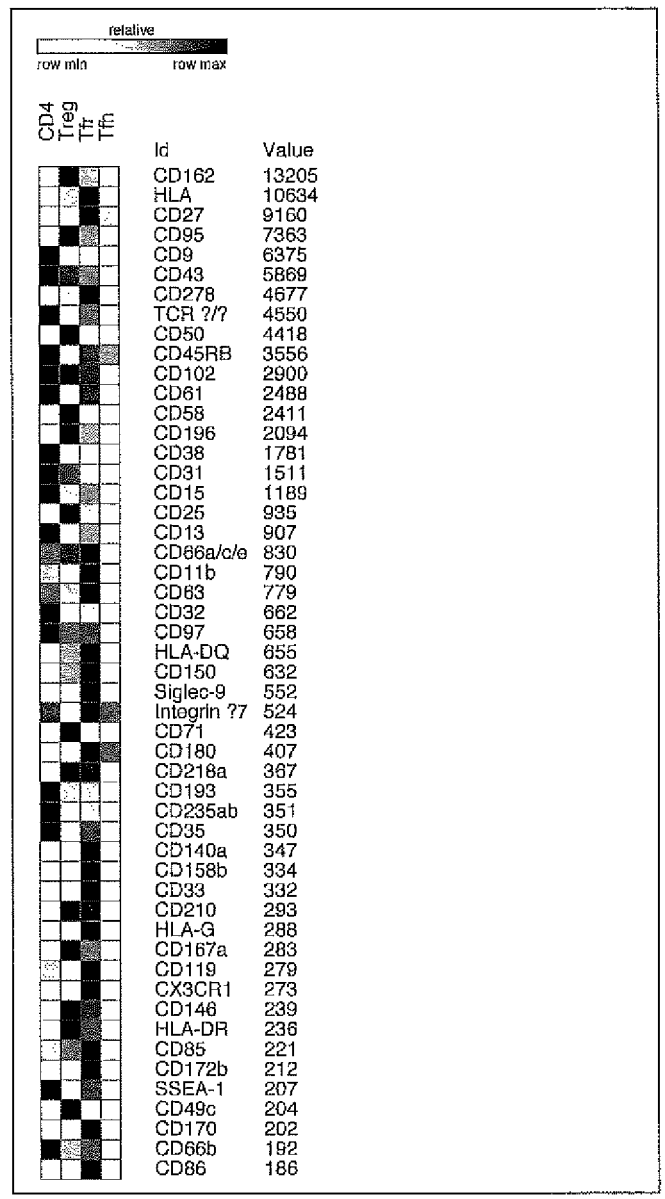

FIG. 24. Surface receptors differentially expressed by human blood TFR cells. Top 56 hits from a survey of surface receptor expression on human blood CD4+CXCR5+ ICOS+FoxP3+CD19− TFR, CD4+CXCR5+ ICOS+FoxP3−CD19− TFH, CXCR5− CD4 (CD4) and CXCR5− Tregs (Treg) are assessed at the protein level by flow cytometry. Hits are sorted based on receptors differentially expressed by TFR and TFH cells. Id indicates gene name. Value indicates mean fluorescence intensity on TFR cells. Heat map indicates relative high expression (black) or low expression (white).

Figure 25:
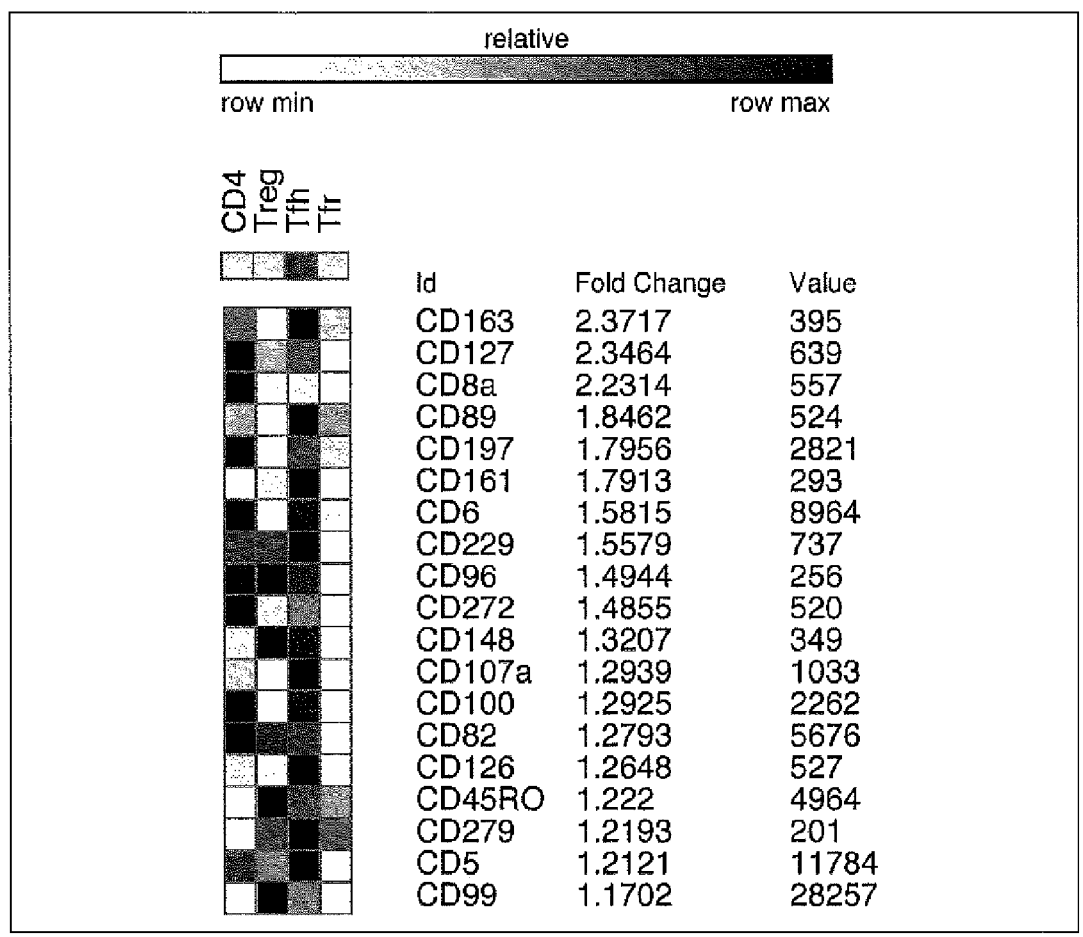

FIG. 25. Surface receptors differentially expressed by human blood TFH cells. Top 19 hits from a survey of surface receptor expression on human blood CD4+CXCR5+ ICOS+FoxP3+CD19−TFR, CD4+CXCR5+ ICOS+FoxP3−CD19− TFH, CXCR5− CD4 (CD4) and CXCR5− Tregs (Treg) are assessed at the protein level by flow cytometry. Hits are sorted based on receptors differentially expressed by TFH and TFR cells. Id indicates gene name. Fold change indicates MFI fold increase on TFH vents TFR cells. Value indicates mean fluorescence intensity on TFR cells. Heat map indicates relative high expression (black) or low expression (white).

Figure 26:
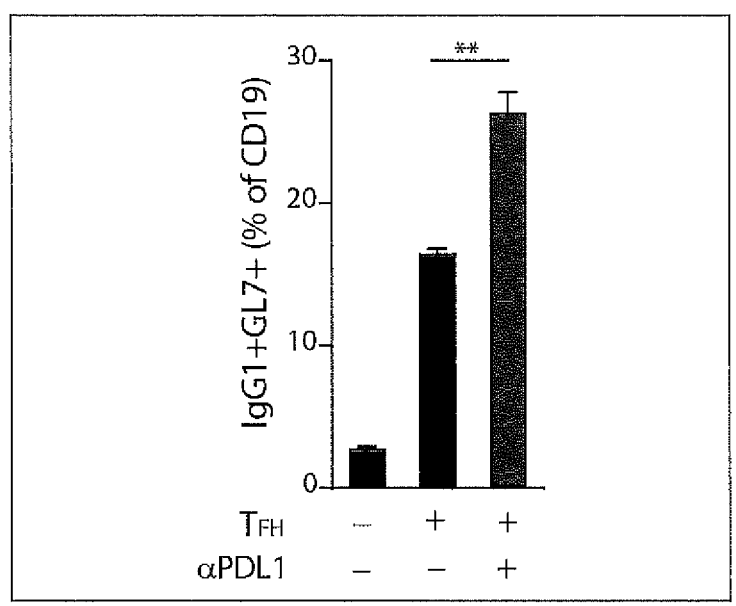

FIG. 26. Blockade of the PD-1 pathway can heighten antibody stimulating capacity of TFH cells. In vitro class switch recombination assay in which murine B cells are plated with sorted murine TFH cells to induce IgG1 class switch recombination. In some wells an anti-PDL1 blocking antibody was added to inhibit the PD-1 pathway.

DETAILED DESCRIPTION OF THE INVENTION

I. Definitions

So that the invention may be more readily understood, certain terms are first defined.

T follicular regulatory (TFR) cells as used herein include, but are not limited to, the following cell surface markers: CD4+ICOS+CXCR5+FoxP3+CD19−. or CD4+ICOS+CXCR5+GITR+CD19−, or CD4+ICOS+CXCR5+CD25hiCD19−. In one embodiment, TFR cells have the following cell surface markers: CD4$^+$CXCR5$^+$ICOS$^+$ and at least one surface marker selected from: GITR$^+$, CD25$^{hi}$, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, TFR cells have the following cell surface markers: CD4$^+$CXCR5$^+$ICOS$^+$ and at least one surface marker selected from: CD27, CD278 (ICOS), CD150, Siglec-9, CD140a, CD158b, CD33.

T follicular helper (TFH) cells as used herein include, but are not limited to the following cell surface markers: CD4+ ICOS+CXCR5+FoxP3−CD19−. In one embodiment, TFH cells have the following cell surface markers: CD4, CXCR5, ICOS positive and at least one marker selected from CD163, CD127, CD8a, CD89, CD197, CD161, CD6, CD229, CD96, CD272, CD148, CD107a, CD100, CD82, CD126, CD45RO, CD279, CD5, and CD99 and optionally wherein the TFH cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, TFH cells have the following cell surface markers: CD4, CXCR5, ICOS positive and at least one marker selected from CD163, CD127, CD161, CD6, CD229, CD272, CD100, CD126, PD-1 (CD279), and optionally wherein the TFH cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

In one embodiment, TFH cells have the following cell surface markers: CD4, CXCR5, ICOS positive and at least one marker selected from CD163, CD127, CD161, CD6, CD229, CD272, CD100, CD126, PD-1 (CD279), and optionally wherein the following markers are expressed a lower levels on TFH cells as compared to the levels of expression on TFR cells wherein such receptors are selected from: GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD8.

T regulatory cells (Tregs) as used herein include, but are not limited to the following cell surface markers: CD4+ GITR+ CXCR5⁻ or CD4+FoxP3+ CXCR5⁻ or CD4+ CD25hi CXCR5⁻.

Populations of TFH or TFR cells referred to herein as "isolated" or purified" from blood refers to cells that have been removed from the body as part of a sample taken from the peripheral blood, organs or tissues of a subject. "Isolated" and "purified" cell compositions may further be enriched for the desired cell type via known procedures for separating desired cell types from other cell populations in a sample including cell sorting. As used herein" enriched" means that the resulting sample comprises more of the desired cell type than other cell types in the sample.

The terms "inhibit", "inhibition, "suppress" and "suppression" in terms of an immune response includes the decrease, limitation or blockage of, for example a particular action, function or interaction (e.g. antibody suppression).

The terms "enhance", "promote" or "stimulate" in terms of an immune response includes an increase, facilitation, proliferation, for example a particular action, function or interaction associated with an immune response (e.g. increase in antibody production).

As used herein, the term "modulate" includes up-regulation and downregulation, e.g., enhancing or inhibiting an immune response. The term "modulate" when used with regard to modulation of a receptor includes up-regulation or downregulation of the biological activity associated with that receptor when the receptor is activated, for example, by its ligand or inhibited, for example, with a blocking antibody.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "T cell" includes CD4+ T cells and CD8+ T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

The term "native" cells or "wild-type" cells as used herein with reference to, for example, TFR cells, TFH cells or other cells, means that the cells are essentially phenotypically and functionally the same as those cells of the same cell-type generally found at the original source of the native or wild type cells, such as, for example, TFR cells normally found in the blood, organs or tissue of a subject.

The term TFR cells with "enhanced suppressive capacity" or "enhanced immune suppressive activity" or "enhanced regulatory capacity" refers to TFR cells that have been activated in the presence of a PD-1 or PD-1 ligand antagonist such that they have enhanced immune suppressive activity as compared to native TFR cells. Enhanced immune suppressive activity may be measured by standard in vivo and in vitro assays such as antibody suppression assays as are known in the art and described herein.

The term TFH cells with "enhanced stimulatory capacity", "enhanced immune stimulatory capacity" or "enhanced antibody stimulatory capacity" refers to TFH cells that have been activated in the presence of a PD-1 or PD-1 ligand antagonist such that they have enhanced stimulatory capacity as compared to native TFR cells. Enhanced stimulatory capacity may be measured, for example, by the novel in vivo and in vitro antibody proliferation assays of the invention as described herein.

As used herein, the term "immune response" includes T cell mediated and/or B cell mediated immune responses and include those immune responses that are mediated by TFR cells or TFH cells. Exemplary immune responses include T cell responses, e.g., cytokine production, and cellular cytotoxicity. In addition, the term immune response includes immune responses that are indirectly affected by T cell activation, e.g., antibody production (humoral responses) and activation of cytokine responsive cells, e.g., macrophages.

A "subject" is preferably a human subject but can also be any mammal, including an animal model, in which modulation of an autoimmune reaction is desired. Mammals of interest include, but are not limited to: rodents, e.g. mice, rats; livestock, e.g. pigs, horses, cows, etc., pets, e.g. dogs, cats: and primates. A subject may also be a donor of peripheral blood T cells who is not the subject in which modulation of an autoimmune reaction is desired also referred to herein as a "healthy donor". A subject may also be referred to herein as a "patient".

The terms "treatment" "treat" and "treating" encompasses alleviation, cure or prevention of at least one symptom or other aspect of a disorder, disease, illness or other condition (collectively referred to herein as a "condition"), or reduction of severity of the condition, and the like. A composition of the invention need not affect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Beneficial or desired clinical results include, but are not limited to, alleviation of symptoms, diminishment of extent of disease, stabilization (i.e., not worsening) of disease, delay or slowing of disease progression, amelioration or palliation of the disease state, remission (whether partial or total, whether detectable or undetectable) and prevention of relapse or recurrence of disease. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

"Treatment" can also mean prolonging survival as compared to expected survival if not receiving treatment. In one embodiment, an indication that a therapeutically effective amount of a composition has been administered to the patient is a sustained improvement over baseline of an indicator that reflects the severity of the particular disorder.

By a "therapeutically effective amount" of a composition of the invention is meant an amount of the composition which confers a therapeutic effect on the treated subject, at a reasonable benefit/risk ratio applicable to any medical treatment. The therapeutic effect is sufficient to "treat" the patient as that term is used herein.

As used herein, "cell therapy" is a method of treatment involving the administration of live cells.

"Adoptive immunotherapy" is a treatment process involving removal of cells from a subject, the processing of the cells in some manner ex-vivo and the infusion of the processed cells into the same subject as a therapy.

As used herein, a vaccine is a composition that provides protection against a viral infection, cancer or other disorder or treatment for a viral infection, cancer or other disorder. Protection against a viral infection, cancer or other disorder will either completely prevent infection or the tumor or other disorder or will reduce the severity or duration of infection, tumor or other disorder if subsequently infected or afflicted with the disorder. Treatment will cause an amelioration in one or more symptoms or a decrease in severity or duration. For purposes herein, a vaccine results from co-infusion (either sequentially or simultaneously) of an antigen and a composition of cells produced by the methods herein. As used herein, amelioration of the symptoms of a particular disorder by administration of a particular composition refers to any lessening, whether permanent or temporary, lasting or transient that can be attributed to or associated with administration of the composition.

As used herein a "vaccination regimen" means a treatment regimen wherein a vaccine comprising an antigen and/or adjuvant is administered to a subject in combination with for example, composition of the invention comprising TFR cells and/or TFH cells, simultaneously, in either separate or combined formulations, or sequentially at different times separated by minutes, hours or days, but in some way act together to provide the desired enhanced immune response to the vaccine in the subject as compared to the subject's immune response in the absence of a TFR and/or TFH composition in accordance with the invention.

The term "adjuvant" is used in its broadest sense as any substance which enhances, increases, upwardly modulates or otherwise facilitates an immune response to an antigen. The immune response may be measured by any convenient means such as antibody titre or level of cell-mediated response.

"Immune-related disease" means a disease in which the immune system is involved in the pathogenesis of the disease. Subsets of immune-related diseases are autoimmune diseases. Autoimmune diseases include, but are not limited to, rheumatoid arthritis, myasthenia gravis, multiple sclerosis, psoriasis, systemic lupus erythematosus, autoimmune thyroiditis (Hashimoto's thyroiditis), Graves' disease, inflammatory bowel disease, autoimmune uveoretinitis, polymyositis, and certain types of diabetes. Other immune-related diseases are provided infra. In view of the present disclosure, one skilled in the art can readily perceive other autoimmune diseases treatable by the compositions and methods of the present invention.

A disease or condition wherein modulation of, and preferably selective modulation of, TFR cells and/or TFH cells is therapeutic, includes diseases wherein suppression of a pathogenic antibody response is desired and diseases where enhancement of a protective antibody response is desired. In some instances, for example, in a disease in which suppression of a pathogenic antibody response is therapeutic, it is contemplated herein that the disease may be treated by selectively upregulating TFR cell-mediated antibody suppression while simultaneously selectively down-regulating TFH cell-mediated immune response.

Examples of diseases or conditions wherein suppression of a pathological antibody response is desired include diseases in which antibodies contribute to, or are primarily responsible for pathogenesis. Such diseases or conditions in which antibodies contribute to and/or are primarily responsible for pathogenesis include, but are not limited to, diabetes (Type 1), multiple sclerosis, systemic lupus erythematosus, allergy, asthma, multiple sclerosis, myasthenia gravis, lupus erythematosus, autoimmune hemolytic, scleroderma and systemic sclerosis, Sjogren's syndrom, undifferentiated connective tissue syndrome, antiphospholipid syndrome, vasculitis (polyarteritis nodosa, allergic granulomatosis and angiitis, Wegner's granulomatosis, hypersensitivity vasculitis, polymyositis systemic lupus erythematosus, collagen diseases, autoimmune hepatitis, primary (autoimmune) sclerosing cholangitis or other hepatic diseases, thyroiditis, glomerulonephritis, Devic's disease, autoimmune throbocytopenic purpura, pemphigus vulgaris, vasculitis caused by ANCA, Goodpasture's syndrome, rheumatic fever, Grave's disease (hyperthyroidism), insulin resistant diabetes, pernicious anemia, celiac disease, hemolytic disease of the newborn, cold aggutinin disease, IgA nephropathology, glomerulonephritis (including post-streptococcal), primary biliary cirhosis, and serum sickness. In one embodiment diseases in which pathogenic antibodies contribute to and/or are primarily responsible for pathogenesis are selected from multiple sclerosis, systemic lupus erythematosus, allergy, myasthenia gravis, collagen diseases, glomerulonephritis, Devic's disease, vasculitis caused by ANCA, and celiac disease.

Examples of diseases or conditions wherein enhancement of a protective antibody response is desired includes those diseases in which the presence of a robust antibody response reduces or eliminates the causes or pathogenesis of the disease. Examples of diseases or conditions benefiting from a protective antibody response include, but are not limited to viral infections and cancer.

While not a disease or condition, enhancement of a protective antibody response is also beneficial in a vaccine or as part of a vaccination regimen as is described herein.

An agent that is an "antagonist" of a cell surface receptor on a TFH cell or a TFR cell is an agent which down regulates or blocks the biological function of the cell surface receptor. As used herein, an agent which is an "antagonist" includes agents that bind or otherwise interfere with ligands of cell surface receptor thereby blocking the ability of the ligand to bind to the cell surface receptor and down-regulate or prevent the biological function of the cell surface receptor.

An agent that is an "agonist" of a cell surface receptor on a TFH cell or a TFR cell is an agent which upregulates or increases the biological function of the cell surface receptor.

II. Starting Population of Cells

In one embodiment TFR cells and TFR precursor cells, for example, T regulatory (Treg) progenitor cells are derived from a mixed cell population containing such cells (e.g. from peripheral blood, tissue or organs). Preferably the mixed cell population containing TFR cells or TFR cell precursors is enriched such that TFR cells or TFR cell precursors comprise more TFR cells than other cell types in the population. In one embodiment, an enriched composition of TFR cells is a composition wherein the TFR cells make up greater than about 50% (e.g., 55%, 60%, 65%, 70%, 75%, 80%, 85%, 90%, 95%, 98%, 99%, 99.5%, 99.9% or more) of the cell population in the composition. In some embodiments, the TFR cells comprise about 90%, 95%, 98%, 99%, 99.5%, 99.9% or more of the cells in the composition, and such compositions are referred to herein as "highly purified" or "substantially homogenous" TFR cell compositions.

While a starting population of TFR cells is described above, it is understood that similar procedures may be applied to obtaining a starting population of TFH cells. Accordingly in some embodiments a mixed cell population containing TFH is enriched such that the composition comprises more TFH cells than other cell types in the population. In one embodiment, an enriched composition of TFH cells is a composition wherein the TFH cells make up greater than about 50% (e.g., 55%, 60%, 65%, 70%, 75%, 80%, 85%, 90%, 95%, 98%, 99%, 99.5%, 99.9% or more) of the cell population in the composition. In some embodiments, the TFH cells comprise about 90%, 95%, 98%, 99%, 99.5%, 99.9% or more of the cells in the composition, and such compositions are referred to herein as "highly purified" or "substantially homogenous" TFH cell compositions. In some embodiments, TFR cells or TFH cells are enriched from a population of cells prior to an activating and/or expanding step. In some embodiments TFR cells or TFH cells are enriched from a population of cells after the activating and/or expanding step.

Such highly purified or substantially homogenous populations of TFR cells or TFH cells may be used for in-vivo and in-vitro diagnoses and examination of TFR cell-mediated, or TFH cell-mediated diseases.

TFR cells can be enriched by targeting for selection of cell surface markers specific for immune suppressive TFR cells and separating using automated cell sorting such as fluorescence-activated cell sorting (FACS), solid-phase magnetic beads, etc. To enhance enrichment, positive selection may be combined with negative selection against cells comprising surface makers specific to non-T-regulatory cell types, such as depletion of CD8, CD11b, CD16, CD19, CD36 and CD56-bearing cells.

In one embodiment TFR cells are sorted via flow cytometry based on surface markers of $CD4^+CXCR5^+ICOS^+GITR^+$, or $CD4^+CXCR5^+ICOS^+CD25^+$. In one embodiment, TFR cells are sorted via flow cytometry based on the following cell surface markers: $CD4^+CXCR5^+ICOS^+$ and at least one surface marker selected from one or more of: $GITR^+$, $CD25^{hi}$, CD162, CD27, CD95, CD9, CD43, CD278, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

TFH cells may be sorted based on surface markers of CD4, CXCR5, ICOS positive; GITR negative, CD25 negative. In one embodiment, TFH cells are sorted via flow cytometry based on the following cell surface markers: CD4, CXCR5, ICOS positive and at least one marker selected from: CD163, CD127, CD8a, CD89, CD197, CD161, CD6, CD229, CD96, CD272, CD148, CD107a, CD100, CD82, CD126, CD45RO, CD279, CD5, and CD99, and optionally wherein the TFH cells are negative for one or more of the following receptors GITR, CD25, CD162, CD27, CD95, CD9, CD43, CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrin?7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86.

It is believed that these sorting methodologies also contribute to the enhanced suppressive capacity of TFH cells and TFR cells alone or in combination with activating such cells in the presence of an antagonist of PD-1 or PD-1 ligand as is described herein.

In one embodiment, an initial population of TFR cells may also be isolated from the peripheral blood of a subject and further enriched for TFR cells. In one embodiment, an initial population of TFH cells may also be isolated from the peripheral blood of a subject and further enriched for TFH cells. Methods of purifying TFR cells or TFH cells from other PBMCs in the blood, using methods such as differential sedimentation through an appropriate medium, e.g. Ficoll-Hypaque [Pharmacia Biotech, Uppsala, Sweden], and/or methods of cell sorting, are well known and examples of such methods are described herein.

In one embodiment the invention provides a composition of TFR cells derived from the peripheral blood of a subject (also referred to herein as "blood TFR cells") wherein the composition comprises about 90%, 95%, 98%, 99%, 99.5%, 99.9% or more of the cells in the composition.

In one embodiment the invention provides a composition of TFH cells derived from the peripheral blood of a patient (also referred to herein as "blood TFH cells") wherein the composition comprises about 90%, 95%, 98%, 99%, 99.5%, 99.9% or more of the cells in the composition. Such high purity compositions of blood TFR cells or blood TFH cells may be used directly in methods of modulating the immune system as described herein. Alternatively such compositions may be further activated and/or expanded prior to use in modulating the immune system as described herein.

III. Activation/Expansion of Starting Population of Cells

In one embodiment, the activation of a starting cell population is achieved by contacting the starting population of TFH cells or TFR cells with T cell stimulatory composition and/or in the presence of a PD-1 or PD-1L antagonist. The activating step may further include an expanding step or the cell population may be expanded separately from the activating step. If an expanding step is desired, the cells are preferably expanded at least 50-fold, and preferably at least 100, 200, 300, 500 and 800-fold.

Preferred stimulatory compositions stimulate the T cells by binding and activating the T cell receptor complex on the cells. In one embodiment, stimulatory compositions may include agents capable of binding and activating selective TFR and selective TFH receptors as described herein. In one embodiment the stimulatory compositions comprise physiological antigen presenting cells (APCs), such as CD19+ B cells (preferably autologous from blood) a TCR/CD3 activator such as a multivalent antibody or ligand for TCR/CD3; a TCR costimulator activator such as multivalent antibody or ligand for CD28, GITR, CD5, ICOS, OX40 or CD40L; and optionally an interleukin such as IL-2. In one embodiment, the TCR/CD3 activator is an anti-CD3 antibody, and the TCR costimulator activator is an anti-CD28 antibody. The anti-CD3 and anti-CD28 antibodies are optionally immobilized on beads as are known in the art and provided in a cell:bead ratio of between 1:1 and 1:2.

In certain embodiments, the stimulatory composition may further include one or more additional agents, e.g., a costimulatory agent, a second regulatory T cell stimulatory agent, or agents that generally promote the survival and/or growth of T cells.

In certain embodiments, the costimulatory agent is an antibody or ligand specific for a T cell costimulator, such as CD28 or ICOS, as described below. In particular embodiments, the costimulatory agent is an agonist antibody, such as an agonist antibody which binds to CD28.

The stimulatory composition alternatively comprises a second regulatory T cell stimulatory agent. Exemplary stimulatory agents include granulocyte colony stimulating factor, interleukins such as IL-2, IL-6, IL-7, IL-13, and IL-15, and hepatocyte growth factor (HGF).

In particular embodiments, one or more components of the stimulatory composition is immobilized on a substrate, such as a cell or bead. Cells suitable for use as substrates include artificial antigen-presenting cells (AAPCs) (Kim, J V et al, Nat Biotechnol. April 2004; 22(4):403-10; and Thomas, A K et al, Clin Immunol. December 2002; 105(3): 259-72). Beads can be plastic, glass, or any other suitable material, typically in the 1-20 micron range.

Examples of PD-1 and PD-1 ligand antagonists are disclosed in U.S. Pat. No. 7,722,868, incorporated herein by reference. Suitable PD-1 and PD-1 ligand antagonists include a PD1-ligand antibody, an anti-PD-1 antibody, a peptide or a small molecule wherein the agent inhibits the interaction between PD-1 and a PD-1 ligand. Other examples of PD-1 or PD-1 ligand antagonists are disclosed, for example in U.S. Pat. Nos. 8,168,757; 8,114,845; 8,008,449; 7,595,048; 7,488,802; and 7,029,674.

Optimal concentrations of each component of the stimulatory compositions, culture conditions and duration can be determined empirically using routine experimentation.

Populations of TFR cells expanded/activated in the presence of a PD-1 or PD-1 ligand antagonist have enhanced suppressive activity as demonstrated by their ability to inhibit TFH-mediated antibody production in vitro and in vivo as demonstrated in appropriate assays as are described herein.

Populations TFH cells expanded/activated in the presence of a PD-1 or PD-1 ligand antagonist have enhanced antibody stimulatory activity as demonstrated by their ability to enhance TFH-mediated antibody production in vitro and in vivo as demonstrated in appropriate assays described herein. Such TFH cells are referred to herein as "TFH cells having enhanced stimulatory capacity".

IV. Modulation of the Immune System

The expanded and/or activated TFR cells and compositions thereof as described herein may be introduced into the subject to treat immune related diseases, for example, by modulating an autoimmune reaction. For example, the subject may be afflicted with a disease or disorder characterized by having an ongoing or recurring autoimmune reaction, such as the diseases/disorders including, but not limited to, lupus erythematosus; myasthenia gravis; autoimmune hepatitis; rheumatoid arthritis; multiple sclerosis; Grave's disease, and graft versus host disease (GVHD).

In one embodiment, if upregulation of an immune response in a subject is desired, such as for example, increasing antibody proliferation in response to a vaccine, an enriched and optionally expanded and/or activated composition comprising a starting population of TFH cells may be administered to a subject.

In one embodiment modulation of the immune system is achieved when upon administration of a composition of the invention, the ratio of TFR cells to TFH cells in a subject is changed as compared to the ratio of TFR cells to TFH cells in a subject prior to administration of a composition of the invention. The ratios of TFR cells to TFH cells in a subject prior to, and after, administration of a composition of the invention may be measured by assaying for the presence of TFR cells or TFH cells in a patient's blood. Examples of suitable assays for measuring the ratio of TFR cells to TFH cells in a patient's blood are described herein.

In one embodiment, if downregulation of a subject's immune response is desired, such as, for example, when the subject has an autoimmune disease and inhibition of an antibody response is desired, a highly purified composition of blood derived TFR cells, or a composition enriched for TFR cells having enhanced suppressive activity may be administered to a patient. After administration of the composition, a blood sample from the patient may be tested to determine if the ratio of TFR cells to TFH cells is high.

In one embodiment, if upregulation of an immune response in a subject is desired, such as for example, increasing antibody proliferation in response to a vaccine, a highly purified composition of blood-derived TFH cells may be administered to a patient. After administration of TFH composition, a blood sample from the patient may be tested to determine if the ratio of TFH cells to TFR cells is high.

Accordingly, the invention provides methods and compositions for adoptive cellular immunotherapy comprising introducing into a patient in need thereof an effective amount of the subject's ex vivo expanded/activated TFR cells, for example. These applications generally involve reintroducing expanded/activated TFR cells extracted from the same patient, though the methods are also applicable to adoptive cellular immunotherapy for treatment of graft-versus-host disease associated with transplantation, particularly bone marrow transplantation using TFRs derived from donor tissue, and/or healthy individuals.

In an exemplary adoptive cell transfer protocol comprises a mixed population of cells is initially extracted from a target donor. Depending on the application, the cells may be extracted during a period of remission, or during active disease. Typically this is done by withdrawing whole blood and harvesting PMBCs by, for example, leukapherisis (leukopheresis). For example, large volume leukapherisis (LVL) has been shown to maximize blood leukocyte yield. Harvests reach $20\times10^6$ cells/L using a continuous flow apheresis device (Spectra, COBE BCT). Symptoms of hypocalcemia are avoided by a continuous infusion of calcium administrated throughout leukapheresis. Typically 15-45 liters of fluid corresponding to about 4 total blood volumes are harvested during a period of time ranging from about 100 to 300 minutes.

The harvested PMBCs may be separated by flow cytometry or other cell separation techniques based on Treg and/or TFR-specific cell markers such as CD4, CD25, CXCR5, ICOS, and GITR and expanded/activated as described herein, and then transfused to a patient, preferably by the intravenous route, typically the cell donor (except in GVHD where the donor and recipient are different), for adoptive immune suppression. Alternatively, the cells may be frozen for storage and/or transport prior to and/or subsequent to expansion.

Effective and optimized dosages and treatment regimens using the expanded and/or enriched and optionally highly pure TFH or TFR cells are known in the art based on previous clinical experience with existing T-cell infusion therapies, and can be further determined empirically.

The preferred route of administration of the TFR and TFH cell compositions to a subject in accordance with the invention is by the intravenous route. However, depending on the application, cell compositions in accordance with the invention may be administered by other routes including, but not limited to, parenteral, oral or by inhalation.

V. Vaccination

The present invention also contemplates a method for enhancing an immune response to an antigen comprising the administration to a subject as part of a vaccination regimen, TFR cells having enhanced suppressive activity, TFR cell compositions derived from peripheral blood and/or TFH cells derived from peripheral blood. The present invention is particularly useful in pharmaceutical vaccines and genetic vaccines in humans.

Adjuvants promote the immune response in a number of ways such as to modify the activities of immune cells that are involved with generating and maintaining the immune response. Additionally, adjuvants modify the presentation of antigen to the immune system. The compositions of the invention may be used as adjuvants in a vaccination regimen.

In one embodiment, compositions of TFR cells in accordance with the invention may be used in a vaccination regimen. Without being limited to a specific theory, it is believed that TFR cells may control germinal center (GC) B cell differentiation into long-lived plasma cells versus memory 8 cells thereby enhancing the immune response to the antigen.

In one embodiment compositions of TFH cells, particularly TFH cells derived from the peripheral blood of a patient (also referred to herein as "blood TFH cells") may be used in a vaccination regimen to enhance TFH cell mediated antibody responses. Without being limited to any, particular theory, it is believed that TFH cells derived from the blood migrate to lymph nodes and interact with cognate B cells rapidly upon antigen exposure, wherein naïve T cells need at least two to four days to differentiate and upregulate CXCR5, Accordingly, TFH cells derived from blood have greater antibody stimulatory capacity.

In one embodiment, it may be desirable to upregulate an immune response or downregulate an immune response as part of a vaccination regimen. This can be accomplished by administering compositions enriched for or highly purified for TFR cells or compositions enriched for or highly purified TFH cells to change the ratio of TFR cells to TFH cells in a subject's blood in combination with the administration of a vaccine.

VI. Novel In-Vivo and In Vitro Assays

The invention also provides in vivo and in vitro assays to analyze the functions of the compositions of TFR cells and TFH cells in accordance with the invention.

In one exemplary embodiment the invention provides an assay to analyze the capacity of T$_{FR}$ cells to inhibit activation of naïve CD4 T cells. Briefly, WT and PD-1$^{-/-}$ mice are immunized with MOG/CFA and T$_{FR}$ cells are sorted from draining lymph nodes and plated 1:1:1 with CFSE-labeled CD4 naïve WT (CD4$^+$CD62L$^+$FoxP3$^-$) responder cells and WT GL7$^-$B220$^+$ B cells from MOG/CFA immunized mice along with anti-CD3 and anti-IgM for 4 days. 3 days later samples are analyzed by flow cytometry. It is understood that any suitable antigen/adjuvant combinations may be used to immunize mice and that the cells may be stimulated by any suitable combinations of stimulatory factors for this assay.

In one exemplary embodiment the invention provides an assay to analyze capacity of T$_{FR}$ cells to inhibit activation of naïve CD4 T cells. WT and PD-1$^{-/-}$ mice are immunized with MOG/CFA and T$_{FR}$ cells and sorted from draining lymph nodes and plated 1:1:1 with CFSE-labeled CD4 naïve WT (CD4$^+$CD62L$^+$FoxP3$^-$) responder cells and WT GL7$^-$B220$^+$ B cells from MOG/CFA immunized mice along with anti-CD3 and anti-IgM for 4 days. 3 days later samples are analyzed by flow cytometry. T responders are analyzed for CD69 expression and proliferation by measuring CFSE dilution.

In one embodiment the invention provides an assay for an in vitro IgG suppression. Briefly, T$_{FR}$ cells are sorted as in the assay to analyze capacity of T$_{FR}$ cells to inhibit activation of naïve CD4 T cells and are plated in a 1:1:1 ratio of T$_{FR}$ (CD4$^+$ICOS$^+$CXCR5$^+$GITR$^+$CD19$^-$), T$_{FH}$ (CD4$^+$ICOS$^+$CXCR5$^+$GITR$^-$CD19$^-$), and B (GL-7$^-$B220$^+$) cells from draining lymph nodes of MOG/CFA immunized mice in the presence of anti-CD3 and anti-IgM for 6 days. Total IgG was measured by ELISA from supernatants. In one embodiment the in-vitro suppression assay may be performed over a range of concentrations of anti-CD3. Naive (CD4$^+$ICOS$^-$CXCR5$^-$CD19$^-$) cells from immunized mice may be included as controls It is understood that any suitable antigen/adjuvant combinations may be used to immunize mice and that the cells may be stimulated by any suitable combinations of stimulatory factors for this assay.

Novel assays of the invention are useful as a diagnostic tool for measuring a subject's TFR cell function and TFH cell function. Such assays are useful in the identification and typing of autoimmune diseases.

The assays of the invention are also useful in measuring the ratio of TFR cells to TFH cells in a patient's blood prior to or during an immune response and/or prior to and after administration of a composition of the invention. Such assays are useful as a diagnostic to assist in determining whether an immune response in a subject should be upregulated or down-regulated or whether an immune modulating treatment regimen has had the desired effect. This assay also may be useful in the diagnosis or progression of specific diseases.

In accordance with the invention, an exemplary assay comprises a method for assaying the TFR cell function or the TFH cell function or both, in a patient comprising the steps of:
 a) Obtaining a sample of peripheral blood from a patient;
 b) Isolating a population of TFH cells and TFR cells from the blood sample;
 c) Contacting the TFH cells and TFR cells with a stimulatory composition comprising antigen present cells (e.g. B cells) in the presence of T-cell receptor stimulating factors and cofactors such as anti-CD3 and anti-IgM, for a time period sufficient to allow the production of antibody such as IgG; and
 d) measuring the total antibody produced using standard assays (e.g. ELISA).

VII. Modulation of TFR and TFH Cell-Mediated Immune Responses Via Selective TFR and TFH Cell Surface Receptors The data in FIG. 23 shows that TFR cells are distinct in their gene expression as compared to Treg cells and TFH cells suggesting that TFR cells are capable of independently regulating immune responses. This knowledge may be applied to diagnose, monitor and treat diseases or conditions wherein TFR-immune responses may be selectively modulated such as in those diseases or conditions in which antibodies play a key role in the pathogenesis and enhanced immune suppression is therapeutic. Examples of such diseases are provided herein supra.

TFR cell function may be modulated by use of an agent such as an agonist or an antagonist of one or more of TFR cell surface receptors as described herein. Use of such an agent in an amount effective to inhibit or induce the differentiation of TFR cells and/or modulate the biological function of TFR cells can affect the TFR cell-mediated immune response.

In one embodiment, the invention provides a method suppressing a pathogenic antibody response in a patient in need thereof comprising, administering to the patient, an agent which modulates at least one receptor which is differentially expressed on TFR cells as compared to TFH cells at an increased mean fluorescence intensity (MFI) fold change of at least 1.17, and wherein the receptor has an MFI of at least 186 on TFR cells and wherein the agent administered in an amount that is effective to modulate the TFR receptor and increase TFR cell-mediated antibody suppression, as compared to the TFR cell-mediated antibody suppression in the absence of the agent. Such differentially expressed receptors are referred to herein as "selective TFR receptors". In one embodiment at least one selective TFR receptor is selected from one or more of: CD162, CD27, CD95, CD9, CD43, CD278 (ICOS), CD50, CD45RB, CD102, CD61, CD58, CD196, CD38, CD31, CD15, CD25, CD13, CD66a/c/e, CD11b CD63, CD32, CD97, HLA-HQ, CD150, Siglec-9, Integrinβ7, CD71, CD180, CD218a, CD193, CD235ab, CD35, CD140a, CD158b, CD33, CD210, HLA-G, CD167a, CD119, CX3CR1, CD146, HLA-DR, CD85, CD172b, SSEA-1, CD49c, CD170, CD66b, and CD86. In one embodiment, selective TFR receptors are selected from one or more of: CD27, CD278 (ICOS), CD150, Siglec-9, CD140a, CD158b, and CD33.

Methods of modulating TFR cell-mediated immune response through antagonizing or agonizing the biological function of a selective TFR receptor are useful in the treatment of diseases and conditions wherein a decreased or increased TFR cell-mediated immune response is useful. Examples of disorders or conditions which may be treated by increasing TFR cell-mediated immune response include those diseases and conditions in which antibodies contribute to and/or are primarily responsible for, pathogenesis such as in those diseases listed previously herein. In one embodiment the disease or condition in which antibodies contribute and/or are primarily responsible for pathogenesis include: multiple sclerosis, systemic lupus erythematosus, allergy, myasthenia gravis, collagen diseases, glomerulonephritis, Devic's disease, vasculitis caused by ANCA, and celiac disease.

In one embodiment, the agent is a blocking antibody capable of blocking/antagonizing a selective TFR receptor, or binding to the ligand of the receptor and thereby blocking its ability to bind its corresponding receptor. The agent may also be a small molecule, or a DNA or RNA molecule (e.g. dsRNA, or antisense molecule) capable of antagonizing or agonizing the biological function of the receptor, for example by causing overexpression of a receptor or by blocking expression of a receptor.

In addition to the known agonists and antagonists of various selective TFR receptors known generally, other agents may be tested for their ability to antagonize or agonize selective TFR receptors using known assays and screens.

Assays and screens of the invention useful for testing various agents for their ability to agonize or antagonize TFR cell surface receptors are used to identify agents of the invention. In one embodiment, the invention provides assays to specifically and sensitively determine the stimulatory function of T$_{FH}$ cells. Complementary assays are also provided which determine the inhibitory capacity of T$_{FR}$ cells. These assays which include both in vitro and in vivo experiments can be used to determine the functional consequences of sending agonist and/or antagonist signals through surface receptors on T$_{FH}$ and T$_{FR}$ cells.

In vitro murine T$_{FH}$ stimulation assays are performed by immunizing/vaccinating mice with an antigen/adjuvant. In some cases live or attenuated virus can be used. Seven to ten days later T$_{FH}$ cells defined as (CD4+ICOS+CXCR5+ FoxP3+CD19−) or (CD4+ICOS+CXCR5+GITR+CD19−) (or alternative T$_{FH}$ marker) are sorted by flow cytometry. T$_{FH}$ cells are incubated with B cells along with anti-CD3 and anti-IgM (or alternatively with specific antigen). Agonists and/or antagonists for TFH surface receptors are also added into cultures. After 7 days antibody production and class switch recombination is assessed by either staining B cells from the culture for activation markers (B7-1, GL7, etc.) or intracellular for IgG isotypes. Activation status of the T$_{FH}$ cell can also be determined. Alternatively, the supernatants can be assessed for presence of IgGs via ELISA. Examples of this assay are included in FIGS. 4A-4M, 20A-20I and 21A-21E. Similar assays are performed using human cells isolated from blood or other tissues.

In vivo murine T$_{FH}$ stimulation assays are performed by immunizing/vaccinating mice with an antigen/adjuvant. In some cases live or attenuated virus can be used. Seven to ten days later T$_{FH}$ cells defined as (CD4+ICOS+CXCR5+FoxP3−CD19−) or (CD4+ICOS+CXCR5+GITR−CD19−) (or alternative T$_{FH}$ marker) are sorted by flow cytometry. Cells are either used right away, or incubated in vitro with agonists or antagonists as in in vitro assays. Cells are adoptively transferred intravenously to mice that are vaccinated or likewise challenged with antigen and/or virus. Ten days later serum is collected from mice and IgGs are detected by ELISA. Within these 10 days agonists or antagonists for T$_{FH}$ surface receptors can be administered.

Examples of this assay are in FIGS. 8A-8K and 21A-21E. These assays can also be used to determine how T$_{FH}$ cells change disease autoimmune pathology. As an example, mice can be immunized with collagen and then T$_{FH}$ cells can be sorted and transferred to a new mouse that is immunized with collagen. The resulting anti-collagen antibodies will cause arthritis which can be measured to determine how T$_{FH}$ cells function within this specific disease. Additionally, these assays can be used to determine TFH stimulation of B cell antibody production in the context of vaccination by using TFH cells from influenza infected mice and then adoptively transfer them to a new mouse that is infected with influenza. Extent of viral infection can be measured as a readout for antibody mediated clearance of virus.

In vitro murine T$_{FR}$ suppression assays are performed by immunizing/vaccinating mice with an antigen/adjuvant. In some cases live or attenuated virus can be used. Seven to ten days later T$_{FH}$ cells defined as (CD4+ICOS+CXCR5+FoxP3−CD19−) or (CD4+ICOS+CXCR5+GITR−CD19−) (or alternative T$_{FH}$ marker) and T$_{FR}$ cells defined as (CD4+ICOS+CXCR5+FoxP3+CD19−) or (CD4+ICOS+CXCR5+GITR+CD19−) (or alternative T$_{FR}$ marker) are sorted by flow cytometry. T$_{FH}$ and/or T$_{FR}$ cells are incubated with B cells along with anti-CD3 and anti-IgM (or alternatively with specific antigen). Agonists and/or antagonists for T$_{FR}$ surface receptors are also added into cultures. After 7 days antibody production and class switch recombination is assessed by either staining B cells from the culture for activation markers (B7-1, GL7, etc.) or intracellular for IgG isotypes. Activation status of the T$_{FH}$ cell can also be determined. Alternatively, the supernatants can be assessed for presence of IgGs via ELISA. Examples of this assay are included in FIGS. 4A-4M, 20A-20I and 21A-21E. Similar assays are performed using human cells isolated from blood or other tissues.

In vivo murine T$_{FR}$ suppression assays are performed by immunizing/vaccinating mice with an antigen/adjuvant. In some cases live or attenuated virus can be used. Seven to ten days later T$_{FH}$ cells defined as (CD4+ICOS+CXCR5+FoxP3+CD19−) or (CD4+ICOS+CXCR5+GITR+CD19−) (or alternative T$_{FH}$ marker) and T$_{FR}$ cells defined as (CD4+ICOS+CXCR5+FoxP3+CD19−) or (CD4+ICOS+CXCR5+GITR+CD19−) (or alternative T$_{FR}$ marker) are sorted by flow cytometry. Cells are either used right away, or incubated in vitro with agonists or antagonists as in in vitro assays. Cells are adoptively transferred intravenously to mice that are vaccinated or likewise challenged with antigen and/or virus. Ten days later serum is collected from mice and IgGs are detected by ELISA. Within these ten days agonists or antagonists for TFR surface receptors can be administered. Examples of this assay are in FIGS. 8A-8K and 21A-21E. These assays can also be used to determine how T$_{FR}$ cells change disease pathology. As an example, mice can be immunized with collagen and then T$_{FH}$ and T$_{FR}$ cells can be sorted and transferred to a new mouse that is immunized with collagen. The resulting anti-collagen antibodies will cause arthritis which can be measured to determine how T$_{FR}$ cells function to suppress the T$_{FH}$ mediated disease.

The present invention further provides agents identified in the assays described herein. Such agents are capable of up antagonizing or agonizing a selected TFR receptor and thereby modulate TFR cell-mediated immune function and to further treat diseases as described herein.

Animal model systems which can be used to screen the effectiveness of the selected agents and test agents of the present invention in protecting against or treating the disease are available. Methods for the testing of systemic lupus erythematosus (SLE) in susceptible mice are known in the art (Knight et al. (1978) J. Exp. Med., 147: 1653; Reinersten et al. (1978) New Eng. J. Med., 299: 515). Myasthenia Gravis (MG) is tested in SJL/J female mice by inducing the disease with soluble AchR protein from another species (Lindstrom et al. (1988) Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds., Grune and Stratton, New York, pp. 179-213; McFarlin et al. (1973) Science, 179: 478: and Satoh et al. (1987) J. hnmunol., 138: 179).

Generally, suitable agents identified and tested as described above will be used in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep, for example, a polypeptide complex such as an antibody in suspension, may be chosen from thickeners such as carboxymethylcellulose, polyvinylpyrrolidone, gelatin and alginates. Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The selected agents of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the agents of the present invention.

The route of administration of pharmaceutical compositions according to the invention may be any of those commonly known to those of ordinary skill in the art. For therapy, including without limitation immunotherapy, the selected agents can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counter-indications and other parameters to be taken into account by the clinician.

In certain therapeutic applications, an adequate amount to accomplish modulation of a TFR and/or TFH cell-mediated immune response will depend upon the severity of the disease and the general state of the patient's own immune system. Generally, if the agent is a blocking antibody, for example, a range from 0.01 mg-100 mg per kilogram of body weight, with doses of 1-10 mg/kg would be suitable.

A composition containing one or more selected agents according to the present invention may be used in prophylactic and therapeutic settings to aid in the modulation of a TFR and/or TFH cell-mediated response. In addition, the agents described herein may be used extracorporeally or in vitro to selectively modulate TFR and/or TFH cell-mediated immune responses.

The invention also provides agents and methods for modulating TFH cell-mediated immune responses. TFH cells are known in the prior art to be a subset of T helper cells that are genetically distinct from other types of T helper cells suggesting that TFR cells may independently regulate immune responses. This knowledge may be applied to diagnose, monitor and treat, for example, diseases or conditions wherein enhancement of a protective antibody response is therapeutic. Such diseases include but are not limited to treating viral infections and treating cancer. Enhancing and preferably selectively enhancing, TFH cell-mediated immune responses are also particularly beneficial as part of a vaccine or vaccination regimen.

TFH cell function may be modulated by use of an agent such as an agonist or an antagonist of one or more of TFH cell surface receptors as described herein. Use of such an agent in an amount effective to inhibit or induce the differentiation of TFH cells and/or modulate the biological function of TFH cells can affect the TFH cell-mediated immune response.

In one embodiment, the invention provides method of increasing a protective antibody response in a patient in need thereof comprising administering to the patient, an agent which modulates at least one receptor which is differentially expressed on TFH cells as compared to TFR cells at an increased mean fluorescence intensity (MFI) fold change of at least 1.17, and wherein the receptor has an MFI of at least 200 on TFH cells and wherein the agent is effective to modulate the receptor and increase the antibody response in the patient as compared to the antibody response when the agent is absent. Such differentially expressed receptors are referred to herein as "selective TFH receptors". In one embodiment at least one selective TFH receptor is selected from one or more of: CD163, CD127, CD8a, CD89, CD197, CD161, CD6, CD229, CD96, CD272, CD148, CD107a, CD100, CD82, CD126, CD45RO, PD-1 (CD279), CD5, and CD99. In one embodiment, at least one selective TFH receptor is selected from one or more of: CD163, CD127, CD161, CD6, CD229, CD272, CD100, CD126, PD-1 (CD279).

In one embodiment, the agent is a blocking/antagonizing antibody capable of blocking a selective TFH receptor, or binding to the ligand of the receptor and thereby blocking its ability to bind its corresponding receptor. The agent may also be a small molecule, or a DNA or RNA molecule (e.g. dsRNA, or antisense molecule) capable of antagonizing or agonizing the receptor.

In addition to the known agonists and antagonists the various selective TFH receptors described herein, other agents may be tested for their ability to antagonize or agonize selective TFH receptors using known assays and screens. Assays and screens for testing various agents for their ability to agonize or antagonize TFH cell surface receptors are described previously herein. Animal models may be used to test modulation of selective TFH receptors as described previously herein.

The present invention further provides agents identified in the assays described herein wherein such agents are capable of antagonizing or agonizing a selective TFH receptor and thereby modulate TFH cell-mediated immune function. Agents for modulating selective TFH receptors may be formulated and administered to patients as described above.

In one embodiment, the invention provides a method of decreasing a pathogenic antibody response in a patient in need thereof comprising administering to the patient a first agent capable of modulating a selective TFR receptor in an amount effective to increase TFR cell-mediated antibody suppression in the patient, in combination with an second agent capable of modulating a selective TFH receptor in an amount effective to decrease TFH cell-mediated antibody production, wherein the pathogenic antibody response is decreased as compared to the pathogenic antibody response in the absence of the first or second agents.

In one embodiment, the invention provides a method of increasing a protective antibody response in a patient in need thereof comprising administering to the patient a first agent capable of modulating a selective TFR receptor in an amount effective to decrease TFR cell-mediated antibody suppression in the patient, in combination with a second agent capable of modulating a selective TFH receptor in an amount effective to increase TFH cell-mediated antibody production, wherein the protective antibody response is increased as compared to the protective antibody response in the absence of the first or second agents.

VIII. Modulation of TFR and TFH Cell-Mediated Immune Responses Via PD-1 Receptors The inventors' discovery that PD-1:PD-L1 interactions limit TFR cell differentiation and function has also elucidated another novel approach to modulating both TFR cell-mediated and TFH cell-mediated immune responses in a patient.

Therefore, in one embodiment the invention provides a method of decreasing a pathogenic antibody response in a patient in need thereof comprising administering to the patient, an agent which modulates the PD-1 receptor on a TFR cell. In one embodiment, the agent is an antagonist of the PD-1 receptor on a TFR cell. In one embodiment, the agent is an antibody capable of blocking the PD-1 receptor on a TFR cell. In one embodiment, the agent is an antibody capable of binding to a ligand selected from PD-L1 or PD-L2 and preventing the ligand from binding to the PD-1 receptor. The agent may also be a small molecule, or a DNA or RNA molecule (e.g., dsRNA, or antisense molecule) capable of antagonizing or agonizing the receptor.

In one embodiment a disease or condition wherein suppression of a pathogenic antibody response is therapeutic includes those diseases listed previously in which antibodies contribute to, or are primarily responsible for pathogenesis.

In another embodiment, the invention provides a method of increasing a protective antibody response in a patient in need thereof comprising administering to the patient, an agent which modulates the PD-1 receptor on a TFH cell. In one embodiment the agent is an agonist of the PD-1 receptor on a TFH cell. The agent may also be a small molecule, or a DNA or RNA molecule (e.g. dsRNA, or antisense molecule) capable of agonizing the PD-1 receptor.

In one embodiment, the invention provides a method of decreasing a pathogenic antibody response in a patient in need thereof comprising administering to the patient a first agent capable of modulating a PD-1 receptor on a TFR cell in an amount effective to increase TFR cell-mediated antibody suppression in the patient, in combination with an second agent capable of modulating a PD-1 receptor on a TFH cell in an amount effective to decrease TFH cell-mediated antibody production, wherein the pathogenic antibody response is decreased as compared to the pathogenic antibody response in the absence of the first or second agents.

In one embodiment, the invention provides a method of increasing a protective antibody response in a patient in need thereof comprising administering to the patient a first agent capable of modulating a PD-1 receptor on a TFR cell in an amount effective to decrease TFR cell-mediated antibody suppression in the patient, in combination with a second agent capable of modulating a PD-1 receptor on a TFH receptor in an amount effective to increase TFH cell-mediated antibody production, wherein the protective antibody response is increased as compared to the protective antibody response in the absence of the first or second agents.

In addition to the known agonists and antagonists of the PD1 receptor generally, other agents may be tested for their ability to antagonize or agonize PD-1 on TFH and TFR cells using known assays and screens. Assays and screens for testing various agents for their ability to agonize or antagonize PD-1 receptors are previously described. Animal models may be used to test modulation of selective TFH receptors as described above.

The present invention further provides agents identified in the assays described herein wherein such agents are capable of antagonizing or agonizing PD-1 receptors and thereby modulate TFR or TFH cell-mediated immune function or both.

Agents for modulating PD-1 receptors on TFR or TFH cells may be formulated and administered to patients as described above.

IX. Examples

Example 1 Introduction

Follicular helper T cells (TFH) are a recently defined subset of CD4 T cells that are essential for helping cognate B cells form and maintain the germinal center (GC) reaction, and for development of humoral immune responses. These cells are universally defined by expression of the chemokine receptor CXCR5, which directs them to the B cell follicles via gradients of the chemokine CXCL13[1]. TFH cells also express the transcription factor Bcl6 (which represses Blimp-1/Prdm1) and high levels of the costimulatory receptor ICOS, which are both critical for their differentiation and maintenance[1-4]. In addition, TFH cells secrete large amounts of IL-21, which aids in GC formation, isotype switching and plasma cell formation[5]. In humans and mice functionally similar TFH cells can be found in secondary lymphoid organs. Significantly, CXCR5+ TFH cells are also present in peripheral blood and seen at elevated levels in individuals with autoantibodies, including systemic lupus erythematosis, myasthenia gravis and juvenile dermatomyositis patients. However, the function of these circulating TFH remains unclear[6-9].

TFH cells also express high levels of programmed death (PD) 1 receptor (CD279). Signaling through PD-1 attenuates TCR signals and inhibits T cell expansion, cytokine production and cytolytic function. In addition, PD-1 promotes the development of induced regulatory T (iTreg) cells from naïve lymphocytes[10-14]. PD-1 has two ligands, PD-L1 (B7-H1) and PD-L2 (B7-DC). PD-L1 is more widely expressed than PD-L2, but PD-L1 and PD-L2 both can be expressed on GC B cells and dendritic cells[15]. Perturbation studies suggest critical roles for this pathway in regulating humoral immune responses. However, there are conflicting reports as to the function of the PD-1 pathway in controlling humoral immunity. Some studies have found that humoral responses are attenuated[16-18], while others have seen that humoral responses are heightened[19, 20] when PD-1:PD-L interactions are prevented.

PD-1 also is found on a newly defined subset of CD4+ CXCR5+ cells called T follicular regulatory (TFR) cells, which are positive for the transcription factors FoxP3, Bcl6 and Prdm1/Blimp1 and function to inhibit the germinal center response[21-23]. These cells originate from natural regulatory T cell precursors, but express similar levels of ICOS, CXCR5 and PD-1 as TFH cells. Since ICOS, CXCR5 and PD-1 have been widely used to identify and purify 'TFH cells', it seems likely that the inability to define clear functions for PD-1 in GC responses derives from experimental systems containing mixtures of stimulatory TFH cells and inhibitory TFR cells. We provide a separate analyses of the function of PD-1 on TFH and TFR cells to elucidate how PD-1 controls humoral immunity and to gain insight into the individual roles of TFR cells and TFH cells in regulating antibody production.

Here we demonstrate that PD-1:PD-L1 interactions inhibit TFR, but not TFH, cell numbers in lymph nodes. PD-1 deficient mice have increased numbers of lymph node TFR cells compared to wild type mice. PD-1 deficient lymph node TFR cells have enhanced ability to suppress activation of naïve T cells, as well as antibody production in vitro. In addition, we show for the first time that TFR cells are present in the peripheral blood of mice, and that these circulating cells can potently regulate humoral immune responses in vivo. Using transfer approaches, we demonstrate that blood TFH cells can promote antibody production, while blood TFR cells can strongly inhibit antibody production in vivo. We further show that the PD-1 pathway inhibits blood TFR cell function and PD-1 deficient blood TFR cells have enhanced suppressive capacity in vivo. Taken together, our studies reveal a new immunoregulatory role for the PD-1:PD-L1 pathway in limiting TFR cell differentiation and function, and further demonstrate the dynamic control of humoral immune responses by migration of TFR cells from the circulation into lymph nodes to control antibody production in vivo.

Methods

Mice.

6-10 week old mice were used for all experiments. WT C57BL/6 and TCRα−/− mice were purchased from The Jackson Laboratory (Bar Harbor, Me.). PD-1−/−, PD-L1−/−, and PD-L2−/− mice on the C57BL/6 background were generated in our laboratory[32-34]. ICOS−/−[35] and CD28−/− mice[36] were generated as described. 2D2 TCR Tg mice Foxp3-IRES-GFP knockin mice (Foxp3.GFP;[37] were generated in our laboratory by crossing 2D2 TCR Tg mice[38] with Foxp3.GFP reporter mice. All mice were used according to the Harvard Medical School Standing Committee on Animals and National Institutes of Animal Healthcare Guidelines. Animal protocols were approved by the Harvard Medical School Standing Committee on Animals.

Immunizations.

For MOG 35-55 immunizations (referred to as "MOG/CFA"), mice were injected subcutaneously with 100 μg of MOG 35-55 (UCLA Biopolymers Facility) emulsified in a 1:1 emulsion of H37RA CFA (Sigma) on the mouse flanks Seven days later mice were euthanized and inguinal lymph nodes (dLN) and/or spleen were harvested for flow cytometric analyses. Blood was collected via cardiac puncture with a 1 cc syringe and immune cells were isolated by sucrose density centrifugation using Lymphocyte Separation Media (LSM). For NP-OVA immunizations, 100 μg $NP_{18}$-OVA (Biosearch Technologies) was used in a 1:1 H37RA CFA emulsion and injected similarly as MOG/CFA.

ELISA.

For in vitro quantitation of antibody production, supernatants were taken from cultures and total IgG was quantified using pan-IgG capture antibody (Southern Biotech) and alkaline phosphatase conjugated pan-IgG detection antibody (Southern Biotech). To assess in vivo antibody production, sera were collected from mice at indicated time points. NP-specific antibody titers were measured by coating ELISA plates with $NP_{16}$-BSA (Biosearch Technologies), and incubating serum for 1 hr followed by alkaline phosphatase-conjugated IgG detection antibodies. A standard curve was generated using antibody from an NP-specific IgG1 hybridoma (a kind gift of Dr. Michael Carroll). This standard curve was used to approximate all IgG subtype antibody levels in the linear range of detection using a Spectramax Elisa plate reader (Molecular Devices).

Flow Cytometry.

Cells from lymphoid organs were isolated and resuspended in staining buffer (PBS containing 1% fetal calf serum and 2 mM EDTA) and stained with directly labeled antibodies from Biolegend against CD4 (RM4-5), ICOS (15F9), CD19 (6D5), PD-1 (RMP1-30), PD-L1 (10F.9G2), CD69 (H1.2F3), from eBioscience against FoxP3 (FJK-165), Bcl6 (mGI191E), and from BD bioscience against FAS (Jo2), GL7, Ki67 (B56). For CXCR5 staining, biotinylated anti-CXCR5 (2G8, BD Biosciences) was used followed by streptavidin-brilliant violet 421 (Biolegend). For intracellular staining, the FoxP3 fix/perm kit was used (eBioscience) after surface staining was accomplished. All flow cytometry was analyzed with an LSR II (BD biosciences) using standard filter sets.

Confocal Microscopy.

Draining lymph nodes were embedded in OCT and 8 μm sections were cut, fixed with 4% paraformaldehyde, and stained before imaging on a Zeiss LSM 510 confocal microscope by acquiring z-stacks of 0.5 um with a 40× oil objective. Germinal center quantitation was calculated by drawing outlines around $GL7^+IgD^-$ areas present within the B cell zone. FoxP3 quantitation was performed by determining germinal center zones and scrolling through z-stack images to identify large FoxP3 positive spots. Axiovision (Zeiss) software was used to measure distances from germinal center borders. For micrograph panels, single z slices were linearly contrasted and merged images were made in Adobe photoshop.

Quantitative PCR.

Q-PCR was performed using standard TaqMAN probes (Applied Biosystems) and an ABI FAST9500 QPCR machine according to the manufacturer's instructions. mRNA levels were normalized to HPRT or β2M, and the $2^{-deltadeltaCT}$ method was used to quantitate mRNA. Each bar graph represents mean values from more than three individual experiments consisting of cells sorted from 5-10 pooled mice.

In Vitro Suppression Assay.

Cell populations were sorted to 99% purity on an Aria II flow cytometer. For TFR suppression assays, sorted cells were counted on an Accuri cytometer (BD biosciences) by gating live cells only, and $1\times10^5$ $GL7^-$ B cells from dLNs of WT mice immunized with MOG/CFA 7 days previously, $1\times10^5$ CFSE labeled $CD4^+CD62L^+FoxP3^-$ T responder cells from unimmunized WT FoxP3 GFP reporter mice, and $1\times10^5$ TFR cells from the draining dLN of 10 pooled mice immunized with MOG/CFA 7 days previously were plated with 2 μg/ml soluble anti-CD3 (2C11, BioXcell) and 5 μg/ml anti-IgM (Jackson Immunoresearch). After 3 days, cells were harvested and stained for CD4 and CD19. T cell responders were identified as CFSE positive, and percent divided was gated as the percent of cells with CFSE diluted compared to unstimulated T responders.

Adoptive Transfers.

For blood TFH/TFR adoptive transfers, 20 to 30 WT mice were immunized with NP-OVA subcutaneously as described above, and 8 days later blood was collected by cardiac puncture. TFH and TFR cells were sorted as described. $4\times10^4$ blood TFH cells alone or together with $2\times10^4$ blood TFR cells were transferred into $CD28^{-/-}$ or $TCR\alpha^{-/-}$ mice unless specified otherwise. These recipient mice were immunized with NP-OVA as described above. Serum and organs were harvested at indicated times and analyzed by ELISA or flow cytometry.

Statistical Analysis.

Unpaired Student's t test was used for all comparisons, data represented as mean+/−SD or SE are shown. P values <0.05 were considered statistically significant. * P<0.05,  P<0.005, * P<0.0005.

Results

PD-1 Controls T Follicular Regulatory Cells

Figure 1A:
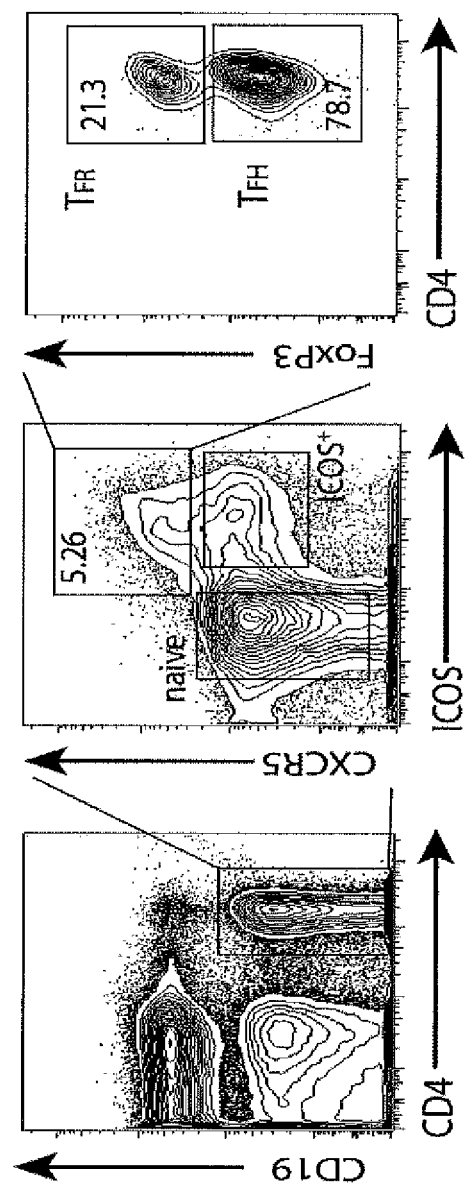
FIG. 1A. PD-1 signaling in FoxP3 Tregs limits the generation of T follicular regulatory cells. Quantitation of T$_{FR}$ cells. WT mice were immunized with MOG/CFA and 7 days later draining lymph nodes were isolated and immediately stained for CD4$^+$FoxP3$^+$ICOS$^+$CXCR5$^+$CD19$^-$ T follicular regulatory cells (T$_{FR}$), CD4$^+$FoxP3$^-$ ICOS$^+$ CXCR5$^+$CD19$^-$ T follicular helper cells (T$_{FH}$), CD4$^+$ICOS$^-$ CXCR5⁻CD19⁻ cells (naive) or CD4⁺ICOS⁺CXCR5⁻CD19⁻ cells (ICOS+). Numbers indicate percentages of cells located within each gate.
Figure 1B:
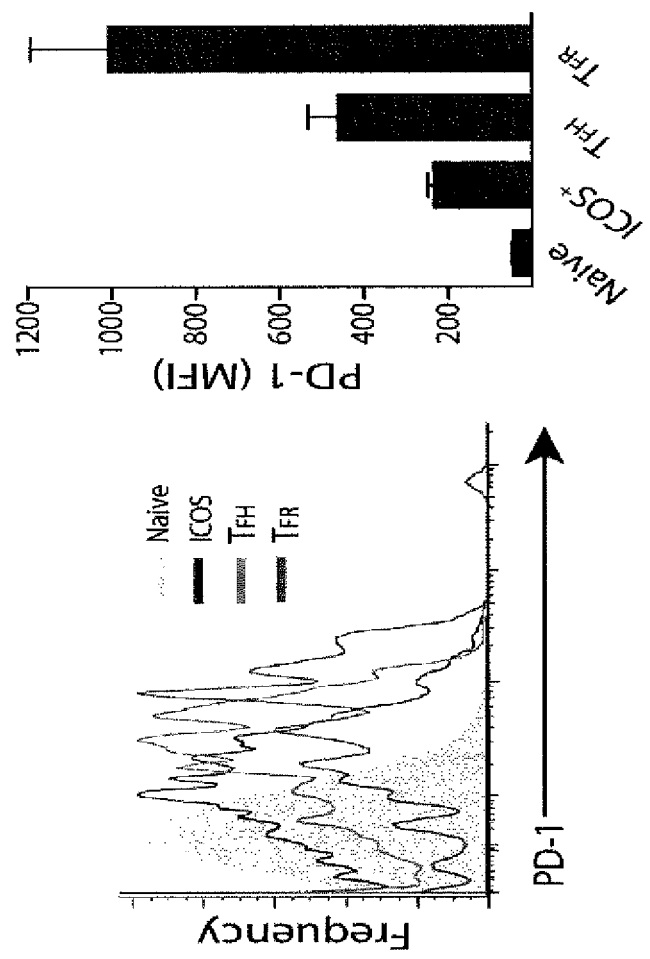
FIG. 1B. PD-1 expression by flow cytometry on WT naive, ICOS+, T$_{FR}$ and T$_{FH}$ cells. Populations were gated as in FIG. 1A. Data represent means of 5 mice per group. All error bars indicate standard error FIG. 1C Gating of T$_{FR}$ cells from total FoxP3⁺ cells in WT and PD-1⁻/⁻ mice immunized with MOG/CFA and analyzed 7 days later and stained as in FIG. 1A.

To analyze the role of PD-1 in controlling T follicular regulatory (TFR) cells, we first compared PD-1 expression on CD4 T cell subsets in draining lymph nodes (dLN) of WT C57BL/6 mice subcutaneously immunized with myelin oligodendrocyte glycoprotein (MOG) peptide 35-55 emulsified in CFA (from herein simply referred to as "MOG/CFA"), an immunization that breaks tolerance and also results in effective TFH cell generation[24]. TFR cells were defined as $CD4^+ICOS^+CXCR5^+FoxP3^+CD19^-$, a gating strategy that separates TFR cells from $CD4^+ICOS^+CXCR5^+FoxP3^-CD19^-$ TFH cells, the cell type that was until recently thought to solely comprise the $CD4^+CXCR5^+$ gate (FIG. 1A). TFH cells showed higher expression of PD-1 compared to $ICOS^+CXCR5^-$ effector-like cells and $ICOS^-CXCR5^-$ naïve (referred to as nave) cells in the draining lymph node on day 7 after immunization. Strikingly, TFR cells had even higher PD-1 expression when compared to the other CD4 T cell subsets examined, including TFH cells (FIG. 1B).

Figure 1C:
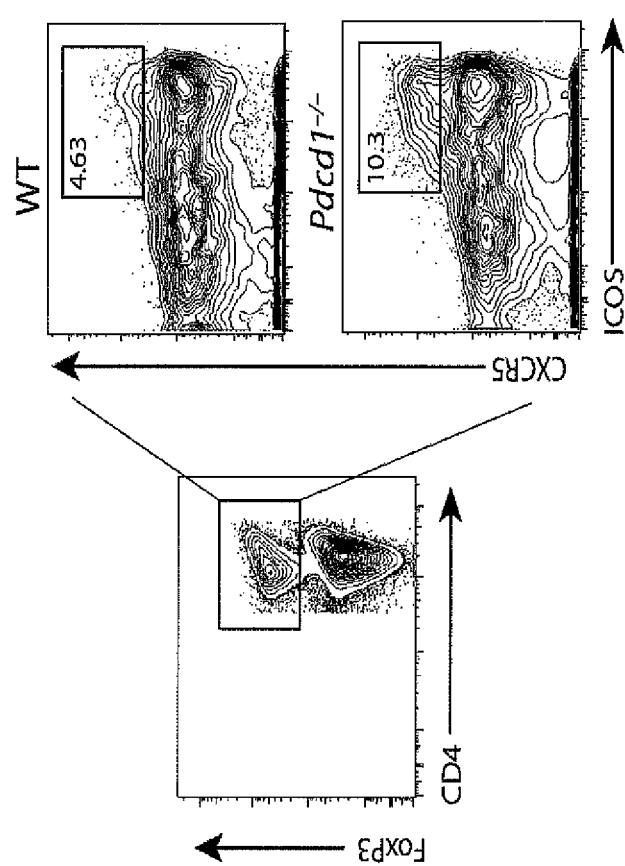
FIG. 1D. Quantitation of WT or PD-1⁻/⁻ T$_{FR}$ cells gated in FIG. 1C and expressed as a percentage of CD4⁺FoxP3⁺ (left), percentage of total CD4 T cells (middle), or percentage of CD4⁺ICOS⁺CXCR5⁺CD19⁻ gate (right). Data represent means of 5 mice per group. All error bars indicate standard error FIG. 1E. Quantitation of T$_{FH}$ cells as a percentage of total CD4 T cells. Data represent means of 5 mice per group. All error bars indicate standard error.
FIG. 1F. PD-1 on FoxP3⁺ cells has a cell-intrinsic role in inhibiting T$_{FR}$ differentiation in vivo. Schematic design of a transfer assay in which 2D2 TCR transgenic CD4⁺FoxP3⁺CXCR5⁻ non-T$_{FR}$ Tregs were transferred into WT mice which were subsequently immunized with MOG/CFA. Draining lymph nodes were harvested 7 days later and analyzed for T$_{FR}$ cells.
FIG. 1G. representative gating of T$_{FR}$ cells from transfer experiments described in FIG. 1F.
FIG. 1H. Quantitation of T$_{FR}$ cells from transfer experiments expressed as a percentage of FoxP3 GFP⁺ cells present on day 7 post immunization per lymph node. All data are representative of at least two independent experiments with at least 5 mice per group. All error bars indicate standard error. * P<0.05, ** P<0.005.
FIG. 1I. Quantitation of T$_{FR}$ cells from transfer experiments expressed as total cell number per lymph node. All data are representative of at least two independent experiments with at least 5 mice per group. All error bars indicate standard error. * P<0.05, ** P<0.005
Figure 1D:
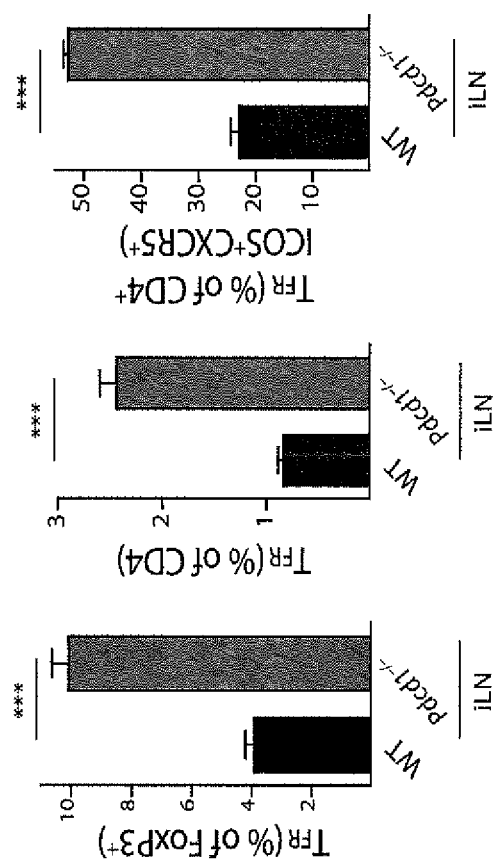
Figure 1E:
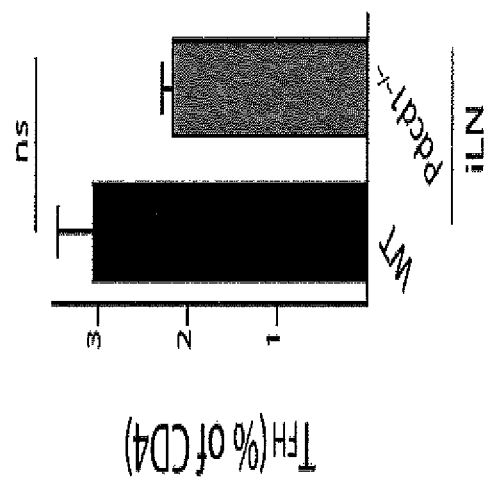

To determine the functional significance of PD-1 expression on TFR cells, we immunized WT and $PD-1^{-/-}$ mice and analyzed TFR cells 7 days later. The percentage of TFR cells contained within the $CD4^+FoxP3^+$ gate was about 4 percent in WT lymph nodes and less than 1 percent of all CD4 T cells. In marked contrast, the percentage of TFR cells in $PD-1^{-/-}$ mice was about 10 percent of the $CD4^+FoxP3^+$ gate and greater than 2 percent of all CD4 T cells (FIGS. 1C-D). Because total numbers of CD4 T cells are typically about two fold higher in the lymph nodes of PD-1 deficient animals, a two-fold increase in T$_{FR}$ cell frequency translates into a ~4-fold increase in absolute numbers of T$_{FR}$ cells (data not shown). When expressed as a percentage of all CD4$^+$ ICOS$^+$CXCR5$^+$ cells (and therefore the percentage of CD4 T cells that respond to CXCL13 and migrate to the B cell zone), PD-1$^{-/-}$ T$_{FR}$ cells comprised half of this population, whereas WT T$_{FR}$ cells comprised only about 20 percent (FIG. 1D). The dramatic increase in the percentage of T$_{FR}$ cells in PD-1$^{-/-}$ mice also was observed when other classical B cell antigens, such as 4-hydroxy-3-nitrophenylacetyl hapten conjugated to ovalbumin (NP-OVA), were used (FIG. 10A-10E). We did not find a significant difference in the percentage of FoxP3$^-$ T$_{FH}$ (from hereon called "T$_{FH}$") cells when expressed as a percentage of all CD4 T cells in WT and PD-1$^{-/-}$ mice on day 7 post immunization (FIG. 1E).

Figures 1F, 1G:
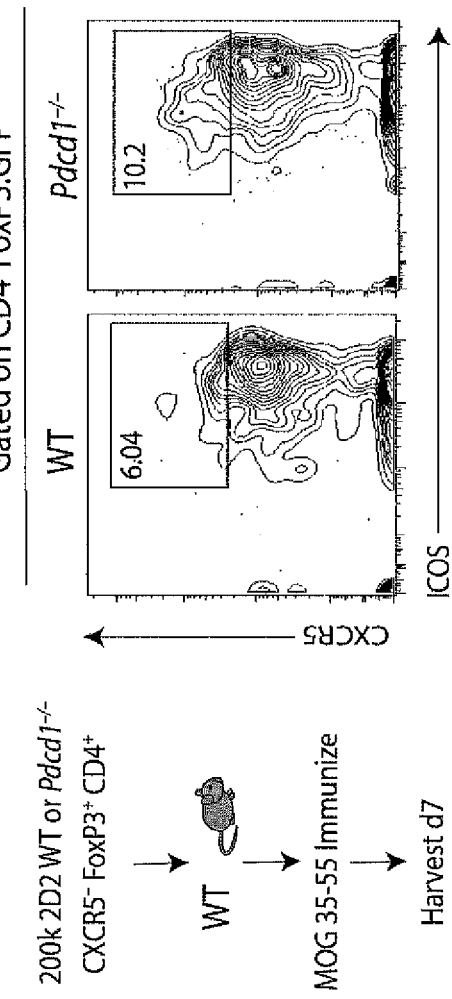
Figure 1H:
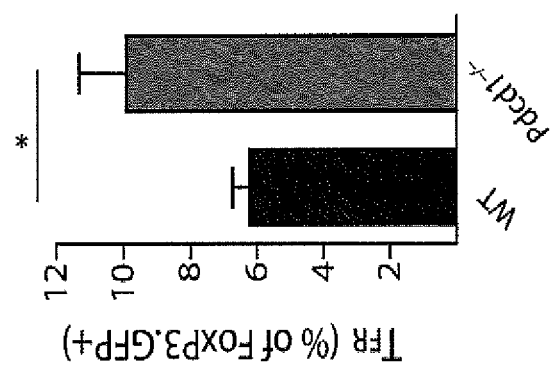
Figure 1I:
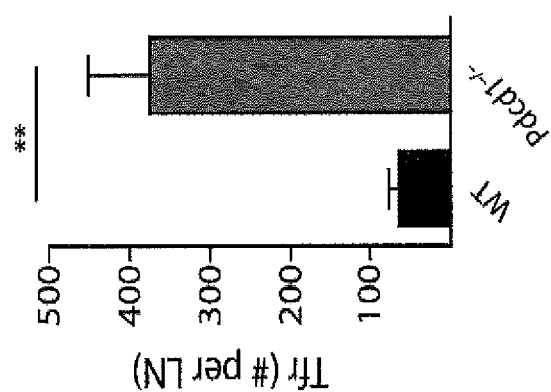

Since PD-1 can be expressed by a number of hematopoietic cell types including T cells, B cells, macrophages and some dendritic cells[15], we next investigated whether PD-1 regulates T$_{FR}$ cells directly by controlling their generation from FoxP3$^+$ T regulatory cells (Treg). To track the fate of FoxP3$^+$ cells following transfer into WT mouse recipients, we used antigen-specific FoxP3$^+$ T cells from TCR transgenic mice for these studies. We sorted FoxP3$^+$ Tregs from WT or PD-1$^{-/-}$ 2D2 (MOG-specific) TCR transgenic FoxP3 GFP reporter mice and transferred 2×10$^5$ 2D2 WT or PD-1$^{-/-}$ CD4$^+$CXCR5$^-$FoxP3$^+$ cells into WT recipient mice. We immunized these recipients with MOG/CFA and analyzed cells in the draining lymph node seven days later (FIG. 1F). There were a greater percentage (FIG. 1H) and absolute number (FIG. 1I) of 2D2 PD-1$^{-/-}$ Tregs upregulating CXCR5 and thus differentiating into T$_{FR}$ cells, compared to 2D2 WT Tregs. The increased percentage of PD-1$^{-/-}$ T$_{FR}$ cells in the immunized transfer recipients was similar, but less pronounced, than the increased percentage in T$_{FR}$ cells seen in immunized intact PD-1 deficient mice (FIG. 1D, H). These results demonstrate that PD-1 controls differentiation of FoxP3$^+$ Tregs into T$_{FR}$ cells.

Figure 2A:
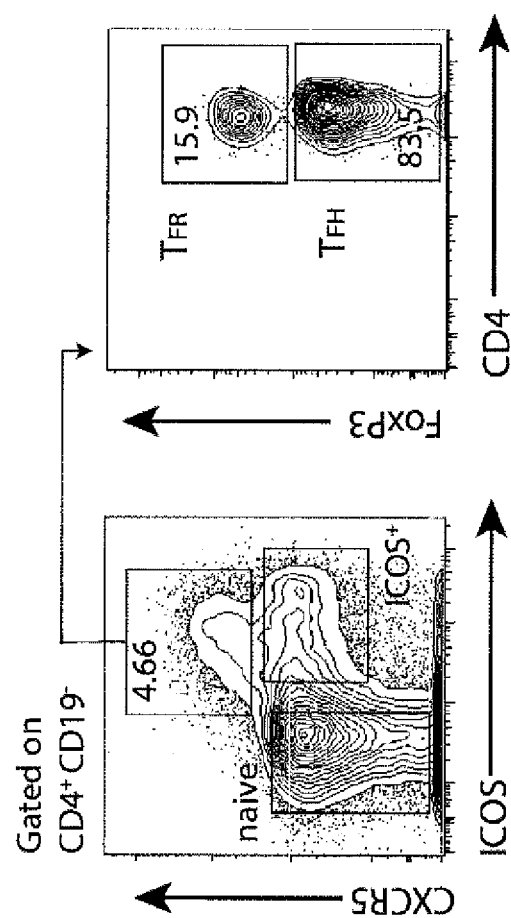
FIG. 2A. PD-1 deficient T$_{FR}$ cells have altered expression of activation markers. T$_{FR}$ cell gating strategy. WT or PD-1⁻/⁻ mice were immunized with MOG/CFA and draining lymph nodes were harvested 7 days later.
Figure 2B:
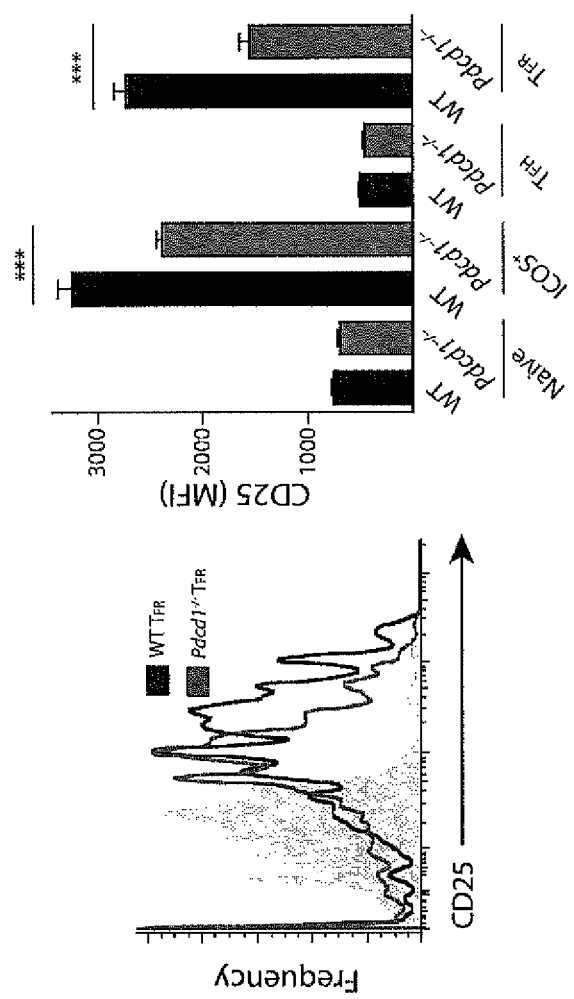
FIG. 2B. CD25 expression on WT and PD-1⁻/⁻ CD4 subsets gated as in FIG. 2A. Overlay histograms of WT and PD-1⁻/⁻ T$_{FR}$ cells (left) and mean fluorescence intensity (MFI) in CD4 subsets gated as in FIG. 1A (right). Data represent means of 5 mice per group.
Figure 2C:
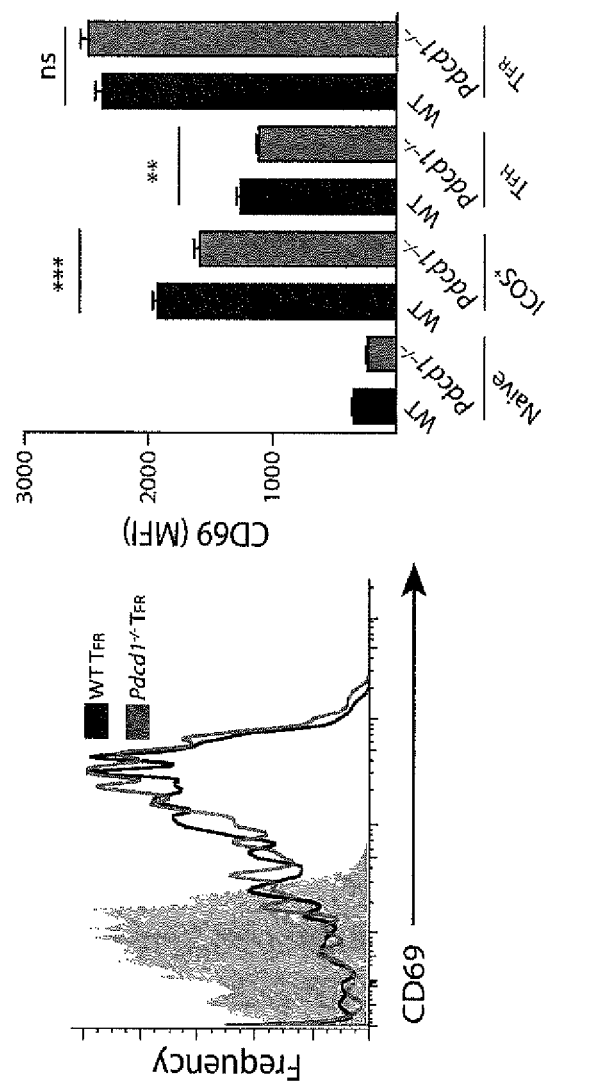
FIG. 2C. CD69 expression on WT and PD-1⁻/⁻ CD4 subsets gated as in FIG. 2A. Overlay histograms of WT and PD-1⁻/⁻ T$_{FR}$ cells (left) and MFI (right). Data represent means of 5 mice per group.
Figure 2D:
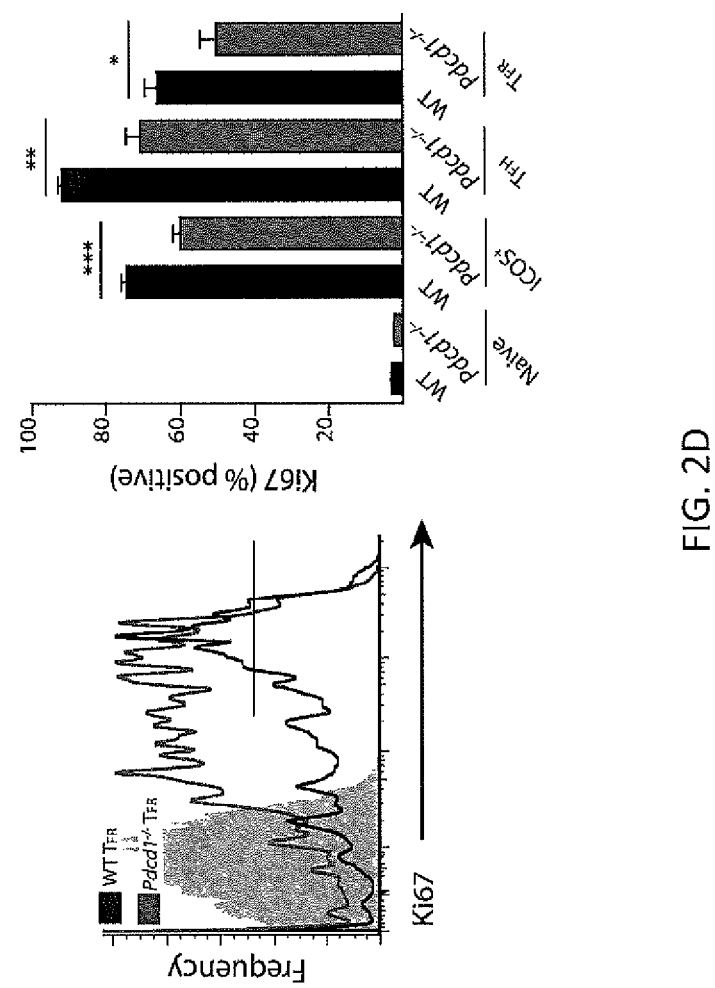
FIG. 2D. Intracellular staining of cell cycle marker Ki67 in populations as in (a). Overlay histograms of WT and PD-1⁻/⁻ T$_{FR}$ cells (left) and percent Ki67 high (right) in CD4 subsets gated as in FIG. 2A. Ki67 high was defined as the highest intensity peak on WT T$_{FR}$ cells and is denoted by a black bar on the histogram. Data represent means of 5 mice per group. All data are representative of at least two independent experiments. All error bars indicate standard error. * P<0.05,  P<0.005, * P<0.0005.

Since CD25 (the alpha chain of the IL-2 receptor) is frequently used as a marker for Tregs, we next compared CD25 expression on WT and PD-1$^{-/-}$ T$_{FR}$ cells directly ex vivo (FIG. 2A). PD-1$^{-/-}$ T$_{FR}$ cells expressed less CD25 than WT T$_{FR}$ cells (FIG. 2B). The attenuated CD25 expression in PD-1 deficient T$_{FR}$ cells is not likely due to decreased activation because the expression of the early activation marker CD69 was virtually identical on WT and PD-1$^{-/-}$ T$_{FR}$ cells (FIG. 2C). To compare the proportion of WT and PD-1$^{-/-}$ T$_{FR}$ cells proliferating at day 7 post immunization, we examined Ki67 expression, a marker widely used to identify cells that are actively dividing. WT ICOS$^+$ CXCR5$^-$ effectors, T$_{FH}$ and T$_{FR}$ gated cells had high expression of Ki67. In contrast, the WT CXCR5$^-$ICOS$^-$ "naïve" cells, lacking CD69 and CD25 expression, had no Ki67 staining consistent with their designation as naïve (FIG. 2D). WT T$_{FR}$ cells expressed significantly higher levels of Ki67 compared to PD-1$^{-/-}$ T$_{FR}$ cells, suggesting that the increased numbers of T$_{FR}$ cells in PD-1 deficient animals reflect increased differentiation, and not maintenance, of T$_{FR}$ cells. Ki67 expression was similarly greater in WT ICOS$^+$ effectors and T$_{FH}$ cells compared to PD-1$^{-/-}$ ICOS$^+$ CXCR5$^-$ effectors and T$_{FH}$ cells. These points to an overall decrease in cell cycling in PD-1$^{-/-}$ effector cells at 7 days after immunization. Other Treg markers such as CD103 and GITR were not altered on T$_{FR}$ cells in PD-1 deficient mice (FIG. 11A-11C). Additionally, there was low, but significant expression of PD-L1 on WT and PD-1$^{-/-}$ T$_{FR}$ cells. Together, these data indicate that PD-1 is important in regulating numbers of T$_{FR}$ cells in vivo.

PD-1 Deficient T$_{FR}$ Cells are Capable of Homing to Germinal Centers

Figure 3A:
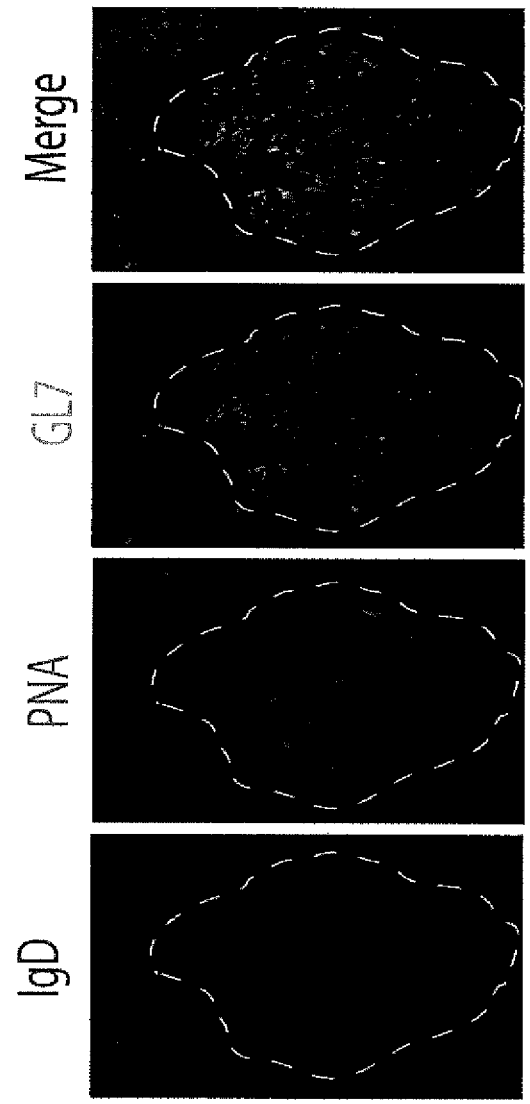
FIG. 3A. PD-1 deficient T$_{FR}$ cells are capable of homing to germinal centers (GCs). Micrographs of draining lymph node sections from WT mice immunized with MOG/CFA and harvested 7 days later. Sections were cut and stained for GL-7 (green), PNA (red) and IgD (blue). GCs were identified by PNA and GL7 positive, but IgD negative, staining GCs are indicated with a white dotted line.
Figure 3B:
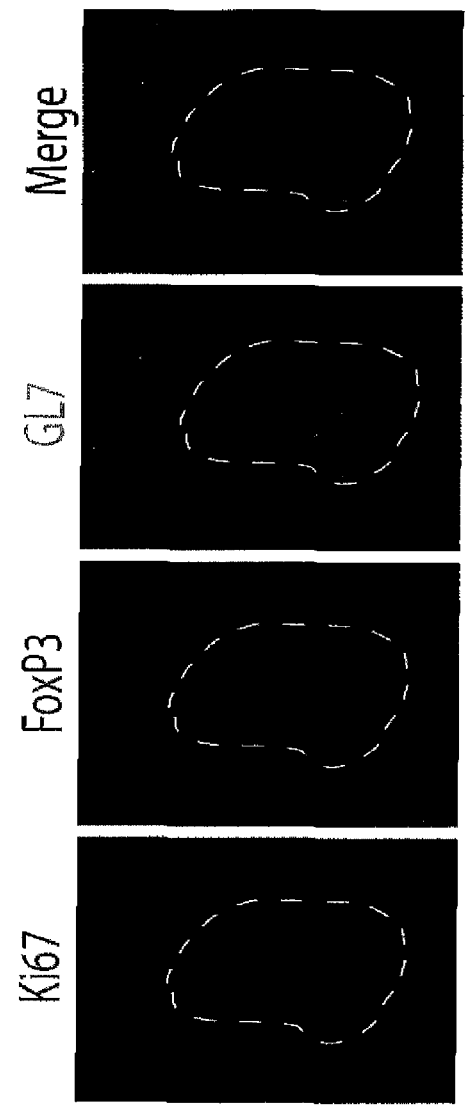
FIG. 3B. Ki67 staining in GCs. Sections were stained for the cell cycle marker Ki67 (blue), FoxP3 (red) and GL7 (green).
Figure 3C:
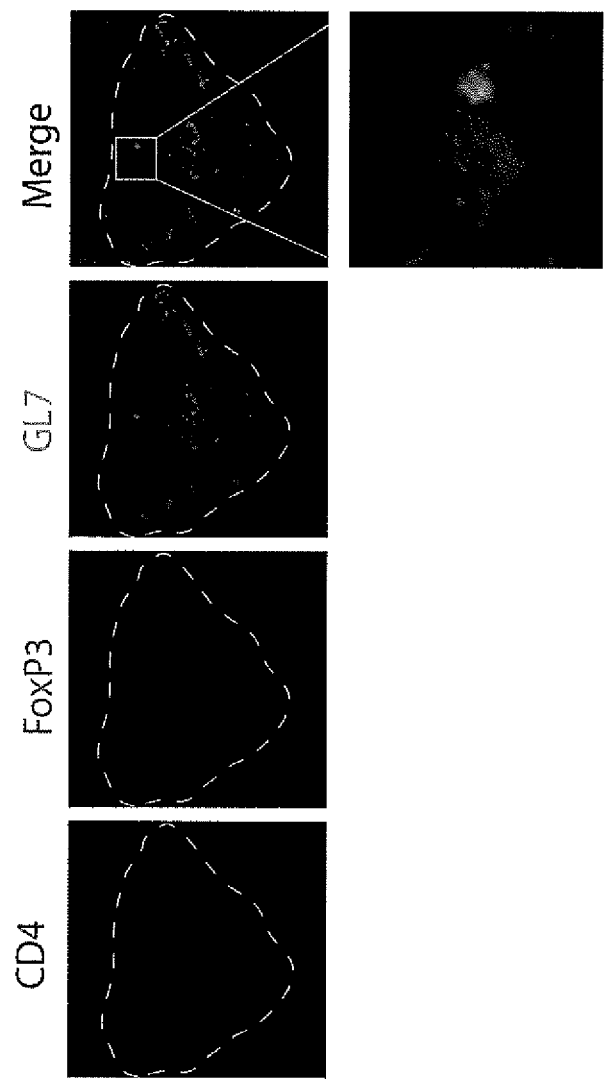
FIG. 3C. Colocalization of CD4 and FoxP3. Sections were stained for CD4 (blue), FoxP3 (red) and GL7 (green). Box indicates magnification highlighting CD4 positive staining on FoxP3⁺ cells.
Figure 3D:
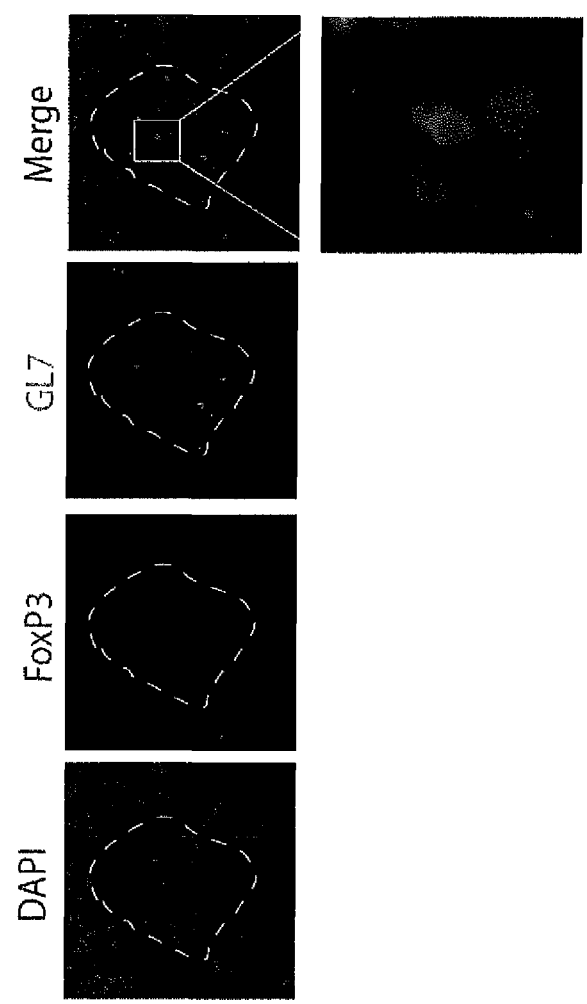
FIG. 3D. Colocalization of FoxP3 in the nucleus. Sections were stained with the nuclear stain DAPI (blue), FoxP3 (red) and GL7 (green). Box indicates magnification highlighting FoxP3 protein within DAPI positive nuclei.

We next compared the capacity of T$_{FR}$ cells from WT and PD-1 deficient animals to enter the germinal center (GC) in order to inhibit the GC response. First, we evaluated GC formation in lymph node sections harvested 7 days after MOG/CFA immunization. GCs were identified by the presence of PNA/GL7 positively stained and IgD negatively stained B cell zones (FIG. 3A). These GCs were determined to be active, based on robust expression of the cell cycle marker Ki67 (FIG. 3B). Similar to previous reports[21, 22], CD4$^+$FoxP3$^+$ T$_{FR}$ cells could be found within GCs of immunized mice (FIG. 3C). The FoxP3 protein within the T$_{FR}$ cells was judged to be largely nuclear based on its co-localization with the DAPI staining (FIG. 3D).

Figure 3E:
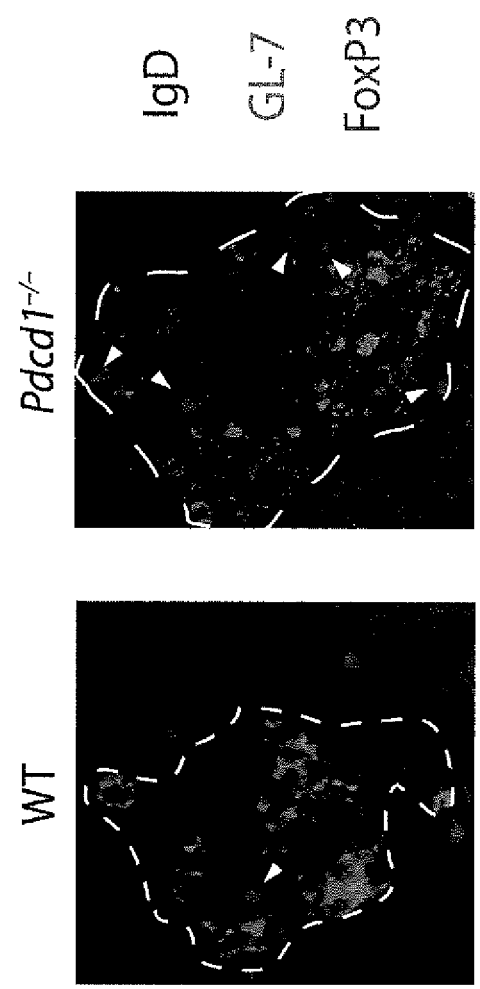
FIG. 3E. Comparison of FoxP3⁺ T$_{FR}$ cells in germinal centers of WT and PD-1⁻/⁻ mice. Representative GC staining in WT and PD-1⁻/⁻ lymph nodes 7 days after immunization with MOG/CFA.
Figures 3F, 3G:
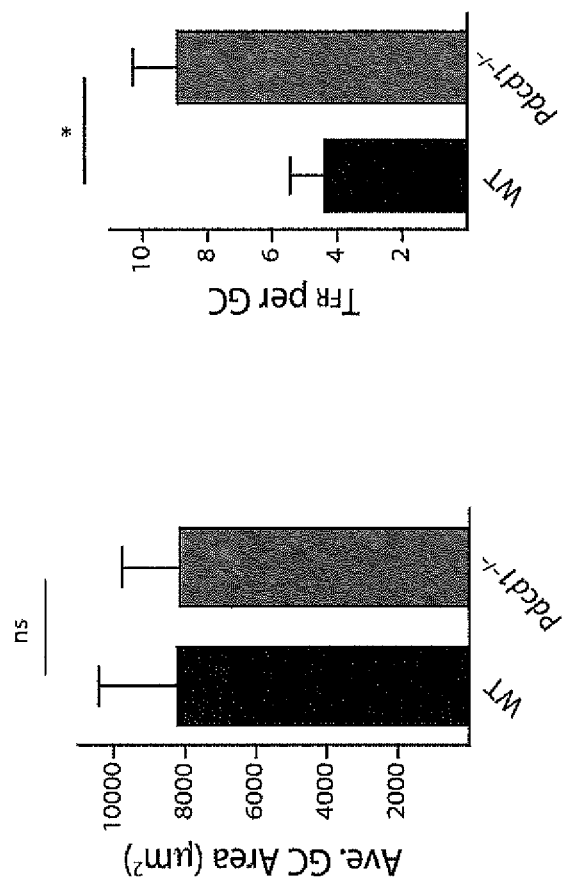
FIG. 3F. Average GC area was determined by calculating the area within the dotted lines according to materials and methods. Data represent mean area per lymph node of 5 individual mice.
FIG. 3G. Numbers of FoxP3⁺ cells contained within GCs. Data represent mean per GC from 5 pooled mice.

We then investigated whether the phenotypically distinct T$_{FR}$ cells from PD-1 deficient mice were able to migrate to GCs similarly to WT T$_{FR}$ cells, because PD-1 blockade can prolong the TCR stop signal and decrease T cell migration[25]. We immunized WT and PD-1 deficient mice with MOG/CFA and 7 days later analyzed lymph node sections for IgD, GL7 and FoxP3 expression (FIG. 3E). Although the average germinal center area (FIG. 3F) and numbers of germinal centers per lymph node (data not shown) were equivalent in WT and PD-1$^{-/-}$ mice, there were slightly more FoxP3$^+$ cells (and therefore T$_{FR}$ cells) located within the GC borders in PD-1$^{-/-}$ mice as in WT mice (FIG. 3G). However, since this increase is proportional to the larger numbers of T$_{FR}$ cells in PD-1 deficient mice determined by flow cytometry, these data demonstrate that PD-1 deficient T$_{FR}$ cells are not defective in homing to GCs and can enter the GC similarly to WT T$_{FR}$ cells.

Figures 3H, 3I:
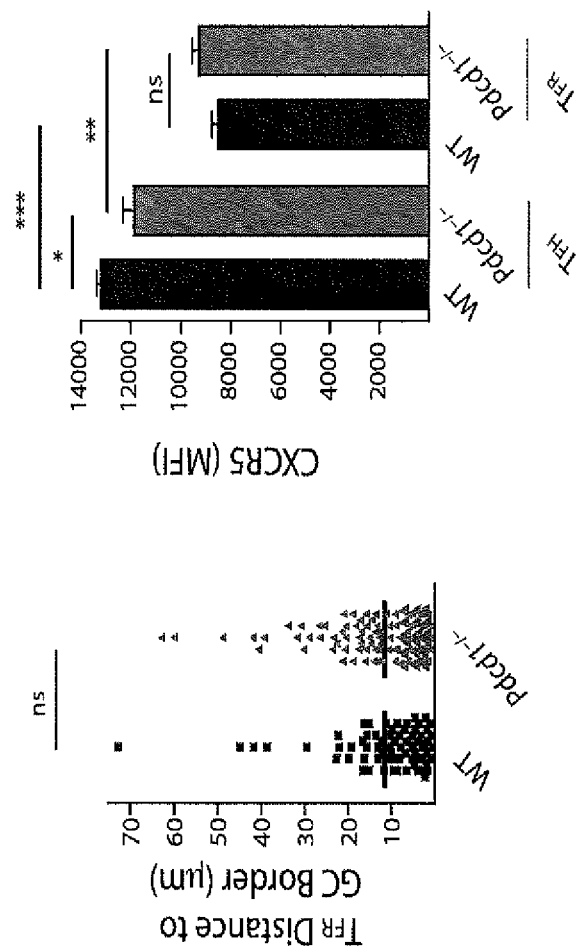
FIG. 3H. Quantitation of the distance of each FoxP3⁺ cell to the GC border. The distance for each FoxP3⁺ cell in FIG. 3E from the GC borders (dotted line in FIG. 3E) was calculated as described in materials and methods.
FIG. 3I CXCR5 expression was quantified on WT and PD-1⁻/⁻ CD4⁺ICOS⁺CXCR5⁺FoxP3⁻CD19⁻ T$_{FH}$ and CD4⁺ICOS⁺CXCR5⁺FoxP3⁺CD19⁻ T$_{FR}$ cells by flow cytometry 7 days after MOG/CFA immunization. Data represent means of 5 mice per group. * P<0.05,  P<0.005, * P<0.0005.

The relative location of FoxP3$^+$ T$_{FR}$ cells within the GC did not differ significantly between WT and PD-1$^{-/-}$ T$_{FR}$ cells (FIG. 3H). In both WT and PD-1$^{-/-}$ mice the FoxP3$^+$ cells tended to reside close to the GC border, with more than half of the FoxP3$^+$ nuclei being positioned within 10 μm of the border. Furthermore, when CXCR5 fluorescence was quantified by flow cytometry in T$_{FR}$ cells, there was similar CXCR5 expression on TFR cells in the WT and PD-1$^{-/-}$ mice, indicating similar potential for these cells to respond to chemokine cues to migrate to GCs (FIG. 3I). Taken together, these data indicate that T$_{FR}$ cells are increased in lymph nodes of immunized PD-1$^{-/-}$ mice, and these PD-1$^{-/-}$ T$_{FR}$ cells are capable of migrating into GCs to regulate B cell responses.

PD-1 Deficient T$_{FR}$ Cells More Potently Inhibit T Cell Activation

Figure 4A:
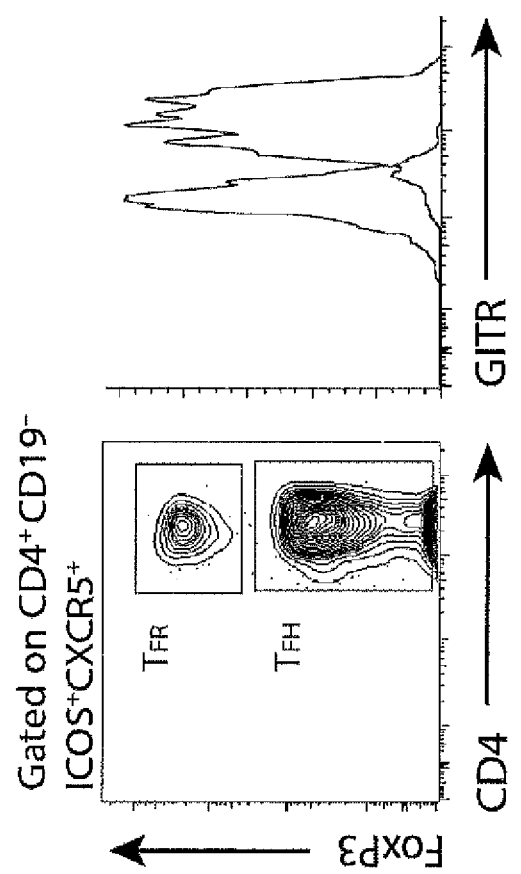
FIG. 4A. PD-1 deficient T$_{FR}$ cells have enhanced regulatory capacity. T$_{FR}$ cells express high levels of GITR. WT mice were immunized with MOG/CFA and 7 days later lymph node cells were isolated and expression of GITR on T$_{FR}$ (CD4FoxP3⁺ICOS⁺CXCR5⁺CD19⁻, blue) and T$_{FH}$ (CD4⁺FoxP3⁻ICOS⁺CXCR5⁺CD19⁻, red) was quantified as shown by histogram overlays.
Figure 4B:
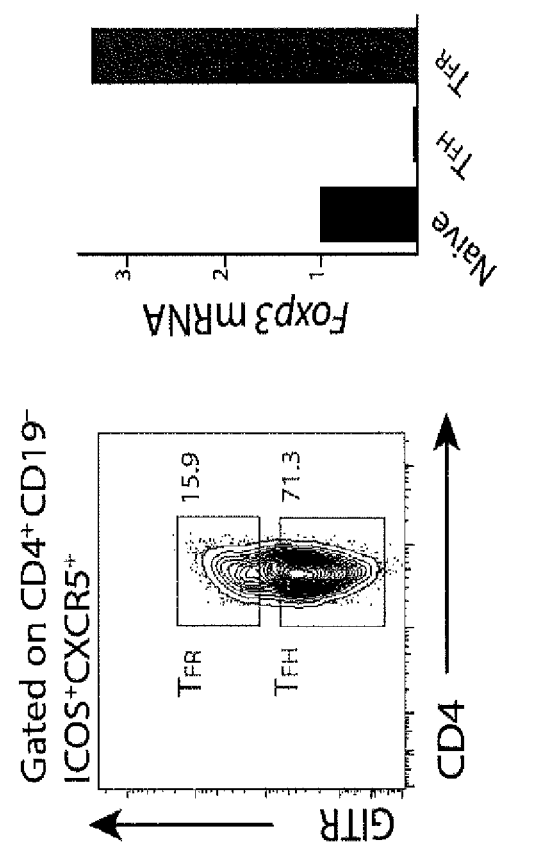
FIG. 4B. Expression of FoxP3 mRNA in sorted T$_{FR}$ (CD4⁺GITR⁺ICOS⁺CXCR5⁺CD19⁻), T$_{FH}$ (CD4⁺GITR⁻ICOS⁺CXCR5⁺CD19⁻) and naive (CD4⁺ICOS⁻CXCR5⁻CD19) cells. Data represent fold change in mRNA normalized to Hprt.
Figure 12:
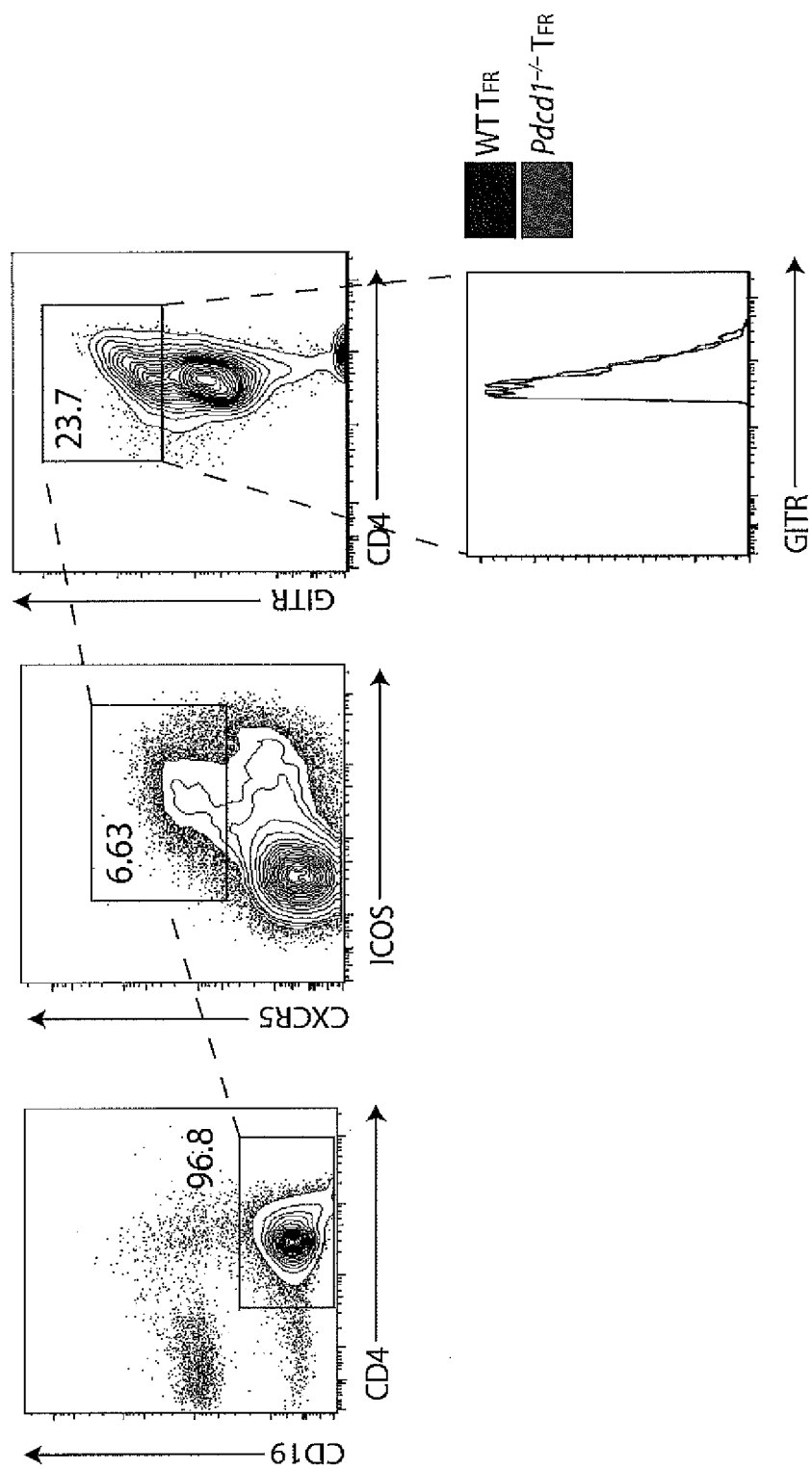
FIG. 12. WT and PD-1 deficient T$_{FR}$ cells express similar levels of GITR. WT and PD-1$^{-/-}$ mice were immunized with NP-OVA and 7 days later populations were sorted according to gating strategy.

We next compared the function of T$_{FR}$ cells from WT and PD-1$^{-/-}$ mice. T$_{FR}$ cells express higher levels of GITR on the cell surface than do T$_{FH}$ cells, which allows for separation of the T$_{FH}$ and T$_{FR}$ cells in a similar manner to intracellular staining for FoxP3 (FIG. 4A). For functional studies, we sorted T$_{FR}$ cells from immunized mice by taking the lymph node CD4$^+$ICOS$^+$CXCR5$^+$CD19$^-$GITR$^+$ population as T$_{FR}$ cells and the CD4$^+$ICOS$^+$CXCR5$^+$CD19$^-$GITR$^-$ population as T$_{FH}$ cells (FIG. 4B). Sorting in this fashion shows robust mRNA for FoxP3 in the GITR$^+$ (T$_{FR}$) population, but essentially no FoxP3 mRNA in the GITR$^-$ (T$_{FH}$) population, validating the use of this gating strategy to isolate T$_{FR}$ and T$_{FH}$ cells for functional assays. Furthermore, this sorting strategy can be used to compare WT and PD-1 deficient T$_{FR}$ cells since GITR expression is identical on WT and PD-1 deficient T$_{FR}$ cells (FIG. 12).

Figures 4C, 4D:
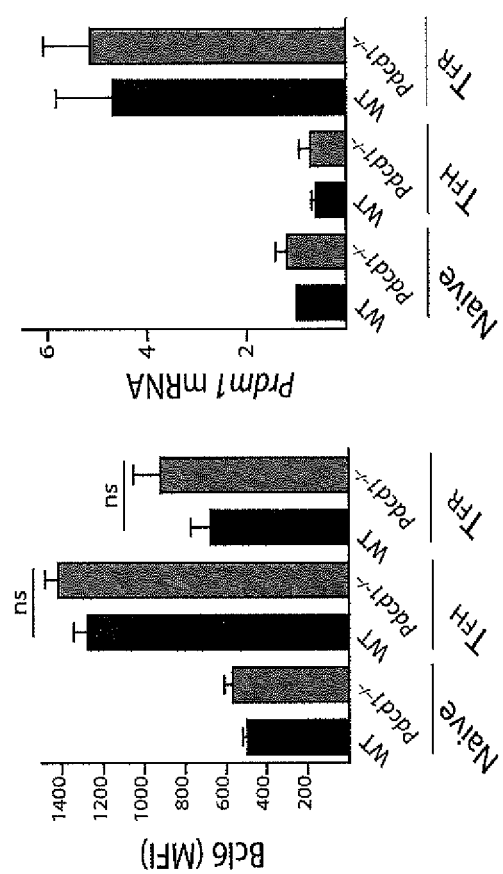
FIG. 4C. Bcl6 expression analyzed by intracellular flow cytometry on T$_{FH}$ and T$_{FR}$ cells from WT (blue) and PD-1⁻/⁻ (green) mice. Data represent means from at least three separate experiments in which cells were sorted from lymph nodes of 10 pooled mice.
FIG. 4D. mRNA expression of blimp-1/Prdm1 from sorted WT (blue) and PD-1⁻/⁻ (green) T$_{FR}$ and T$_{FH}$ cells and in CD4–ICOS⁻CXCR5⁻ (naive) cells quantified by qPCR analysis. Data represent means from at least three separate experiments in which cells were sorted from lymph nodes of 10 pooled mice.
Figures 4E, 4F:
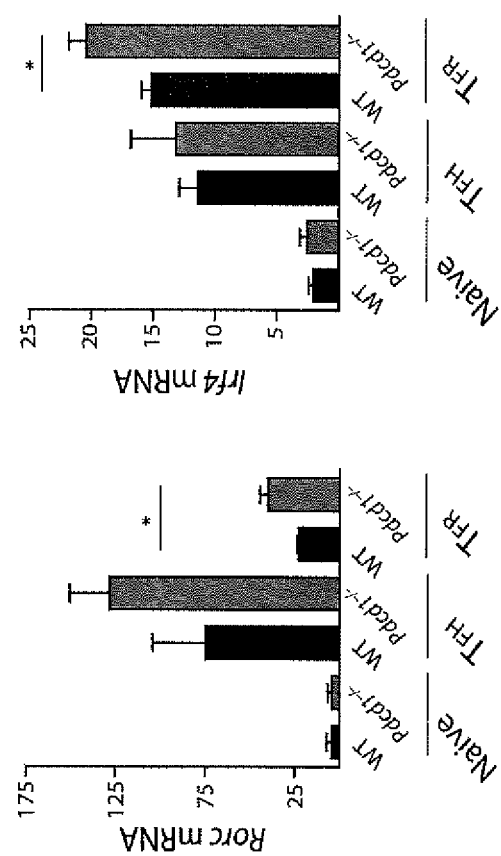
FIG. 4E. mRNA expression of Rorc from sorted WT (blue) and PD-1⁻/⁻ (green) T$_{FR}$ and T$_{FH}$ cells and in CD4-ICOS⁻CXCR5⁻ (naive) cells quantified by qPCR analysis. Data represent means from at least three separate experiments in which cells were sorted from lymph nodes of 10 pooled mice.
FIG. 4F. mRNA expression of Irf4 from sorted WT (blue) and PD-1⁻/⁻ (green) T$_{FR}$ and T$_{FH}$ cells and in CD4-ICOS⁻CXCR5⁻ (naive) cells quantified by qPCR analysis. Data represent means from at least three separate experiments in which cells were sorted from lymph nodes of 10 pooled mice.

T$_{FR}$ cells express high Blimp1/Prdm1 and moderate levels of Bcl6[21]. Bcl6 and Blimp1 reciprocally modulate each other[2]; Bcl6 inhibition of Blimp1 is essential for maintenance of the T<sub>FH</sub> phenotype, whereas Blimp1 is important in Treg homeostasis in general[26, 27]. Since relative expression of Bcl6 and Blimp1 determines function of T<sub>FR</sub> subsets, we compared Bcl6 expression in T<sub>FR</sub> cells from WT and PD-1$^{-/-}$ mice using flow cytometry to analyze intracellular Bcl6 expression at the protein level. Although T<sub>FR</sub> cells expressed less Bcl6 at the protein level than T<sub>FH</sub> cells, WT and PD-1$^{-/-}$ T<sub>FR</sub> had similar Bcl6 levels (FIG. 4C). We next compared the expression of Blimp1 (encoded by Prdm1) on T<sub>FR</sub> cells from WT and PD-1$^{-/-}$ mice. At the mRNA level, we did not find any consistent differences in Blimp1/Prdm1 expression between WT and PD-1$^{-/-}$ T<sub>FR</sub> cells (FIG. 4D). Since FoxP3 can directly interact with and negatively regulate the function of Rorγt[28], we also examined Rorc (which encodes Rorγt) in WT and PD-1$^{-/-}$ T<sub>FR</sub> cells. Rorc mRNA levels were lower in T<sub>FR</sub> cells compared to T<sub>FH</sub> cells, but Rorc expression was increased in PD-1$^{-/-}$ T<sub>FR</sub> cells relative to WT T<sub>FR</sub> cells (FIG. 4E). In addition, we compared expression of the transcription factor IRF4 in WT and PD-1$^{-/-}$ T<sub>FR</sub> cells, since Blimp1 and IRF4 synergistically control the differentiation and effector functions of regulatory T cells[26]. We found an increase in IRF4 mRNA in PD-1$^{-/-}$ T<sub>FR</sub> cells compared to WT T<sub>FR</sub> cells (FIG. 4F).

IRF4 is essential for the suppressive capacity of regulatory T cells[26]. To determine if increased IRF4 mRNA in PD-1$^{-/-}$ T<sub>FR</sub> cells translates into an increase in suppression of naïve T cell proliferation, we set up an in vitro suppression assay in which we cultured sorted WT GL7$^-$ B cells, CFSE labeled WT nave CD4$^+$CD62L$^+$FoxP3$^-$ responder T cells, and either WT or PD-1$^{-/-}$ T<sub>FR</sub> cells sorted from mice immunized with MOG/CFA together with anti-CD3 and anti-IgM (FIG. 4G). The responder T cells highly upregulated CD69 after 3 days of culture with WT B cells. However, when WT T<sub>FR</sub> cells were added in a 1:1:1 ratio, the CD69 expression on the responder T cells was much lower, consistent with the function of T<sub>FR</sub> cells in suppressing T cell activation (FIG. 4H). CD69 upregulation was inhibited to an even greater extent in responder T cells that were cultured with PD-1$^{-/-}$ T<sub>FR</sub> cells. Moreover, PD-1$^{-/-}$ T<sub>FR</sub> attenuated the proliferation of responder T cells (FIG. 4I), in contrast to WT T<sub>FR</sub> cells, which did not inhibit the proliferation of responder T cells during the day 3 culture period.

Figures 4J, 4K:
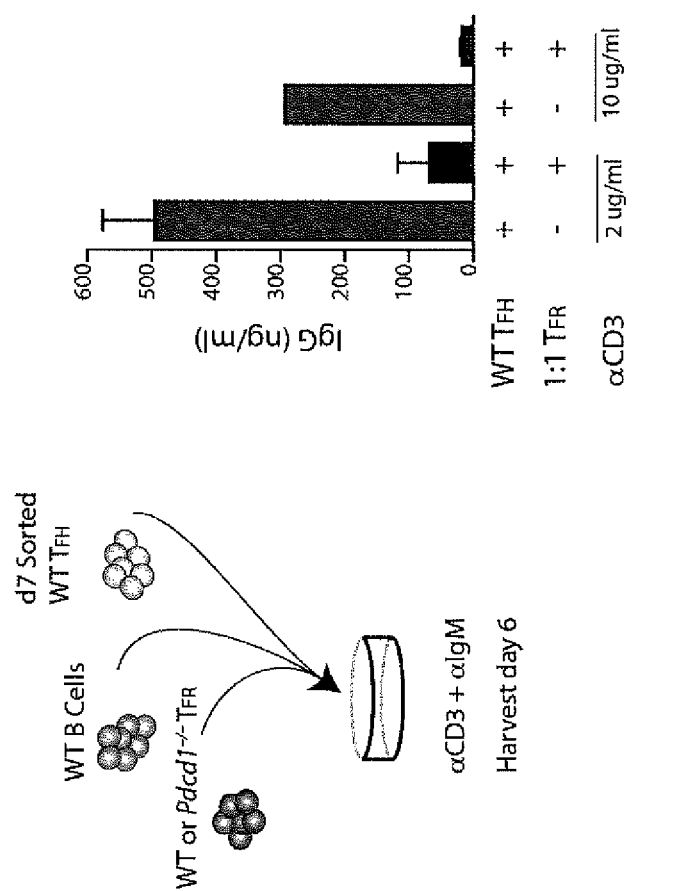
FIG. 4J. In vitro IgG suppression assay design. T$_{FR}$ cells sorted as in FIG. 4G were plated in a 1:1:1 ratio of T$_{FR}$ (CD4$^+$ICOS$^+$CXCR5$^+$GITR$^+$CD19$^-$), T$_{FH}$ (CD4$^+$ICOS$^+$CXCR5$^+$GITR$^-$CD19), and B (GL-7$^-$B220$^+$) cells from draining lymph nodes of MOG/CFA immunized mice in the presence of anti-CD3 and anti-IgM for 6 days. Total IgG was measured by ELISA from supernatants.
FIG. 4K. Suppression assay using two concentrations of anti-CD3.
Figures 4L, 4M:
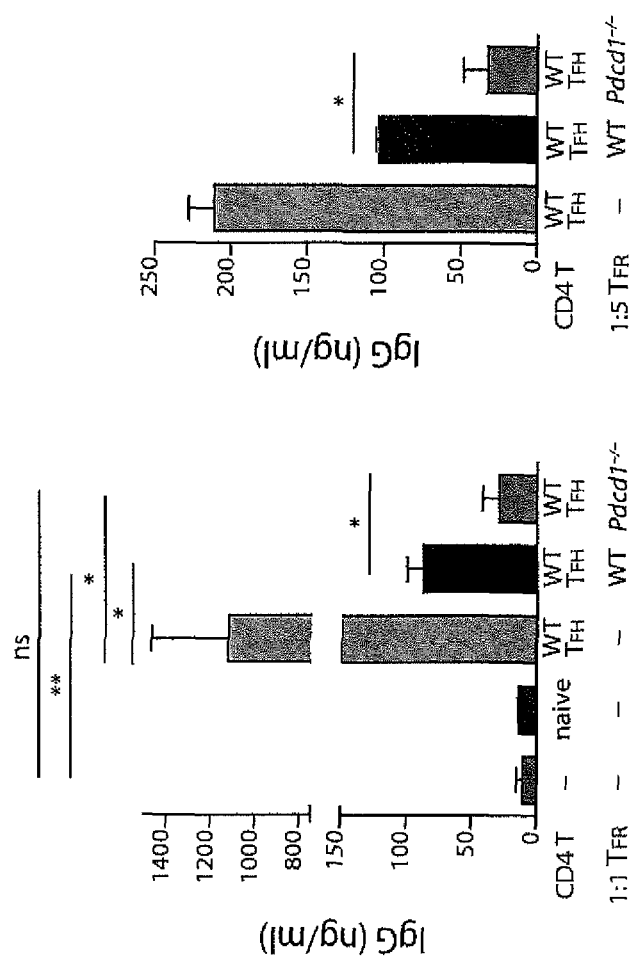
FIG. 4L. PD-1 deficient T$_{FR}$ cells suppress IgG production to a greater extent than WT T$_{FR}$ cells at a 1:1 T$_{FR}$:T$_{FH}$ ratio. Naive (CD4$^+$ICOS$^-$CXCR5$^-$CD19$^-$) cells from immunized mice were included as controls. Data indicates means+/−standard error of replicate wells and is representative of at least two experiments. * P<0.05,  P<0.005, * P<0.0005.
FIG. 4M. PD-1 deficient T$_{FR}$ cells suppress IgG production to a greater extent than WT T$_{FR}$ cells at a 1:5 T$_{FR}$:T$_{FH}$ ratio. Data indicates means+/−standard error of replicate wells and is representative of at least two experiments. * P<0.05,  P<0.005, * P<0.0005.
Figures 13A, 13B:
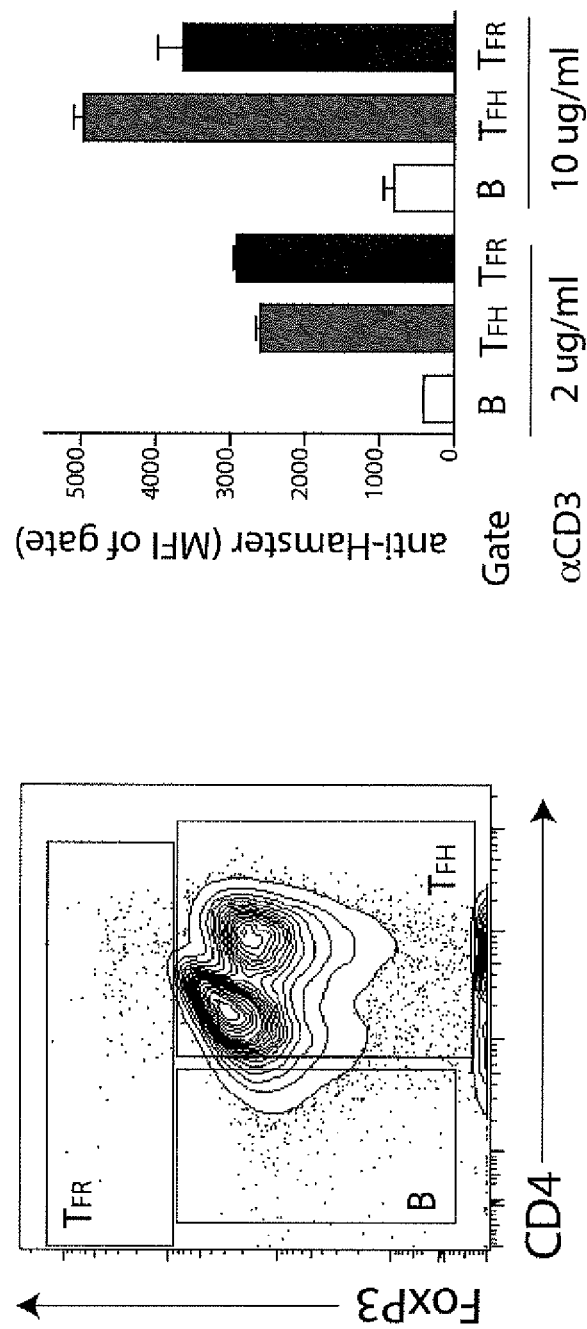
FIG. 13A. T$_{FH}$ and T$_{FR}$ cells can bind similar levels of anti-CD3. Gating of T$_{FH}$, T$_{FR}$ and B cells from in vitro suppression assays as in FIG. 4K.
FIG. 13B. Cells gated as in FIG. 13A were stained with an anti-hamster secondary antibody to quantify the amount of anti-CD3 bound to the surface of the cells.

Although T<sub>FR</sub> cells are thought to inhibit the germinal response in vivo, it is unclear whether T<sub>FR</sub> cells directly inhibit T cell differentiation, T<sub>FH</sub> cell function, B cell activation or all three. To assess the capability of T<sub>FR</sub> cells to suppress B cell antibody production in vitro, we cultured WT GL7$^-$ B cells with WT FoxP3$^-$ T<sub>FH</sub> cells for 6 days in the presence or absence of T<sub>FR</sub> cells, anti-IgM and anti-CD3 (FIG. 4J). WT B cells produced large amounts of IgG when cultured with WT FoxP3$^-$ T<sub>FH</sub> cells plus anti-IgM and anti-CD3 (FIG. 4K). No significant IgG was present when CD4$^+$FoxP3$^-$ naïve T cells were used in these experiments (FIG. 4L). When T<sub>FR</sub> cells were added to the wells along with T<sub>FH</sub> cells, almost no IgG was produced. The T<sub>FR</sub>-mediated suppression was not due to sequestering of anti-CD3 because there was equally good suppression at the two doses of anti-CD3 tested (FIG. 4K), and the anti-CD3 could still be found on the surface of the T<sub>FH</sub> cells at the end of the suppression assay (FIG. 13A-FIG. 13B). PD-1$^{-/-}$ T<sub>FR</sub> cells suppressed IgG production more than WT T<sub>FR</sub> cells at both a 1:1 (FIG. 4L) and a 1:5 (FIG. 4M) T<sub>FR</sub>:T<sub>FH</sub> ratio, with PD-1 deficient T<sub>FR</sub> cells resulting in a 50% greater reduction in IgG production compared to WT T<sub>FR</sub> cells. Taken together, these data demonstrate not only that are there increased T<sub>FR</sub> cells in PD-1 mice, but that these PD-1$^{-/-}$ T<sub>FR</sub> cells have increased suppressive capacity.

PD-1 Controls Blood T Follicular Regulatory Cells

Figure 5A:
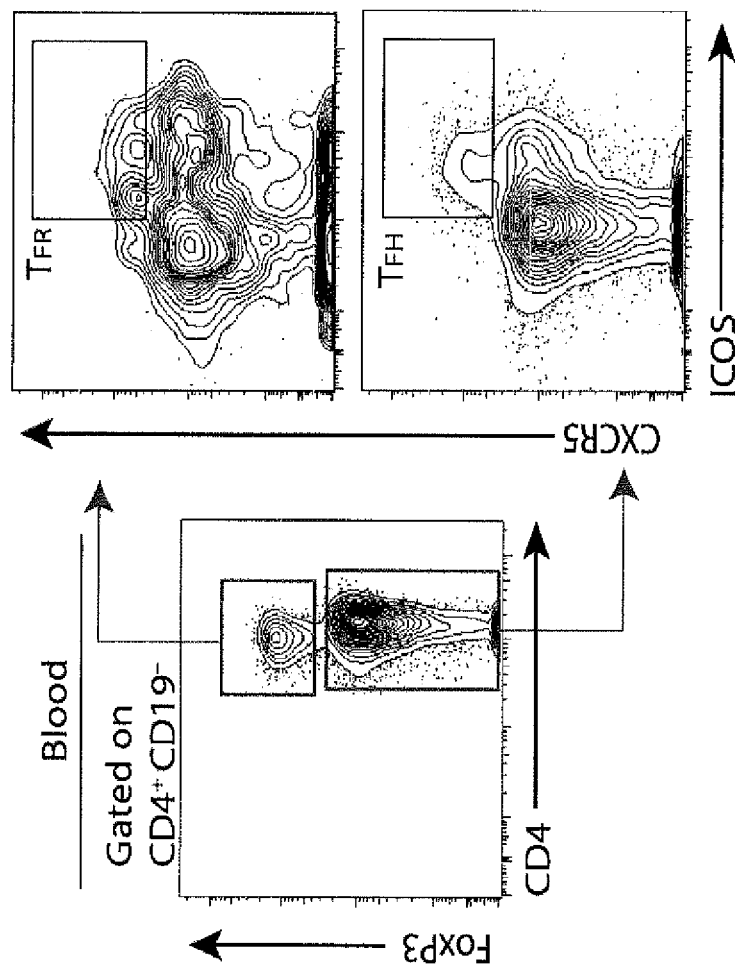
FIG. 5A. PD-1 controls circulating blood T$_{FR}$ cells. Gating strategy to identify circulating T$_{FH}$ and T$_{FR}$ cells from blood. WT mice were immunized with MOG/CFA and blood was collected 7 days later by cardiac puncture. T$_{FH}$ and T$_{FR}$ populations were gated as shown.

One possible explanation for the increase in T<sub>FR</sub> cells in lymph nodes of immunized PD-1 deficient mice is that PD-1$^{-/-}$ T<sub>FR</sub> cells are unable to exit the lymph node. Studies have demonstrated that functional T<sub>FH</sub> cells can be found in the blood of humans as well as mice[6, 7, 9], but whether T<sub>FR</sub> cells circulate in the blood of humans or mice is not yet known. Strikingly, we found a significant population of T<sub>FH</sub> cells, as well as a smaller population of T<sub>FR</sub> cells, in the blood of WT mice immunized with MOG/CFA (FIGS. 5A-B). When we compared the kinetics of T<sub>FH</sub> and T<sub>FR</sub> cell expansion in the lymph node and blood of mice following MOG/CFA immunization, we found that both T<sub>FR</sub> and T<sub>FH</sub> cells increase in the draining lymph node of WT immunized mice over a 10 day period, and that T<sub>FH</sub> cells, but not T<sub>FR</sub> cells, increase substantially by percentage in the blood over this time (FIG. 5B). Thus, without antigenic stimulus, the blood T<sub>FR</sub>:T<sub>FH</sub> ratio is fairly high (sometimes greater than 1:1) but upon addition of a stimulus, blood T<sub>FH</sub> cells expand more than blood T<sub>FR</sub> cells so that the T<sub>FR</sub>:T<sub>FH</sub> ratio is about 1:5. To investigate whether WT blood T<sub>FH</sub> and T<sub>FR</sub> cells are quiescent or are actively in cell cycle, we compared Ki67 expression in draining lymph node and blood T<sub>FH</sub> and T<sub>FR</sub> cells 7 days after immunization. T<sub>FH</sub> cells from the draining lymph node had higher Ki67 expression than those found in the blood (FIG. 5C). Blood T<sub>FH</sub> and T<sub>FR</sub> and draining lymph node T<sub>FR</sub> cells expressed similar levels of Ki67.

Figure 5D:
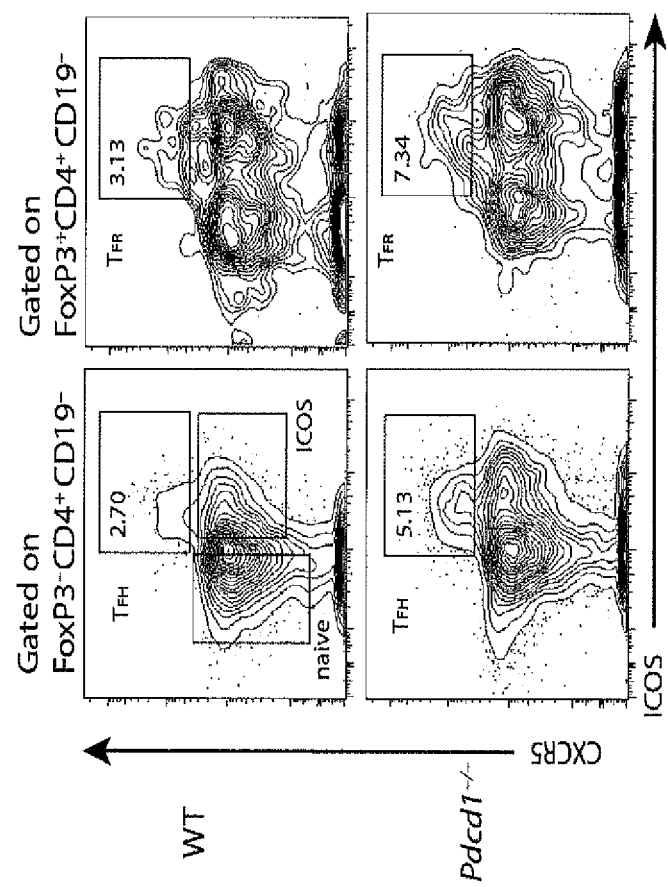
FIG. 5D. Comparison of blood T$_{FH}$ and T$_{FR}$ cells in WT and PD-1$^{-/-}$ mice immunized as in FIG. 5A and harvested 7 days after immunization. Blood T$_{FH}$ cells are shown gated on FoxP3$^-$CD4$^+$CD19$^-$ (left) and T$_{FR}$ cells are shown gated on FoxP3$^+$CD4$^+$CD19$^-$ (right).
Figures 5E, 5F:
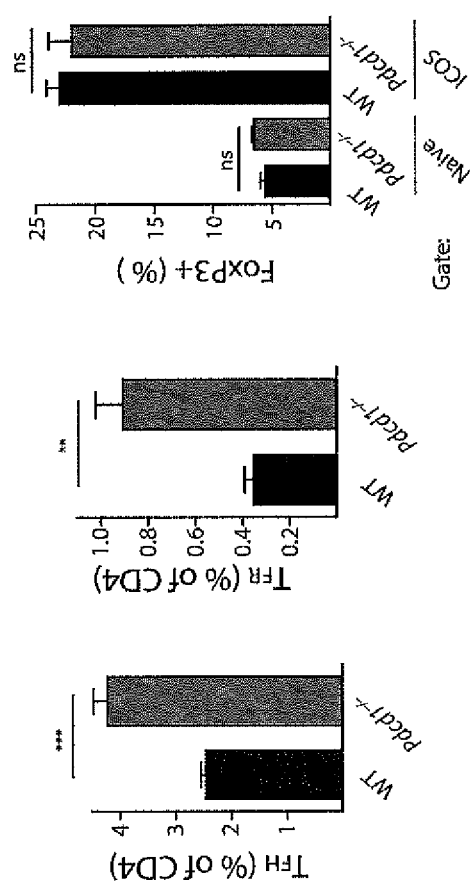
FIG. 5E. Comparison of blood T$_{FH}$ and T$_{FR}$ cells in WT and PD-1$^{-/-}$ mice immunized as in FIG. 5A and harvested 7 days after immunization. Quantitation of blood T$_{FH}$ and T$_{FR}$ cells from immunized WT and PD-1$^{-/-}$ mice gated as in FIG. 5D and expressed as a percent of CD4$^+$CD19$^-$ cells. All data indicates means+/−standard error of 5 mice and is representative of at least two independent experiments. * P<0.05,  P<0.005, * P<0.0005.
FIG. 5F. Comparison of blood T$_{FH}$ and T$_{FR}$ cells in WT and PD-1$^{-/-}$ mice immunized as in FIG. 5A and harvested 7 days after immunization. Quantitation of CXCR5$^-$ FoxP3$^+$ cells from immunized WT and PD-1$^{-/-}$ mice, expressed as a percentage of CXCR5$^-$ CD4$^+$ cells. All data indicates means+/−standard error of 5 mice and is representative of at least two independent experiments. * P<0.05,  P<0.005, * P<0.0005.

Next we investigated whether T<sub>FR</sub> cells in the blood were inhibited to the same degree by PD-1 signaling as lymph node T<sub>FR</sub> cells. We immunized WT and PD-1$^{-/-}$ mice with MOG/CFA and 7 days later analyzed the blood for T<sub>FH</sub> and T<sub>FR</sub> cells. In WT mice ~2-3 percent of CD4$^+$FoxP3$^-$CD19$^-$ cells in the blood were T<sub>FR</sub> cells, but in the PD-1$^{-/-}$ mice this increased to ~4-5 percent (FIG. 5D). This increase in PD-1$^{-/-}$ T<sub>FH</sub> cells in blood markedly contrasts with the lymph node, where PD-1$^{-/-}$ mice have similar, if not less, T<sub>FH</sub> cells compared to WT mice (FIG. 1E). Importantly, T<sub>FR</sub> cells comprised ~3 percent of all FoxP3 positive cells in the blood of WT mice, but more than 7 percent of FoxP3 positive cells in the blood of PD-1$^{-/-}$ mice (FIGS. 5D-E). The increase in FoxP3$^+$ cells seems to be specific to the blood T<sub>FR</sub> subset, as the percentage of FoxP3$^+$ cells in the ICOS$^+$CXCR5$^-$ (ICOS$^+$) and ICOS$^-$CXCR5$^-$ naïve cell gates were not increased in PD-1$^{-/-}$ mice (FIG. 5F). Taken together, these data indicate that both T<sub>FR</sub> and T<sub>FH</sub> cells are present in the blood of mice, and both subsets are repressed by PD-1 signals.

Figure 14A:
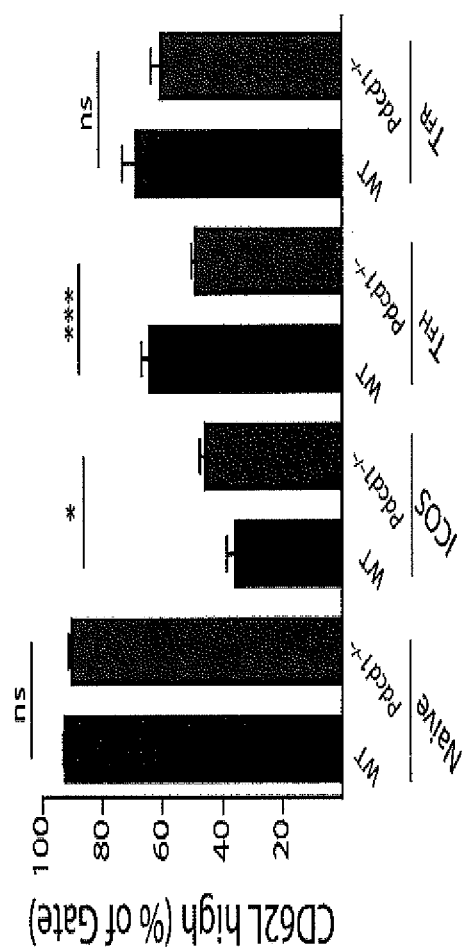
FIG. 14A. Blood T$_{FH}$ and T$_{FR}$ cells express central memory homing markers. WT and PD-1$^{-/-}$ mice were immunized with MOG/CFA and 7 days later populations from blood were analyzed for CD62L expression.
Figure 14B:
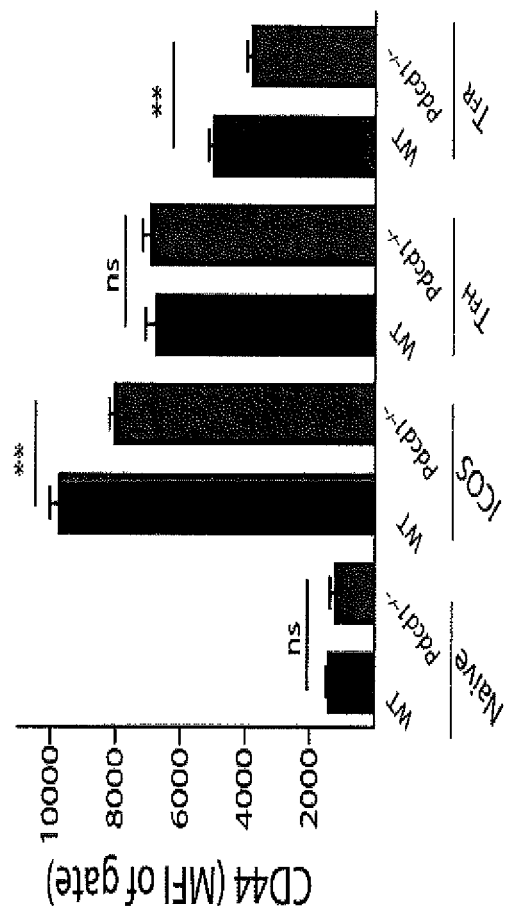
FIG. 14B. Blood T$_{FH}$ and T$_{FR}$ cells express central memory homing markers. WT and PD-1$^{-/-}$ mice were immunized with MOG/CFA and 7 days later populations from blood were analyzed for CD44 expression.
Figure 14C:
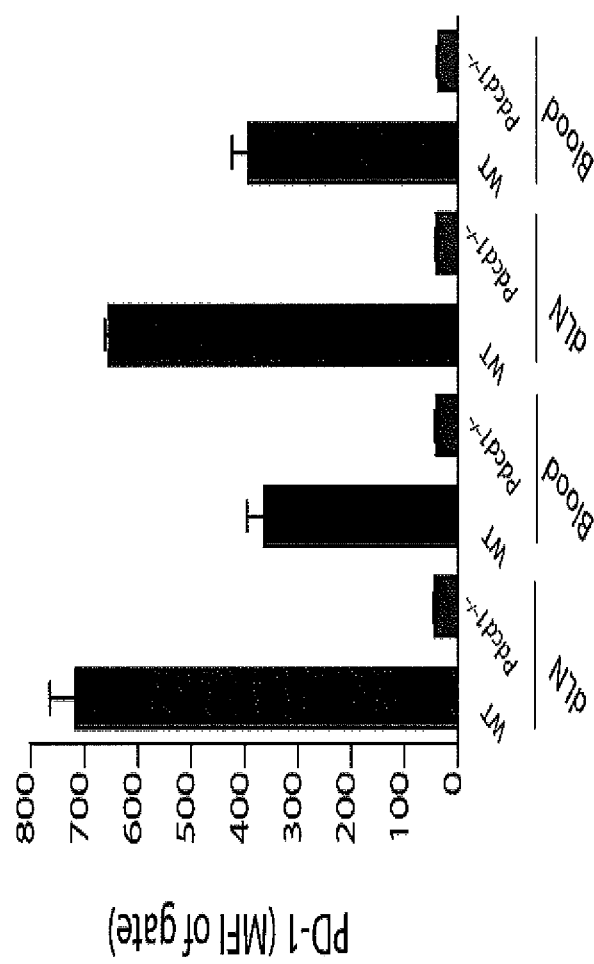
FIG. 14C. PD-1 expression was compared on WT and PD-1 deficient mice from draining lymph node and blood T$_{FH}$ and T$_{FR}$ cells 7 days after NP-OVA immunization.

To investigate whether blood T<sub>FH</sub> and T<sub>FR</sub> cells have a central memory phenotype, we analyzed surface expression of CD62L and CD44. About 60% of WT and PD-1$^{-/-}$ blood T<sub>FR</sub> cells had high expression of CD62L (FIG. 14A). This contrasts with the greater than 90% of ICOS$^-$CXCR5$^-$ naïve cells that had high CD62L expression. PD-1$^{-/-}$ T<sub>FH</sub> cells had lower CD62L compared to WT T<sub>FH</sub> cells. CD44 was highly expressed on all WT and PD-1$^{-/-}$ blood T<sub>FR</sub> cells, but PD-1$^{-/-}$ blood T<sub>FR</sub> cells had slightly lower surface expression (FIG. 14B). Furthermore, PD-1 was expressed at lower levels on blood T<sub>FR</sub> cells than lymph node T<sub>FR</sub> cells (FIG. 14C). Taken together, these data indicate that blood T<sub>FR</sub> cells can have a central memory homing phenotype.

Figure 6A:
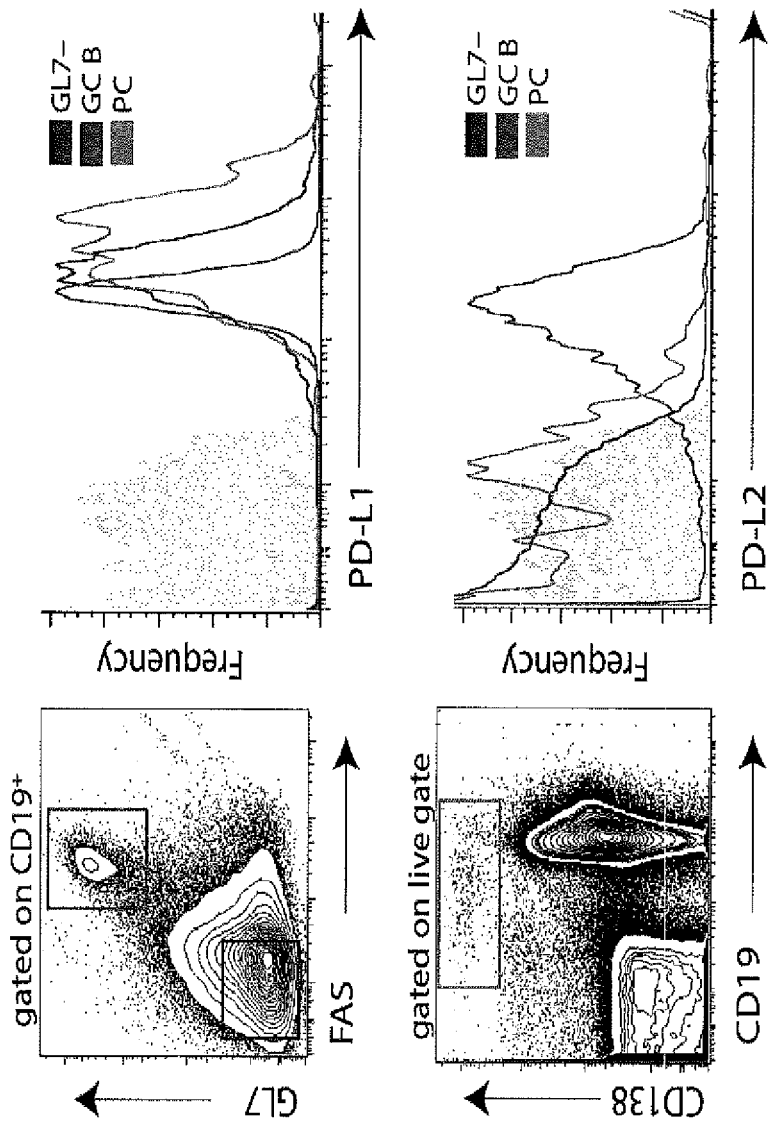
FIG. 6A. PD-L1 but not PD-L2 controls blood T$_{FR}$ cells. PD-L1 and PD-L2 expression on B cell subsets. WT mice were immunized with NP-OVA subcutaneously and 12 days later germinal center B (GC B), GL7$^-$, and plasma cells (PC) from draining lymph nodes were analyzed for PD-L1 (top) and PD-L2 (bottom) expression.
Figure 6B:
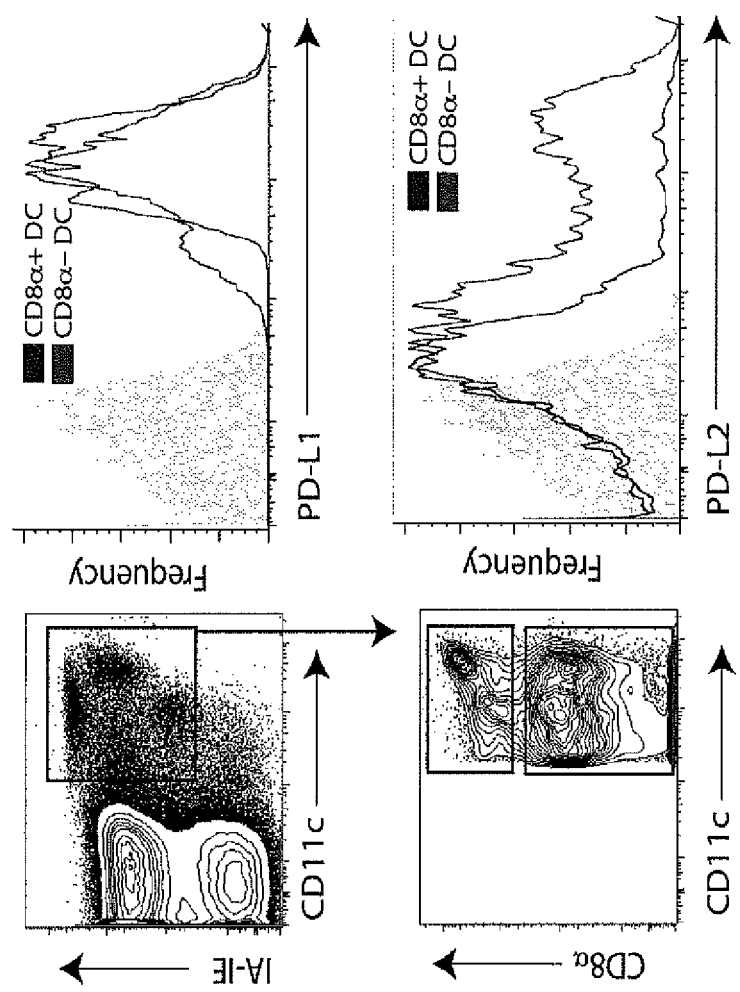
FIG. 6B PD-L1 and PD-L2 expression on dendritic cells (DC). WT mice were immunized with NP-OVA and 3 days later CD8α$^+$ DC and CD8α$^-$ DC subsets from draining lymph nodes were analyzed for PD-L1 (top) and PD-L2 (bottom) expression.

The increase in T<sub>FR</sub> cells in PD-1$^{-/-}$ mice led us to investigate which PD-1 ligand is critical for controlling lymph node and blood T<sub>FR</sub> generation. We first compared PD-L1 and PD-L2 expression on B cells and DCs present in dLNs of immunized WT mice because both B cells and dendritic cells (DCs) contribute to proper T<sub>FH</sub> differentiation and maintenance in the lymph node[1]. It is not yet clear whether B cells, DC or both are needed for T$_{FR}$ differentiation and/or maintenance. To study GC B cells, we immunized mice with NP-OVA subcutaneously and 12 days later compared PD-L1 and PD-L2 expression on FAS$^+$GL7$^+$CD19$^+$ GC B cells, as well as CD138$^+$ positive plasma cells (PC) from the dLN. We found that all B cell subsets expressed high levels of PD-L1, but only GC B cells expressed high levels of PD-L2 (FIG. 6A). To quantify PD-L1 and PD-L2 expression on DCs, we immunized mice with NP-OVA and analyzed DC populations from the draining lymph node 3 days later. Both CD8α$^+$ and CD8α$^-$ DC populations expressed high levels of PD-L1 and moderate levels of PD-L2 (FIG. 6B). A subpopulation of CD8α$^-$ DCs expressed high levels of PD-L2.

Figures 6C, 6D:
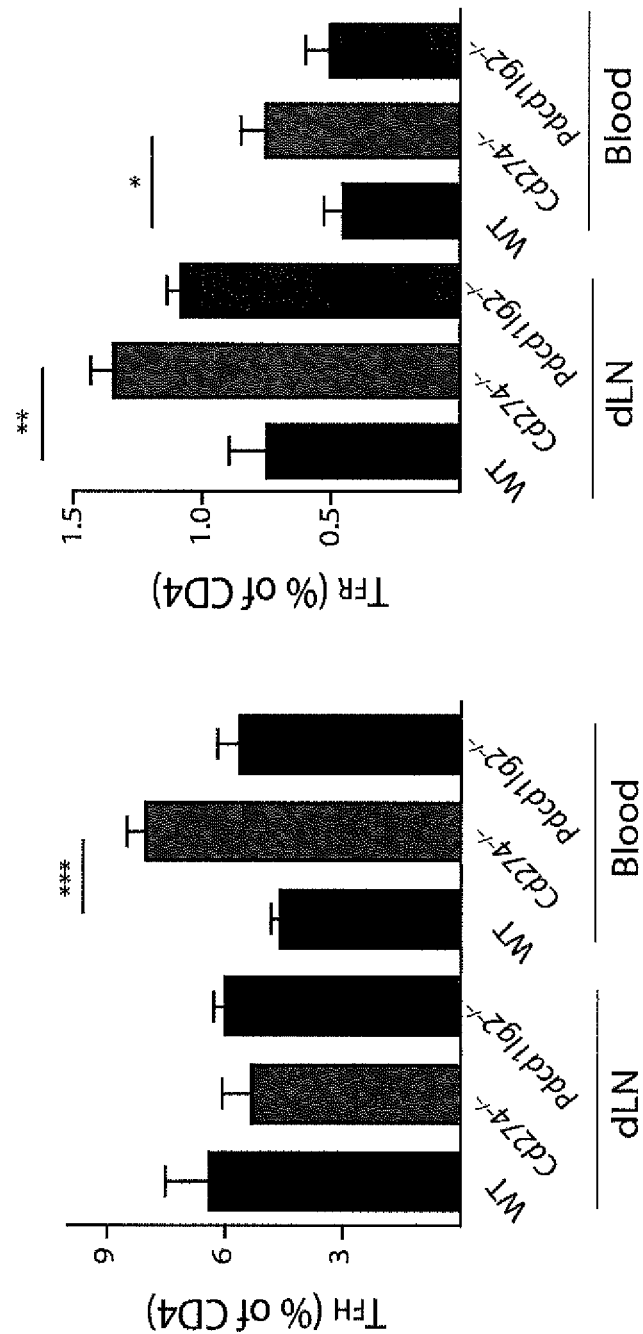
FIG. 6C. Lymph node and blood T$_{FH}$ and T$_{FR}$ cells in PD-1 ligand deficient mice. WT, PD-L1$^{-/-}$ and PD-L2$^{-/-}$ mice were immunized with MOG/CFA, and 7 days later draining lymph nodes and blood were harvested and analyzed for T$_{FH}$ CD4 T cells. Data represent means of 5 mice per group. All data are representative of at least two independent experiments. * P<0.05,  P<0.005, * P<0.0005.
FIG. 6D. Lymph node and blood T$_{FH}$ and T$_{FR}$ cells in PD-1 ligand deficient mice. WT, PD-L1$^{-/-}$ and PD-L2$^{-/-}$ mice were immunized with MOG/CFA, and 7 days later draining lymph nodes and blood were harvested and analyzed for T$_{FR}$ CD4 T cells. Data represent means of 5 mice per group. All data are representative of at least two independent experiments. * P<0.05,  P<0.005, * P<0.0005.
Figure 6E:
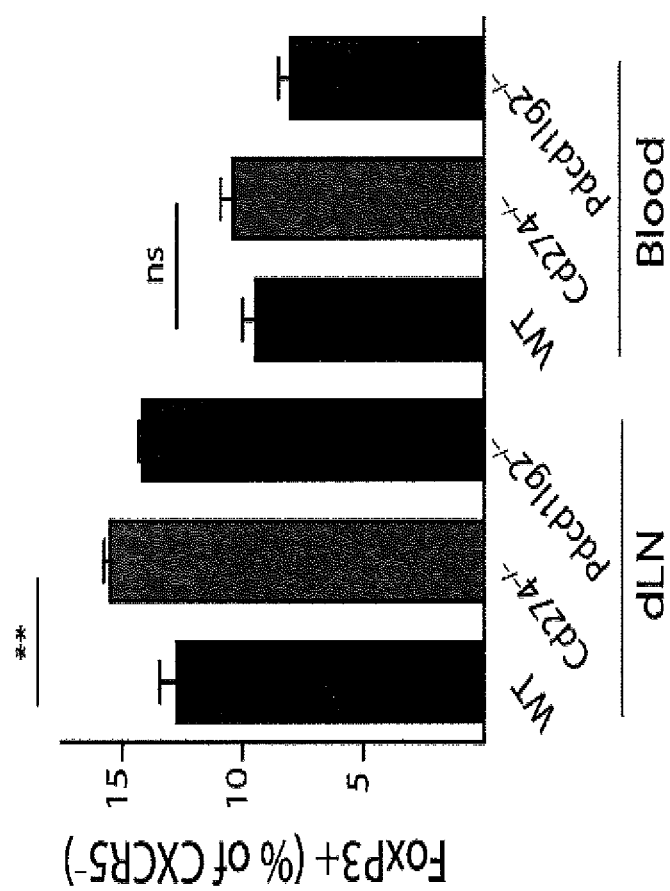
FIG. 6E. Lymph node and blood T$_{FH}$ and T$_{FR}$ cells in PD-1 ligand deficient mice. WT, PD-L1$^{-/-}$ and PD-L2$^{-/-}$ mice were immunized with MOG/CFA, and 7 days later draining lymph nodes and blood were harvested and analyzed for CXCR5$^-$ FoxP3$^+$ CD4 T cells. Data represent means of 5 mice per group. All data are representative of at least two independent experiments. * P<0.05,  P<0.005, * P<0.0005.

To determine which ligand is important for T$_{FH}$ and T$_{FR}$ generation, we immunized WT, PD-L1$^{-/-}$ and PD-L2$^{-/-}$ mice with MOG/CFA, and analyzed T$_{FH}$ and T$_{FR}$ cells 7 days post-immunization in the draining lymph node and blood. The percentages of lymph node T$_{FH}$ cells in PD-L1$^{-/-}$ and PD-L2$^{-/-}$ mice were comparable to WT mice (FIG. 6C) and PD-1$^{-/-}$ mice (FIG. 1E). PD-L1$^{-/-}$, but not PD-L2$^{-/-}$ mice, had greater blood T$_{FH}$ cell numbers, which was similar to PD-1$^{-/-}$ mice (FIG. 5E). T$_{FR}$ cells, however, were increased in the lymph nodes as well as the blood of PD-L1$^{-/-}$, but not PD-L2$^{-/-}$ mice (FIG. 6D). Similar to PD-1$^{-/-}$ mice, PD-L1$^{-/-}$ mice did not exhibit any increases in non-T$_{FR}$ FoxP3$^+$ effector cells within the blood (FIG. 6E). These studies demonstrate that PD-L1, but not PD-L2, is responsible for controlling lymph node and blood T$_{FR}$ cells.

Blood T$_{FH}$ and T$_{FR}$ Cells Require CD28 and ICOS Signals

Figure 7A:
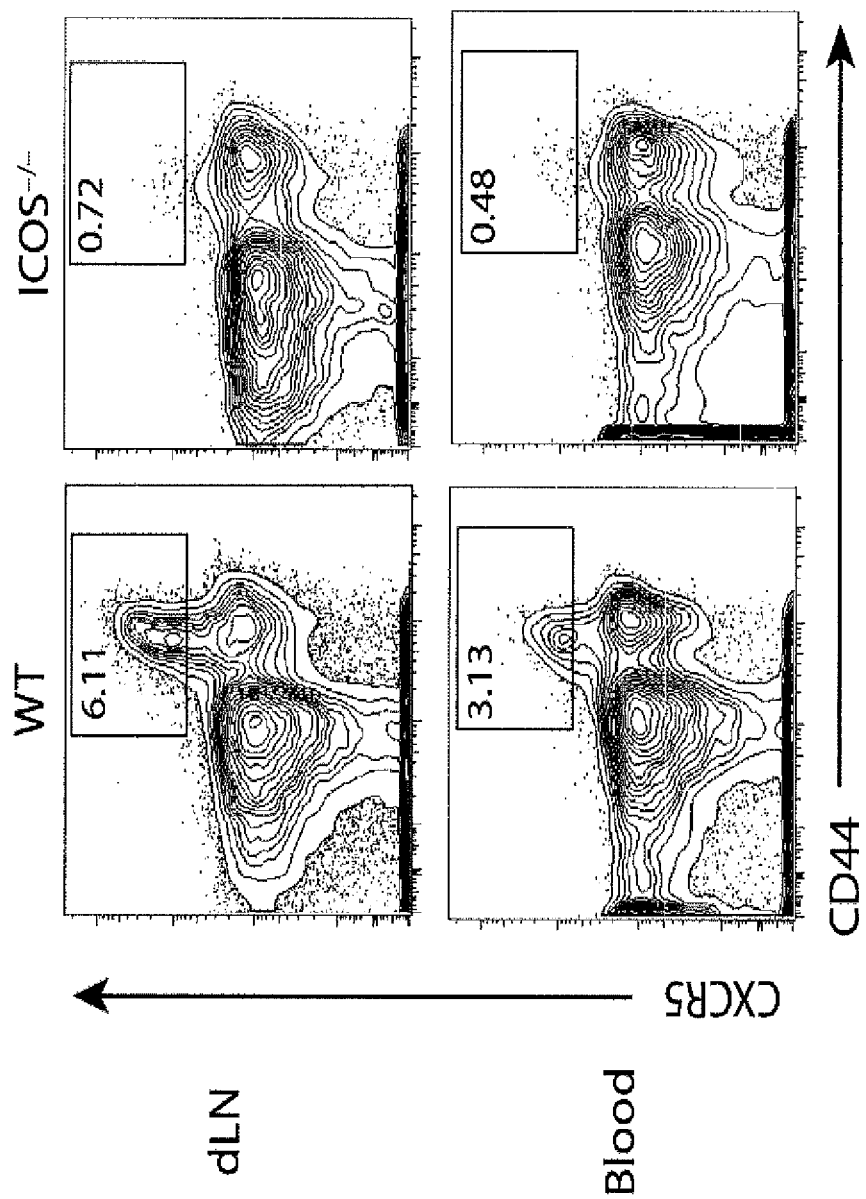
FIG. 7A. Blood T$_{FR}$ cells require ICOS and CD28 costimulation. T$_{FH}$ and T$_{FR}$ gating in WT and ICOS$^{-/-}$ mice. Mice were immunized with MOG/CFA and 7 days later draining lymph nodes (dLN) and blood were harvested. T$_{FH}$ cells were gated as CD4$^+$CD44$^+$CXCR5$^+$FoxP3$^-$CD19$^-$, and T$_{FR}$ cells as CD4$^+$CD44$^+$CXCR5$^+$FoxP3$^+$CD19$^-$ cells.
Figures 7B, 7C:
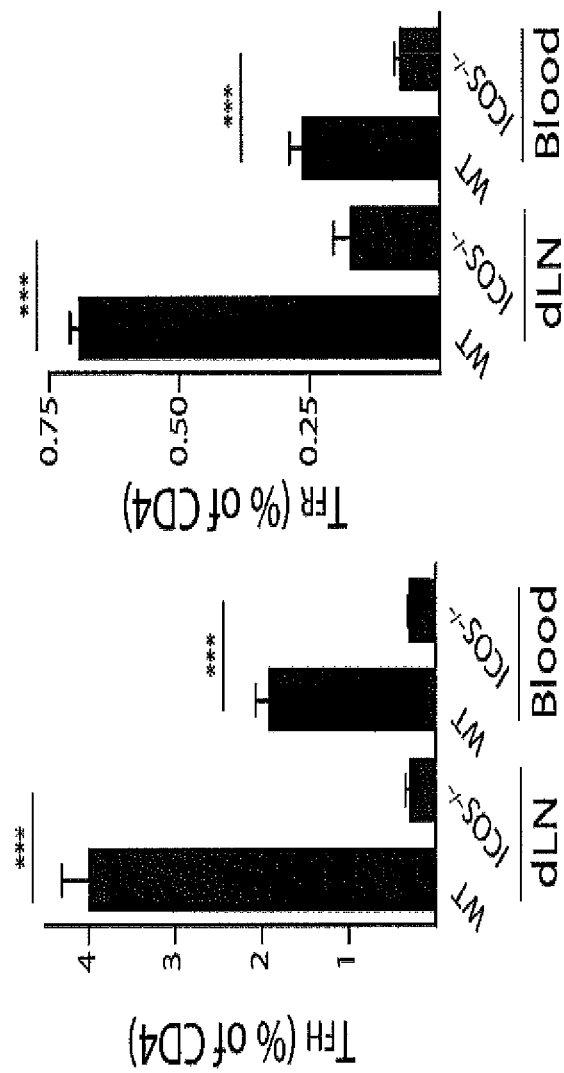
FIG. 7B T$_{FH}$ quantitation in lymph nodes (dLN) and blood of WT and ICOS$^{-/-}$ mice as in FIG. 7A.
FIG. 7C T$_{FR}$ quantitation in lymph nodes (dLN) and blood of WT and ICOS$^{-/-}$ mice as in FIG. 7A.
Figure 7D:
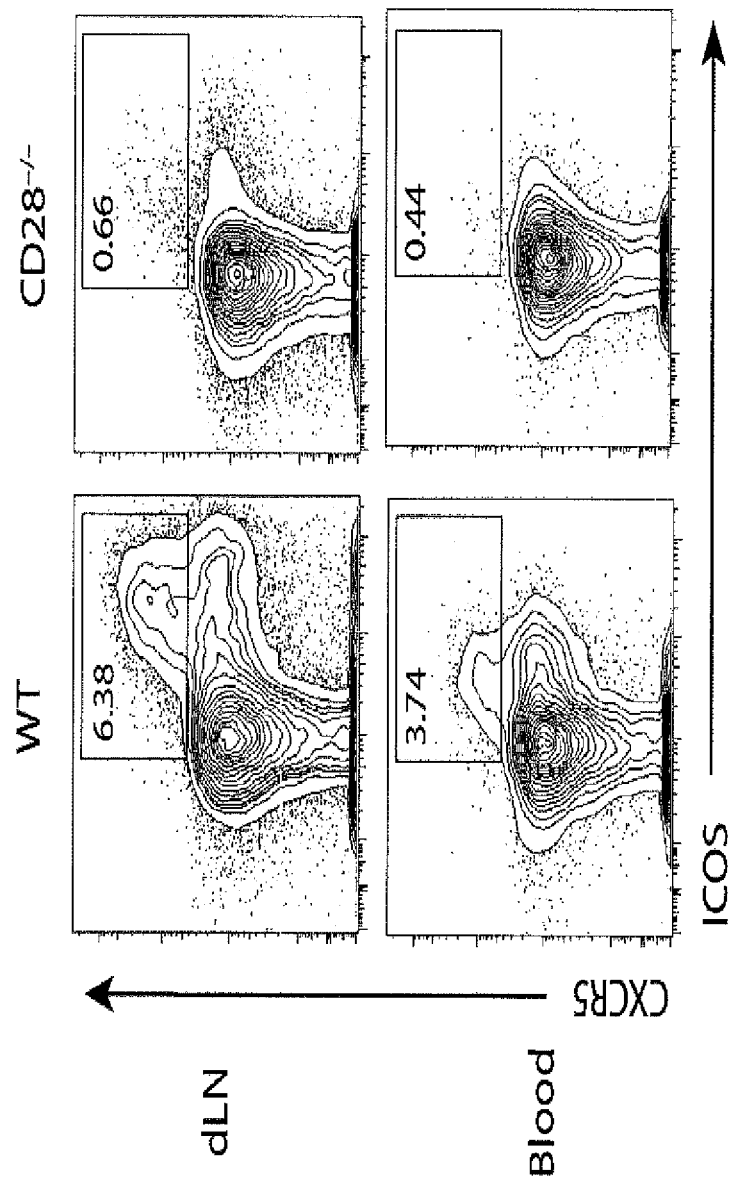
FIG. 7D. T$_{FH}$ and T$_{FR}$ gating strategy in WT and CD28$^{-/-}$ mice. Mice were immunized as in FIG. 7A and T$_{FH}$ cells were gated as CD4$^+$ ICOS$^+$CXCR5$^+$FoxP3$^-$ CD19$^-$ and T$_{FR}$ cells as CD4$^+$ICOS$^+$CXCR5$^+$FoxP3$^+$CD19$^-$.
Figures 7E, 7F:
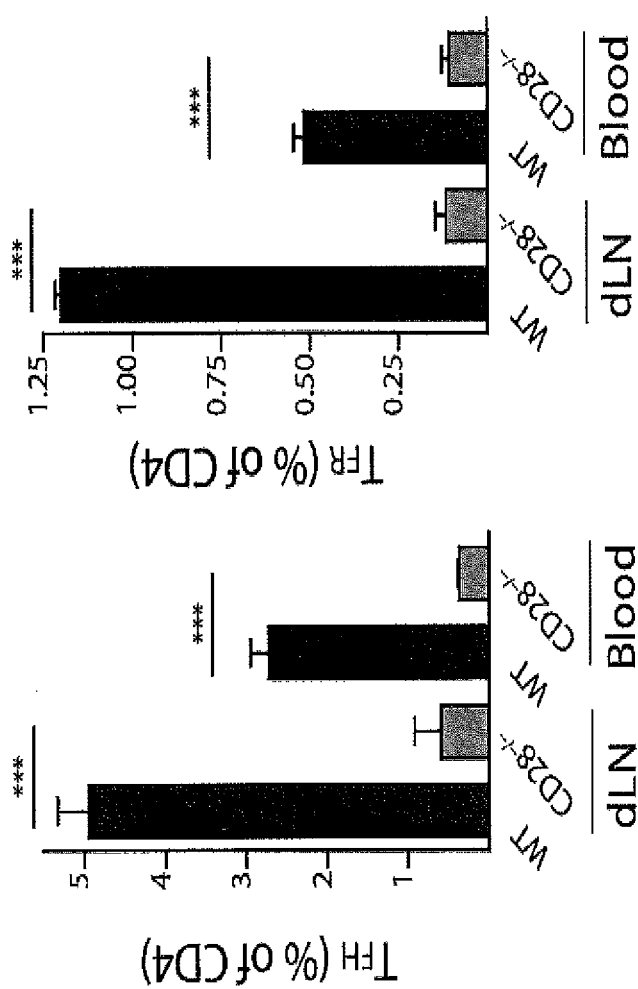
FIG. 7E. T$_{FH}$ quantitation in lymph nodes and blood of WT and CD28$^{-/-}$ mice gated as in FIG. 7D. All data are representative of at least two independent experiments. * P<0.05,  P<0.005, * P<0.0005.
FIG. 7F. T$_{FR}$ quantitation in lymph nodes and blood of WT and CD28$^{-/-}$ mice gated as in FIG. 7D. All data are representative of at least two independent experiments. * P<0.05,  P<0.005, * P<0.0005.

We further investigated the costimulatory requirements for blood T$_{FR}$ cells, focusing on the effects of CD28 and ICOS costimulation on CD4$^+$ICOS$^+$CXCR5$^+$FoxP3$^+$CD19$^-$ T$_{FR}$ populations in the blood due to the important roles of these costimulatory receptors in controlling lymph node T$_{FH}$ and T$_{FR}$ cells. CD28$^{-/-}$ mice are deficient in lymph node T$_{FH}$ and T$_{FR}$ cells[21]. ICOS$^{-/-}$ mice are deficient in lymph node T$_{FH}$ cells[24]. We analyzed CD28 and ICOS deficient animals for the presence of T$_{FR}$ cells in the lymph nodes and blood 7 days after immunization with MOG/CFA. In WT mice, there were fewer T$_{FH}$ and T$_{FR}$ cells in the blood compared to the draining lymph node (FIGS. 7A-B). Numbers of T$_{FR}$ (and T$_{FH}$) cells were greatly attenuated in the blood, as well as lymph nodes, of ICOS deficient mice (FIGS. 7A-C). CD28 deficient mice had similar severe deficiencies in T$_{FR}$ and T$_{FH}$ cell percentages in both lymph nodes and blood (FIGS. 7E-F). Thus, ICOS and CD28 supply essential costimulatory signals for T$_{FR}$ and T$_{FH}$ cells in the blood as well as the lymph nodes.

Figure 8A:
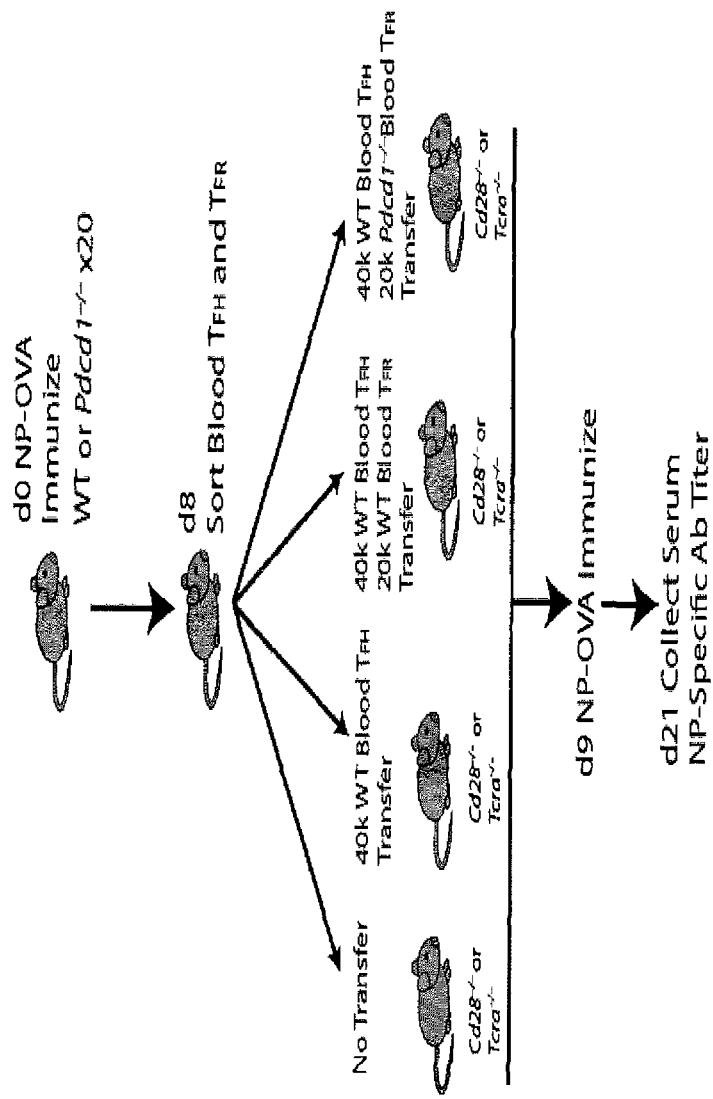
FIG. 8A. PD-1 deficient blood T$_{FR}$ cells more potently regulate antibody production in vivo. Experimental strategy to assess blood T$_{FH}$ and T$_{FR}$ cell function by transfer of blood T$_{FH}$ and/or T$_{FR}$ cells into mice that lack both lymph node and blood T$_{FH}$/T$_{FR}$ cells. Blood T$_{FH}$ and/or T$_{FR}$ cells were isolated from 20 pooled mice immunized with NP-OVA 8 days previously and CD4$^+$CXCR5$^+$GITR$^-$CD19$^-$ T$_{FH}$ and CD4$^+$CXCR5$^+$GITR$^+$CD19$^-$ T$_{FR}$ cells were purified by cell sorting; recipient CD28$^{-/-}$ or TCRα$^{-/-}$ mice received either no cells, 4×10$^4$ T$_{FH}$ cells, or 4×10$^4$ T$_{FH}$ plus 2×10$^4$ T$_{FR}$ cells. One day later recipients were immunized with NP-OVA. 12 days later sera were collected and NP-specific antibody titers quantified by ELISA.

PD-1 Deficient Blood T$_{FR}$ Cells More Potently Regulate Antibody Production In Vivo We next investigated the function of blood T$_{FR}$ cells in humoral immune responses. Because T$_{FH}$ cells in human blood can function in B cell activation and antibody production in vitro[6, 7], we analyzed whether circulating blood T$_{FR}$ cells contribute to suppression of antibody production in vivo. To assess this, we designed transfer experiments in which we immunized >20 WT donor mice with NP-OVA subcutaneously and 8 days later sorted T$_{FR}$ (CD4$^+$ICOS$^+$CXCR5$^+$GITR$^+$CD19$^-$) and T$_{FH}$ (CD4$^+$ICOS$^+$CXCR5$^+$GITR$^-$CD19$^-$) cells from the blood (FIG. 8A). We transferred these cells into CD28$^{-/-}$ or TCRα$^{-/-}$ mice because they lack both blood and lymph node T$_{FH}$ and T$_{FR}$ cells. This approach enabled us to determine if blood T$_{FR}$ and T$_{FH}$ cells could regulate humoral responses. Since the transferred blood T$_{FH}$ and T$_{FR}$ cells are the only follicular T cells in CD28$^{-/-}$ and TCRα$^{-/-}$ recipients, any responses in the draining lymph node would be due to trafficking of the blood T$_{FR}$ and T$_{FH}$ cells.

Figure 8B:
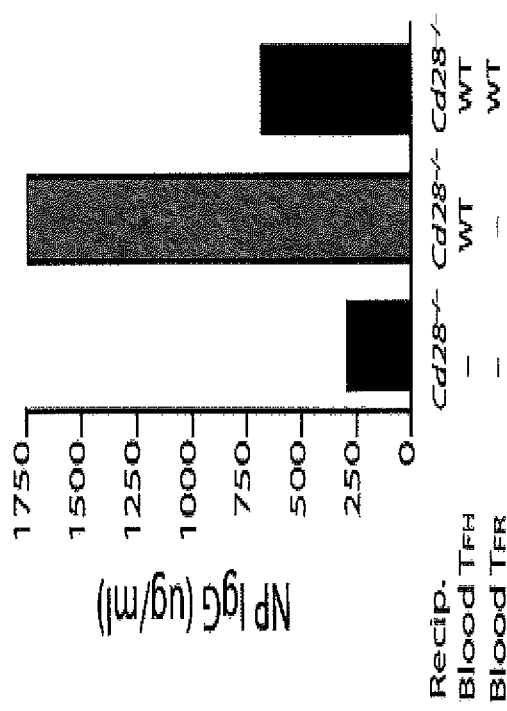
FIG. 8B. WT blood T$_{FR}$ cells potently suppress antibody production. NP-specific antibody titers from experiments as in FIG. 8A in which WT T$_{FH}$ or WT T$_{FH}$ plus WT T$_{FR}$ cells were transferred into CD28$^{-/-}$ recipients.
Figure 8C:
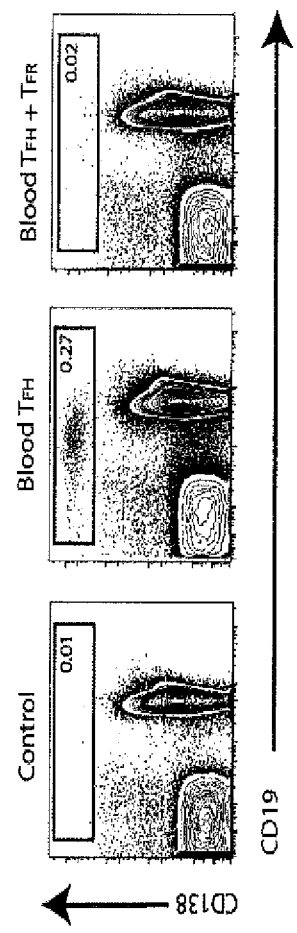
FIG. 8C. CD138$^+$ plasma cell percentages in draining lymph nodes of CD28$^{-/-}$ recipients following no transfer (Control), Blood T$_{FH}$ transfer (Blood T$_{FH}$) or Blood T$_{FH}$ plus T$_{FR}$ cell transfer (Blood T$_{FH}$+T$_{FR}$) 24 days after immunization. Cells are gated as a percentage of CD11b$^-$CD11c$^-$Ly6c$^-$ (dump) cells.
Figure 8D:
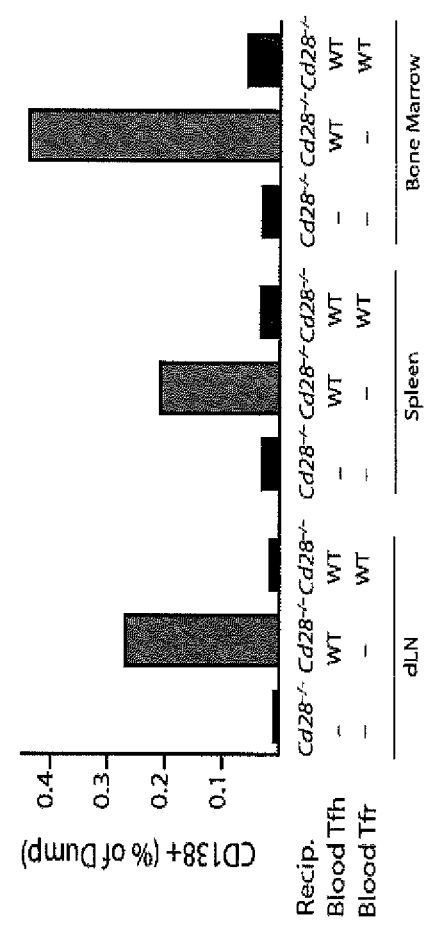
FIG. 8D. Quantitation of CD138 plasma cells as gated in FIG. 8C in draining lymph node, spleen and bone marrow.

Initially, we adoptively transferred 4×10$^4$ T$_{FH}$ cells alone or together with 2×10$^4$ T$_{FR}$ cells into CD28$^{-/-}$ mice (approximately a two-fold higher ratio of T$_{FR}$:T$_{FH}$ cells than is found in blood after immunization). We immunized recipients 1 day later with NP-OVA and analyzed NP-specific IgG titers 12 days after immunization (FIG. 8A). Without blood T$_{FH}$ or T$_{FR}$ cell transfer, CD28$^{-/-}$ mice were unable to produce significant amounts of NP-specific IgG (FIG. 8B). The transfer of blood T$_{FH}$ cells alone resulted in a substantial increase in NP-specific IgG titers. Transfer of blood T$_{FH}$ cells led to substantial production of IgG1, but also smaller increases in other isotypes (data not shown). Significantly, transfer of blood T$_{FR}$ cells along with blood T$_{FH}$ cells resulted in robust inhibition of NP-specific antibody production, demonstrating the potent regulatory capacity of blood T$_{FR}$ cells in suppressing antibody production (FIG. 8B). To evaluate the impact of T$_{FR}$ cells on plasma cell generation, draining lymph nodes, spleens and bone marrow were harvested 24 days after immunization and plasma cells were quantified. CD138$^+$ plasma cells were absent from the lymph nodes of immunized CD28$^{-/-}$ mice (FIGS. 8C-D). Transfer of blood T$_{FH}$ cells resulted in a sizable population of plasma cells in the draining lymph node, spleen and bone marrow (FIGS. 8C-D). Blood T$_{FR}$ cells almost completely prevented plasma cell formation/survival in all organs tested.

Figure 8E:
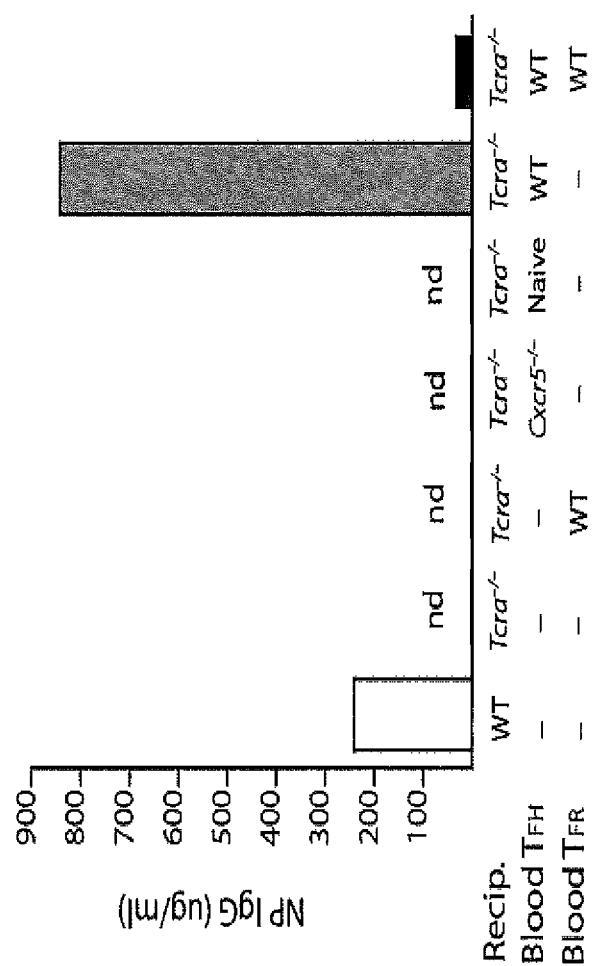
FIG. 8E. Blood T$_{FH}$ and/or T$_{FR}$ Transfer into TCRα$^{-/-}$ recipients using experimental design as in FIG. 8A. Comparison of NP-specific antibody titers in (1) WT control mice, (2) TCRα$^{-/-}$ recipients given no cells, (3) TCRα$^{-/-}$ recipients given WT blood T$_{FR}$ cells alone, (4) TCRα$^{-/-}$ recipients given total blood CD4 T cells from CXCR5$^{-/-}$ mice immunized with NP-OVA 8 days previously, (5) TCRα$^{-/-}$ recipients given blood CD4$^+$FoxP3$^-$ cells from unimmunized FoxP3-GFP mice, (6) TCRα$^{-/-}$ recipients given WT blood T$_{FH}$ cells, and (7) TCRα$^{-/-}$ recipients given WT blood T$_{FH}$ cells plus T$_{FR}$ cells. NP specific IgG levels were determined by ELISA.
Figures 8F, 8G:
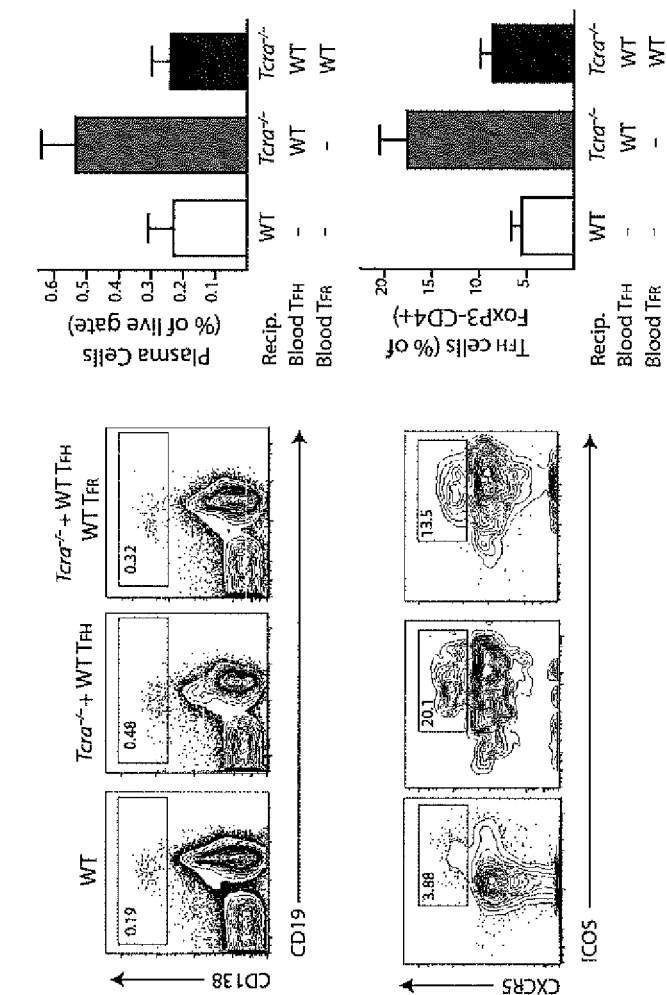
FIG. 8F. CD138$^+$ plasma cells from the spleen (gated as a percent of live cells) were quantified from experiments in FIG. 8E 12 days after secondary immunization. Error bars indicate standard error of at least three separate experiments.
FIG. 8G. CD4FoxP3$^-$ T$_{FH}$ cells from the draining lymph node pre-gated on CD4$^+$FoxP3$^-$ were quantified from experiments in FIG. 8E 12 days after secondary immunization. Error bars indicate standard error of at least three separate experiments.
Figures 8H, 8I:
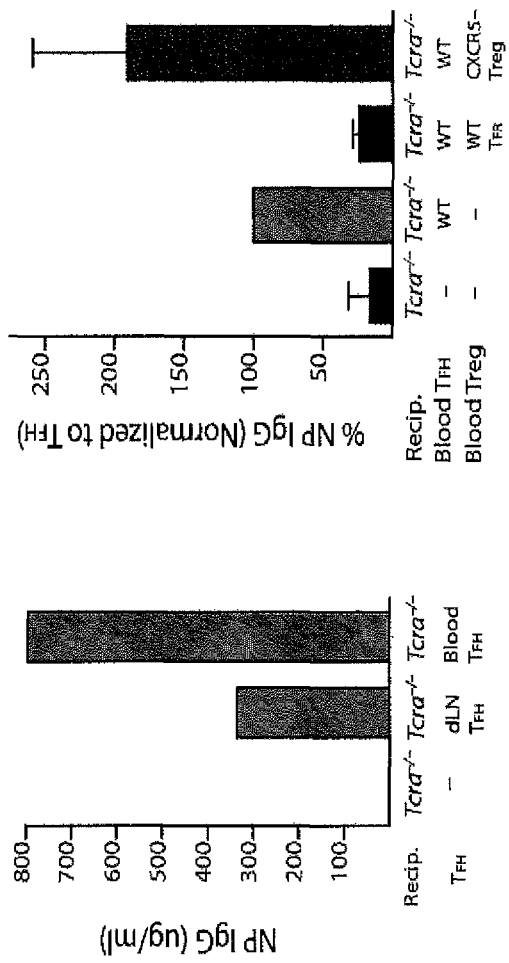
FIG. 8H. Blood T$_{FH}$ cells can have an enhanced ability to stimulate antigen-specific antibody production compared to lymph node T$_{FH}$ cells. Blood T$_{FH}$ cells and draining lymph node T$_{FH}$ cells were isolated from WT mice immunized with NP-OVA 8 days previously and 4×10$^6$ cells were transferred into TCRα$^{-/-}$ mice and immunized as in FIG. 8E.
FIG. 8I. Blood T$_{FR}$ cell suppression is aided by the follicular program. Blood T$_{FH}$ cells were transferred to TCRα$^{-/-}$ mice along with blood CXCR5– FoxP3 GFP$^+$ cells from FoxP3 reporter mice or blood T$_{FR}$ cells. Antibody titers were quantified 12 days after NP-OVA immunization and NP IgG levels are expressed as a percent of T$_{FH}$ transfer group. Data indicate standard error of at least three independent experiments.
Figure 8J:
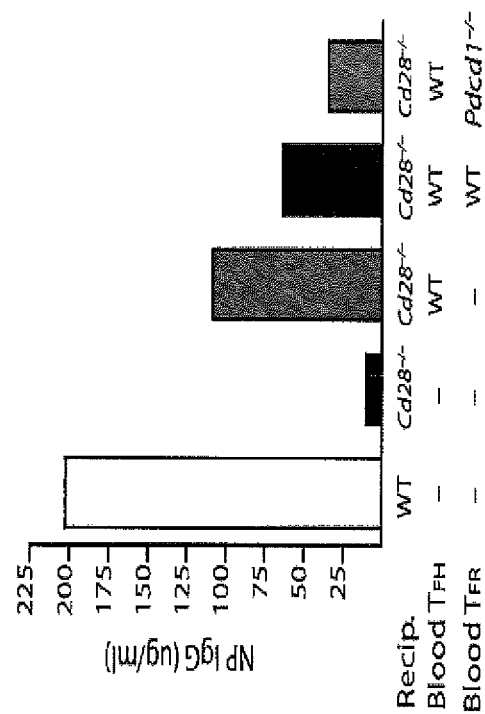
FIG. 8J. PD-1 deficient blood T$_{FR}$ cells more potently suppress antibody production in vivo compared to WT T$_{FR}$ cells. 4×10$^4$ WT blood T$_{FH}$ and 1.5×10$^4$ WT or PD-1 deficient blood T$_{FR}$ cells from mice immunized with NP-OVA 8 days previously were transferred into CD28$^{-/-}$ mice. Recipient mice were immunized with NP-OVA, and NP specific antibody titers were measured from serum 12 days later. Data are representative of two independent experiments.
Figure 8K:
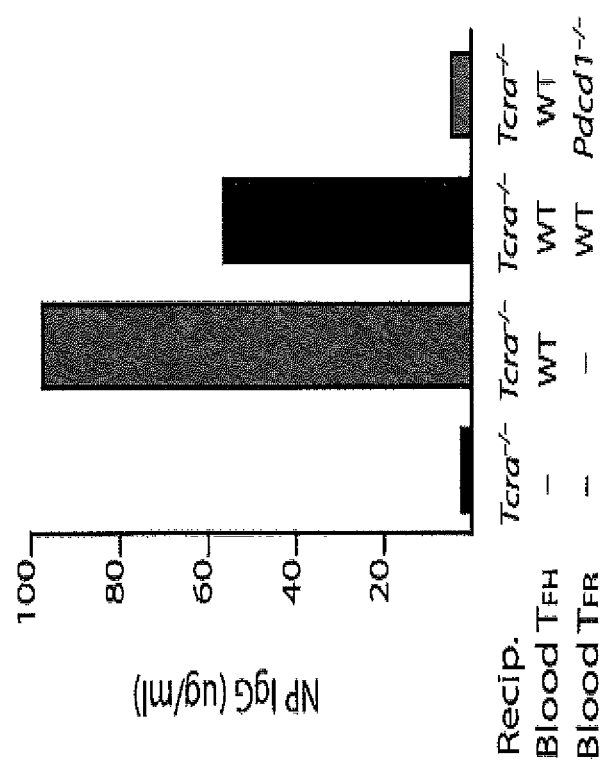
FIG. 8K. PD-1 deficient blood T$_{FR}$ cells more potently suppress antibody production in vivo compared to WT T$_{FR}$ cells. 4×10$^4$ WT blood T$_{FH}$ and 1.5×10$^4$ WT or PD-1 deficient blood T$_{FR}$ cells from mice immunized with NP-OVA 8 days previously were transferred into TCRα$^{-/-}$ mice. Recipient mice were immunized with NP-OVA, and NP specific antibody titers were measured from serum 12 days later. Data are representative of two independent experiments.
Figure 9:
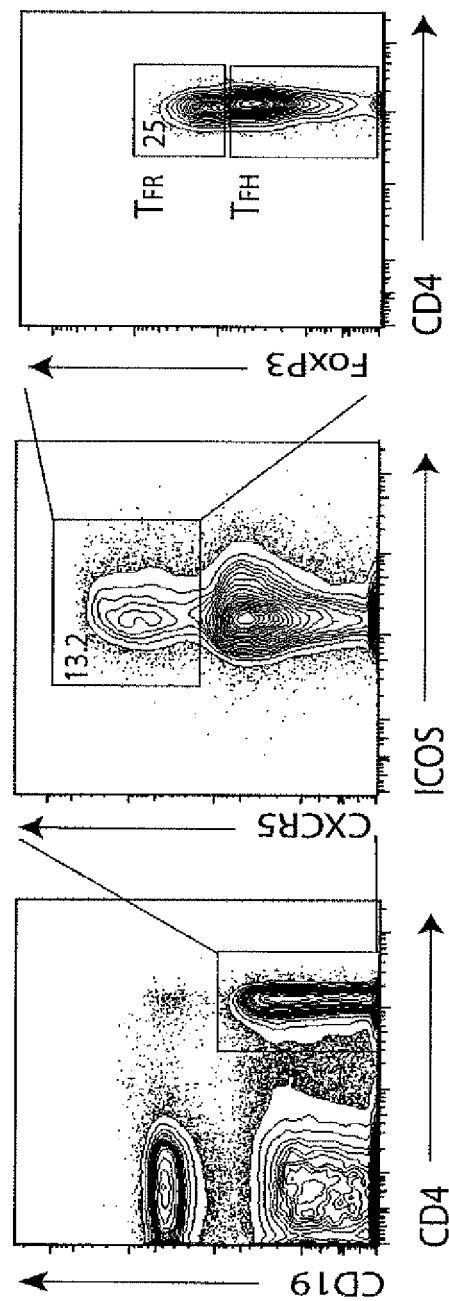
FIG. 9. Blood Tfh and Tfr cells are present in human blood. Peripheral blood mononuclear cells were isolated from the blood of a healthy individual by sucrose density centrifugation and stained for indicated proteins and were analyzed by flow cytometry. Numbers indicate percentages contained within gates.
Figure 10A:
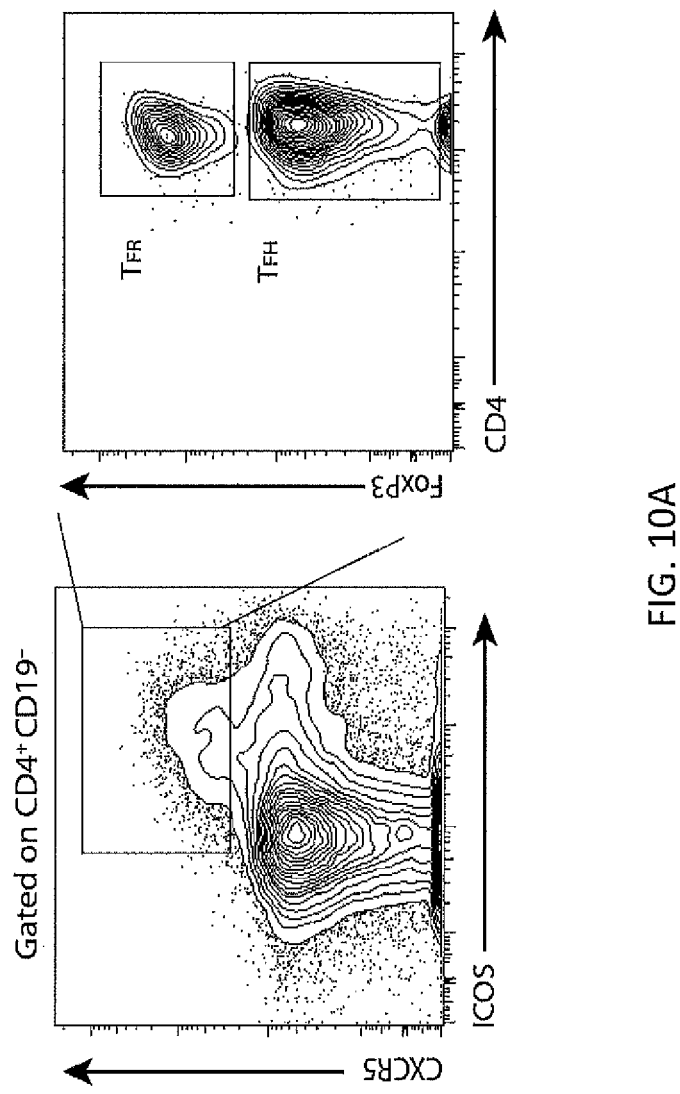
FIG. 10A. PD-1 controls T$_{FR}$ cells in NP-OVA immunized mice. WT or PD-1$^{-/-}$ mice were immunized with NP-OVA emulsified in CFA and 7 days later draining lymph nodes were stained for CD4$^+$FoxP3$^+$ICOS$^+$CXCR5$^+$CD19$^-$ T follicular regulatory cells (T$_{FR}$) and CD4$^+$FoxP3$^-$ICOS$^+$CXCR5$^+$CD19$^-$ T follicular helper cells (T$_{FH}$) using gating strategy shown.
Figures 10B, 10C:
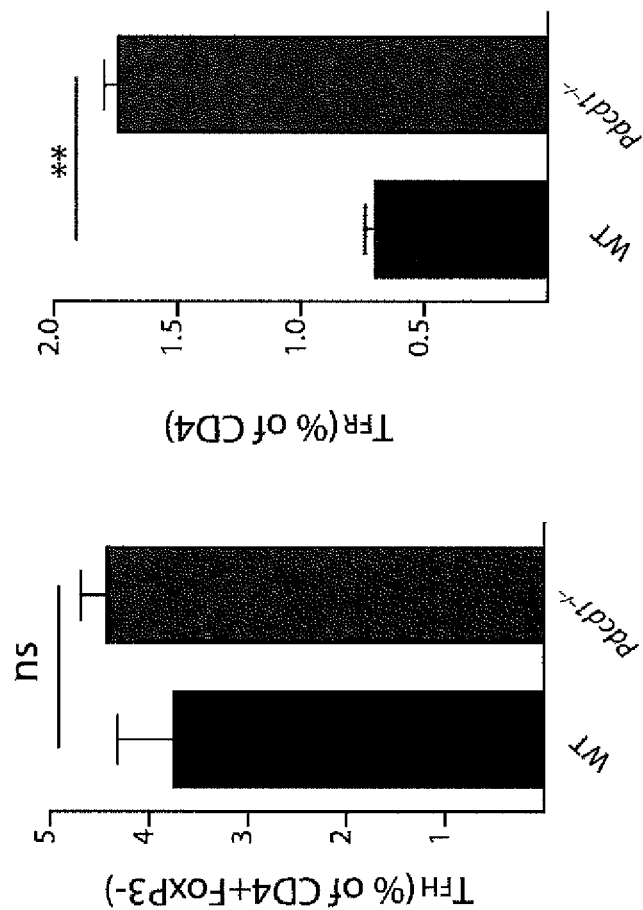
FIG. 10B. T$_{FH}$ cells were gated and expressed as a percentage of CD4$^+$FoxP3$^-$ cells.
FIG. 10C. T$_{FR}$ cells were gated and expressed as a percentage of all CD4$^+$ cells.
Figures 10D, 10E:
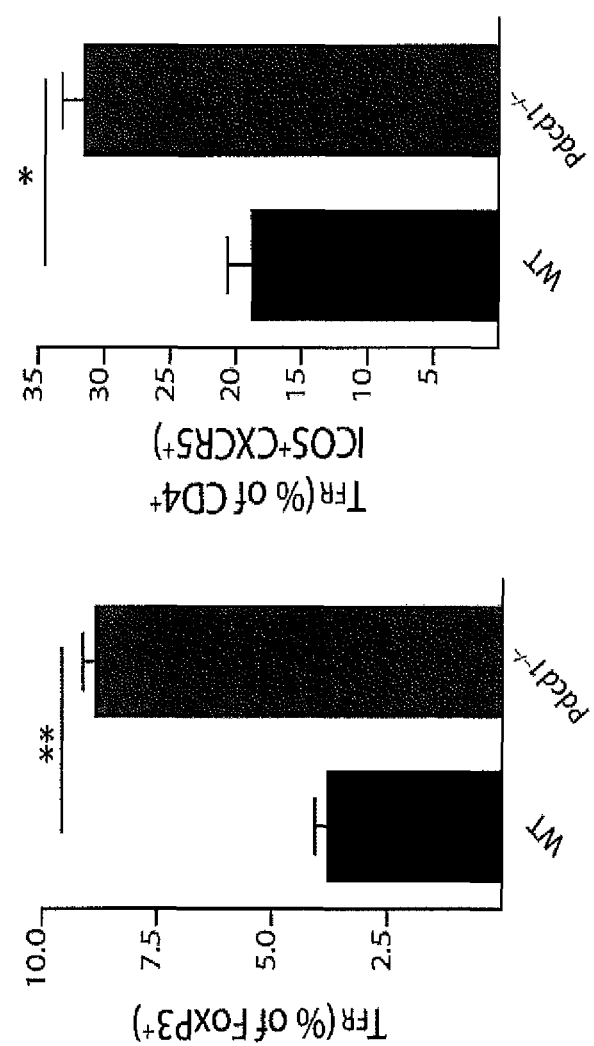
FIG. 10D. T$_{FR}$ cells were gated and expressed as a percentage of CD4$^+$FoxP3$^+$ cells.
FIG. 10E. T$_{FR}$ cells were gated and expressed as a percentage of CD4$^+$CXCR5$^+$ICOS$^+$ cells.

Next we transferred blood T$_{FH}$ and/or T$_{FR}$ cells into TCRα$^{-/-}$ recipients. Transfer of 4×10$^4$ T$_{FH}$ cells resulted in high levels of NP-specific IgG and at a greater titer than an immunized WT mouse in most experiments (FIG. 8E). The robust antibody production elicited by blood T$_{FH}$ cells depends on the "follicular program" because transfer of total CD4 T cells from CXCR5$^{-/-}$ mice or CD4$^+$CXCR5$^-$FoxP3$^-$ naïve cells resulted in near background levels of antibody production in these experiments (FIG. 8E). When blood T$_{FR}$ cells were transferred together with blood T$_{FH}$ cells, the NP-specific antibody titers were markedly reduced, demonstrating the suppressive capacity of these cells (FIG. 8E). The blood T$_{FR}$ cells resulted in both lower plasma cell percentages (FIG. 8F), as well as lower percentages of T$_{FH}$ cells within the lymph node (FIG. 8G). When we compared the functions of blood T$_{FH}$ cells and draining lymph node T$_{FH}$ cells following transfer into TCRα$^{-/-}$ recipients, we found that blood T$_{FH}$ cells have an increased capacity to promote NP-specific IgG production (FIG. 8H). T$_{FR}$ suppression of T$_{FH}$ cells also depends on the "follicular program" in these cells because neither blood CD25$^+$CD62L$^+$ Tregs from CXCR5$^{-/-}$ mice (data not shown) nor blood CXCR5$^-$ FoxP3 GFP$^+$ Tregs from FoxP3 reporter mice possess the same suppressive capacity as WT blood T$_{FR}$ cells (FIG. 8I).

Finally, we investigated the suppressive capacity of PD-1 deficient blood T$_{FR}$ cells in vivo since we have found that PD-1 deficient lymph node T$_{FR}$ cells more potently suppress antibody production in vitro. We adoptively transferred 4×10$^4$ blood T$_{FH}$ cells alone or together with 1.5×10$^4$ blood T$_{FR}$ cells from WT or PD-1 deficient mice into either CD28$^{-/-}$ or TCRα$^{-/-}$ recipients and immunized as in FIG. 8A. PD-1 deficient T$_{FR}$ cells inhibited antibody production to a greater extent than WT T$_{FR}$ cells in CD28$^{-/-}$ (FIG. 8J) as well as TCRα$^{-/-}$ (FIG. 8K) recipients, demonstrating that they have increased suppressive capacity. Together, these data show that blood T$_{FR}$ cells potently inhibit antibody production in vivo and PD-1 deficiency results in enhanced T$_{FR}$ cell suppressive capacity.

Discussion

A mechanistic understanding of T$_{FR}$ cell differentiation and function is provided to gain insight into how humoral immune responses are regulated by T$_{FH}$ and T$_{FR}$ cells. Although T$_{FR}$ cells originate from different precursors than T$_{FH}$ cells, T$_{FR}$ and T$_{FH}$ cells have nearly identical surface receptors. The shared expression of ICOS, CXCR5 and PD-1 by T$_{FR}$ and T$_{FH}$ cells means that functional studies of T$_{FH}$ cells have, in fact, examined mixtures of stimulatory T$_{FH}$ cells and inhibitory T$_{FR}$ cells. The PD-1 pathway regulates many effector arms of the immune response, however biological complexity has led to inconsistencies regarding the role of this pathway in humoral immune responses[16-20]. In this Example 1, we identify a new mechanism by which PD-1 regulates humoral immunity: PD-1 controls the generation and function of suppressive T$_{FR}$ cells. We found that lack of PD-1, or its ligand PD-L1, resulted in greater numbers of T$_{FR}$ cells in the draining lymph node of immunized mice. These PD-1$^{-/-}$ lymph node T$_{FR}$ cells expressed more IRF4 and showed an enhanced ability to suppress antibody production. We also discovered that T$_{FR}$ cells are present in the blood of mice, and that PD-1 controls the numbers of blood T$_{FR}$ cells, as evidenced by the substantial increases in PD-1 deficient mice. Importantly, we demonstrated a functional role for blood T$_{FH}$ cells in promoting antibody production and blood T$_{FR}$ cells in suppressing antibody production in vivo. PD-1 deficient blood T$_{FR}$ cells more potently suppress antibody production compared to WT blood T$_{FR}$ cells. Thus, PD-1 limits the development and function of T$_{FR}$ cells in lymph nodes and in the circulation.

We have found that PD-1 signaling inhibits the numbers of T$_{FR}$ cells, but not T$_{FH}$ cells, in the lymph node, skewing the T$_{FR}$ to T$_{FH}$ ratio. It is possible that the greater suppressive capacity of PD-1$^{-/-}$ T$_{FR}$ cells, together with the increased ratio of T$_{FR}$ to T$_{FH}$ cells in PD-1$^{-/-}$ mice, results in inhibition of PD-1$^{-/-}$ T$_{FH}$ cells. Alternatively, there may be alterations in PD-1$^{-/-}$ T$_{FH}$ cells that promote their departure from the lymph node and homing to other sites to perform effector functions. These hypotheses are not mutually exclusive. Some studies have described increases in lymph node/spleen T$_{FH}$ cells in PD-1 deficient mice; however the contribution of T$_{FR}$ cells in these studies was not assessed[16, 18, 19]. It is likely that increased T$_{FR}$ cells in PD-1/PD-L1 knockout mice may have contributed to the increases in T$_{FH}$ cells observed in these studies, and may explain, at least in part, conflicting data regarding the role of PD-1 in regulating T$_{FH}$ cells and germinal center reactions. For example, Kawamoto et al. described increased CD4$^+$CXCR5$^+$ (T$_{FH}$) cells in the Peyer's patches of PD-1 deficient mice. However, upon transfer, these cells were non-functional in supporting IgA production. Increases in T$_{FR}$ cells contained within the T$_{FH}$ gate in PD-1 deficient Peyer's patches may explain these data.

TFR cells depend on SAP, CD28 and Bcl6 for differentiation[21, 22]. However, the pathways that limit T$_{FR}$ cell differentiation are less clear. To date, only the transcription factor Blimp1 has been shown to inhibit T$_{FR}$ cell differentiation[21]. Here we identify PD-1 as the first surface receptor that inhibits T$_{FR}$ cell development and function. We also show that PD-1 predominantly interacts with PD-L1, and not PD-L2, to inhibit T$_{FR}$ generation. Our adoptive transfer studies demonstrate a cell intrinsic role for PD-1 in T$_{FR}$ cell differentiation from FoxP3$^+$ Treg cells. Therefore, the increase in T$_{FR}$ cells in PD-1 deficient mice appears to reflect increased differentiation and not maintenance. We observed a general trend for a decrease in cell cycling of CD4 PD-1$^{-/-}$ effector cells, because ICOS$^+$CXCR5$^+$FoxP3$^-$ and ICOS$^+$CXCR5$^-$ effector cells also had diminished Ki67 expression, at least at day 7 after immunization, which may temporally correspond to a maintenance phase. Based on these data, we believe that, rather than simply inhibiting responses, the PD-1:PD-L pathway can act as a molecular switch that controls cell fate decisions in naïve CD4 T cells. Integration of signals through PD-1, the TCR and cytokine receptors may direct CD4 T cell subset differentiation. Likewise, PD-1 may limit differentiated effector T cell expansion, cytokine production and/or survival depending on how signals through the TCR, PD-1 and cytokine receptors are integrated. Thus, the PD-1 pathway can influence CD4 T cell lineage commitment in distinct ways, depending on molecular cues and the local environment. For instance, PD-L1 can promote induced Treg (iTreg) differentiation from naïve T cell precursors[10-14, 29]. However, we find that PD-1 inhibits differentiation of T$_{FR}$ cells. T$_{FR}$ cells arise from natural T regulatory cell (nTreg) precursors (shown here and previously[21]). Therefore, our studies suggest that PD-1 may have distinct roles in iTreg and nTreg differentiation. In addition genetic background may contribute to the effects of PD-1 deficiency.

Because of the recent discovery of T$_{FR}$ cells, there is a lack of fundamental knowledge about T$_{FR}$ cell biology, so we developed novel assays to analyze mechanisms by which PD-1 regulates T$_{FR}$ cell function. T$_{FR}$ cells have the potential to directly inhibit activation of naïve T cells, T$_{FH}$ cell function, and/or B cell activation. T$_{FR}$ cells might regulate T$_{FH}$ or B cell responses either inside the B cell follicle and/or control activation and differentiation of T cells outside the B cell follicle. Here, we present the first specific assays for T$_{FR}$ cell function in vitro and show that sorted wild type T$_{FR}$ cells from the lymph node are extremely potent at inhibiting antibody production, but not very effective at suppressing activation of naïve T cells. PD-1$^{-/-}$ T$_{FR}$ cells inhibit naïve T cell activation and attenuate antibody production in vitro to a greater extent than WT T$_{FR}$ cells. Our studies also demonstrate the dynamic control of antibody production by lymph node T$_{FH}$ and T$_{FR}$ cells. Initially, our attempts to activate B cells in vitro with total CD4$^+$CXCR5$^+$ cells resulted in little IgG secretion. However, when we separated T$_{FH}$ cells from T$_{FR}$ cells and used these T$_{FH}$ cells in such experiments, we could detect robust IgG production. Of note, during an immune response to peptide/CFA, the in vivo dLN T$_{FR}$:T$_{FH}$ ratio is ~1:5. When we cultured T$_{FR}$ and T$_{FH}$ cells at this ratio, little antibody production was observed.

T$_{FR}$ cells tend to be present predominantly at the borders of germinal centers, which may be explained by their relatively lower expression of CXCR5 compared to T$_{FH}$ cells, though other chemokines also may have roles. It is possible that close proximity of T$_{FR}$ cells to germinal center borders enables them to interact with T$_{FH}$ cells as they enter. This could make T$_{FR}$ cells the "gate-keepers" of the germinal center, inhibiting T$_{FH}$ cells as they enter and gain access to B cells undergoing somatic hypermutation and class switch recombination. Furthermore, our studies suggest that the balance between T$_{FR}$ and T$_{FH}$ cells within the germinal center itself may modulate the type and extent of humoral responses. The relative roles of T$_{FR}$ and T$_{FH}$ cells also may depend on the source or strength of antigenic stimulus, cytokine milieu, and tissue microenvironment, and further work is needed to investigate these issues.

Surprisingly, we found substantial populations of T$_{FR}$ cells in the blood of mice. There are a number of reports describing T$_{FH}$ cells in the circulation of humans[6, 7] and one in mice[9]. To our knowledge, our work is the first description of T$_{FR}$ cells in the blood of any organism. In humans, blood T$_{FH}$ cells have been shown to provide B cell help for the production of antibody in vitro. Some studies show more efficient B cell antibody production by blood T$_{FH}$ cells compared to blood CXCR5$^-$ cells[6,7] whereas other studies find no differences between blood T$_{FH}$ and CXCR5$^-$ cells[30]. Differences might relate to mixtures of blood T$_{FH}$ and T$_{FR}$ cells and their relative ratios in these experiments. Since most work describing blood T$_{FH}$ cells was done in humans, little is known about the requirements for blood T$_{FH}$ differentiation and function. Here we show that murine blood T$_{FH}$ and T$_{FR}$ cell generation requires signals through ICOS and CD28, two costimulatory receptors essential for controlling T$_{FH}$ cells in the lymph node. Previous work showed that CD28 is essential for T$_{FR}$ cells in lymph nodes[21]. Here we demonstrate lymph node T$_{FR}$ cell generation also requires ICOS signaling.

Our transfer studies show that blood T$_{FR}$ cells are functional and can regulate antibody production in vivo. To study T$_{FH}$ and T$_{FR}$ function, we transferred blood T$_{FH}$ cells alone or with T$_{FR}$ cells into CD28$^{-/-}$ or TCRα$^{-/-}$ mice, which lack both blood and lymph node T$_{FH}$ and T$_{FR}$ cells. This approach allowed us to analyze T$_{FH}$ and T$_{FR}$ cell function separately from differentiation. Our transfer studies demonstrate effective and specific control of humoral responses by blood T$_{FH}$ and T$_{FR}$ cells. Blood T$_{FR}$ cells are extremely potent at inhibiting T$_{FH}$ cell mediated antibody production, even when relatively few cells are transferred. We hypothesize that blood T$_{FR}$ cells may represent a central memory pool that can be utilized to modulate humoral immunity, analogous to recently reported FoxP3$^+$ cells with regulatory memory to self-antigens[31] and similar to a proposed role for blood T$_{FH}$ cells[7]. High expression of CD62L and CD44 on blood T$_{FR}$ cells along with their ability to home back to lymph nodes strongly support this idea. Blood T$_{FH}$ cells may migrate to lymph nodes and interact with cognate B cells rapidly upon antigen exposure, whereas naïve T cells need at least two to four days to differentiate and upregulate CXCR5. Additionally, blood T$_{FR}$ cells homing to lymph nodes would be able to suppress early B cell responses, before dLN nTregs could fully differentiate into T$_{FR}$ cells.

Beyond their ability to directly suppress antibody responses, T$_{FR}$ cells may be instrumental in determining B cell fates and control whether an immune response generates long-lived plasma cells or memory B cells. For example, cytokines produced by T$_{FR}$ cells may direct GC B cell differentiation into plasma cells versus memory B cells. PD-1 and PD-1 ligand deficiency result in decreased numbers of long-lived plasma cells[16], and further work is needed to determine if this is related to the enhanced PD-1$^{-/-}$ T$_{FR}$ cell numbers and suppressive capacity. If T$_{FR}$ cells can direct B cell fates, this would have implications for rational design of vaccines. We have also identified some of the potential relative roles of T$_{FH}$ and T$_{FR}$ cells in autoimmunity. For example, PD-1 deficiency on autoimmune-prone backgrounds accelerates disease pathologies. It is possible that autoimmune-prone backgrounds may lead to inhibition of T$_{FR}$ differentiation and function. This information will be important for therapeutic strategies using T$_{FR}$ cells. By expanding either T$_{FH}$ or T$_{FR}$ cells from patient blood in vitro, it may be possible to enhance antibody responses by transferring T$_{FH}$ cells or to inhibit systemic autoimmunity by transferring T$_{FR}$ cells.

In summary, we define a new role for PD-1 in regulating immune responses, by inhibiting differentiation and function of T follicular regulatory cells in both lymph node and blood. Our research has provided a better understanding of T$_{FR}$ and T$_{FH}$ interactions, and has the potential to provide novel insights into mechanisms that regulate humoral immunity and applications of those mechanisms in, for example, a vaccination regimen. Our understanding of how PD-1 regulates humoral immunity suggests suggest strategies for manipulating this pathway to enhance protective immunity and long-term memory or to inhibit systemic autoimmunity.

References

1. Crotty, S. Follicular helper CD4 T cells (TFH). *Annu Rev Immunol* 29, 621-663 (2011).
2. Johnston, R. J. et al. Bcl6 and Blimp-1 are reciprocal and antagonistic regulators of T follicular helper cell differentiation. *Science* 325, 1006-1010 (2009).
3. Nurieva, R. I. et al. Bcl6 mediates the development of T follicular helper cells. *Science* 325, 1001-1005 (2009).
4. Choi, Y. S. et al. ICOS receptor instructs T follicular helper cell versus effector cell differentiation via induction of the transcriptional repressor Bcl6. *Immunity* 34, 932-946 (2011).
5. Nurieva, R. I. et al. Generation of T follicular helper cells is mediated by interleukin-21 but independent of T helper 1, 2, or 17 cell lineages. *Immunity* 29, 138-149 (2008).
6. Morita, R. et al. Human blood CXCR5(+)CD4(+) T cells are counterparts of T follicular cells and contain specific subsets that differentially support antibody secretion. *Immunity* 34, 108-121 (2011).
7. Schaerli, P. et al. CXC chemokine receptor 5 expression defines follicular homing T cells with B cell helper function. *J Exp Med* 192, 1553-1562 (2000).
8. Saito, R. et al. Altered expression of chemokine receptor CXCR5 on T cells of myasthenia gravis patients. *Journal of neuroimmunology* 170, 172-178 (2005).
9. Simpson, N. et al. Expansion of circulating T cells resembling follicular helper T cells is a fixed phenotype that identifies a subset of severe systemic lupus erythematosus. *Arthritis and rheumatism* 62, 234-244 (2010).
10. Polanczyk, M. J., Hopke, C., Vandenbark, A. A. & Ofiher, H. Treg suppressive activity involves estrogen-dependent expression of programmed death-1 (PD-1). *Int Immunol* 19, 337-343 (2007).
11. Wang, L. et al. Programmed death 1 ligand signaling regulates the generation of adaptive Foxp3+CD4+ regulatory T cells. *Proc Natl Acad Sci USA* 105, 9331-9336 (2008).
12. Francisco, L. M. et al. PD-L1 regulates the development, maintenance, and function of induced regulatory T cells. *J Exp Med* 206, 3015-3029 (2009).
13. Wang, C., Li, Y., Proctor, T. M., Vandenbark, A. A. & Offner, H. Downmodulation of programmed death 1 alters regulatory T cells and promotes experimental autoimmune encephalomyelitis. *Journal of neuroscience research* 88, 7-15 (2010).
14. Amarnath, S. et al. The PDL1-PD1 axis converts human TH1 cells into regulatory T cells. *Science translational medicine* 3, 111ra120 (2011).
15. Francisco, L. M., Sage, P. T. & Sharpe, A. H. The PD-1 pathway in tolerance and autoimmunity. *Immunol Rev* 236, 219-242 (2009).
16. Good-Jacobson, K. L. et al. PD-1 regulates germinal center B cell survival and the formation and affinity of long-lived plasma cells. *Nature immunology* 11, 535-542 (2010).
17. Hamel, K. M. et al. B7-H1 expression on non-B and non-T cells promotes distinct effects on T- and B-cell responses in autoimmune arthritis. *Eur J Immunol* 40, 3117-3127 (2010).
18. Kawamoto, S. et al. The inhibitory receptor PD-1 regulates IgA selection and bacterial composition in the gut. *Science* 336, 485-489 (2012).

19. Hams, E. et al. Blockade of B7-H1 (programmed death ligand 1) enhances humoral immunity by positively regulating the generation of T follicular helper cells. *J Immunol* 186, 5648-5655 (2011).
20. Velu, V. et al. Enhancing SIV-specific immunity in vivo by PD-1 blockade. *Nature* 458, 206-210 (2009).
21. Linterman, M. A. et al. Foxp3+ follicular regulatory T cells control the germinal center response. *Nat Med* 17, 975-982 (2011).
22. Chung, Y. et al. Follicular regulatory T cells expressing Foxp3 and Bcl-6 suppress germinal center reactions. *Nat Med* 17, 983-988 (2011).
23. Wollenberg, I. et al. Regulation of the germinal center reaction by Foxp3+ follicular regulatory T cells. *J Immunol* 187, 4553-4560 (2011).
24. Bauquet, A. T. et al. The costimulatory molecule ICOS regulates the expression of c-Maf and IL-21 in the development of follicular T helper cells and TH-17 cells. *Nature immunology* 10, 167-175 (2009).
25. Fife, B. T. et al. Interactions between PD-1 and PD-L1 promote tolerance by blocking the TCR-induced stop signal. *Nature immunology* 10, 1185-1192 (2009).
26. Cretney, E. et al. The transcription factors Blimp-1 and IRF4 jointly control the differentiation and function of effector regulatory T cells. *Nature immunology* 12, 304-311 (2011).
27. Martins, G. A. et al. Transcriptional repressor Blimp-1 regulates T cell homeostasis and function. *Nature immunology* 7, 457-465 (2006).
28. Zhou, L. et al. TGF-beta-induced Foxp3 inhibits T(H)17 cell differentiation by antagonizing RORgammat function. *Nature* 453, 236-240 (2008).
29. Beswick, E. J., Pinchuk, I. V., Das, S., Powell, D. W. & Reyes, V. E. Expression of the programmed death ligand 1, B7-H1, on gastric epithelial cells after *Helicobacter pylori* exposure promotes development of CD4+CD25+FoxP3+ regulatory T cells. *Infect Immun* 75, 4334-4341 (2007).
30. Kim, C. H. et al. Subspecialization of CXCR5+ T cells: B helper activity is focused in a germinal center-localized subset of CXCR5+ T cells. *J Exp Med* 193, 1373-1381 (2001).
31. Rosenblum, M. D. et al. Response to self antigen imprints regulatory memory in tissues. *Nature* 480, 538-542 (2011).
32. Keir, M. E., Freeman, G. J. & Sharpe, A. PD-1 regulates self-reactive CD8+ T cell responses to antigen in lymph nodes and tissues. *Journal of Immunology* 179, 5064-5070 (2007).
33. Latchman, Y. E. et al. PD-L1-deficient mice show that PD-L1 on T cells, antigen-presenting cells, and host tissues negatively regulates T cells. *Proc Natl Acad Sci USA* 101, 10691-10696 (2004).
34. Keir, M. E. et al. Tissue expression of PD-L1 mediates peripheral T cell tolerance. *J Exp Med* 203, 883-895 (2006).
35. McAdam, A. J. et al. ICOS is critical for CD40-mediated antibody class switching. *Nature* 409, 102-105 (2001).
36. Shahinian, A. et al. Differential T cell costimulatory requirements in CD28-deficient mice. *Science* 261, 609-612 (1993).
37. Bettelli, E. et al. Reciprocal developmental pathways for the generation of pathogenic effector TH17 and regulatory T cells. *Nature* 441, 235-238 (2006).
38. Bettelli, E. et al. Myelin oligodendrocyte glycoprotein-specific T cell receptor transgenic mice develop spontaneous autoimmune optic neuritis. *J Exp Med* 197, 1073-1081 (2003).

Example 2. T Follicular Regulatory Cell (TFR) Cellular Therapy Strategies

1.) Enrichment and Injection of TFR Cells from Blood.

In order to skew the TFH:TFR balance, TFR cells will be purified from peripheral blood. First, lymphocytes from peripheral blood will be isolated by sucrose density centrifugation and stained with fluorescently labeled antibodies. TFR cells will be purified and separated from TFH cells by flow cytometry. TFR cells will be sorted via flow cytometry based on surface markers of CD4$^+$CXCR5$^+$ICOS$^+$GITR$^+$ and then administered intravenously to patients. These patients include a) individuals with autoimmune diseases with pathogenic antibodies (such as systemic lupus erythematosis) as a means to inhibit immunopathology related to these pathogenic antibodies, b) individuals undergoing transplantation (to prevent pathogenic effects of antibodies during transplant rejection), c) patients undergoing gene therapy or stem cell therapy to prevent development of antibodies that would abrogate the intended beneficial effects of the transferred gene or cell.

2.) Enrichment/Activation and Injection of TFR Cells from Blood.

In order to skew the TFH:TFR balance and to promote heightened suppressive function of TFR cells, TFR cells will be sorted and activated in vitro prior to administration into patients. Lymphocytes from peripheral blood will be isolated by sucrose density centrifugation and stained with fluorescently labeled antibodies. TFR cells will be sorted via flow cytometry based on surface markers of CD4$^+$CXCR5$^+$ICOS$^+$GITR$^+$ and activated in vitro by using a soluble anti-CD3 antibody along with autologous CD19+ B cells from blood to trigger TCR signaling and activation. After activation, TFR cells will be given to patients intravenously.

3.) Enhanced Activation of TFR Cells by Blocking PD-1 Pathway.

In order to skew the TFH:TFR balance and to promote heightened suppressive function of TFR cells, TFR cells will be sorted and activated in vitro in the presence of PD-1 or PD-L1 antagonists, which should enhance TFR cell numbers and suppressive capacity. Lymphocytes from peripheral blood will be isolated by sucrose density centrifugation and stained with fluorescently labeled antibodies. TFR cells will be sorted via flow cytometry based on surface markers of CD4$^+$CXCR5$^+$ICOS$^+$GITR$^+$ and activated in vitro by using a soluble anti-CD3 antibody along with autologous CD19+ B cells from blood to trigger TCR signaling. PD-1 antagonists (monoclonal antibodies and/or small molecule inhibitors) are added during activation to enhance activation of TFR cells. After activation, TFR cells are administered to patients intravenously.

4.) Enrichment and Injection of Tfr Cells to Induce Long Term Memory During Vaccination.

The goal of this strategy is to skew TFH:TFR balance in the blood during B cell memory development and preferentially promote development of long lived B cell memory cells by inhibiting plasma cell differentiation. TFR cells will be sorted via flow cytometry and injected intravenously into individuals at the time of vaccination. Lymphocytes from peripheral blood will be isolated by sucrose density centrifugation and stained with fluorescently labeled antibodies. TFR cells will be sorted via flow cytometry based on surface markers of CD4+CXCR5+ICOS+GITR+ and reinjected intravenously.

5.) Induction of T<sub>FR</sub> Cells from nTreg Precursors by Blocking PD-1 Pathway In Vitro.

In order to generate de novo T<sub>FR</sub> cells from Treg progenitors, naïve Tregs are sorted from human blood by CD4+CXCR5−GITR+ (or CD25+). These cells are activated with autologous CD19+ B cells with anti-CD3. During this activation, PD-1 antagonists (blocking antibodies or small molecule inhibitors) are used to block the PD-1 pathway. T<sub>FR</sub> cells are then sorted by flow cytometry as CD4+CXCR5+ICOS+GITR+ or and injected into patients.

Example 3. Summary

T Follicular Regulatory (T<sub>FR</sub>) cells inhibit whereas T Follicular Helper (T<sub>FH</sub>) cells stimulate antibody production. Both T<sub>FR</sub> and T<sub>FH</sub> cells are found in blood, however relatively little is known about the developmental signals for these cells or their functions. Here we demonstrate a new mechanism of control of antibody responses mediated by T<sub>FR</sub> and T<sub>FH</sub> cells. We find that circulating T<sub>FH</sub> and T<sub>FR</sub> cells are distinct from lymph node effector T<sub>FR</sub>/T<sub>FH</sub> cells, and represent memory-like cells that have specialized function to patrol diverse sites of potential antigen encounter. Circulating T<sub>FH</sub> cells can be potently activated by DCs, home to germinal centers and produce large amounts of cytokines Although memory-like circulating T<sub>FR</sub> cells can be potently activated in lymph nodes, they have a lower capacity to suppress B cell responses than lymph node T<sub>FR</sub> cells. Therefore, memory-like circulating T<sub>FH</sub> cells are able to provide quick and robust systemic B cell help.

Follicular helper T (T<sub>FH</sub>) cells are a subset of CD4+ T cells that stimulate and maintain the germinal center reaction, enabling B cells to produce high affinity antibodies. T<sub>FH</sub> cells are defined by CXCR5, the chemokine receptor which directs them to the B cell zone via gradients of the chemokine CXCL13 (Breitfeld et al., 2000; Crotty, 2011). T<sub>FH</sub> cells express the transcription factor Bcl6 which facilitates CXCR5 expression, as well as production of IL-21, a key cytokine that helps B cells to undergo affinity maturation and produce antibody (Johnston et al., 2009; Nurieva et al., 2008; Nurieva et al., 2009). In addition, T<sub>FH</sub> cells can produce other cytokines including IFNγ IL-17 and IL-4 that are thought to influence the germinal center reaction by helping with selection of antibody isotypes during class switch recombination. Significant plasticity in cytokine production exists within in the T<sub>FH</sub> lineage, so distinguishing T<sub>FH</sub> from Th1, Th2 and Th17 cells can be challenging (Cannons et al.). Lymph node (LN) T<sub>FH</sub> differentiation is thought to be a two step process: T cells are initially primed by dendritic cells and subsequently interact with B cells in the germinal center, culminating in full effector potential (Crotty, 2011; Goenka et al., 2011; Haynes et al., 2007; Poholek et al., 2010).

Follicular regulatory T (T<sub>FR</sub>) cells are a newly defined population of CXCR5+ CD4 T cells that until recently were hidden within T<sub>FH</sub> gating strategies. Like T<sub>FH</sub> cells, T<sub>FR</sub> cells express high levels of CXCR5, the costimulatory molecule ICOS, and the coinhibitory molecule PD-1 (Chung et al., 2011; Linterman et al., 2011; Sage et al., 2013; Wollenberg et al., 2011). Importantly, T<sub>FR</sub> cells are thought to originate from thymic Treg (tTreg) precursors, in contrast to T<sub>FH</sub> cells which develop from naïve T cells (Chung et al., 2011; Sage et al., 2013).

T<sub>FR</sub> and T<sub>FH</sub> cells have diametrically opposing roles in regulating humoral immune responses; T<sub>FH</sub> cells stimulate humoral immunity, whereas T<sub>FR</sub> cells potently suppress humoral immune responses (Chung et al., 2011; Linterman et al., 2011; Sage et al., 2013; Wollenberg et al., 2011). The mechanisms by which T<sub>FR</sub> cells suppress the germinal center reaction are still unclear. It is not known whether T<sub>FR</sub> cells suppress T<sub>FH</sub> cells, germinal center B cells, or both. Understanding how T<sub>FR</sub> cells inhibit humoral immunity has the potential to enable improved vaccination strategies.

T<sub>FH</sub> and T<sub>FR</sub> cells are not only present in LNs, but also in the circulation. Circulating T<sub>FH</sub> cells from humans can provide help to B cells in vitro (Morita et al., 2011; Schaerli et al., 2000), and circulating T<sub>FH</sub> cells from mice can potently stimulate B cells in vivo (Sage et al., 2013). A subset of human blood T<sub>FH</sub> cells with CXCR5 expression comparable to lymph node T<sub>FH</sub> cells but lower levels of PD-1 and ICOS expression has been postulated to represent memory cells (Breitfeld et al., 2000; Morita et al., 2011; Rasheed et al., 2006). Therefore, it is possible that circulating T<sub>FH</sub> cells may give rise to memory T<sub>FH</sub> cells (Fazilleau et al., 2007; Hale et al., 2013; Sage et al., 2013). Although there is evidence for the presence of memory T<sub>FH</sub> cells, the origin and function of these cells is not yet clear (Fazilleau et al., 2007; Hale et al., 2013; Luthje et al., MacLeod et al., 2011; Marshall et al., 2011). If blood T<sub>FH</sub> and T<sub>FR</sub> cells possess properties of memory cells, then they could serve as attractive candidates for immune monitoring and cellular therapy (Morita et al., 2011; Sage et al., 2013; Saito et al., 2005; Schaerli et al., 2000; Simpson et al., 2010).

Elucidating the relationships between lymph node T<sub>FH</sub> and T<sub>FR</sub> cells and circulating T<sub>FH</sub> and T<sub>FR</sub> cells may provide insights into T<sub>FH</sub> (and T<sub>FR</sub>) memory cell development and function (Crotty, 2011). Although lymph node T<sub>FR</sub> and T<sub>FH</sub> cells depend on CD28, ICOS and B cells for development, the specific cues for blood T<sub>FH</sub> and T<sub>FR</sub> cell development and maintenance are not yet clear. Circulating T<sub>FH</sub> cells in humans appear to differ from lymph node T<sub>FH</sub> cells by microarray analysis, however these differences may be due to decreased activation in the blood or contaminating T<sub>FR</sub> cells (Rasheed et al., 2006). The most straightforward explanation for the presence of T<sub>FH</sub> and T<sub>FR</sub> cells in the circulation is that some T<sub>FH</sub> and T<sub>FR</sub> cells from the germinal center "decide" to leave the lymph node. If this hypothesis is true, then circulating T<sub>FH</sub> and T<sub>FR</sub> cells would require lymph node T<sub>FH</sub> and T<sub>FR</sub> cells for their development. In support of this hypothesis, T<sub>FH</sub> and T<sub>FR</sub> cells are completely missing from the lymph nodes and blood of CD28 and ICOS deficient mice (Bauquet et al., 2009; Bossaller et al., 2006; Sage et al., 2013). However, there are data that are inconsistent with this hypothesis. PD-1 deficient mice have increased T<sub>FH</sub> cells in the blood, but not in the lymph node (Sage et al., 2013). In addition, lymph node T<sub>FH</sub> and T<sub>FR</sub> cells develop with similar kinetics as blood T<sub>FH</sub> and T<sub>FR</sub> cells (Sage et al., 2013). Moreover, recent tracking experiments suggest that GC T<sub>FH</sub> cells are unable to gain access to the circulation (Shulman et al., 2013). These findings suggest that circulating and lymph node T<sub>FH</sub> and T<sub>FR</sub> cells may develop independently.

Here we demonstrate that "memory-like" blood T<sub>FR</sub> and T<sub>FH</sub> cells are distinct and specialized cellular subsets that potently and systemically control antibody production. Memory-like blood T<sub>FH</sub> and T<sub>FR</sub> populations differ from lymph node T<sub>FR</sub> and T<sub>FH</sub> "effector" cells in several ways. Memory-like blood T<sub>FH</sub> and T<sub>FR</sub> cells can circulate throughout the body patrolling for antigen, in contrast to LN T<sub>FH</sub> and T<sub>FR</sub> cells. After homing to lymph nodes, blood T<sub>FH</sub> cells require repriming with dendritic cells to be completely functional; these activated T<sub>FH</sub> cells produce enhanced amounts of cytokines and dominate the CXCR5 population compared to lymph node T$_{FH}$ cells. In addition, we find that blood T$_{FR}$ cells have decreased suppressive capacity in vitro, compared to lymph node T$_{FR}$ cells. Since blood T$_{FH}$ cells are more potently activated and blood T$_{FR}$ cells are less suppressive, the blood CD4$^+$CXCR5$^+$ population as a whole is poised to form a quick memory-like response throughout the body wherever re-exposure to antigen may occur. Taken together, these studies identify a novel mechanism by which circulating T$_{FH}$ cells control B cell responses in vivo.

Results

Figures 15A, 15B:
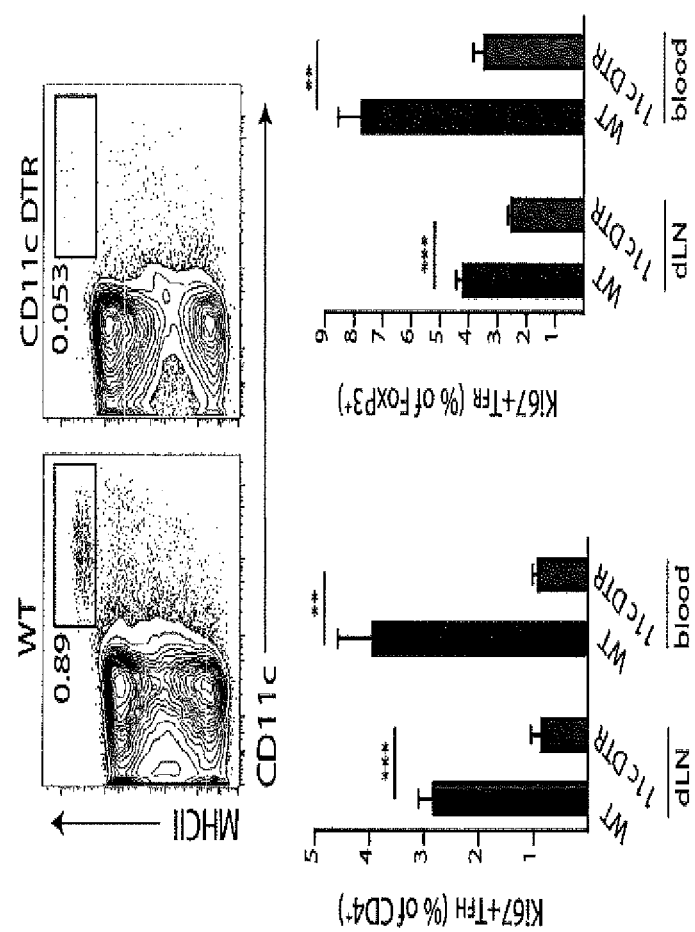
FIG. 15A. Circulating T$_{FH}$ and T$_{FR}$ cells require dendritic cells for development. WT or CD11c$^{DTR}$ bone marrow chimeras were immunized with NP-OVA subcutaneously and diphtheria toxin (DT) was administered (or not) on days 0, 2, 4, and 6 to deplete DCs.
FIG. 15B. Draining lymph node analysis of CD11c$^+$MHC II$^+$ DCs Quantification of Ki67+ T$_{FH}$ (CD4$^+$ICOS$^+$CXCR5$^+$ FoxP3$^-$Ki67$^+$CD19$^-$) and T$_{FR}$ (CD4$^+$ICOS$^+$CXCR5$^+$ FoxP3$^+$Ki67$^+$CD19$^-$) cells in the draining lymph node and blood. Data are means+/−standard error with 5 mice per group. Data are representative of at least 2 independent experiments.

Differentiation of Circulating T$_{FH}$ and T$_{FR}$ Cells Require Priming by Dendritic Cells We recently demonstrated that T follicular regulatory (T$_{FR}$) and T follicular helper (T$_{FH}$) cells are present in the blood of mice. To determine if blood and lymph node T$_{FH}$ and T$_{FR}$ cells have phenotypic differences, we first compared the expression of CXCR5 and other cell surface markers on murine T$_{FH}$ and T$_{FR}$ cells from lymph node and blood. Initially, we analyzed CXCR5 and ICOS expression on circulating and lymph node cells 7 days after subcutaneous immunization with NP-OVA in CFA, an immunization that causes robust differentiation of both T$_{FH}$ and T$_{FR}$ cells (Sage et al., 2013). T$_{FH}$ cells, defined as CD4$^+$ICOS$^+$CXCR5$^+$FoxP3$^-$CD19$^-$, greatly expanded in the draining lymph nodes (dLN) and blood of immunized mice compared to unimmunized controls (FIG. 15A-B). The blood T$_{FH}$ cells had lower, but still substantial, expression of CXCR5 (FIG. 22A-FIG. 22E). Expression of the essential T$_{FH}$ costimulatory molecule ICOS was much lower on blood T$_{FH}$ compared to LN T$_{FH}$ cells (FIG. 22A-FIG. 22E). Intracellular staining of the cell cycle marker Ki67 revealed that fewer blood T$_{FH}$ cells were in cell cycle compared to dLN T$_{FH}$ cells. However, blood T$_{FH}$ cells had much higher Ki67 expression than the total CD4 T cell population (FIG. 22E).

T$_{FR}$ cells, defined as CD4$^+$ICOS$^+$CXCR5$^+$FoxP3$^+$CD19$^-$ cells, differentiated significantly in both the dLN and blood after immunization (FIG. 22F-FIG. 22G). Draining LN T$_{FR}$ cells expressed lower levels of CXCR5 than dLN T$_{FH}$ cells. Blood T$_{FR}$ cells expressed even lower levels of CXCR5 than dLN T$_{FR}$ cells (FIG. 22H). ICOS expression was also greatly attenuated in blood T$_{FR}$ cells compared to dLN T$_{FR}$ cells (FIG. 22I). However, Ki67 intracellular staining revealed that there were similar proportions of dLN and blood T$_{FR}$ cells in cell cycle (FIG. 22J). Taken together, these data indicate that circulating T$_{FH}$ and T$_{FR}$ cells are phenotypically distinct from dLN T$_{FH}$ and T$_{FR}$ cells and express less CXCR5 and ICOS.

Next we analyzed the developmental cues necessary for circulating T$_{FH}$ and T$_{FR}$ cells. LN T$_{FH}$ cells depend on dendritic cells for initial differentiation (Goenka et al.) and require B cells for maintenance of the T$_{FH}$ phenotype, as well as optimal CXCR5 and ICOS expression (Choi et al., 2011; Kerfoot et al., 2011; Poholek et al., 2010). LN T$_{FR}$ cells also depend on B cells for differentiation (Linterman et al., 2011). To determine if dendritic cells are necessary for the generation of circulating T$_{FH}$ and T$_{FR}$ cells, we utilized CD11c DTR bone marrow chimeric mice to deplete dendritic cells. We used bone marrow chimeric mice for these in vivo studies to circumvent the lethality related to stromal expression of CD11c in the brain. We administered diphtheria toxin every 2 days starting on day 0 during an NP-OVA immunization, and compared the generation of blood and dLN T$_{FH}$ and T$_{FR}$ cells 7 days post immunization. Diphtheria toxin administration resulted in depletion of most, but not all, dendritic cells in the dLN of CD11cDTR mice (FIG. 15A). Depletion of dendritic cells led to significantly lower percentages of Ki67$^+$ T$_{FH}$ and T$_{FR}$ cells in both the dLN and blood, suggesting that dendritic cells are key for differentiation of both dLN and blood T$_{FH}$ and T$_{FR}$ cells (FIG. 15B).

Figure 15C:
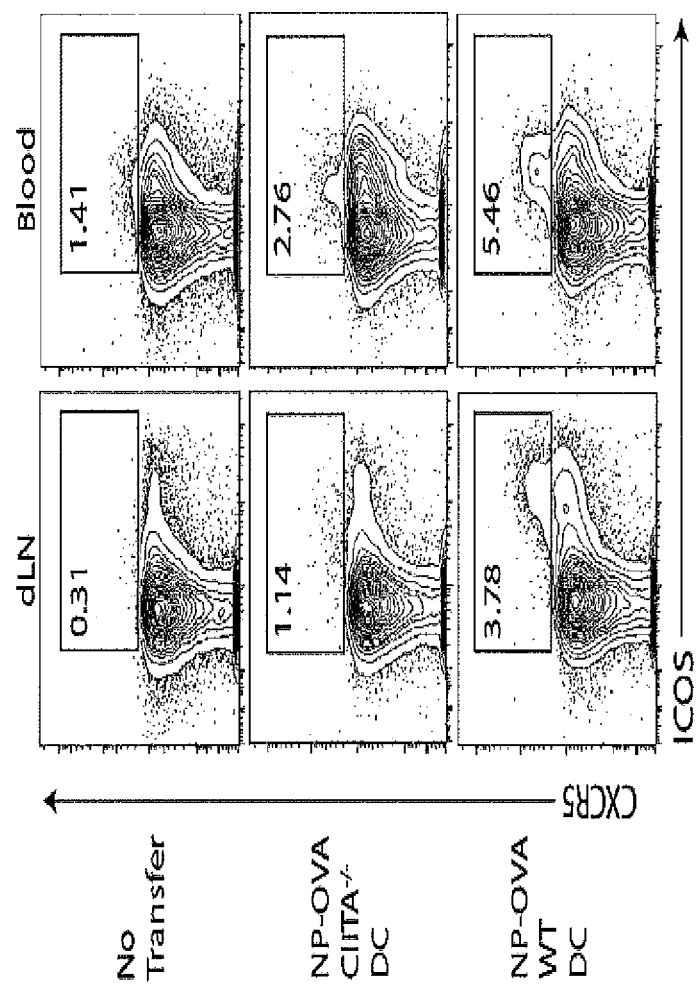
FIG. 15C WT or Ciita$^{-/-}$ bone marrow derived dendritic cells (BMDCs) were pulsed with NP-OVA in an overnight in vitro culture, washed and adoptively transferred subcutaneously to WT mice. 5 days later draining lymph nodes and blood were analyzed for ICOS and CXCR5 expression on CD4 T cells. WT mice that received no transfer were included as controls. Plots are pregated on CD4$^+$CD19$^-$. Representative plots are shown.
Figure 15D:
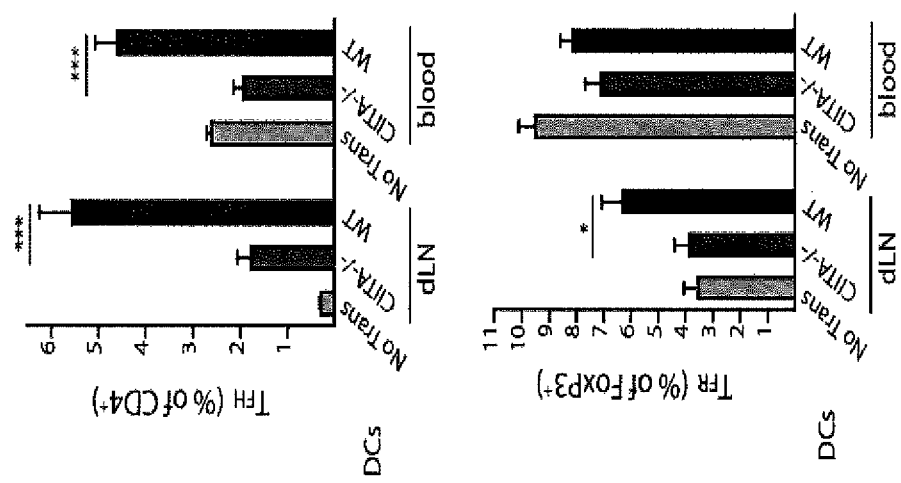
FIG. 15D. Quantification of draining lymph node and blood T$_{FH}$ (top) and T$_{FR}$ (bottom) cells in BMDC adoptive transfer experiments as in FIG. 15C. Data are means+/−standard error with 5 mice per group. Data are representative of at least 2 independent experiments.

Next, we investigated whether antigen presentation by dendritic cells was sufficient for development of circulating T$_{FH}$ and T$_{FR}$ cells by comparing antigen presentation by WT and MHC II deficient (Ciita$^{-/-}$) dendritic cells using adoptive transfer approaches. We differentiated WT or Ciita$^{-/-}$ bone marrow derived dendritic cells (BMDCs) with GM-CSF, activated them with LPS and pulsed them overnight with NP-OVA. After washing the cells thoroughly, we adoptively transferred these Ag-pulsed BMDCs subcutaneously into WT mice, and analyzed the dLN and blood for T$_{FH}$ and T$_{FR}$ cell development 5 days later. When NP-OVA-pulsed WT BMDCs were adoptively transferred, there were substantial increases in percentages of total CD4$^+$CXCR5$^+$ cells in both the dLN and blood (FIG. 15C). When T$_{FH}$ cells were quantified, we found that transfer of antigen-pulsed WT BMDCs caused a significant increase in the proportions of T$_{FH}$ cells in both the lymph node and blood (FIG. 15D). In contrast, adoptive transfer of NP-OVA-pulsed MHC II-deficient BMDCs resulted in modest increases in percentages of CXCR5$^+$ cells in the dLN and blood (FIG. 15C-D). Antigen-pulsed WT BMDCs also stimulated a significant increase in the proportion of T$_{FR}$ cells in the lymph node. However, Ag-pulsed WT BMDC did not result in increased blood T$_{FR}$ cells, suggesting that cues for blood T$_{FR}$ cell generation can be supplied by subcutaneous immunization but not DC transfer approaches.

Figure 15E:
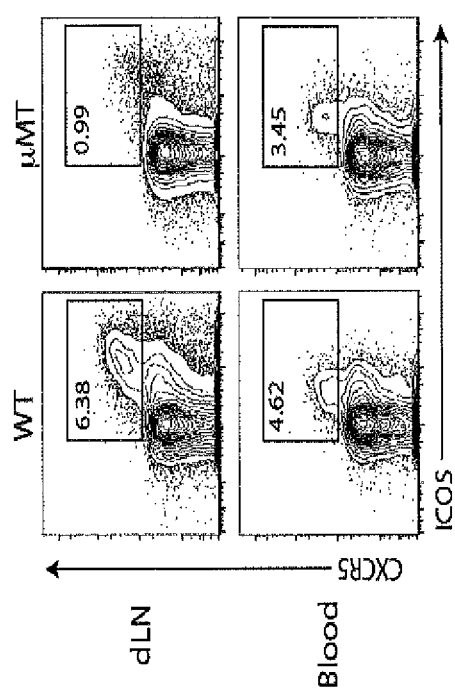
FIG. 15E. mMT mice have normal circulating T$_{FH}$ and T$_{FR}$ cells. WT or Ighm$^{-/-}$ "mMT" mice were immunized with NP-OVA subcutaneously and 7 days later ICOS$^+$CXCR5$^+$ CD4 T cells were identified. Plots are pregated on CD4$^+$ CD19$^-$. Representative plots are shown.
Figure 15F:
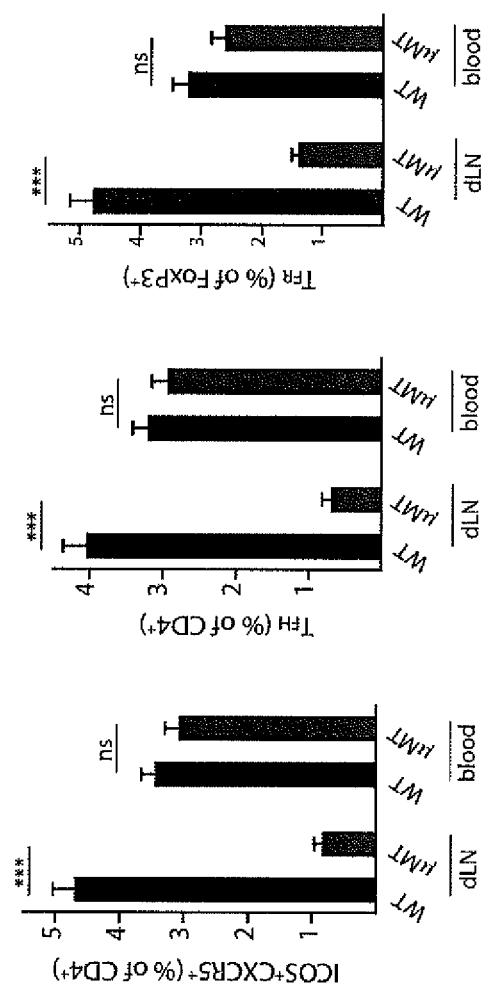
FIG. 15F. Quantification of total lymph node or blood CD4$^+$ICOS$^+$CXCR5$^+$ (left; as gated in FIG. 15D), T$_{FH}$ (middle), or T$_{FR}$ (right) cells. Data are means+/−standard error with 5 mice per group. Data are representative of at least 2 independent experiments.
Figure 15G:
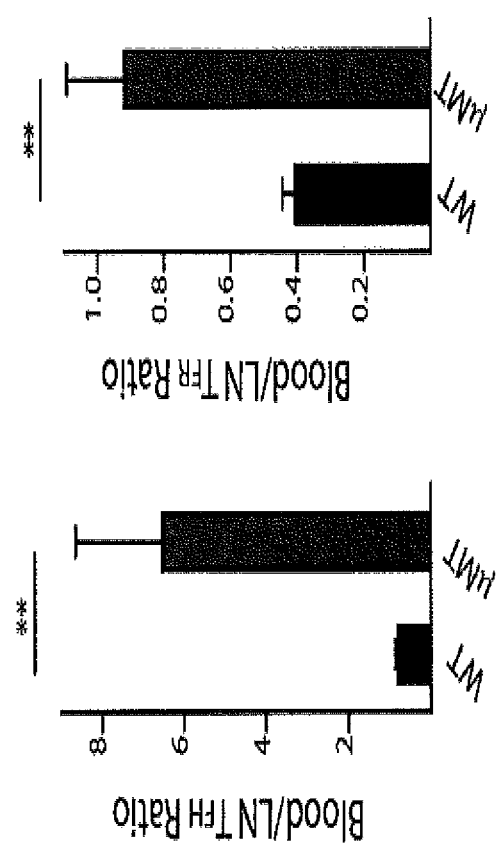
FIG. 15G. Analysis of the blood:lymph node ratio of T$_{FH}$ and T$_{FR}$ cells in WT and μMT mice immunized as in FIG. 15E. Data are means+/−standard error with 5 mice per group. Data are representative of at least 2 independent experiments.

Since B cells are required for full differentiation of dLN T$_{FH}$ and T$_{FR}$ cells, we next tested whether B cells are required for the generation of circulating T$_{FH}$ and T$_{FR}$ cells. We immunized WT and "µMT" mice (that lack mature B cells due to the lack of surface IgM expression) with NP-OVA, and compared dLN and circulating T$_{FH}$ and T$_{FR}$ cells. Similar to previous reports, the percentages of T$_{FH}$ cells and T$_{FR}$ cells in the dLN were severely attenuated in µMT mice compared to WT mice (FIG. 15E-F) (Poholek et al., 2010). Surprisingly, the percentages of T$_{FH}$ and T$_{FR}$ cells within the blood of µMT mice were equivalent to those of WT mice, suggesting that blood T$_{FH}$ and T$_{FR}$ cells require distinct cues for development compared to LN T$_{FH}$ and T$_{FR}$ cells. Furthermore, since blood T$_{FH}$ and T$_{FR}$ cell numbers did not increase in the µMT mice compared to WT mice, it is unlikely that the absence of dLN T$_{FH}$ and T$_{FR}$ cells is due to migration of these cells into the blood. Since the lack of mature B cells attenuated T$_{FH}$ and T$_{FR}$ numbers in the dLN but not the blood, the µMT mice have a blood:LN T$_{FH}$ ratio 6 times higher than that of WT mice and a blood:LN T$_{FR}$ ratio 2 fold higher than WT mice (FIG. 15G). Taken together, these data indicate that circulating T$_{FH}$ and T$_{FR}$ cells require signals from DCs for their generation.

Blood T$_{FH}$ and T$_{FR}$ Cells Exit the Lymph Node Via S1P Signals

Figure 16A:
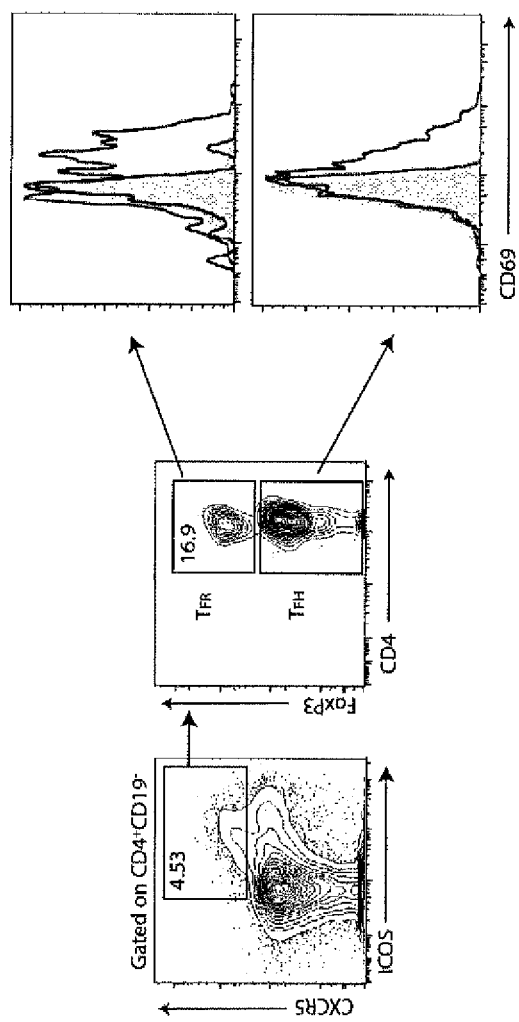
FIG. 16A. Circulating T$_{FH}$ and T$_{FR}$ cells depend on SIP signals to exit the lymph node. Analysis of CD69 expression on T$_{FH}$ and T$_{FR}$ cells. Gating of T$_{FH}$ and T$_{FR}$ cells from the lymph node and blood of WT mice immunized with NP-OVA 7 days previously (left). Plots are pregated on CD4$^+$ CD19$^-$. Histograms (right) show CD69 expression on T$_{FH}$ and T$_{FR}$ cells from lymph node (blue) and blood (red) or on CD4$^+$ICOS$^-$CXCR5$^-$ cells. Data are means+/−standard error with 5 mice per group; data are representative of at least 2 independent experiments.
Figure 16B:
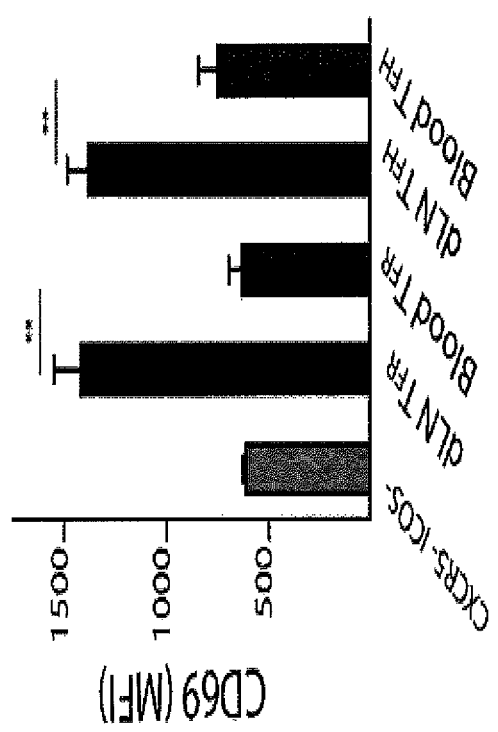
FIG. 16B. Quantification of CD69 on lymph node and blood T$_{FH}$ and T$_{FR}$ cells as in FIG. 16A. CD4$^+$ICOS$^-$ CXCR5$^-$CD19$^-$ cells are included as controls. Data are means+/−standard error with 5 mice per group; data are representative of at least 2 independent experiments.

To further understand the relationship between LN and blood T$_{FH}$ and T$_{FR}$ cells, we next investigated the cues responsible for exit of T$_{FH}$ and T$_{FR}$ cells from the dLN and entry into the circulation. Sphingosine-1-phosphate (S1P) levels control T cell exit from the lymph node into the efferent lymph (Matloubian et al., 2004). High levels of S1P in blood and lymph act as a chemoattractant for T cells. This directed migration can be blocked by expression of CD69 on newly activated cells, which downregulates S1P receptors (Cyster and Schwab, 2011; Shiow et al., 2006). Based on these data, we hypothesized that blood T$_{FH}$ and T$_{FR}$ cells would have low CD69 expression. To test this hypothesis, we compared CD69 expression on T$_{FH}$ and T$_{FR}$ cells from the dLN and blood of mice that were immunized with NP-OVA 7 days previously. Blood T$_{FH}$ and T$_{FR}$ cells had ~2-3 fold lower CD69 expression compared to T$_{FH}$ and T$_{FR}$ cells from the lymph node (FIG. 16A-B).

Figure 16C:
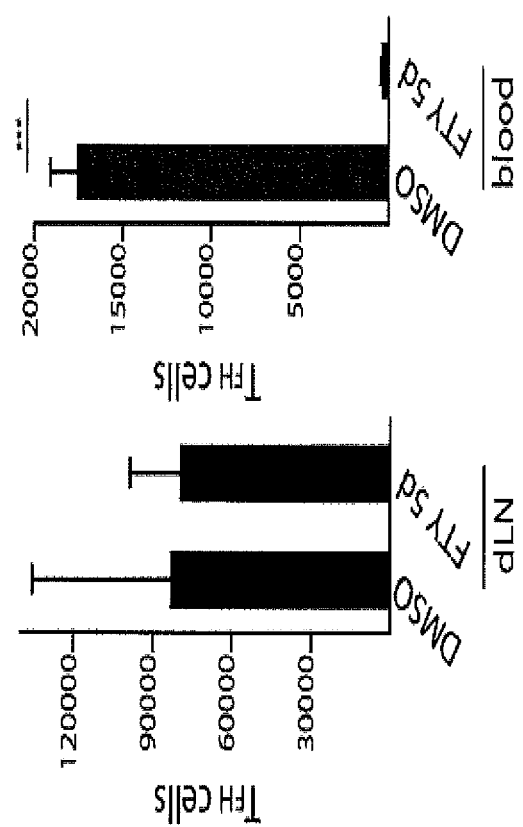
FIG. 16C. Quantification of numbers of T$_{FH}$ cells in the lymph node (left; blue) and blood per ml (right; red) after FTY720 treatment for 5 days (on days 2, 4, and 6 post immunization followed by analysis on day 7) are shown. Data are means+/−standard error with 5 mice per group; data are representative of at least 2 independent experiments.
Figure 16D:
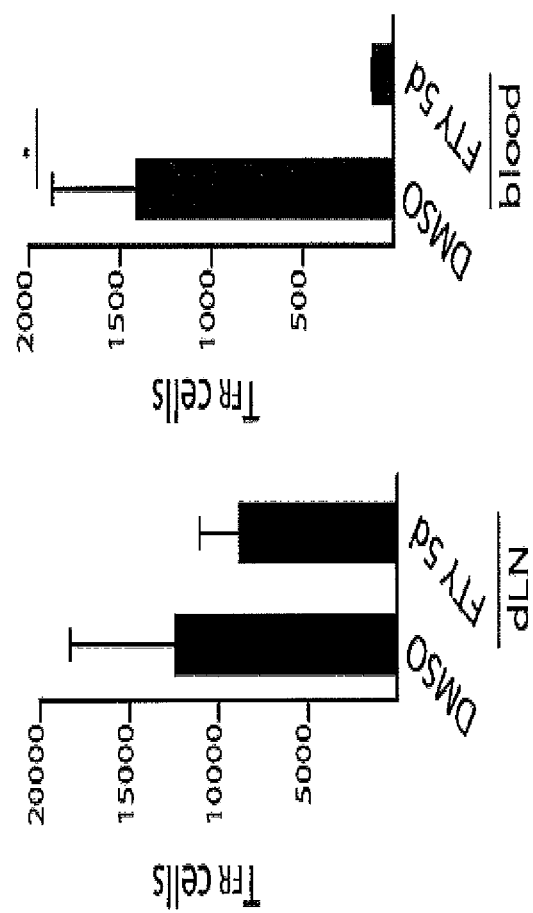
FIG. 16D. Quantification of numbers of T$_{FR}$ cells in the lymph node (left; blue) and blood (right; red) after FTY720 treatment for 5 days, as in FIG. 16C. Data are means+/− standard error with 5 mice per group; data are representative of at least 2 independent experiments.
Figure 16E:
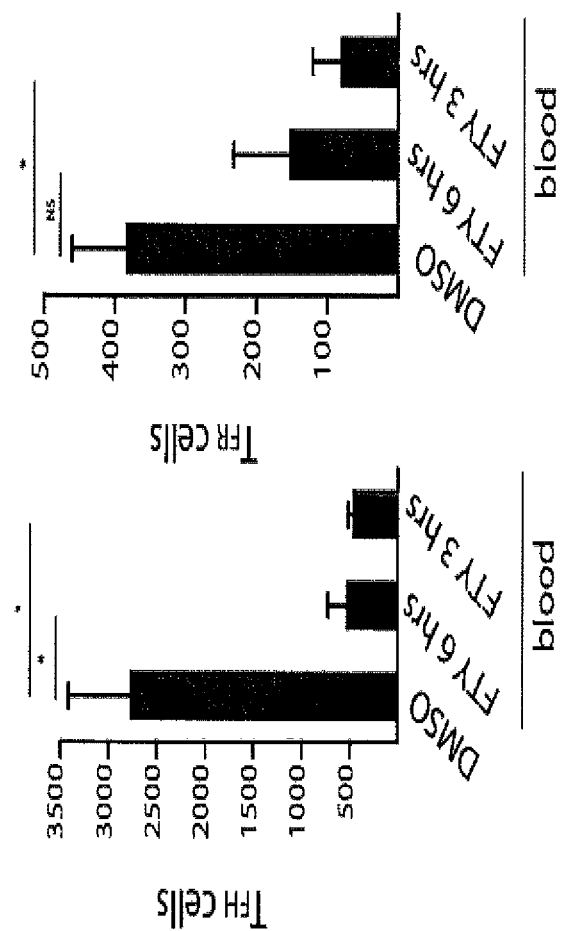
FIG. 16E. Numbers of T$_{FH}$ (left) and T$_{FR}$ (right) cells (per ml blood) after FTY720 treatment during the last 3 or 6 hours of a 7 day immunization. Data are means+/−standard error with 5 mice per group; data are representative of at least 2 independent experiments.

To test whether T$_{FH}$ and T$_{FR}$ cells utilize S1P signals to exit the lymph node via the efferent lymphatic system, we used FTY720 which prevents cells from responding to S1P gradients and prevents lymphocyte egress from lymphoid tissues (Cyster, 2005; Cyster and Schwab, 2011). We immunized mice with NP-OVA and then administered FTY720 to mice every 2 days (starting on day 2) and harvested organs 7 days after NP-OVA immunization. Blood T$_{FH}$ cells were virtually absent in mice that received the FTY720 treatment (FIG. 16C). T$_{FR}$ cells showed a similar dependence on SIP signals and very few were present in the blood after FTY720 administration (FIG. 16D). However, the numbers of dLN T$_{FH}$ and T$_{FR}$ cells were not significantly changed by FTY720 treatment. To investigate the kinetics of blood T$_{FH}$ and T$_{FR}$ circulation, we immunized mice with NP-OVA and administered FTY720 on day 7 after immunization and analyzed T$_{FH}$ and T$_{FR}$ cells after 3 or 6 hours after FTY720 administration. When we treated mice with FTY720 only for 3 or 6 hours prior to analysis, there was also a marked attenuation of both T$_{FH}$ and T$_{FR}$ numbers, demonstrating T$_{FH}$ and T$_{FR}$ cells exit the blood quickly, within only a few hours (FIG. 16E).

Figure 16F:
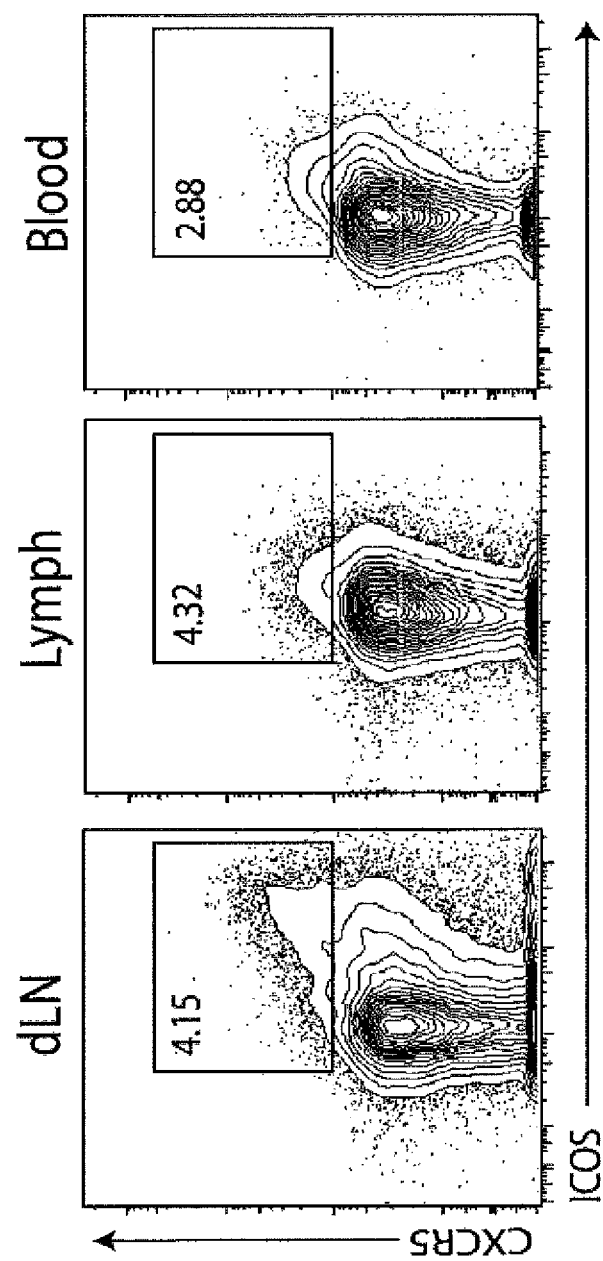
FIG. 16F. Representative plots of total CD4$^+$ICOS$^+$ CXCR5$^+$ cells from the draining lymph node (dLN), efferent lymph (lymph) and blood of WT mice immunized 7 days previously. Plots are pregated on CD4+CD19−. Data are representative from at least 3 replicates.
Figure 16G:
FIG. 16G. Quantification of percentages of T$_{FH}$ and T$_{FR}$ cells in the draining lymph node (blue), efferent lymph (green) and blood (red) of WT mice immunized 7 days previously. Data are representative from at least 3 replicates.
Figure 16H:
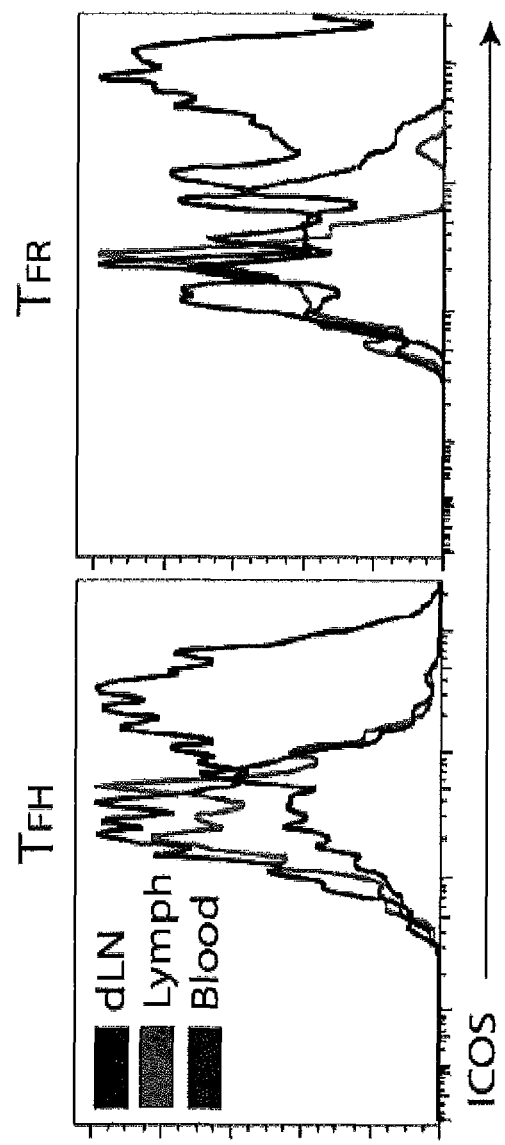
FIG. 16H. Histograms showing ICOS expression on draining lymph node (blue), lymph (green) and blood (red) T$_{FH}$ (left) and T$_{FR}$ (right) cells as in FIG. 16G.

To analyze T$_{FH}$ and T$_{FR}$ cell exit from the dLN and entry into efferent lymph, we conducted experiments in which the efferent lymph was collected via a thoracic duct cannulation method (Massberg et al., 2007). We detected robust percentages of both T$_{FH}$ and T$_{FR}$ cells in the lymph (FIG. 16F-G). The percentages of T$_{FH}$ cells in lymph and dLN were similar and the percentages of T$_{FR}$ cells in lymph and blood were similar (FIG. 16F-G). Lymph T$_{FH}$ and T$_{FR}$ cells had lower levels of ICOS compared to dLN T$_{FH}$ and T$_{FR}$ cells, but levels similar to blood T$_{FH}$ and T$_{FR}$ cells (FIG. 16H). Thus, both T$_{FH}$ and T$_{FR}$ cells have low ICOS expression upon exiting the dLN and entering the lymph, but do not further downregulate ICOS after entry into the circulation. Taken together, these data indicate that both T$_{FH}$ and T$_{FR}$ cells use SIP signals to leave the dLN, and their circulation in the blood is transient, on the order of hours.

Figure 17A:
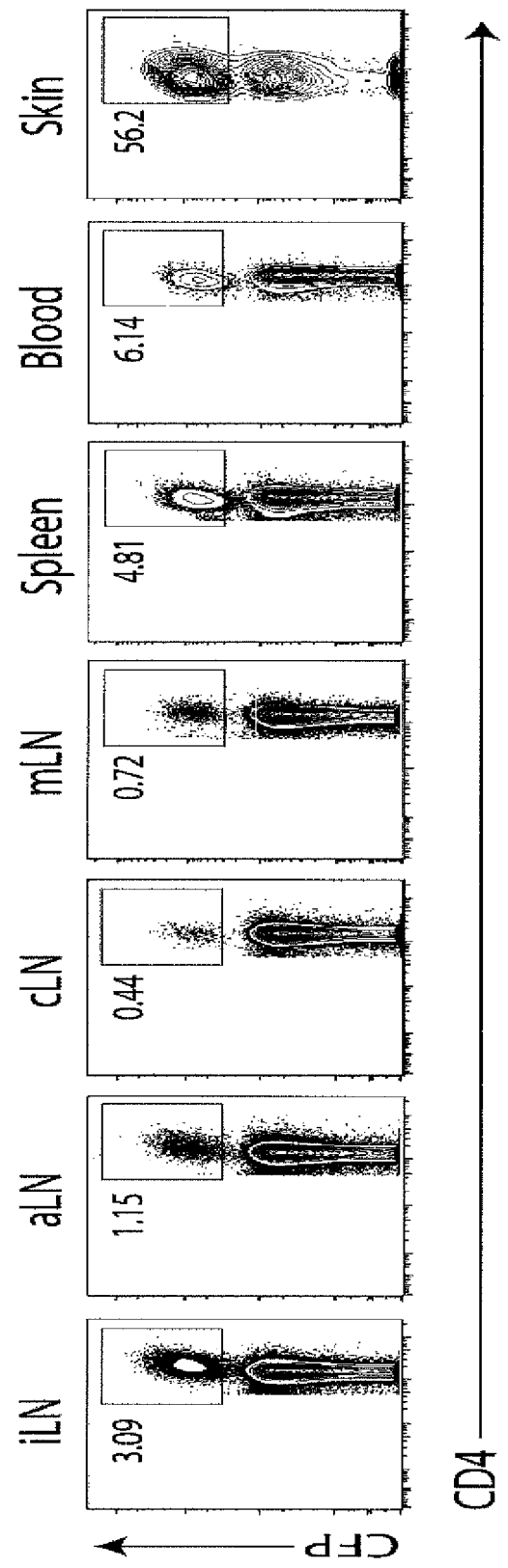
FIG. 17A. Circulating T$_{FH}$ and T$_{FR}$ cells migrate to diverse secondary lymphoid organs and tissues. 20, Actin$^{CFP}$-Fox$^{GFP}$ mice were immunized with NP-OVA subcutaneously and 7 days later 2×10$^4$ sorted blood CD4$^+$CXCR5$^+$ CD19$^-$ cells were adoptively transferred into CD28 deficient mice which were immunized with NP-OVA. Organs were harvested 7 days later for analyses. Transferred cells from indicated organs were identified as CFP positive according to gates: iLN; draining inguinal lymph node, aLN; axillary lymph node, cLN; cervical lymph node, mLN; mesenteric lymph node, Skin; skin around site of immunization. Plots are pregated on CD4$^+$CD19$^-$.
Figure 17B:
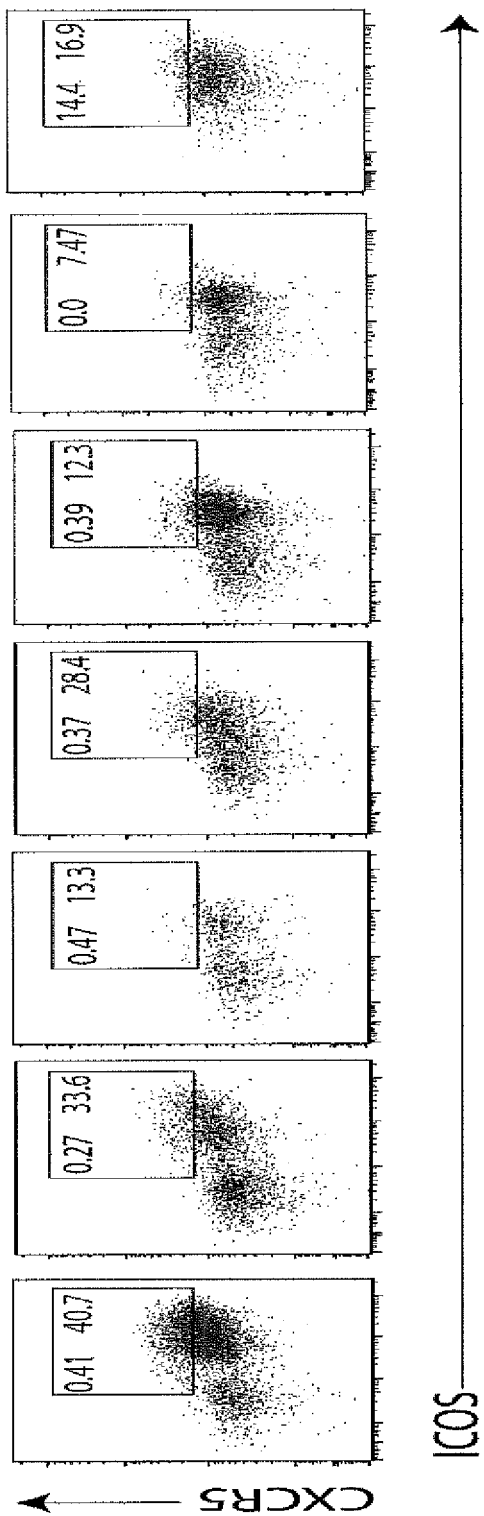
FIG. 17B. Dual color overlay plots showing ICOS and CXCR5 expression on CFP positive transferred cells (red) or endogenous CD28 deficient CD4 T cells (blue) in organs as in FIG. 17A.

Circulating T$_{FH}$ and T$_{FR}$ Cells Migrate to Diverse Lymph Nodes and Tissues To test the hypothesis that circulating T$_{FH}$ and T$_{FR}$ cells represent a memory pool of cells that can migrate to diverse secondary lymphoid organs where they can be reactivated to become effector cells, we next investigated blood T$_{FH}$ and T$_{FR}$ cell trafficking in vivo. To monitor blood T$_{FH}$ and T$_{FR}$ cell behavior in vivo we crossed Actin-CFP mice with FoxP3-IRES-GFP mice to create mice that report FoxP3 expression but can also be tracked in vivo by CFP expression (these mice are referred to as Actin$^{CFP}$-FoxP3$^{GFP}$ mice). We immunized 20 Actin$^{CFP}$-FoxP3$^{GFP}$ mice with NP-OVA and 7 days later sorted total CD4$^+$ICOS$^+$CXCR5$^+$CD19$^-$ cells to keep blood T$_{FH}$ and T$_{FR}$ cells in endogenous proportions. We transferred these cells into CD28$^{-/-}$ recipients, which cannot generate dLN or blood T$_{FH}$ and T$_{FR}$ cells. Transfer into CD28$^{-/-}$ recipients allowed us to transfer very small numbers (2×10$^4$) of cells, yet avoid homeostatic proliferation since CD28$^{-/-}$ mice have substantial T cell populations (Sage et al., 2013). We immunized CD28$^{-/-}$ recipients with NP-OVA subcutaneously and 7 days later isolated lymphoid organs and other tissues and analyzed transferred cells. We found significant populations of transferred cells in all lymph nodes tested, demonstrating that blood T$_{FH}$ and T$_{FR}$ cells have homing properties similar to central memory cells (FIG. 17A). Surprisingly, more than half of the CD4 T cells in the skin around the immunization site were transferred blood CXCR5$^+$ cells, demonstrating that circulating T$_{FH}$ and T$_{FR}$ cells can home to peripheral tissues as well as lymphoid organs. When we examined the transferred cells for ICOS and CXCR5 expression we found that the transferred cells in the lymph nodes and skin highly upregulated ICOS surface expression. However, ICOS expression remained low in the blood and spleen, similar to levels of ICOS expression on sorted blood CXCR5$^+$ cells prior to transfer (FIG. 11A-FIG. 11C, 17A). In comparison, CD28$^{-/-}$ recipient CD4 T cells had very low ICOS expression. CXCR5 expression was maintained on about 40 percent of transferred cells in the draining (inguinal) lymph node. Other organs, particularly the blood, showed lower CXCR5 expression.

Figure 17C:
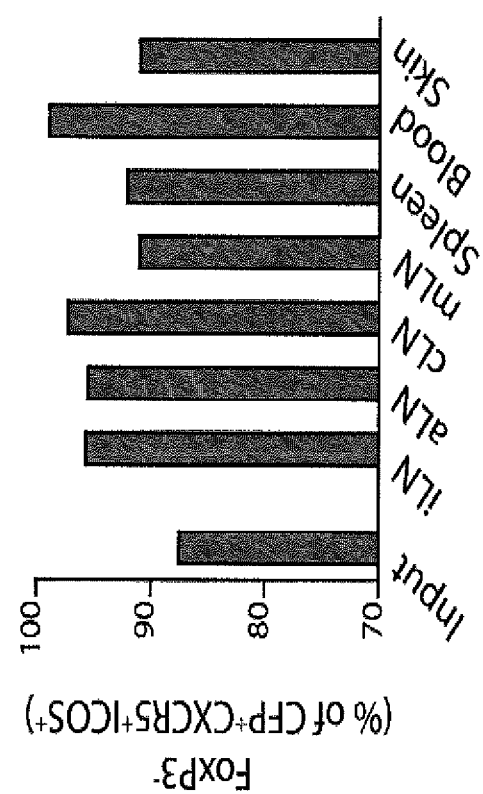
FIG. 17C. Quantification of the percentage of T$_{FH}$ cells of the CFP$^+$CXCR5$^+$ICOS$^+$ transferred cells as in FIG. 17B.
Figure 17D:
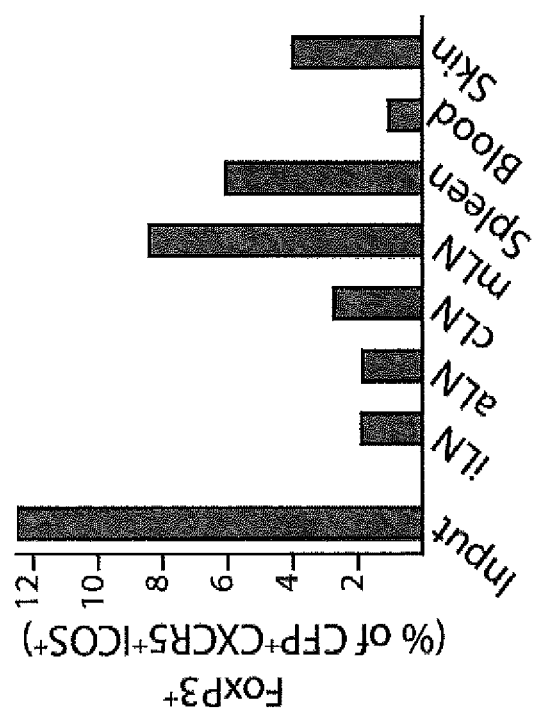
FIG. 17D. Quantification of FoxP3+ cell percentages of the CFP$^+$CXCR5$^+$ICOS$^+$ transferred cells.
Figure 17E:
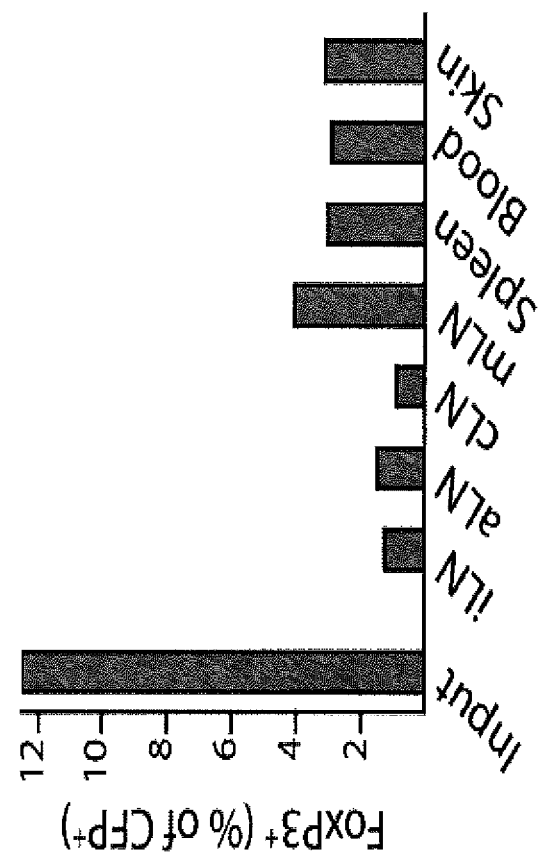
FIG. 17E. Quantification of the percentage of FoxP3+ cells from the total transferred CFP$^+$ population gated as in FIG. 17A.

To determine specifically where T$_{FH}$ and T$_{FR}$ cells homed, we used FoxP3$^{GFP}$ to identify T$_{FR}$ cells in the CFP$^+$ transferred population. The FoxP3$^-$ T$_{FH}$ cells predominated in the transferred population (FIG. 17C). Compared to the percentage of T$_{FR}$ cells in the input population, the percentage of T$_{FR}$ cells in the CXCR5$^+$CFP$^+$ gate in the various lymphoid organs was much lower (FIG. 17D). Therefore, blood T$_{FR}$ cells are more short-lived or proliferate less after homing to various tissues than blood T$_{FH}$ cells. The highest proportion of T$_{FR}$ to T$_{FH}$ cells in the recipients was in the mesenteric lymph node. The overall reduction in T$_{FR}$ cells was not due to CXCR5 downregulation on T$_{FR}$ cells, since this decrease was also seen when FoxP3$^+$ cells were gated on the total CFP transferred population (FIG. 17E).

Figure 17F:
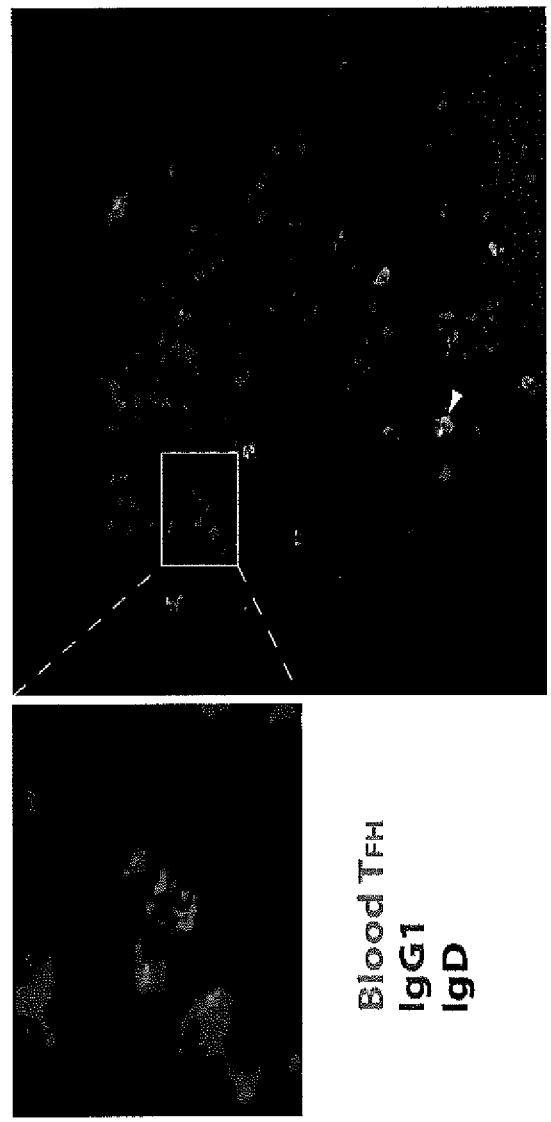
FIG. 17F Interaction of blood T$_{FH}$ cells with IgG1$^+$ B cells upon homing to lymph nodes. 2×10$^4$ blood T$_{FH}$ (CD4$^+$ICOS$^+$ CXCR5$^+$GITR$^-$CD19$^-$) cells from NP-OVA immunized CD45.2 mice were adoptively transferred to CD45.1 mice that were then NP-OVA immunized. 7 days later dLN were stained for CD45.2 (Blood T$_{FH}$), IgG1 or IgD.
Figure 17G:
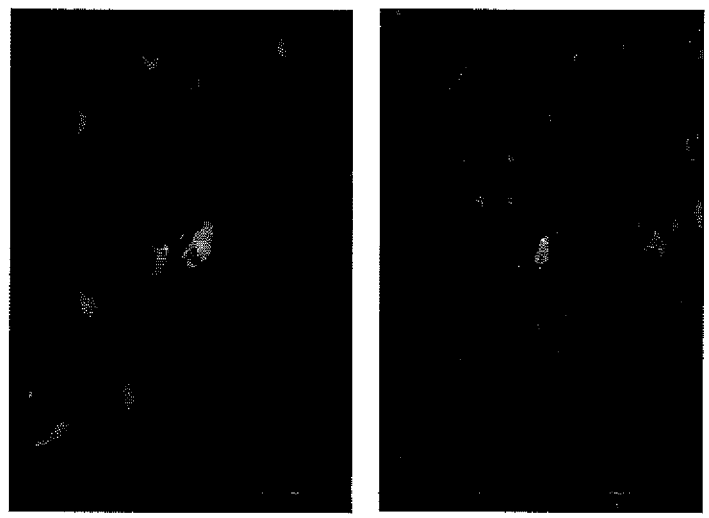
FIG. 17G. Interaction of blood T$_{FR}$ cells with IgG1$^+$ B cells upon homing to lymph nodes. 1×10$^4$ blood T$_{FR}$ (CD4$^+$ ICOS$^+$CXCR5$^+$GITR$^+$CD19$^-$) cells from NP-OVA immunized CD45.2 mice were adoptively transferred to CD45.1 mice that were then NP-OVA immunized. 7 days later dLNs were stained for CD45.2 (Blood T$_{FR}$), FoxP3 or IgG1. Data are from transfers of T$_{FH}$ or T$_{FR}$ cells from 20 pooled mice into a single mouse recipient and representative of at least 2 individual experiments.

To determine if blood T$_{FH}$ and T$_{FR}$ cells are capable of migrating to the B cell zone in order to perform effector functions after homing to lymph nodes, we analyzed the location of transferred cells in dLNs of recipient mice. We immunized CD45.2 WT mice with NP-OVA, transferred sorted blood T$_{FH}$ cells (CD4+ICOS+CXCR5+GITR−CD19−, a gating strategy we have established previously (Sage et al., 2013)) to CD45.1 recipients that were subsequently immunized with NP-OVA. 7 days later we found CD45.2+ blood T$_{FH}$ cells interacting with IgG1+ class switched B cells both within germinal centers and outside germinal centers in the interfollicular zone of the dLN of recipient mice (FIG. 17F). Likewise, when we transferred blood T$_{FR}$ cells (CD4+ICOS+CXCR5+GITR+CD19−) into recipient mice that were subsequently immunized, we found transferred blood T$_{FR}$ cells interacting with IgG1$^+$ class switched B cells in the interfollicular zone, and sometimes directly in the germinal centers of the dLN of recipient mice (FIG. 17G). Taken together, these data indicate the circulating T$_{FH}$ and T$_{FR}$ cells are capable of homing to numerous secondary lymphoid organs and tissues to perform effector functions.

Figure 18A:
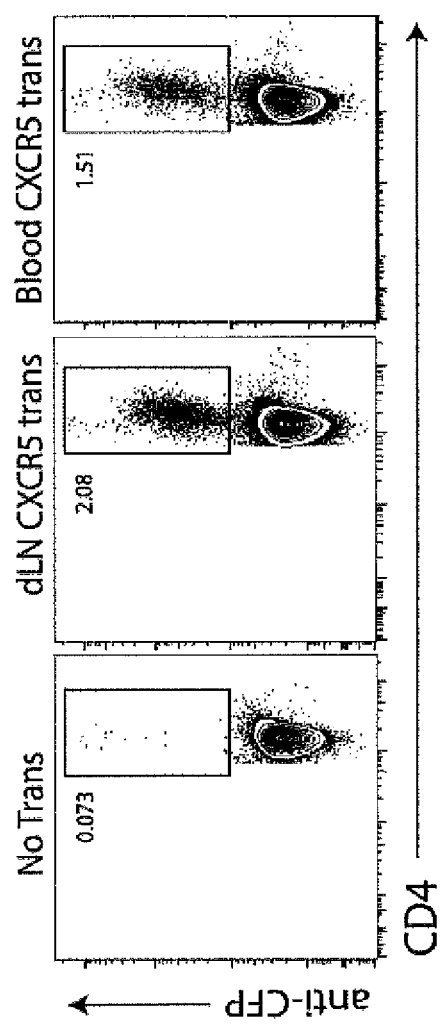
FIG. 18A. Circulating T$_{FH}$ and T$_{FR}$ cells show enhanced activation upon reentering lymphoid organs of immunized mice in vivo. 20, Actin$^{CFP}$-Fox$^{GFP}$ mice were immunized with NP-OVA subcutaneously and 7 days later 2×10$^4$ sorted lymph node or blood CD4$^+$CXCR5$^+$CD19$^-$ cells were adoptively transferred to CD28 deficient mice that were then immunized. 7 days later CFP positive cells in draining lymph nodes were analyzed by flow cytometry. CD28 deficient mice that received no transfer ("No Trans") were used as controls.

Circulating T$_{FH}$ and T$_{FR}$ Cells are More Potently Activated after Transfer In Vivo Next we compared the function of circulating T$_{FH}$ and T$_{FR}$ cells with LN T$_{FH}$ and T$_{FR}$ cells. We hypothesized that if blood T$_{FH}$ and T$_{FR}$ cells have characteristics of memory cells, they would have increased ability to be activated in vivo compared to dLN T$_{FH}$ and T$_{FR}$ cells. To investigate this issue, we immunized Actin$^{CFP}$-FoxP3$^{GFP}$ mice with NP-OVA and 7 days later sorted total CD4$^+$CXCR5$^+$CD19$^-$ cells from the dLN and blood and adoptively transferred these cells intravenously into CD28$^{-/-}$ recipients, which were immunized with NP OVA. As in FIG. 18A, we could readily detect small populations of transferred cells in the dLN of recipients 7 days later based on the presence of CFP (FIG. 18A).

Figure 18B:
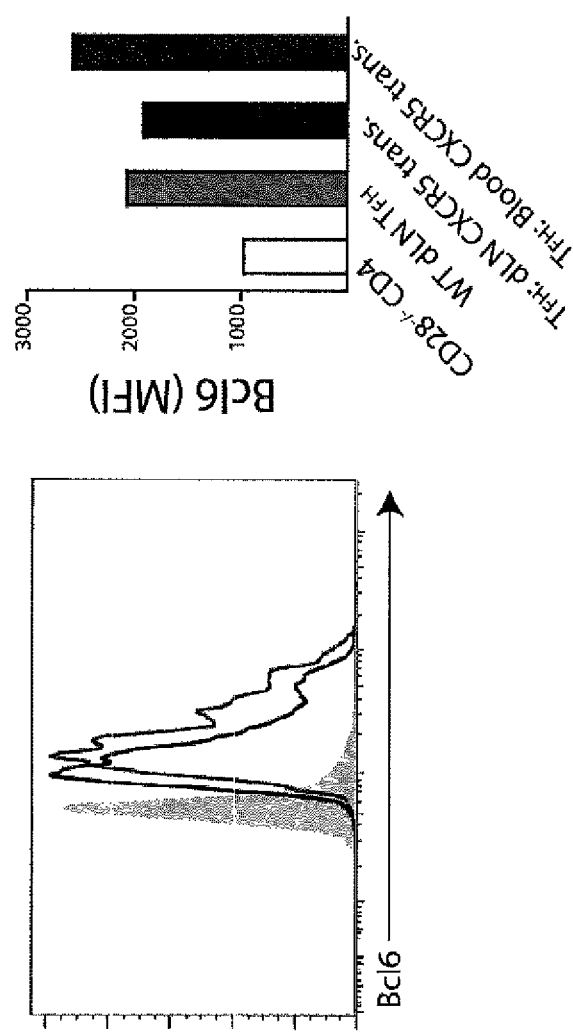
FIG. 18B. Bcl6 expression in dLN FoxP3−CFP+ (TFH) cells in CD28−/− recipients of dLN CXCR5 or blood CXCR5 cells as described in FIG. 18A. WT dLN TFH (CD4+ICOS+CXCR5+FoxP3−CD19−) cells from WT mice immunized 7 days previously were used as positive controls and CD28−/− CD4 T cells from immunized LN were used as negative controls for Bcl6 expression, and shown for comparison.
Figure 18C:
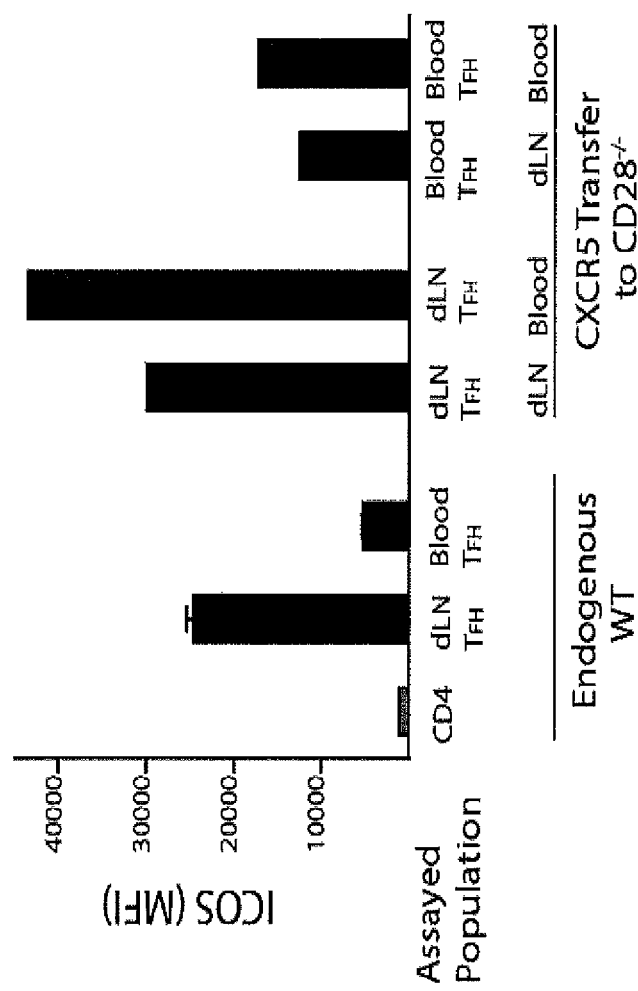
FIG. 18C. ICOS expression on lymph node or blood FoxP3−CFP+ (TFH) cells (assayed population) which originated from either dLN or blood CXCR5 transfers (CXCR5 Transfer) as in FIG. 18A. Total CD4 T cells, dLN and blood TFH from WT immunized mice were included for comparison.
Figure 18D:
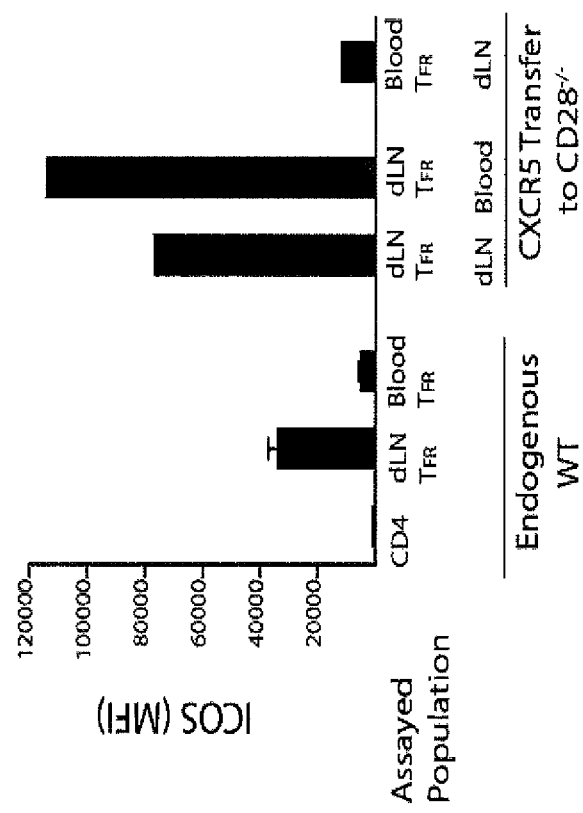
FIG. 18D. ICOS expression on lymph node or blood FoxP3+CFP+ (TFR) cells (assayed population) which originated from either dLN or blood CXCR5 transfers (CXCR5 Transfer) as in FIG. 18C.
Figures 18E, 18F:
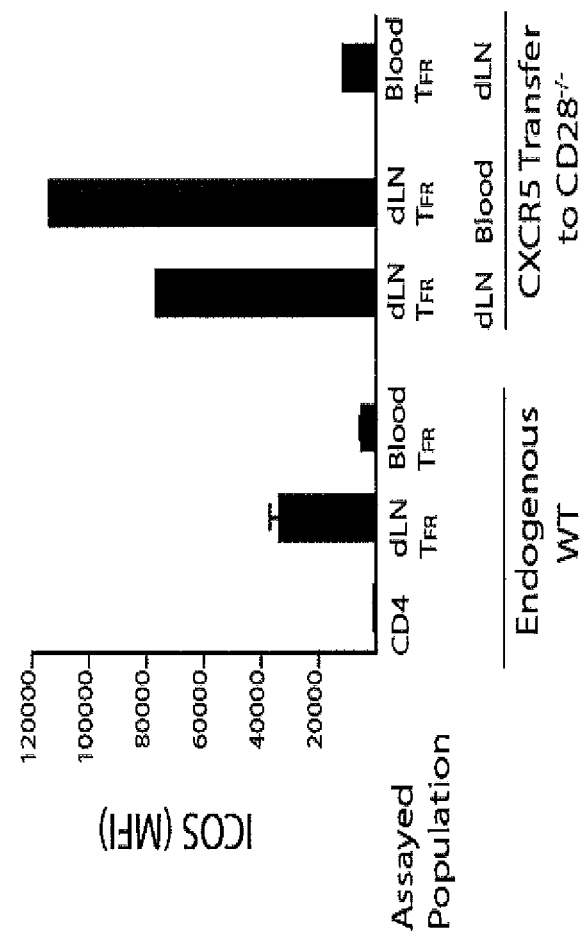
FIG. 18E. CXCR5 expression on lymph node or blood FoxP3−CFP+ (TFH) cells as in FIG. 18C.
FIG. 18F. CXCR5 expression on lymph node or blood FoxP3+CFP+ (TFR) cells as in FIG. 18D.

Since Bcl6 expression is essential for T$_{FH}$ cell function, we investigated if blood T$_{FH}$ cells could upregulate Bcl6 after entering and being activated in the dLN. We found slightly higher Bcl6 expression in transferred blood T$_{FH}$ cells compared to transferred dLN cells (FIG. 18B). These findings indicate that circulating T$_{FH}$ cells can become effector T$_{FH}$ cells upon homing back to a lymph node during an immune response. Next we compared ICOS expression on transferred dLN and blood cells ("CXCR5 Transfer") in the dLN or blood (the "assayed population") of immunized CD28$^{-/-}$ recipients. We also compared ICOS expression on dLN and blood T$_{FH}$ and T$_{FR}$ cells from immunized WT mice ("endogenous WT") in order to facilitate comparisons. ICOS is expressed at a very low level on endogenous WT blood T$_{FH}$ cells from WT mice (FIG. 18C). ICOS expression was dramatically increased on blood T$_{FH}$ cells after homing back to the lymph node (dLN T$_{FH}$ assayed population, blood CXCR5 transfer) compared both to endogenous WT blood T$_{FH}$ cells and even dLN transferred T$_{FH}$ cells (dLN T$_{FH}$ assayed population, dLN CXCR5 transfer) (FIG. 18C). The increased ICOS expression on circulating T$_{FH}$ cells was not unique to the T$_{FH}$ subset, because blood T$_{FR}$ cells that were found in the dLN also greatly upregulated ICOS expression compared to endogenous blood T$_{FR}$ cells and transferred LN T$_{FR}$ cells (FIG. 18D). CXCR5 expression was similar in blood T$_{FH}$ cells upon rehoming to the lymph node and transferred lymph node T$_{FH}$ and T$_{FR}$ cells in the lymph node (FIG. 18E). Blood T$_{FR}$ cells had slightly lower CXCR5 upon rehoming to the lymph node compared to transferred LN T$_{FR}$ cells in the LN (FIG. 18F).

Figure 18G:
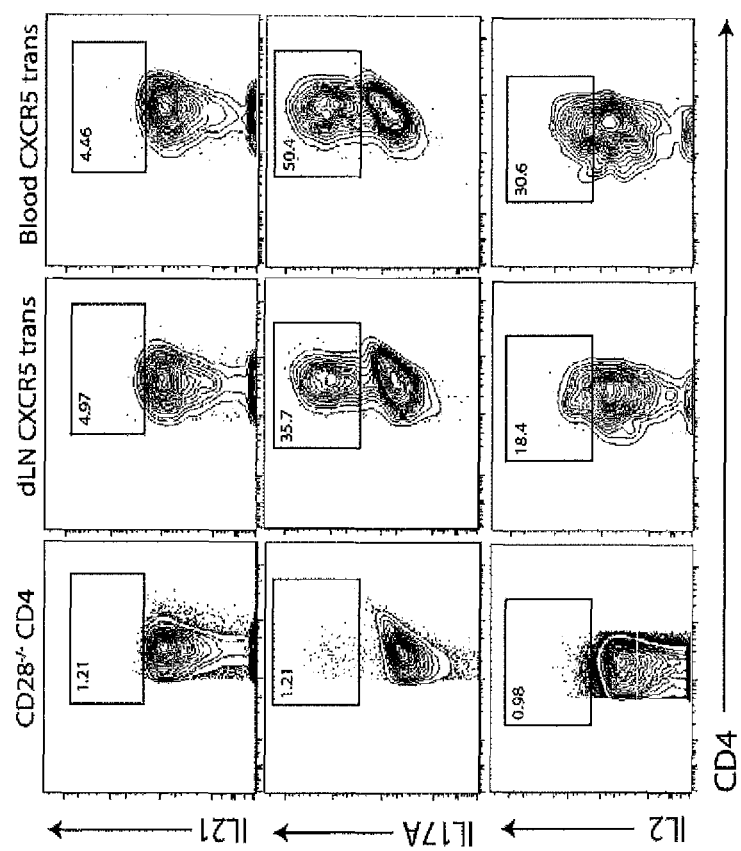
FIG. 18G. Intracellular cytokine production of IL-21, IL-17A or IL-2 by transferred FoxP3−CFP+ (TFH cells) from dLN or blood CXCR5 transfers as in FIG. 18A. Data are from transfers of TFH or TFR cells from 20 pooled mice into a single mouse recipient and representative of at least 2 individual experiments.

To determine if the increase in Bcl6 and ICOS translated into an increase in effector cytokine production by the circulating T$_{FH}$ cells, we compared cytokines produced by the transferred dLN or blood T$_{FH}$ cells found in the dLN after immunization. We found no difference in the very low, but detectable, intracellular IL-21 expression in the transferred blood T$_{FH}$ cells and transferred dLN T$_{FH}$ cells. In contrast, there was a substantial increase in intracellular IL-17A produced by transferred circulating T$_{FH}$ cells compared to transferred dLN T$_{FH}$ cells (FIG. 18G). Intracellular IL-2 expression was also ~2 fold higher in transferred circulating T$_{FH}$ cells, compared to transferred dLN T$_{FH}$ cells (FIG. 18G). Taken together, these data indicate that circulating T$_{FH}$ cells (and T$_{FR}$ cells) can be potently re-activated upon homing to secondary lymphoid organs, consistent with a memory phenotype.

Figure 19A:
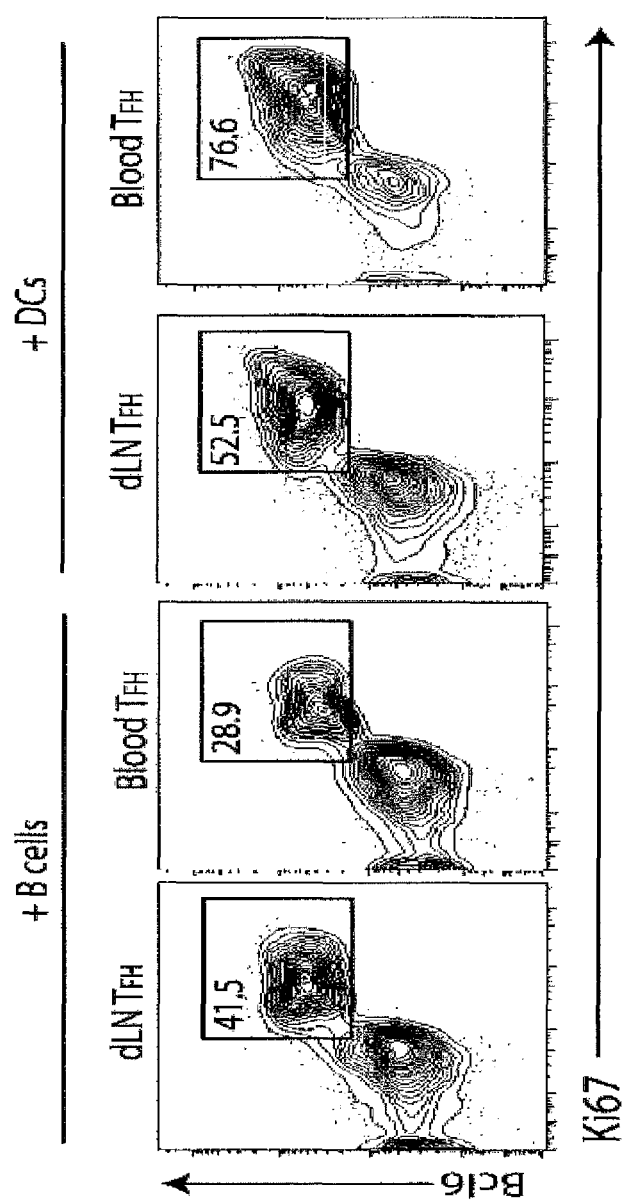
FIG. 19A. Circulating TFH cells Require Dendritic Cells for Restimulation and Have Memory PropertiesIn vitro activation assay in which draining lymph node (dLN) or blood TFH cells (sorted as CD4+ICOS+CXCR5+GITR−CD19−) were plated with B cells or DCs (isolated from lymph nodes of WT mice immunized 7 days previously) in the presence of anti-IgM and anti-CD3 for 6 days. Cells were stained for CD4+CD19− and intracellularly for Bcl6 and Ki67. Plots are pregated on CD4+CD19−. Data indicate means+/−standard error of at least 3 individual experiments.
Figure 19B:
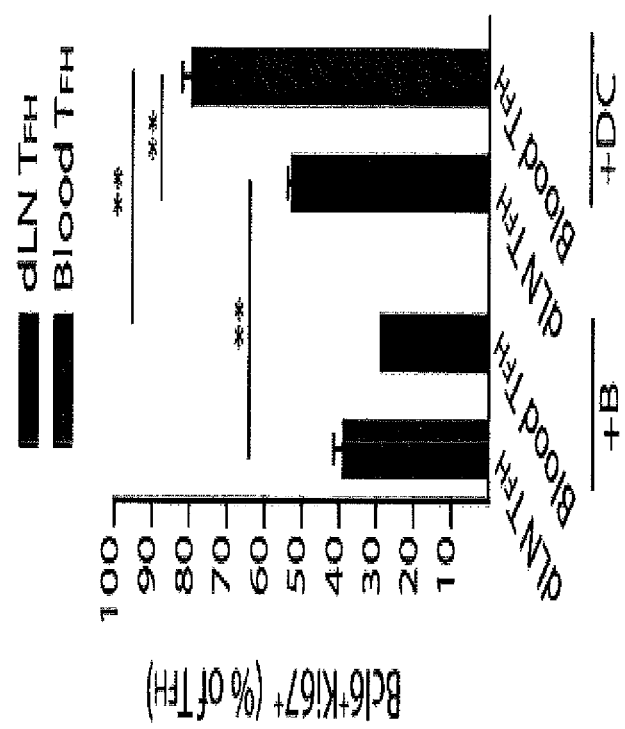
FIG. 19B. Quantification of data presented in FIG. 19A. Data indicate means+/−standard error of at least 3 individual experiments.
Figure 19C:
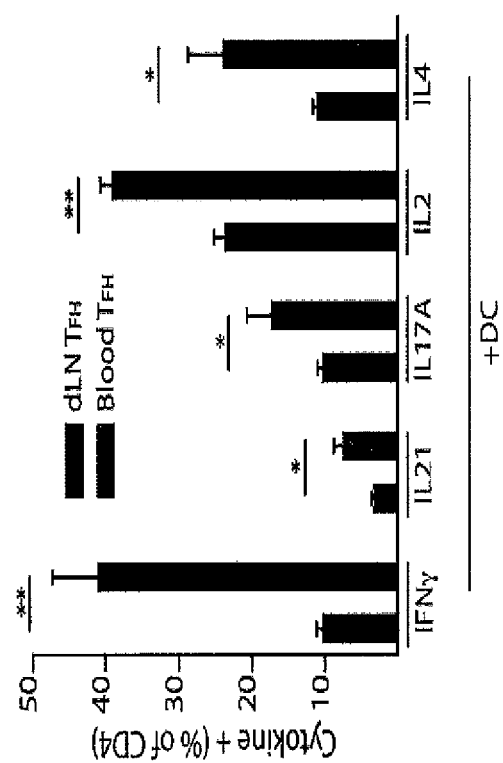
FIG. 19C. Intracellular cytokine staining of samples as in FIG. 19A except samples were stimulated with PMA/Iono for 4 hours in the presence of golgistop. Data indicate means+/−standard error of at least 3 individual experiments.

Circulating T$_{FH}$ Cells Require Dendritic Cells for Restimulation and have Memory Properties Next we investigated the signals required for reactivation of blood T$_{FH}$ cells. We determined if dendritic cells and/or B cells were necessary for reactivation of circulating T$_{FH}$ cells using in vitro systems to sensitively evaluate activation and effector functions of T$_{FH}$ cells. We immunized 20 WT mice with NP-OVA subcutaneously and 7 days later purified dLN and circulating T$_{FH}$ cells by sorting CD4$^+$ICOS$^+$CXCR5$^+$GITR$^-$CD19$^-$ cells, as we previously reported (Sage et al., 2013)). We compared the reactivation of these T$_{FH}$ cells following culture with B cells or dendritic cells (also sorted from dLN of immunized mice) in the presence of anti-CD3 and anti-IgM. We evaluated Bcl6 and Ki67 expression to compare the activation and effector potential of dLN and circulating T$_{FH}$ cells. When cultured with B cells, dLN T$_{FH}$ cells had a higher percentage of Bcl6$^+$Ki67$^+$ cells than circulating T$_{FH}$ cells (FIG. 19A-B). Culturing dLN T$_{FH}$ cells with DCs only modestly increased the percentage of Bcl6$^+$Ki67$^+$ cells, as compared to culture with B cells. In contrast, culture of circulating T$_{FH}$ cells with DCs led to a greatly enhanced percentage of Bcl6$^+$Ki67$^+$ cells, as compared to circulating T$_{FH}$ cells cultured with B cells or lymph node T$_{FH}$ cells cultured with DCs (FIG. 19B). We next investigated if the increased Bcl6 expression in the circulating T$_{FH}$ cells cultured with DCs was associated with enhanced cytokine production. We found profound increases in intracellular IFNγ as well as smaller increases in IL-21, IL-17A, IL-2 and IL-4 in circulating T$_{FH}$ cells compared to lymph node T$_{FH}$ cells cultured with DCs (FIG. 19C).

Figure 19D:
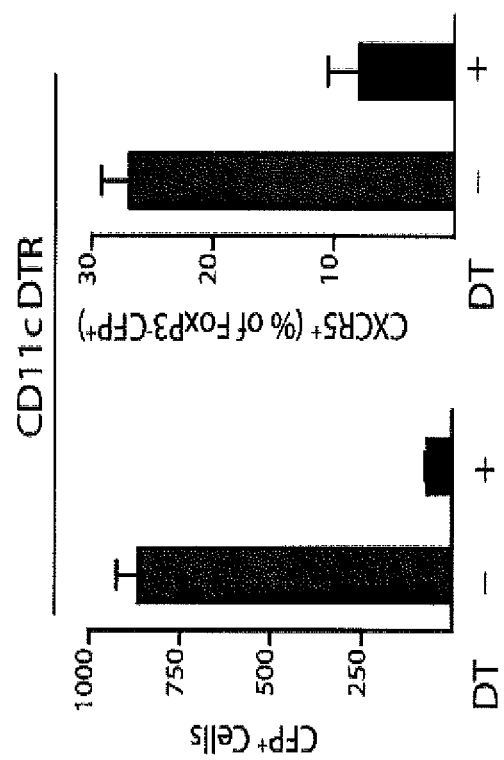
FIG. 19D. Blood TFH cells require DCs for expansion in vivo. 1.5×10^4 blood CD4+CXCR5+CD19− cells from immunized Actin^CFP-Fox^GFP mice were adoptively transferred to CD11 cDTR bone marrow chimeric mice that were immunized with NP-OVA and treated or not with DT on days 0, 3 and 5. 7 days after immunization the draining lymph nodes were harvested for flow cytometric analysis of total CFP+ cells (left) and expression of CXCR5 on CFP+ FoxP3− cells (right). data from transfer of TFH or TFR cells from 20 pooled mice into 3 recipients.
Figure 19E:
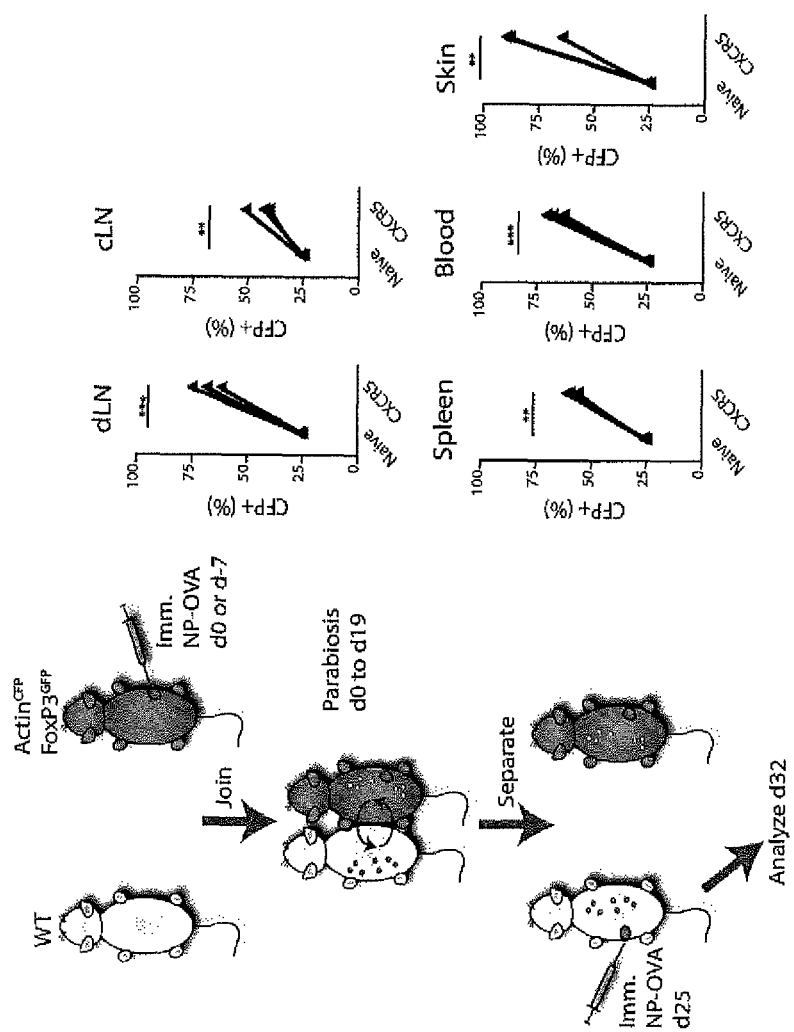
FIG. 19E. Circulating Memory blood CXCR5+ cells dominate the germinal center reaction upon homing to dLNs after challenge. Schematic diagram of parabiosis experiments (left). Actin^CFP Fox^GFP mice were immunized subcutaneously with NP-OVA at d0 or d7. At d0, mice were surgically joined to WT mice and circulatory systems were allowed to freely exchange for 19 days. Mice were then separated and 6 days later the WT "recipient" was immunized with NP-OVA. 7 days later organs were harvested for presence of CFP+ cells. Comparison of CFP+ cells in the non-draining lymph node naïve gate or CXCR5 gate in specified organs (right). Data from 3 individual mice/parabiotants.

To determine if blood T$_{FH}$ cells require DCs for persistence in vivo, we adoptively transferred 1.5×10$^4$ blood CD4$^+$CXCR5$^+$CD19$^-$ cells from immunized Actin$^{CFP}$-FoxP3$^{GFP}$ mice into CD11cDTR bone marrow chimeric mice that were immunized with NP-OVA. We administered diphtheria toxin (DT) on days 0, 3 and 5 during a 7 day immunization to deplete DCs and measured the number of transferred cells 7 days later. We found that DC depletion resulted in fewer CFP$^+$ cells persisting, as well as a lower percentage of cells expressing CXCR5 on the transferred cells (FIG. 19D). Taken together, these data indicate that circulating T$_{FH}$ cells need to be restimulated by dendritic cells and these T$_{FH}$ cells have a superior ability to produce T$_{FH}$ cytokines We next determined if blood T$_{FH}$ and T$_{FR}$ cells could persist in vivo similarly to memory T cells and dominate a GC reaction upon re-exposure to antigen by conducting parabiosis experiments. Actin$^{CFP}$-Fox$^{GFP}$ mice were immunized with NP-OVA and the circulatory systems of these mice were surgically joined to WT mice, allowing transfer of blood T$_{FH}$ and T$_{FR}$ cells to the adjoining mouse (FIG. 19E). After being joined for 19 days, chimerism was confirmed, and mice were separated. The WT "non-immunized" mouse was then immunized with NP-OVA and 7 days later organs were harvested and analyzed. We compared the percent of CFP+ cells in the naïve as well as the CXCR5+ICOS+ populations. The CFP+ population in the naïve gate (from the non-draining lymph node) is indicative of baseline chimerism, and contributions above this percentage in the CXCR5+ICOS+ gate are indicative of increased blood T$_{FH}$/T$_{FR}$ cells in the germinal center. We found significantly enhanced CFP+ cells in the CXCR5+ICOS+ gate in the draining lymph node and less so in the non-draining (cervical) lymph node (FIG. 19E). We also found substantial increases in the CFP population in the spleen, blood and (more dramatically) in the skin. Together these data demonstrate that the blood memory-like CXCR5+ population can out compete and dominate the GC reaction upon re-exposure to antigen.

Figure 19F:
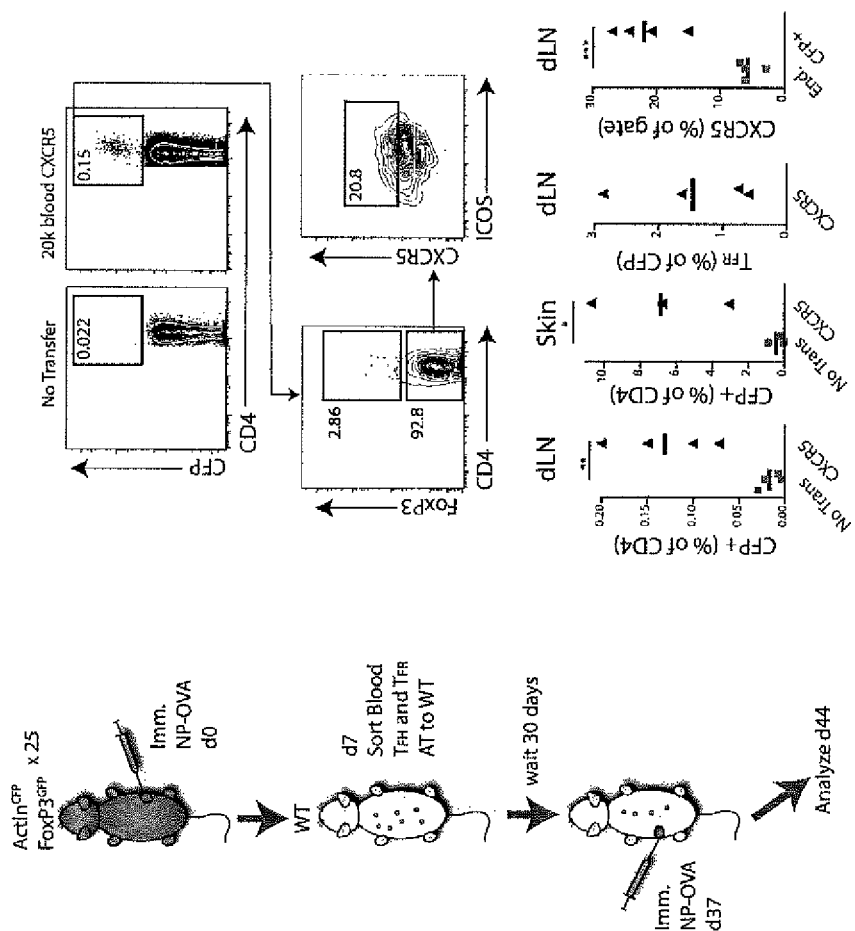
FIG. 19F. Blood TFH and TFR cells persist for 30 days in vivo. 2×10^4 blood CFP+ICOS+CXCR5+CD19− (TFH+TFR) cells were adoptively transferred to WT mice that were immunized with NP-OVA 30 days later (left). Typical flow cytometry plots and quantification of data (right). "End"=endogenous CD4 T cells. Adoptive transfer recipients are compared to mice that did not receive CFP+ cells, "No Trans". Data from 25 pooled mice transferred to a single mouse recipient and repeated 4 times.

Next we used adoptive transfer approaches to analyze T$_{FH}$ and T$_{FR}$ cells at memory time points. We transferred total blood CXCR5+ cells from NP-OVA immunized Actin$^{CFP}$-Fox$^{GFP}$ mice to WT mice. After 30 days, WT recipients were immunized with NP-OVA and draining lymph nodes were harvested 7 days later. We found a small, but substantial population of CFP positive cells in the draining lymph node (FIG. 19F). Although the majority of these cells were T$_{FH}$ cells, there was a very small population of T$_{FR}$ cells that persisted. The T$_{FH}$ cells had high ICOS expression and a sizeable population that maintained CXCR5 expression, suggesting functionality. Taken together these data indicate that blood T$_{FH}$ and T$_{FR}$ cells need to be reactivated by DCs, can dominate the GC reaction upon exposure to antigen, and can persist in vivo similar to memory cells.

T$_{FR}$ Cells Potently Suppress T Cell and B Cell Activation

Next we compared the suppressive functions of lymph node and blood Tfr cells. Since the mechanisms by which T$_{FR}$ cells exert their suppressive effects are not well understood, we first developed a series of sensitive in vitro suppression assays for analyzing T$_{FR}$ cell suppression. We immunized more than 20 WT mice with NP-OVA subcutaneously and 7 days later sorted T$_{FH}$ (CD4$^+$ICOS$^+$CXCR5$^+$ GITR$^-$CD19$^-$) and T$_{FR}$ (CD4$^+$ICOS$^+$CXCR5$^+$GITR$^+$CD19$^-$) cells from the dLN. We cultured T$_{FH}$ cells (with or without T$_{FR}$ cells) together with total B cells or dendritic cells (sorted from the dLN of immunized mice) for 6 days in the presence of anti-IgM and anti-CD3. CXCR5 remained highly expressed on T$_{FH}$ cells whether cultured with B cells or DCs (FIG. 20A). The addition of T$_{FR}$ cells did not cause downregulation of CXCR5 on T$_{FH}$ cells, suggesting that T$_{FR}$ cells do not suppress T$_{FH}$ cells by diverting them away from the germinal center by downregulation of chemokine receptors (FIG. 20A). Bcl6 expression was highly expressed on the T$_{FH}$ cells when cultured with dendritic cells or B cells (FIG. 20B). However, Bcl6 expression in the T$_{FH}$ cells was attenuated profoundly in the presence of T$_{FR}$ cells and DCs (but not B cells), suggesting that T$_{FR}$ cell repriming by DCs may increase T$_{FR}$ suppressive capacity. T$_{FH}$ Ki67 expression also was strongly suppressed by T$_{FR}$ cells in both B cell and DC culture conditions, suggesting that a key T$_{FR}$ cell suppression mechanism is inhibition of cell cycling in T$_{FH}$ cells (FIG. 20C).

To determine if T$_{FH}$ cytokine production was also suppressed by T$_{FR}$ cells, we analyzed T$_{FH}$ cells from in vitro cultures for cytokine production by intracellular staining We found that T$_{FR}$ cells suppressed IFNg, IL-21, IL-10 and TNFα (FIG. 20D). T$_{FR}$ cells had no effect on IL-17A or IL-2 and caused an increase in IL-4. Thus, T$_{FR}$ cells are selective in the T$_{FH}$ cytokines that they suppress, at least in this in vitro model. Together, these studies suggest that T$_{FR}$ cells exert their suppressive effects by inhibiting T$_{FH}$ cell proliferation and cytokine production.

We next investigated whether T$_{FR}$ cells also affect B cell function. We cultured dLN T$_{FH}$ and B cells with or without T$_{FR}$ cells in the presence of anti-CD3 and anti-IgM for 6 days and then analyzed the B cells from these cultures. The germinal center B cell marker GL7 was highly upregulated on B cells when cultured with T$_{FH}$ cells, but markedly reduced when T$_{FR}$ cells were present in co-cultures (FIG. 20E-F). Importantly, this in vitro suppression depends on the "T$_{FR}$ program" as FoxP3+CXCR5− cells sorted from unimmunized lymph nodes did not attenuate the expression of GL7 on B cells in contrast to T$_{FR}$ cells (FIG. 20F). Furthermore, Ki67 expression was greatly attenuated in B cells when cocultured with T$_{FH}$ and T$_{FR}$ cells as compared to culture with T$_{FH}$ cells alone, demonstrating potent suppression of B cell activation by T$_{FR}$ cells (FIG. 20G). T$_{FR}$ cells also inhibited IgG1 expression in B cells. A substantial portion of B cells class switched to IgG1 when cultured with T$_{FH}$ cells but this was abrogated in the presence of T$_{FR}$ cells (FIG. 20H-I). B cell class switch recombination suppression was dependent on the T$_{FR}$ program, since non-T$_{FR}$ Tregs could not suppress IgG1 levels on B cells (FIG. 20I). Taken together these data indicate that lymph node T$_{FR}$ cells can suppress T$_{FH}$ cell activation, as well as B cell activation and antibody production in vitro.

Weaker B Cell Suppression by Blood T$_{FR}$ Cells

Finally, since blood T$_{FH}$ cells can be reactivated more potently than LN T$_{FH}$ cells, we compared the suppressive functions of blood T$_{FR}$ cells and dLN T$_{FR}$ cells. We compared the abilities of dLN T$_{FR}$ and blood T$_{FR}$ cells to suppress dLN T$_{FH}$ cells and B cells using the assays described above. T$_{FH}$ cells promoted IgG1 and GL7 expression in B cells (FIG. 21A). Blood T$_{FR}$ cells were able to greatly suppress IgG1 expression in B cells, but were less potent than dLN T$_{FR}$ cells. Additionally, blood T$_{FR}$ cells were able to attenuate GL7 expression, but this was not as robust as the attenuation by dLN T$_{FH}$ cells (FIG. 21B). Thus, dLN T$_{FR}$ cells potently suppress B cell activation but blood T$_{FR}$ cells suppress B cell responses to a somewhat lesser extent than dLN T$_{FR}$ cells. Additionally, a lower percentage of blood T$_{FR}$ cells expressed Ki67, compared to dLN T$_{FR}$ cells, regardless of culture with B cells or DCs (FIG. 21C). Therefore, unlike blood T$_{FH}$ cells, blood T$_{FR}$ cells are not more potently activated by DCs than dLN T$_{FR}$ cells.

Since blood T$_{FH}$ cells are more potent than LN T$_{FH}$ cells and blood T$_{FR}$ cells are less inhibitory than LN T$_{FR}$ cells in vitro, we next compared the effect of the total blood CXCR5 (T$_{FH}$/T$_{FR}$ cells) population on B cell activation in vivo compared to dLN CXCR5 cells. We sorted total CXCR5+ cells from dLNs or blood of immunized Actin$^{CFP}$ Fox$^{GFP}$ mice (which had the same T$_{FH}$/T$_{FR}$ ratios) and adoptively transferred these cells to CD28$^{-/-}$ recipient mice that were immunized as in FIG. 18A. When we analyzed the draining lymph node 10 days after adoptive transfer, we detected a greater percentage of both GC B cells and plasma cells in the mice that received blood CXCR5+ cells (FIG. 21D-E). Taken together, these data indicate that stimulatory blood T$_{FH}$ cells are poised to provide a quick and robust memory-like response in secondary lymphoid organs.

Discussion

In this study we have determined that "memory-like" blood T$_{FH}$ and T$_{FR}$ cells differ from "effector" dLN T$_{FH}$ and T$_{FR}$ cells because they provide systemic B cell control in secondary lymphoid organs and not just at the site of differentiation. We demonstrate that blood T$_{FH}$ and T$_{FR}$ cells have distinct phenotypes and require different cues for generation compared to lymph node T$_{FH}$ and T$_{FR}$ cells. Additionally, we show that circulating T$_{FH}$ and T$_{FR}$ cells can be potently activated by DCs in diverse secondary lymphoid organs and tissues. Finally, beyond their ability to home to and patrol diverse sites of possible antigen encounter, we find that blood T$_{FH}$ and T$_{FR}$ cells may provide effector functions differing from LN T$_{FH}$ and T$_{FR}$ cells upon reactivation. Therefore, blood T$_{FH}$ and T$_{FR}$ cells constitute distinct subsets that share many hallmarks of memory cells and the blood T$_{FH}$ cells can provide a quick and robust response to stimulate humoral immunity.

We find that dendritic cell signals are important for blood T$_{FH}$ and T$_{FR}$ development, but T$_{FH}$ and T$_{FR}$ cell numbers are not altered in mice that lack mature B cells. This contrasts with lymph node T$_{FH}$ and T$_{FR}$ cells that are lacking in μMT mice (Haynes et al., 2007; Johnston et al., 2009; Linterman et al., 2011; Poholek et al., 2010). However, it is important to note that the μMT mouse has an altered lymph node structure and blood T$_{FH}$/T$_{FR}$ cell behavior may be a consequence of these alterations. Nevertheless, our studies suggest that circulating memory-like T$_{FH}$ and T$_{FR}$ cells are not derived from lymph node T$_{FH}$ and T$_{FR}$ cells, but differentiate in parallel with lymph node T$_{FH}$ and T$_{FR}$ cells.

The signals that elicit dLN versus circulating memory-like T$_{FH}$ and T$_{FR}$ differentiation are not clear. Full T cell activation in general is thought to occur through multiple serial contacts with dendritic cells leading to full activation (Mempel et al., 2004). We hypothesize that two fates emerge for follicular CD4 T cells during differentiation with DCs. Subsets of T$_{FH}$ and T$_{FR}$ cells that have lower CXCR5 expression and low CD69 after priming exit the lymph node via S1P gradients and are destined to become blood memory cells. T$_{FH}$ and T$_{FR}$ cells with higher CXCR5 and high CD69 after priming follow CXCL13 gradients and migrate to the B cell zone, where full differentiation and maintenance of the T$_{FH}$ and T$_{FR}$ effector phenotype occurs. Therefore, within the "window" for T$_{FH}$ and T$_{FR}$ differentiation, subtle differences in TCR and/or costimulation can push the fate of the cells towards an effector or memory T$_{FH}$/T$_{FR}$ cell phenotype. Importantly, when T$_{FH}$ and T$_{FR}$ cells enter the efferent lymph, they already have a surface phenotype similar to blood T$_{FH}$ and T$_{FR}$ cells, suggesting that the circulating/memory T$_{FH}$ and T$_{FR}$ cell phenotype is acquired during differentiation and not after entry into the circulation. These data also demonstrate that circulating T$_{FH}$ and T$_{FR}$ cells do not originate from GC T$_{FH}$ cells. This is consistent with a recent study which demonstrated that GC T$_{FH}$ cells can move between the GC and interfollicular regions, but do not enter the circulation (Shulman et al., 2013).

Our studies with the SIP agonist FTY720, as well as our transfer and tracking experiments, suggest that T$_{FH}$ and T$_{FR}$ cells recirculate from the blood to secondary lymphoid organs and tissues rather quickly, on the order of hours. We hypothesize that the function of circulating T$_{FH}$ cells is to probe various organs for antigen and provide specialized and robust B cell help during secondary antigen exposure or systemic infections. Relatively lower expression of CXCR5 on circulating T$_{FH}$ and T$_{FR}$ cells may allow these cells to better patrol T cell zones for DCs presenting antigen, while LN T$_{FH}$ and T$_{FR}$ cells may get "stuck" in the B cell follicle due to high CXCL13 levels present there. Circulating T$_{FR}$ cells may help to regulate circulating T$_{FH}$ responses to ensure that antigen-specific B cell responses are generated, but limit hyperactivation or antibody production in distal secondary lymphoid organs.

We previously showed that blood T$_{FH}$ cells stimulate more IgG production in vivo than dLN T$_{FH}$ cells (Sage et al., 2013). Here we demonstrate that upon reactivation by dendritic cells (but not B cells), blood T$_{FH}$ cells produce more cytokines, particularly IFNγ compared to dLN T$_{FH}$ cells. Classical experiments have demonstrated that IFNγ can inhibit B cell class switching from IgG1 to IgG2a, and recent studies have suggested that directed IFNγ production, presumably by T$_{FH}$ cells, has a similar effect (Reinhardt et al., 2009). However, in our experiments, blood T$_{FH}$ cells do not skew antibody isotypes away from IgG1 to any particular isotype in vivo or in vitro (data not shown). Although IFNγ is the cytokine that is most highly expressed by blood T$_{FH}$ cells compared to dLN T$_{FH}$ cells, there are slight increases in other cytokines as well. This suggests that blood T$_{FH}$ cells have an increased effector function upon restimulation by DCs and are not simply Th1-skewed T$_{FH}$ cells. The distinct cytokine profile of blood T$_{FH}$ cells may lead to specialized differentiation and/or function of germinal center B cells or plasma cells.

Far less is known about the signals necessary for the differentiation and function of T$_{FR}$ cells than T$_{FH}$ cells (Chung et al., 2011; Linterman et al., 2011; Sage et al., 2013; Wollenberg et al., 2011). LN T$_{FR}$ cell development follows many of the same cues as T$_{FH}$ cells, such as the B cell requirement in the lymph node as well as CD28 and ICOS costimulation (Linterman et al., 2011; Sage et al., 2013). It has been suggested that subsets of Treg cells (such as T$_{FR}$ cells) may use T helper transcription factors that are not normally expressed by Tregs to help position themselves near T helper cells and/or to program T helper specific suppression (Josefowicz et al., 2012). For example, adipose tissue-resident Tregs, similar to other cells present in adipose tissue, depend on PPAR-γ (Cipolletta et al., 2012). We previously showed that the T$_{FR}$ program is essential for suppression of antibody production as CXCR5 Tregs could not suppress antibody production in vivo (Sage et al., 2013). The exact mechanisms of T$_{FR}$ cell suppression are not known (Josefowicz et al., 2012). Here we show that lymph node T$_{FR}$ cells potently suppress activation of T$_{FH}$ cells, but do not suppress CXCR5 or Bcl6 expression in T$_{FH}$ cells cultured with B cells. Draining LN T$_{FR}$ cells can also suppress IFNγ, IL21, IL10 and TNFα expression by T$_{FH}$ cells. Interestingly, dLN T$_{FR}$ cells were unable to suppress IL17A or IL2 production in dLN T$_{FH}$ cells, at least in in vitro models. In addition, we find that dLN T$_{FR}$ cells potently suppress dLN T$_{FH}$-mediated B cell activation, class switch recombination and germinal center markers. Importantly, non-T$_{FR}$ FoxP3$^+$ Tregs were not able to suppress GL7 or class switching to IgG1. Since these in vitro assays do not depend on distinct T and B cell zones, the inability of non-T$_{FR}$ cells to suppress B cells suggests a "T$_{FR}$ program" beyond CXCR5 expression that is essential for T$_{FR}$ cell suppressive functions.

It is not currently known if T regulatory cells can possess immunological memory. One report showed that self-reactive Tregs can possess some form of regulatory memory at least within the skin (Rosenblum et al., 2011). Here we demonstrate that memory-like blood T$_{FR}$ cells can home to diverse secondary lymphoid organs, including the skin. Within the skin T$_{FR}$ cells may inhibit effector T cells or provide specific suppression of memory-like T$_{FH}$ cells and antibody secreting cells (ASCs). It also is possible that T$_{FR}$ cells may suppress formation of ectopic follicles that can arise during certain inflammatory conditions within the tissue (Peters et al.). We hypothesize that the main role of blood T$_{FR}$ cells is to provide systemic control of humoral immunity during an immune response by migrating throughout the body to organs that may be exposed to antigens. Blood T$_{FR}$ cells may function to ensure proper T$_{FH}$ control and thereby limit excessive or inappropriate B cell help. Additionally, blood T$_{FR}$ cells may prevent humoral autoimmunity by raising the threshold for B cell activation in situations where an abundance of proinflammatory cytokines might bypass the need for T$_{FH}$ help.

Since blood T$_{FR}$ cells require distinct cues compared to lymph node T$_{FR}$ cells, it is likely that blood T$_{FR}$ cells may be programmed differently than lymph node T$_{FR}$ cells. We show here that both lymph node and blood T$_{FR}$ cells are able to attenuate B cell activation but blood T$_{FR}$ cells are less suppressive. This difference may be due to differential programming during development. Further experiments are needed to investigate these issues. Importantly, the T$_{FH}$:T$_{FR}$ ratio, which is important in controlling humoral immunity (Sage et al., 2013), is roughly similar between LN and blood T$_{FH}$:T$_{FR}$ cells. Therefore, functional differences between blood and LN CXCR5$^+$ cells can be attributed to cell intrinsic differences in the T$_{FH}$ and T$_{FR}$ compartments. By interrogating these cells individually, we show that blood T$_{FH}$ cells are more potently activated upon restimulation (compared to LN T$_{FH}$ cells) and blood T$_{FR}$ cells are less suppressive (compared to LN T$_{FR}$ cells). Additionally, in memory experiments, the T$_{FH}$ to T$_{FR}$ ratio is skewed towards the T$_{FH}$ cell. The combination of these cell intrinsic and extrinsic differences allow circulating memory T$_{FH}$ cells to quickly respond to antigen and activate B cells in lymph nodes after a secondary exposure to antigen. We show in parabiosis experiments that the CXCR5+ population of the non-immunized parabiotic mouse is dominated by blood derived CXCR5+ cells after immunization, demonstrating that the blood-derived CXCR5+ population controls the GC response more potently than newly generated LN CXCR5 cells. We hypothesize this is a key mechanism by which quick and efficient secondary responses are generated upon re-exposure to antigen in distant tissues. Understanding the mechanisms of T$_{FH}$ and T$_{FR}$ cell memory should provide insights into strategies for developing long-lasting B cell memory to vaccines and for controlling pathogenic B cell responses.

Experimental Procedures

Mice.

6-8 week old mice were used for all experiments. WT C57BL/6, CIITA$^{-/-}$, Itax-DTR (CD11c-DTR), Ighm$^{-/-}$ (mMT) and Actin$^{CFP}$ mice were purchased from The Jackson Laboratory (Bar Harbor, Me.). CD28$^{-/-}$ mice were generated as described (Shahinian et al., 1993). Actin$^{CFP}$ FOX$^{GFP}$ mice were generated by crossing Actin$^{CFP}$ mice with Fox-IRES-GFP mice (Bettelli et al., 2006). For CD11c-DTR experiments, bone marrow chimeras were made by irradiating WT recipient mice with 600 rads twice, separated by 3 hours, and adoptively transferring $7 \times 10^6$ bone marrow cells. Mice were used after 8 weeks of reconstitution, and reconstitution was confirmed by flow cytometry. Mice were injected with 1 mg diphtheria toxin (Sigma) intraperitoneally every 2 days starting at day 0 after immunization and harvested on day 7. In some experiments WT mice were injected intraperitoneally with 25 mg/kg FTY720 (Cayman Chemical) every 2 days starting at day 2 after immunization. Alternatively, mice were injected with the FTY720 3 or 6 hours before harvesting organs. Thoracic duct cannulation was performed as described previously (Massberg et al., 2007). All mice were used according to the Harvard Medical School Standing Committee on Animals and National Institutes of Animal Healthcare Guidelines. Animal protocols were approved by the Harvard Medical School Standing Committee on Animals.

Immunizations

For NP-OVA immunizations, 100 µg NP$_{18}$-OVA (Biosearch Technologies) in a 1:1 H37RA CFA (DIFCO) emulsion was injected subcutaneously on the mouse flanks Seven days later mice were euthanized and inguinal lymph nodes (dLN) were harvested, blood was collected via cardiac puncture with a 1 cc syringe and immune cells were isolated by sucrose density centrifugation using Lymphocyte Separation Media (LSM).

Bone Marrow Derived Dendritic Cells

Bone marrow derived dendritic cells (BMDCs) were made by culturing total bone marrow cells in the presence of 30 ng/ml GM-CSF (Peprotech) for 7 days. During the last 24 hours, 20 ng/ml of LPS (sigma) and 20 µg/ml of NP-OVA were added to the cultures. Cells were harvested, washed extensively and counted on an Accuri cytometer. $1 \times 10^6$ cells were subcutaneously injected in 100 ul PBS on the flank of WT mice. 5 days later the inguinal lymph node and blood were harvested and analyzed for T$_{FH}$ and T$_{FR}$ cells.

Flow Cytometry

Cells from lymphoid organs were isolated and resuspended in staining buffer (PBS containing 1% fetal calf serum and 2 mM EDTA) and stained with directly labeled antibodies from Biolegend against CD4 (RM4-5), ICOS (15F9), CD19 (6D5), CD69 (H1.2F3) CD11c (N418), MHC II (M5/114.15.2), IL17A (TC11-18H10.1), IL2 (JES6-5H4), IFNg (XMG1.2), IL4 (11B11), TNFα (MP6-XT22), CD138 (281-2), from eBioscience against FoxP3 (FJK-165), Bcl6 (mGI191E), IL21 (FFA21), from BD bioscience against GL7, Ki67 (B56) and IgG1 (A85-1), and from Abcam, goat anti-GFP. For CXCR5 staining, biotinylated anti-CXCR5 (2G8, BD Biosciences) was used followed by streptavidin-brilliant violet 421 (Biolegend). For intracellular staining of transcription factors and Ki67, the FoxP3 fix/perm kit was used (eBioscience) after surface staining was accomplished. For intracellular cytokine staining, cells were incubated with 1 µg/ml ionomycin (Sigma) and 500 ng/ml PMA (Sigma) in the presence of Golgistop (BD biosciences) for 4 hours prior to staining. All flow cytometry was analyzed with an LSR II (BD biosciences) using standard filter sets.

Adoptive Transfers

For CXCR5$^+$ T cell transfers, 20 Actin$^{CFP}$ Fox$^{GFP}$ mice were immunized with NP-OVA subcutaneously as described above, and 7 days later dLN or blood was collected. $2 \times 10^5$ CFP$^+$CD4$^+$ICOS$^+$CXCR5$^+$ cells were adoptively transferred to CD28$^{-/-}$ or WT mice that were then immunized subcutaneously with NP-OVA. For memory experiments, recipients were immunized after 30 days. 7 days later organs were harvested. Skin from the immunization site was digested with 500 U/ml collagenase (Worthington Biochemical). Transferred cells were identified by either CFP expression or intracellularly with an anti-GFP polyclonal antibody (Abcam).

Parabiosis

For parabiosis, age- and sex-matched Actin-$^{GFP}$ Fox-$^{GFP}$ mice and C57Bl/6 mice were anesthetized by ketamine/xylazine (i.p.) and surgically joined at the olecranons and knees as described previously (Massberg et al., 2007). Briefly, the lateral sides of each mouse were shaved and wiped with depilatory cream, and incisions were made along the lateral aspect of each mouse from the olecranon to the knee. The subcutaneous fascia was bluntly dissected to expose loose ventral and dorsal skin flaps for connection. Mice were first joined together at the olecranons and knees by a double ligature using 4-0 braided silk suture. Next, the ventral and dorsal skin flaps overlying the olecranon and knee region were joined by continuous 6-0 braided silk suture. Finally, the remaining dorsal and ventral skin flaps between the olecranons and knees were connected by staples. Parabiotic mice were separated after 19 days by reversal of the above procedure. Mice were immunized with NP-OVA subcutaneously on the non-joined side 6 days later. Chimerism among different leukocyte populations was calculated as the average of the percent of CFP+ cells in the WT mouse in the non-draining lymph nodes.

In Vitro Suppression Assay

All populations were sorted to 98% purity on a FACS Aria using standard detectors. Cells were counted on an Accuri cytometer (BD biosciences) by gating live cells only. For T$_{FH}$ stimulation assays, $2 \times 10^4$ dLN or blood CD4$^+$ICOS$^+$ CXCR5$^+$CD19$^-$ GITR$^-$ T$_{FH}$ cells were plated with $5 \times 10^4$ CD19$^+$ B cells or $2 \times 10^4$ CD3$^-$CD19$^-$CD11c$^+$ DCs, all from dLNs of WT mice immunized with NP-OVA 7 days previously. For DCs, dLNs were digested with 500 U/ml Collagenase I (Worthington Biochemical) before isolation. T$_{FH}$ plus B or DCs were cultured in the presence of 2 µg/ml soluble anti-CD3 (2C11, BioXcell) and 5 µg/ml anti-IgM (Jackson Immunoresearch) for 5-6 days. Cells were then harvested and stained for flow cytometry. Intracellular expression of Bcl6 and Ki67 were used as readouts for T$_{FH}$ cell activation and functional potential. Intracellular expression of IgG1 was used as a readout for B cell class switch recombination. For T$_{FR}$ suppression assays, $1 \times 10^4$ CD4$^+$ ICOS$^+$CXCR5$^+$CD19$^-$GITR$^+$ T$_{FR}$ cells from either the dLN or blood of WT mice immunized with NP-OVA 7 days previously were added to the wells of T$_{FH}$ stimulation assays. Cells were harvested 5-6 days later.

Confocal Microscopy

Confocal microscopy was performed as described previously (Sage et al., 2013). Briefly, organs were harvested and embedded and frozen in OCT medium (Tissue-Tek). 10 um sections were cut, fixed and stained using the FoxP3 kit (ebioscience). Samples were imaged using an Olympus confocal microscope using standard configurations.

Statistical Analysis

Unpaired Student's t test was used for all comparisons, data represented as mean+/−SD or SE are shown. P values <0.05 were considered statistically significant. * P<0.05,  P<0.005, * P<0.0005.

(G) Quantification of lymph node and blood T$_{FR}$ cells from plots in (F). Total CD4$^+$FoxP3$^+$CD19$^−$ cells "Total FoxP3+" are included as controls. (H-J) CXCR5 (H), ICOS (I), Ki67 (J) expression on lymph node and blood T$_{FR}$ cells gated as in (F). Data are means+/−standard error with 5 mice per group. Data are representative of at least 3 independent experiments.

References

Bauquet, A. T., Jin, H., Paterson, A. M., Mitsdoerffer, M., Ho, I. C., Sharpe, A. H., and Kuchroo, V. K. (2009). The costimulatory molecule ICOS regulates the expression of c-Maf and IL-21 in the development of follicular T helper cells and TH-17 cells. Nature immunology 10, 167-175.

Bettelli, E., Carrier, Y., Gao, W., Korn, T., Strom, T. B., Oukka, M., Weiner, H. L., and Kuchroo, V. K. (2006). Reciprocal developmental pathways for the generation of pathogenic effector TH17 and regulatory T cells. Nature 441, 235-238.

Bossaller, L., Burger, J., Draeger, R., Grimbacher, B., Knoth, R., Plebani, A., Durandy, A., Baumann, U., Schlesier, M., Welcher, A. A., et al. (2006). ICOS deficiency is associated with a severe reduction of CXCR5+CD4 germinal center Th cells. J Immunol 177, 4927-4932.

Breitfeld, D., Ohl, L., Kremmer, E., Ellwart, J., Sallusto, F., Lipp, M., and Forster, R. (2000). Follicular B helper T cells express CXC chemokine receptor 5, localize to B cell follicles, and support immunoglobulin production. J Exp Med 192, 1545-1552.

Cannons, J. L., Lu, K. T., and Schwartzberg, P. L. (2013). T follicular helper cell diversity and plasticity. Trends Immunol.

Choi, Y. S., Kageyama, R., Eto, D., Escobar, T. C., Johnston, R. J., Monticelli, L., Lao, C., and Crotty, S. (2011). ICOS receptor instructs T follicular helper cell versus effector cell differentiation via induction of the transcriptional repressor Bcl6. Immunity 34, 932-946.

Chung, Y., Tanaka, S., Chu, F., Nurieva, R. I., Martinez, G. J., Rawal, S., Wang, Y. H., Lim, H., Reynolds, J. M., Zhou, X. H., et al. (2011). Follicular regulatory T cells expressing Foxp3 and Bcl-6 suppress germinal center reactions. Nat Med 17, 983-988.

Cipolletta, D., Feuerer, M., Li, A., Kamei, N., Lee, J., Shoelson, S. E., Benoist, C., and Mathis, D. (2012). PPAR-gamma is a major driver of the accumulation and phenotype of adipose tissue Treg cells. Nature 486, 549-553.

Crotty, S. (2011). Follicular helper CD4 T cells (TFH) Annu Rev Immunol 29, 621-663.

Cyster, J. G. (2005). Chemokines, sphingosine-1-phosphate, and cell migration in secondary lymphoid organs. Annu Rev Immunol 23, 127-159.

Cyster, J. G., and Schwab, S. R. (2011). Sphingosine-1-Phosphate and Lymphocyte Egress from Lymphoid Organs. Annu Rev Immunol.

Fazilleau, N., Eisenbraun, M. D., Malherbe, L., Ebright, J. N., Pogue-Caley, R. R., McHeyzer-Williams, L. J., and McHeyzer-Williams, M. G. (2007). Lymphoid reservoirs of antigen-specific memory T helper cells. Nature immunology 8, 753-761.

Goenka, R., Barnett, L. G., Silver, J. S., O'Neill, P. J., Hunter, C. A., Cancro, M. P., and Laufer, T. M. (2011). Cutting edge: dendritic cell-restricted antigen presentation initiates the follicular helper T cell program but cannot complete ultimate effector differentiation. J Immunol 187, 1091-1095.

Hale, J. S., Youngblood, B., Latner, D. R., Mohammed, A. U., Ye, L., Akondy, R. S., Wu, T., Iyer, S. S., and Ahmed, R. (2013). Distinct Memory CD4 T Cells with Commitment to T Follicular Helper- and T Helper 1-Cell Lineages Are Generated after Acute Viral Infection. Immunity.

Haynes, N. M., Allen, C. D., Lesley, R., Ansel, K. M., Killeen, N., and Cyster, J. G. (2007). Role of CXCR5 and CCR7 in follicular Th cell positioning and appearance of a programmed cell death gene-1high germinal center-associated subpopulation. J Immunol 179, 5099-5108.

Johnston, R. J., Poholek, A. C., DiToro, D., Yusuf, I., Eto, D., Barnett, B., Dent, A. L., Craft, J., and Crotty, S. (2009). Bcl6 and Blimp-1 are reciprocal and antagonistic regulators of T follicular helper cell differentiation. Science 325, 1006-1010.

Josefowicz, S. Z., Lu, L. F., and Rudensky, A. Y. (2012). Regulatory T cells: mechanisms of differentiation and function. Annu Rev Immunol 30, 531-564.

Kerfoot, S. M., Yaari, G., Patel, J. R., Johnson, K. L., Gonzalez, D. G., Kleinstein, S. H., and Haberman, A. M. (2011). Germinal center B cell and T follicular helper cell development initiates in the interfollicular zone. Immunity 34, 947-960.

Linterman, M. A., Pierson, W., Lee, S. K., Kallies, A., Kawamoto, S., Rayner, T. F., Srivastava, M., Divekar, D. P., Beaton, L., Hogan, J. J., et al. (2011). Foxp3+ follicular regulatory T cells control the germinal center response. Nat Med 17, 975-982.

Luthje, K., Kallies, A., Shimohakamada, Y., Belz, G. T., Light, A., Tarlinton, D. M., and Nutt, S. L. (2012). The development and fate of follicular helper T cells defined by an IL-21 reporter mouse. Nature immunology 13, 491-498.

MacLeod, M. K., David, A., McKee, A. S., Crawford, F., Kappler, J. W., and Marrack, P. (2011). Memory CD4 T cells that express CXCR5 provide accelerated help to B cells. J Immunol 186, 2889-2896.

Marshall, H. D., Chandele, A., Jung, Y. W., Meng, H., Poholek, A. C., Parish, I. A., Rutishauser, R., Cui, W., Kleinstein, S. H., Craft, J., and Kaech, S. M. (2011). Differential expression of Ly6C and T-bet distinguish effector and memory Th1 CD4(+) cell properties during viral infection. Immunity 35, 633-646.

Massberg, S., Schaerli, P., Knezevic-Maramica, I., Kollnberger, M., Tubo, N., Moseman, E. A., Huff, I. V., Junt, T., Wagers, A. J., Mazo, I. B., and von Andrian, U. H. (2007). Immunosurveillance by hematopoietic progenitor cells trafficking through blood, lymph, and peripheral tissues. Cell 131, 994-1008.

Matloubian, M., Lo, C. G., Cinamon, G., Lesneski, M. J., Xu, Y., Brinkmann, V., Allende, M. L., Proia, R. L., and Cyster, J. G. (2004). Lymphocyte egress from thymus and peripheral lymphoid organs is dependent on SIP receptor 1. Nature 427, 355-360.

Mempel, T. R., Henrickson, S. E., and Von Andrian, U. H. (2004). T-cell priming by dendritic cells in lymph nodes occurs in three distinct phases. Nature 427, 154-159.

Morita, R., Schmitt, N., Bentebibel, S. E., Ranganathan, R., Bourdery, L., Zurawski, G., Foucat, E., Dullaers, M., Oh, S., Sabzghabaei, N., et al. (2011). Human blood CXCR5 (+)CD4(+) T cells are counterparts of T follicular cells and contain specific subsets that differentially support antibody secretion. Immunity 34, 108-121.

Nurieva, R. I., Chung, Y., Hwang, D., Yang, X. O., Kang, H. S., Ma, L., Wang, Y. H., Watowich, S. S., Jetten, A. M., Tian, Q., and Dong, C. (2008). Generation of T follicular helper cells is mediated by interleukin-21 but independent of T helper 1, 2, or 17 cell lineages. Immunity 29, 138-149.

Nurieva, R. I., Chung, Y., Martinez, G. J., Yang, X. O., Tanaka, S., Matskevitch, T. D., Wang, Y. H., and Dong, C. (2009). Bcl6 mediates the development of T follicular helper cells. Science 325, 1001-1005.

Peters, A., Pitcher, L. A., Sullivan, J. M., Mitsdoerffer, M., Acton, S. E., Franz, B., Wucherpfennig, K., Turley, S., Carroll, M. C., Sobel, R. A., et al. (2011). Th17 cells induce ectopic lymphoid follicles in central nervous system tissue inflammation. Immunity 35, 986-996.

Poholek, A. C., Hansen, K., Hernandez, S. G., Eto, D., Chandele, A., Weinstein, J. S., Dong, X., Odegard, J. M., Kaech, S. M., Dent, A. L., et al. (2010). In vivo regulation of Bcl6 and T follicular helper cell development. J Immunol 185, 313-326.

Rasheed, A. U., Rahn, H. P., Sallusto, F., Lipp, M., and Muller, G. (2006). Follicular B helper T cell activity is confined to CXCR5(hi)ICOS(hi) CD4 T cells and is independent of CD57 expression. Eur J Immunol 36, 1892-1903.

Reinhardt, R. L., Liang, H. E., and Locksley, R. M. (2009). Cytokine-secreting follicular T cells shape the antibody repertoire. Nature immunology 10, 385-393.

Rosenblum, M. D., Gratz, I. K., Paw, J. S., Lee, K., Marshak-Rothstein, A., and Abbas, A. K. (2011). Response to self antigen imprints regulatory memory in tissues. Nature 480, 538-542.

Sage, P. T., Francisco, L. M., Carman, C. V., and Sharpe, A. H. (2013). The receptor PD-1 controls follicular regulatory T cells in the lymph nodes and blood. Nature immunology 14, 152-161.

Saito, R., Onodera, H., Tago, H., Suzuki, Y., Shimizu, M., Matsumura, Y., Kondo, T., and Itoyama, Y. (2005). Altered expression of chemokine receptor CXCR5 on T cells of myasthenia gravis patients. Journal of neuroimmunology 170, 172-178.

Schaerli, P., Willimann, K., Lang, A. B., Lipp, M., Loetscher, P., and Moser, B. (2000). CXC chemokine receptor 5 expression defines follicular homing T cells with B cell helper function. J Exp Med 192, 1553-1562.

Shahinian, A., Pfeffer, K., Lee, K. P., Kundig, T. M., Kishihara, K., Wakeham, A., Kawai, K., Ohashi, P. S., Thompson, C. B., and Mak, T. W. (1993). Differential T cell costimulatory requirements in CD28-deficient mice. Science 261, 609-612.

Shiow, L. R., Rosen, D. B., Brdickova, N., Xu, Y., An, J., Lanier, L. L., Cyster, J. G., and Matloubian, M. (2006). CD69 acts downstream of interferon-alpha/beta to inhibit S1P1 and lymphocyte egress from lymphoid organs. Nature 440, 540-544.

Shulman, Z., Gitlin, A. D., Targ, S., Jankovic, M., Pasqual, G., Nussenzweig, M. C., and Victora, G. D. (2013). T Follicular Helper Cell Dynamics in Germinal Centers. Science.

Simpson, N., Gatenby, P. A., Wilson, A., Malik, S., Fulcher, D. A., Tangye, S. G., Manku, H., Vyse, T. J., Roncador, G., Huttley, G. A., et al. (2010). Expansion of circulating T cells resembling follicular helper T cells is a fixed phenotype that identifies a subset of severe systemic lupus erythematosus. Arthritis and rheumatism 62, 234-244.

Wollenberg, I., Agua-Doce, A., Hernandez, A., Almeida, C., Oliveira, V. G., Faro, J., and Graca, L. (2011). Regulation of the germinal center reaction by Foxp3+ follicular regulatory T cells. J Immunol 187, 4553-4560.

Example 4 Comparison of T$_{FR}$ and Treg Gene Expression Signatures

T$_{FR}$ (CD4+ICOS+CXCR5+GITR+CD19−) cells were sorted from the lymph nodes of 20 pooled, WT or PD-1 deficient mice 7 days after subcutaneous immunization with NP-OVA in CFA. Similarly, CD4+CXCR5−FoxP3+ Tregs were sorted from the lymph nodes of unimmunized FoxP3 reporter mice. Each sort was performed in triplicate. RNA was isolated using standard procedures, was amplified and reverse transcription was performed. Samples were run on mouse affymetrix gene expression arrays. Data was then normalized. Top 100 hits were determined by comparing WT T$_{FR}$ to Tregs and ranked by signal-to-noise. PD-1 deficient T$_{FR}$ cells, which have enhanced suppressive capacity, are added as an additional signature of T$_{FR}$ cells. Results are shown in FIG. 23.

Example 5 Surface Receptors Differentially Expressed by Human Blood T$_{FR}$ Cells Fresh human peripheral blood mononuclear cells were isolated by sucrose density centrifugation from normal human blood. Cells were surface stained with anti-CD4, anti-CXCR5, and anti-CD19. Cells were then plated on 96-well plates that contained antibodies to surface receptors in the screen. Cells were then fixed, permeabilized and intracellularly stained with anti-FoxP3. Populations were analyzed by flow cytometry as CD4 (CD4+CXCR5−FoxP3−CD19−), Treg (CD4+CXCR5− FoxP3+CD19−), T$_{FH}$ (CD4+CXCR5+FoxP3−CD19−) and T$_{FR}$ (CD4+CXCR5+FoxP3+CD19−). Top 56 hits (of T$_{FR}$ versus T$_{FH}$ cell with a fold increase of at least 1.2) are shown in FIG. 24, sorted on mean fluorescence intensity on T$_{FR}$ cells (value).

Example 6 Surface Receptors Differentially Expressed by Human Blood T$_{FH}$ Cells Fresh human peripheral blood mononuclear cells were isolated by sucrose density centrifugation from normal human blood. Cells were surface stained with anti-CD4, anti-CXCR5, and anti-CD19. Cells were then plated on 96-well plates that contained antibodies to surface receptors in the screen. Cells were then fixed, permeabilized and intracellularly stained with anti-FoxP3. Populations were analyzed by flow cytometry as CD4 (CD4+CXCR5−FoxP3−CD19−), Treg (CD4+CXCR5−FoxP3+CD19−), T$_{FH}$ (CD4+CXCR5+FoxP3−CD19−) and T$_{FR}$ (CD4+CXCR5+FoxP3+CD19−). Top 19 hits (T$_{FH}$ versus T$_{FR}$) are shown in FIG. 25, sorted by fold increase of expression on T$_{FH}$ versus T$_{FR}$ cell. Value indicates expression (in mean fluorescence intensity) on T$_{FR}$ cells.

Example 7 Blockade of the PD-1 Pathway can Heighten Antibody Stimulating Capacity of T$_{FH}$ Cells Murine CD4+ICOS+CXCR5+GITR−CD19− T$_{FH}$ cells were sorted from the lymph nodes of WT mice (that were immunized subcutaneously with NP-OVA in CFA 7 days previously) on an Aria cell sorter. T$_{FH}$ cells were plated with CD19+ B cells (isolated from lymph nodes of mice immunized with NP-OVA 7 days previously) in the presence of 5 ug/ml anti-IgM and 2 ug/ml anti-CD3 for 6 days. Anti-PDL1 was also added to some wells. After 6 days, cells from cultures were harvested, surface stained with anti-CD4, -CD19, -GL7, and -I-A followed by fixation/permeabilization, and intracellularly stained with anti-IgG1. Cells were analyzed by flow cytometric analysis. B cells were identified by surface expression of CD19 and IA. Ig class switched B cells were identified by coexpression of GL7 and IgG1. Results are shown in FIG. 26.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method of preparing a composition comprising TFR cells having enhanced immune suppressive activity comprising the steps of:
   a) obtaining an initial population of cells comprising TFR cells, T regulatory (Treg) progenitor cells or both;
   b) activating the cells ex vivo in the presence of a PD-1 antagonist or PD-1 ligand antagonist, or both; and
   c) isolating activated TFR cells from the population wherein the isolated TFR cells have enhanced immune suppressive activity.

2. The method of claim 1, wherein the initial population of cells is isolated from the peripheral blood, tissues or organs of one or more subjects.

3. The method of claim 1, further comprising sorting TFR cells and Treg progenitor cells from the cell population prior to activation of the cell population or after activation of the cell population.

4. The method of claim 1, wherein the activation step comprises expanding the cell population.

5. The method of claim 1, wherein the activation step comprises contacting the cell population with a stimulatory composition.

6. The method of claim 5, wherein the stimulatory composition comprises an anti-CD3 antibody, physiological antigen presenting cells (APCs), purified CD19+ B cells, and anti-CD28 antibody.

7. The method of claim 5, wherein stimulatory composition comprises beads coated with CD3 antibody, the anti-CD28 antibody or any combination thereof.

8. The method of claim 1, wherein the PD-1 antagonist or PD-1 ligand antagonist is selected from: a PD1-ligand antibody, an anti-PD-1 antibody, a peptide or a small molecule or any combination thereof, wherein the antagonist inhibits the interaction between PD-1 and a PD-1 ligand.

9. The method of claim 1, wherein the isolating step comprises sorting TFR cells based on surface markers of $CD4^+CXCR5^+ICOS^+GITR^+$ or $CD4^+CXCR5^+ICOS^+CD25^{hi}$.

10. A composition comprising T follicular regulatory (TFR) cells having enhanced immune suppressive activity prepared by the method of claim 1.

11. The composition of claim 10, wherein the TFR cells are characterized by their ability to more potently inhibit antibody production in vitro and in vivo.

12. The composition of claim 11, wherein the TFR cells are characterized by their ability to more potently inhibit T follicular helper (TFH) cell-mediated antibody production in vitro and in vivo.

13. The composition of claim 10, wherein the TFR cells are characterized by their ability to more potently inhibit T-follicular helper (TFH) cell function in vitro and in vivo.

14. The composition of claim 10, wherein the TFR cells having enhanced suppressive activity are characterized by their ability to more potently inhibit an antibody response in vitro and in vivo as compared to native TFR cells.

15. The composition of claim 10, wherein the TFR cells are at least two-fold more potent than native TFR.

* * * * *

UNITED STATES PATENT AND TRADEMARK OFFICE
CERTIFICATE OF CORRECTION

PATENT NO. : 9,885,016 B2
APPLICATION NO. : 14/707596
DATED : February 6, 2018
INVENTOR(S) : Sharpe et al.

Page 1 of 1

It is certified that error appears in the above-identified patent and that said Letters Patent is hereby corrected as shown below:

In the Specification

Delete the paragraph beginning at Column 1, Line number 14 and replace it with the following paragraph:
This invention was made with government support under AI078897, AI070085, AI040614, and HL007627 awarded by the National Institutes of Health. The government has certain rights in the invention.

Signed and Sealed this
Twenty-first Day of January, 2025

Coke Morgan Stewart
*Acting Director of the United States Patent and Trademark Office*